(12) United States Patent
Jeanmart et al.

(10) Patent No.: US 9,096,560 B2
(45) Date of Patent: *Aug. 4, 2015

(54) 5-HETEROCYCLYLALKYL-3-HYDROXY-2-PHENYLCYCLOPENT-2-ENONES AS HERBICIDES

(75) Inventors: Stephane André Marie Jeanmart, Bracknell (GB); Russell Colin Viner, Bracknell (GB); John Benjamin Taylor, Bracknell (GB); William Guy Whittingham, Bracknell (GB); Jeffrey Steven Wailes, Bracknell (GB); Sarah Margaret Targett, Bracknell (GB); Christopher John Mathews, Bracknell (GB); Mangala Govenkar, Goa (IN); Matthew Robert Cordingley, Bracknell (GB); Claire Janet Russell, Bracknell (GB); Melloney Tyte, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 358 days.

This patent is subject to a terminal disclaimer.

(21) Appl. No.: 13/002,343

(22) PCT Filed: Jul. 1, 2009

(86) PCT No.: PCT/EP2009/058250
§ 371 (c)(1),
(2), (4) Date: Mar. 25, 2011

(87) PCT Pub. No.: WO2010/000773
PCT Pub. Date: Jan. 7, 2010

(65) Prior Publication Data
US 2011/0263428 A1   Oct. 27, 2011

(30) Foreign Application Priority Data

Jul. 3, 2008   (GB) .................... 0812310.1

(51) Int. Cl.
*C07D 309/04*   (2006.01)
*A01N 43/08*   (2006.01)
(Continued)

(52) U.S. Cl.
CPC .............. *C07D 309/04* (2013.01); *A01N 43/08* (2013.01); *A01N 43/10* (2013.01); *A01N 43/16* (2013.01); *A01N 43/18* (2013.01); *A01N 43/20* (2013.01); *A01N 43/28* (2013.01); *A01N 43/32* (2013.01); *A01N 43/36* (2013.01); *A01N 43/40* (2013.01); *A01N 43/56* (2013.01); *A01N 43/80* (2013.01); *A01N 43/84* (2013.01); *A01N 43/90* (2013.01);
(Continued)

(58) Field of Classification Search
CPC ....... A01N 43/08; A01N 43/10; A01N 43/16; A01N 43/18; A01N 43/20; A01N 43/28; A01N 43/32; A01N 43/36; A01N 43/40; A01N 43/56; A01N 43/80; A01N 43/84; A01N 43/90; A01N 47/00; A01N 47/06; A01N 47/16; A01N 47/38; A01N 53/00; A01N 55/00; C07F 7/0812; C07D 211/32; C07D 211/04; C07D 211/96; C07D 207/08; C07D 207/48; C07D 307/12; C07D 309/04; C07D 317/26; C07D 319/12; C07D 335/02; C07D 401/06; C07D 405/06; C07D 409/06; C07D 413/06; C07D 491/18
USPC ......... 540/118, 119, 130, 138, 139, 140, 193, 540/225, 248, 249, 250, 283, 285, 287, 288, 540/291, 292, 293, 294, 295; 544/130; 546/194, 209, 211, 213, 214, 226, 237, 546/256; 548/248, 432, 517, 524, 527, 531, 548/539, 542; 549/13, 28, 214, 378, 415, 549/425, 427, 454, 498, 554; 504/118, 119, 504/130, 138, 139, 140, 193, 225, 248, 249, 504/250, 283, 285, 287, 288, 291, 292, 293, 504/294, 295

See application file for complete search history.

(56) References Cited

U.S. PATENT DOCUMENTS 4,175,135 A   11/1979   Haines
4,209,532 A   6/1980   Wheeler
(Continued)

FOREIGN PATENT DOCUMENTS

CA   2322158 A1   8/2000
CA   2352526 A1   5/2001
(Continued)

OTHER PUBLICATIONS

Mio et al. "Preparation of . . . " CA133:362702 (2000).*
RN 306948-06-1 CAS (2000).*
Translation WO2000068196, p. 2-225 (2000).*
Mio et al. "preparation of . . . " CA133:362702(2000).*
Patani et al. "Bioisosterism . . . " Chem. Rev. v.96 p. 3147-3176 (1996).*
(Continued)

*Primary Examiner* — Celia Chang
(74) *Attorney, Agent, or Firm* — R. Kody Jones

(57) ABSTRACT

Compounds of formula (I), wherein the substituents are as defined in claim 1, are suitable for use as herbicides.

23 Claims, No Drawings

(51) Int. Cl.

| | | |
|---|---|---|
| *A01N 43/10* | (2006.01) | |
| *A01N 43/16* | (2006.01) | |
| *A01N 43/18* | (2006.01) | |
| *A01N 43/20* | (2006.01) | |
| *A01N 43/28* | (2006.01) | |
| *A01N 43/32* | (2006.01) | |
| *A01N 43/36* | (2006.01) | |
| *A01N 43/40* | (2006.01) | |
| *A01N 43/56* | (2006.01) | |
| *A01N 43/80* | (2006.01) | |
| *A01N 43/84* | (2006.01) | |
| *A01N 43/90* | (2006.01) | |
| *A01N 47/00* | (2006.01) | |
| *A01N 47/06* | (2006.01) | |
| *A01N 47/16* | (2006.01) | |
| *A01N 47/38* | (2006.01) | |
| *A01N 53/00* | (2006.01) | |
| *A01N 55/00* | (2006.01) | |
| *C07D 207/08* | (2006.01) | |
| *C07D 207/48* | (2006.01) | |
| *C07D 211/32* | (2006.01) | |
| *C07D 211/94* | (2006.01) | |
| *C07D 211/96* | (2006.01) | |
| *C07D 307/12* | (2006.01) | |
| *C07D 317/26* | (2006.01) | |
| *C07D 319/12* | (2006.01) | |
| *C07D 335/02* | (2006.01) | |
| *C07D 401/06* | (2006.01) | |
| *C07D 405/06* | (2006.01) | |
| *C07D 409/06* | (2006.01) | |
| *C07D 413/06* | (2006.01) | |
| *C07D 491/18* | (2006.01) | |
| *C07F 7/08* | (2006.01) | |

(52) U.S. Cl.
CPC ............... *A01N 47/00* (2013.01); *A01N 47/06* (2013.01); *A01N 47/16* (2013.01); *A01N 47/38* (2013.01); *A01N 53/00* (2013.01); *A01N 55/00* (2013.01); *C07D 207/08* (2013.01); *C07D 207/48* (2013.01); *C07D 211/32* (2013.01); *C07D 211/94* (2013.01); *C07D 211/96* (2013.01); *C07D 307/12* (2013.01); *C07D 317/26* (2013.01); *C07D 319/12* (2013.01); *C07D 335/02* (2013.01); *C07D 401/06* (2013.01); *C07D 405/06* (2013.01); *C07D 409/06* (2013.01); *C07D 413/06* (2013.01); *C07D 491/18* (2013.01); *C07F 7/0812* (2013.01)

(56) References Cited

U.S. PATENT DOCUMENTS

| | | | | |
|---|---|---|---|---|
| 4,256,659 A | 3/1981 | Wheeler | | |
| 4,283,348 A | 8/1981 | Wheeler | | |
| 4,338,122 A | 7/1982 | Wheeler | | |
| 4,409,153 A | 10/1983 | Hodakowski | | |
| 4,489,012 A | 12/1984 | Hodakowski | | |
| 4,526,723 A | 7/1985 | Wheeler et al. | | |
| 4,551,547 A | 11/1985 | Wheeler | | |
| 4,659,372 A | 4/1987 | Wheeler | | |
| 5,684,205 A * | 11/1997 | Norman et al. | ............... | 568/316 |
| 5,808,135 A | 9/1998 | Fischer et al. | | |
| 5,840,661 A | 11/1998 | Fischer et al. | | |
| 6,251,833 B1 | 6/2001 | Erdelen et al. | | |
| 6,358,887 B1 | 3/2002 | Fischer et al. | | |
| 6,458,965 B1 | 10/2002 | Lieb et al. | | |
| 6,515,184 B1 | 2/2003 | Fischer et al. | | |
| 6,569,810 B1 | 5/2003 | Fischer et al. | | |
| 6,642,180 B1 * | 11/2003 | Fischer et al. | ............... | 504/246 |
| 6,806,264 B2 * | 10/2004 | Lieb et al. | ............... | 514/183 |
| 6,894,005 B1 | 5/2005 | Maetzke et al. | | |
| 7,718,706 B2 * | 5/2010 | Lieb et al. | ............... | 514/681 |
| 7,947,704 B2 * | 5/2011 | Bretschneider et al. | ...... | 514/294 |
| 8,013,172 B2 * | 9/2011 | Fischer et al. | ............... | 548/544 |
| 8,058,210 B2 | 11/2011 | Lieb et al. | | |
| 8,084,649 B2 | 12/2011 | Muehlebach et al. | | |
| 8,193,120 B2 * | 6/2012 | Ruther et al. | ............... | 504/318 |
| 8,202,875 B2 * | 6/2012 | Fischer et al. | ............... | 514/256 |
| 8,541,617 B2 * | 9/2013 | Fischer et al. | ............... | 560/105 |
| 8,629,084 B2 * | 1/2014 | Fischer et al. | ............... | 504/283 |
| 8,735,322 B2 * | 5/2014 | Mathews et al. | ............... | 504/103 |
| 8,791,303 B2 * | 7/2014 | Foley et al. | ............... | 568/327 |
| 2003/0199572 A1 | 10/2003 | Lieb et al. | | |
| 2003/0216260 A1 | 11/2003 | Ruther et al. | | |
| 2005/0164883 A1 | 7/2005 | Maetzke et al. | | |
| 2006/0058194 A1 | 3/2006 | Fischer et al. | | |
| 2006/0166829 A1 | 7/2006 | Fischer et al. | | |
| 2007/0015664 A1 | 1/2007 | Fischer et al. | | |
| 2007/0298969 A1 | 12/2007 | Fischer et al. | | |
| 2008/0167188 A1 | 7/2008 | Fischer et al. | | |
| 2009/0137393 A1 | 5/2009 | Fischer et al. | | |
| 2009/0227563 A1 | 9/2009 | Fischer et al. | | |
| 2009/0239906 A1 | 9/2009 | Fischer et al. | | |
| 2009/0298828 A1 | 12/2009 | Fischer et al. | | |
| 2009/0305891 A1 | 12/2009 | Fischer et al. | | |
| 2010/0009859 A1 | 1/2010 | Fischer et al. | | |
| 2010/0113270 A1 | 5/2010 | Mathews et al. | | |
| 2010/0210466 A1 | 8/2010 | Muehlebach et al. | | |
| 2010/0216638 A1 | 8/2010 | Mathews et al. | | |
| 2012/0035053 A1 * | 2/2012 | Mathews et al. | | |
| 2012/0065064 A1 * | 3/2012 | Taylor et al. | | |
| 2012/0178623 A1 | 7/2012 | Foley et al. | | |
| 2012/0202691 A1 * | 8/2012 | Jeanmart et al. | | |
| 2013/0053385 A1 * | 2/2013 | Jeanmart et al. | ............ | 514/235.5 |
| 2014/0011845 A1 * | 1/2014 | Jeanmart et al. | ............... | 514/326 |

FOREIGN PATENT DOCUMENTS

| | | |
|---|---|---|
| CA | 2382432 A1 | 2/2002 |
| CA | 2382435 A1 | 2/2002 |
| CA | 2404868 A1 | 9/2002 |
| CA | 2456776 A1 | 2/2004 |
| CA | 2636352 | 7/2008 |
| DE | 2813341 A1 | 10/1978 |
| DE | 3239368 | 4/1984 |
| DE | 3239368 A1 | 4/1984 |
| EP | 0701988 | 3/1996 |
| EP | 0701988 A1 | 3/1996 |
| WO | WO96/01798 A1 | 1/1996 |
| WO | WO96/03366 A1 | 2/1996 |
| WO | 9625395 | 8/1996 |
| WO | WO96/25395 A1 | 8/1996 |
| WO | WO96/35664 A1 | 11/1996 |
| WO | 97/14667 | 4/1997 |
| WO | WO97/14667 A1 | 4/1997 |
| WO | WO98/39281 A1 | 9/1998 |
| WO | WO99/43649 A1 | 9/1999 |
| WO | WO99/47525 A1 | 9/1999 |
| WO | WO99/48869 A1 | 9/1999 |
| WO | 00/15615 | 3/2000 |
| WO | WO0068195 * | 4/2000 |
| WO | WO00/47585 A1 | 8/2000 |
| WO | WO0068196 | 11/2000 |
| WO | WO01/09092 A1 | 2/2001 |
| WO | WO01/17972 A2 | 3/2001 |
| WO | WO01/17973 A2 | 3/2001 |
| WO | 0174770 | 10/2001 |
| WO | WO01/74770 A1 | 10/2001 |
| WO | WO0196333 * | 12/2001 |
| WO | WO03013249 A1 | 2/2003 |
| WO | WO2004/037749 A2 | 5/2004 |
| WO | 2004/058712 | 7/2004 |
| WO | WO2004/080962 A1 | 9/2004 |
| WO | WO2004/111042 A1 | 12/2004 |
| WO | WO2005/092897 A2 | 10/2005 |
| WO | WO2006/024411 A2 | 3/2006 |

(56) References Cited

FOREIGN PATENT DOCUMENTS

| WO | WO2006029799 A1 | 3/2006 |
|---|---|---|
| WO | WO2007/068427 A2 | 6/2007 |
| WO | WO2007/080066 | 7/2007 |
| WO | WO2007/096058 A1 | 8/2007 |
| WO | WO2007/121868 | 11/2007 |
| WO | WO2007/140881 | 12/2007 |
| WO | WO2008/071405 | 6/2008 |
| WO | WO2008/110307 | 9/2008 |
| WO | WO2008/110308 | 9/2008 |
| WO | WO2008/145336 A1 | 12/2008 |

OTHER PUBLICATIONS

M. Muchlebach et al., "Discovery and SAR of pinoxaden: a new broad spectrum, postemergence cereal herbicide," in Pesticide Chemistry. Crop Protection, Public Health, Environmental Safety, ed. H. Ohkawa et al., Jun. 2007, Wiley-VCH Verlag, Weinheim, pp. 101-110.

J. Wenger and T. Nidermann, "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

J. Wenger, T. Nidermann and C. Mathews, "Chapter 11: Acetyl-CoA Carboxylase Inhibitors", in Modern Crop Protection Compounds, Second Edition, ed. W. Kraemer et al., Wiley-VCH Verlag, Weinheim, available online Jan. 2012, pp. 447-477.

Chemical Abstracts Reg. No. 52883-96-7, Jun. 11, 2003, "4-cyclopentene-1,3-dione,2-(5-chloro-2-methoxyphenyl)".

Chemical Abstracts Reg. No. 299968-82-4, Oct. 27, 2000, "4-cyclopentene-1,3-dione,2-(2-bromophenyl)".

W. Ried et al., "Ringweiterungen und Umlagerungen von 3-alkyl-4-phenylcyclobutendionen", Chemische Berichte, vol. 115, 1982, pp. 783-790 (see p. 785 compound 7).

Zora et al., Organometallics, vol. 18, No. 21, 1999, pp. 4429-4436 (see p. 4430, compds 4D-4H).

SciFinder record dated Jun. 9, 2014, regarding CAS Registry No. 306948-06-1 disclosing 3-(2,6-dimethylphenyl)-1,5-dihydro-4-hydroxy-5,5-dimethyl-1-[(tetrahydro-3-furanyl)methyl]-2H-pyrrol-2-one.

* cited by examiner

5-HETEROCYCLYLALKYL-3-HYDROXY-2-PHENYLCYCLOPENT-2-ENONES AS HERBICIDES

This application is a 371 of International Application No. PCT/EP2009/058250 filed Jul. 1, 2009, which claims priority to GB 0812310.1 filed Jul. 3, 2008, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting undesired plant growth.

Cyclic diones compounds having herbicidal action are described, for example, in WO01/74770 and WO96/03366.

Novel cyclopentadione compounds, and derivatives thereof, having herbicidal and growth-inhibiting properties have now been found.

The present invention accordingly relates to compounds of formula (I)

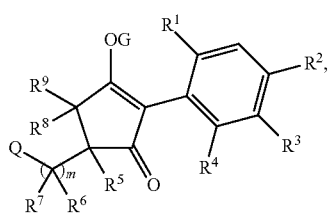

wherein
$R^1$ is hydrogen, methyl, ethyl, n-propyl, iso-propyl, halomethyl, haloethyl, halogen, vinyl, ethynyl, methoxy, ethoxy, halomethoxy, haloethoxy, cyclopropyl or halocyclopropyl, $R^2$ and $R^3$ are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_2$-$C_6$haloalkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, $R^4$ is hydrogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl or cyano,
$R^5$, $R^6$, $R^7$, $R^8$ and $R^9$ are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$haloalkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl, $C_1$-$C_3$alkylsulfonyl, or benzyl or benzyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or $C_3$-$C_6$cycloalkyl$C_1$-$C_3$alkyl in which a ring or chain methylene group is optionally replaced by an oxygen or sulfur atom or
$R^6$ and $R^7$ or $R^8$ and $R^9$ together with the carbon atoms to which they are attached form an optionally substituted 3- to 8-membered ring, optionally containing an oxygen, sulphur or nitrogen atom, or
$R^5$ and $R^6$ together form a bond,
Q is $C_3$-$C_8$ saturated or mono-unsaturated heterocyclyl containing at least one heteroatom selected from O, N and S, unsubstituted or substituted by a residue of formula =O, =N—$R^{10}$ or $C_1$-$C_4$alkyl, $C_1$-$C_4$haloalkyl, $C_1$-$C_4$alkoxy$C_1$-$C_2$alkyl, $C_3$-$C_6$cycloalkyl, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, where $R^{10}$ is $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_1$-$C_6$haloalkylsulfinyl or $C_1$-$C_6$haloalkylsulfonyl,
m is 1, 2 or 3,
where $R^6$ or $R^7$ can have different meanings when m is 2 or 3, and
G is hydrogen or an agriculturally acceptable metal, sulfonium, ammonium or latentiating group.

In the substituent definitions of the compounds of the formula I, each alkyl moiety either alone or as part of a larger group (such as alkoxy, alkylthio, alkylcarbonyl, alkylaminocarbonyl and dialkylaminocarbonyl is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$ alkyl groups, but are preferably $C_1$-$C_4$ alkyl groups, and, more preferably, $C_1$-$C_2$alkyl groups. Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

The term "heteroaryl" preferably refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3- benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

Preferred examples of heteroaromatic radicals include pyridyl, pyrimidinyl, triazinyl, thienyl, furyl, oxazolyl, isoxazolyl, 2,1,3-benzoxadiazolyl and thiazolyl.

Another group of preferred heteroaryls comprises furyl, thienyl, pyrazolyl, 1,2,3-triazolyl, 1,2,4-triazolyl, pyridyl, pyrimidinyl, pyridazinyl, pyrazinyl, quinolinyl, isoquinolinyl, cinnolinyl, quinazolinyl or quinoxalinyl.

The term "heterocyclyl" preferably refers to a non-aromatic, preferably monocyclic or bicyclic ring systems containing up to 8 atoms including at least one (preferably one or two) heteroatoms selected from O, S and N. Examples of such rings include 1,3-dithiane, 1,3-dioxane, 1,4-dioxane, morpholine, thiomorpholin, piperazine, tetrahydropyran, piperidine, thiane, 1,3-dioxolane, tetrahydrofuran, tetrahydrothiophene, pirolidine, imidazoline, azetidine, oxetane, thietane, aziridine, epoxide and thiirane.

Preferred examples of heterocyclic radicals include 1,3-dioxane, morpholine, thiomorpholin, tetrahydropyran, 1,3-dioxolane, tetrahydrofuran and tetrahydrothiophene Cycloalkyl includes preferably cyclopropyl, cyclobutyl, cyclopentyl and cyclohexyl.

For substituted heterocyclyl groups such as the rings formed by $R^6$ and $R^7$, and $R^8$ and $R^9$, respectively, it is preferred that one or more substituents are independently selected from halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected $C_1$-$C_6$alkyl groups. When heterocyclic rings are formed by joining two groups on an N atom, the resulting rings are suitably pyrrolidine, piperidine, thiomorpholine and morpholine each of which may be substituted by one or two independently selected $C_1$-$C_6$alkyl groups.

The invention relates also to the salts which the compounds of formula I are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methyl-nonylamine, methylpentadecylamine, methyloctadecylamine, ethylbutylamine, ethylheptyl-amine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Agriculturally acceptable metals are alkali metal or alkaline earth metal ions, for example sodium, potassium, magnesium and calcium ions, and transition metal ions, for example copper and iron atoms. Suitable ammonium ions are $NH_4^+$, alkylammonium, dialkylammonium, triakylammonium and tetraalkylammonium ions. Suitable sulfonium ions are trialkylsulfonium ions, for example trimethylsulfonium ions.

It should be understood that in those compounds of formula I, where G is a metal, ammonium or sulfonium as mentioned above and as such represents a cation, the corresponding negative charge is largely delocalised across the O—C=C—C=O unit.

The latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photoloysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X)$—$X^c$—$R^b$, $C(X^d)$—N$(R^c)$—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_6$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino, $R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_8$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —$C(X^a)$—$R^a$ or —$C(X^b)$—$X^c$—$R^b$, and the meanings of $X^a$, $R^a$, $X^b$, $X^c$ and $R^b$ are as defined above.

It is preferred that G is hydrogen, an alkali metal or alkaline earth metal, where hydrogen is especially preferred.

Depending on the nature of the substituents, compounds of formula (I) may exist in different isomeric forms. When G is hydrogen, for example, compounds of formula (I) may exist in different tautomeric forms:

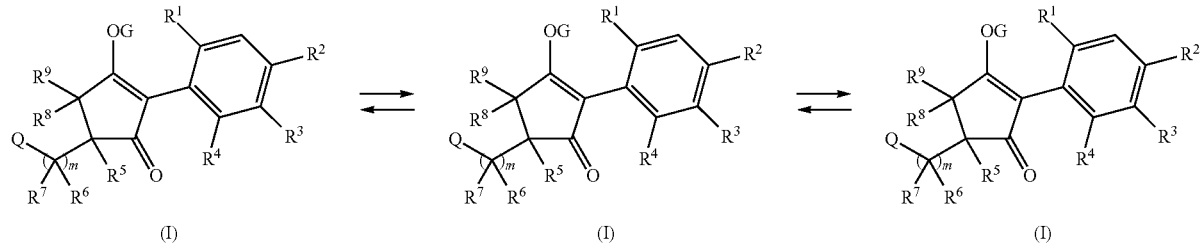

(I)

halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, This invention covers all such isomers and tautomers and mixtures thereof in all proportions. Also, when substituents contain double bonds, cis- and trans-isomers can exist. These isomers, too, are within the scope of the claimed compounds of the formula (I).

In a preferred group of compounds of the formula (I), $R^1$ is methyl, ethyl or methoxy.

Preferably, $R^2$ and $R^3$ are independently hydrogen, halogen, $C_1$-$C_6$alkyl, $C_1$-$C_6$alkoxy, $C_2$-$C_6$alkenyl, $C_2$-$C_6$alkynyl, $C_2$-$C_6$haloalkynyl, phenyl or phenyl substituted by $C_1$-$C_4$alkyl, $C_1$-$C_3$haloalkyl, cyano, nitro, halogen or $C_1$-$C_3$alkylsulfonyl, and, more preferably, $R^2$ and $R^3$ are independently hydrogen, chlorine, bromine, methyl, methoxy, ethyl, ethoxy, ethenyl, ethynyl, phenyl or phenyl substituted by methyl, trifluoromethyl, cyano, nitro, fluorine, chlorine or methylsulfonyl.

In another group of preferred compounds of formula (I), $R^2$ and $R^3$ are independently thienyl, thienyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, furyl, furyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyrazolyl, pyrazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, thiazolyl, thiazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, oxazolyl, oxazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, isothiazolyl, isothiazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, isoxazolyl, isoxazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, triazolyl, triazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, oxadiazolyl, oxadiazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, thiadiazolyl, thiadiazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, tetrazolyl, tetrazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyridyl, pyridyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyrimidinyl, pyrimidinyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyridazinyl, pyridazinyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyrazinyl or pyrazinyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, triazinyl or triazinyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

Preferably, $R^3$ is hydrogen.

Preferably, $R^4$ is hydrogen, methyl, ethyl, n-propyl, isopropyl, halomethyl, haloethyl, halogen, vinyl, ethynyl, methoxy, ethoxy, halomethoxy or haloethoxy, and more preferably $R^4$ is hydrogen, methyl, ethyl, chlorine, bromine, ethenyl, ethynyl, methoxy or ethoxy.

Preferably, $R^1$, $R^2$ and $R^4$ are methyl and $R^3$ is hydrogen.

In another preferred group of the compounds of the formula (I), $R^5$ is hydrogen, halogen, $C_1$-$C_6$alkyl, $C_1$-$C_6$haloalkyl, $C_1$-$C_6$alkoxy or $C_1$-$C_6$haloalkoxy, and, more preferably, $R^5$ is hydrogen or methyl.

Preferably, in the compounds of the formula (I), $R^6$ and $R^7$ independently are hydrogen, halogen, $C_1$-$C_6$alkyl, $C_1$-$C_6$haloalkyl, $C_1$-$C_6$alkoxy or $C_1$-$C_6$haloalkoxy, and, more preferably, $R^6$ and $R^7$ independently are hydrogen or methyl.

In another preferred group of the compounds of the formula (I) $R^8$ and $R^9$ independently are hydrogen, halogen, $C_1$-$C_6$alkyl, $C_1$-$C_6$haloalkyl, $C_1$-$C_6$alkoxy or $C_1$-$C_6$haloalkoxy, and, more preferably, $R^8$ and $R^9$ independently are hydrogen or methyl.

Preferred saturated or mono-unsaturated rings Q are those of the formula

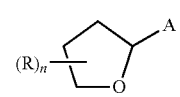 $Q_1$

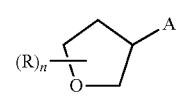 $Q_2$

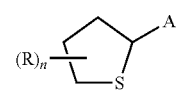 $Q_3$

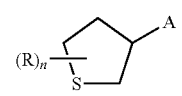 $Q_4$

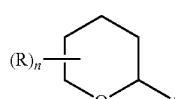 $Q_5$

 $Q_6$

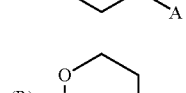 $Q_7$

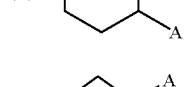 $Q_8$

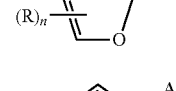 $Q_9$

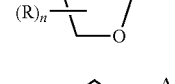 $Q_{10}$

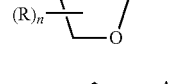 $Q_{11}$

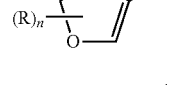 $Q_{12}$

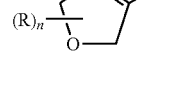 $Q_{13}$

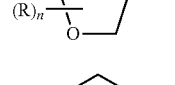 $Q_{14}$

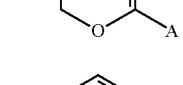 $Q_{15}$

-continued
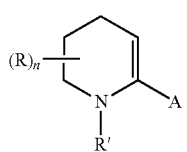 Q16
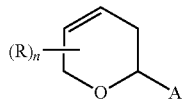 Q17
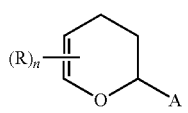 Q18
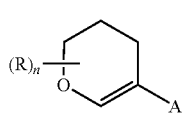 Q19
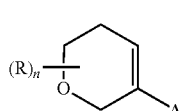 Q20
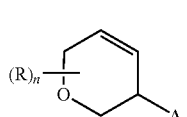 Q21
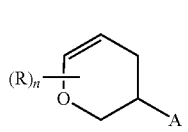 Q22
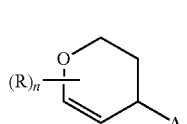 Q23
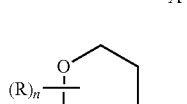 Q24
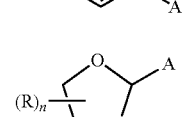 Q25
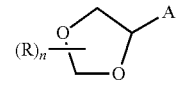 Q26
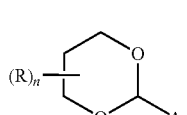 Q27
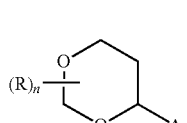 Q28
-continued
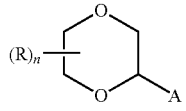 Q29
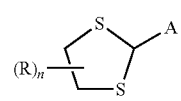 Q30
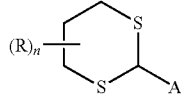 Q31
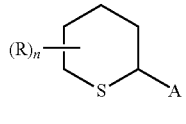 Q32
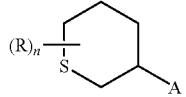 Q33
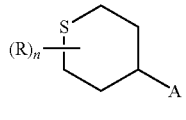 Q34
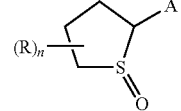 Q35
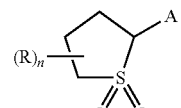 Q36
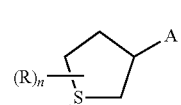 Q37
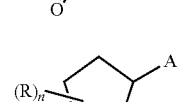 Q38
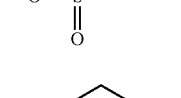 Q39
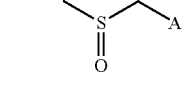 Q40
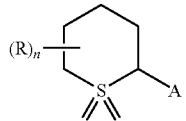

-continued
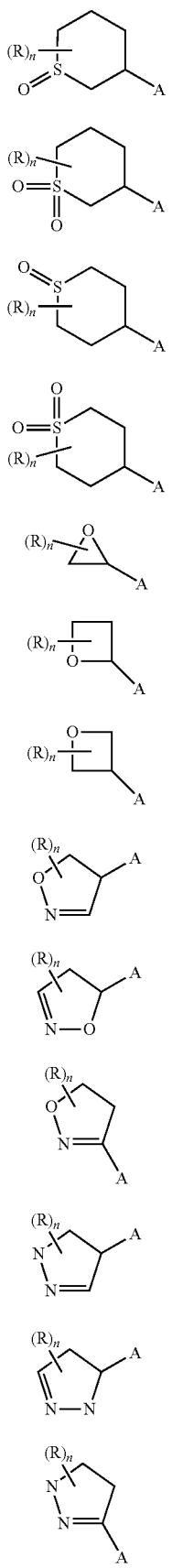
Q41
Q42
Q43
Q44
Q45
Q46
Q47
Q48
Q49
Q50
Q51
Q52
Q53
-continued
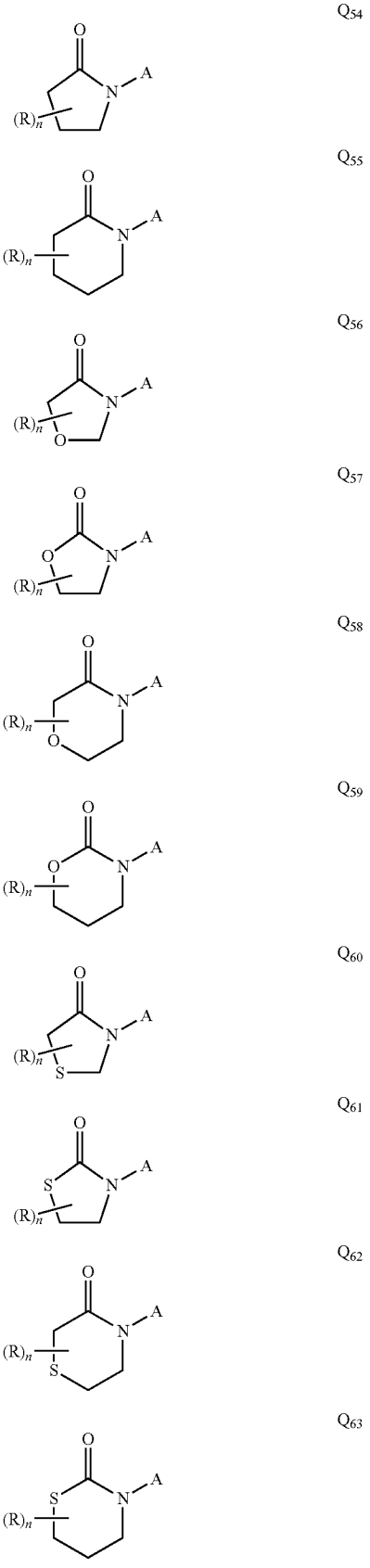
Q54
Q55
Q56
Q57
Q58
Q59
Q60
Q61
Q62
Q63

-continued
| | |
|---|---|
| 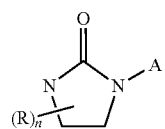 | $Q_{64}$ |
| 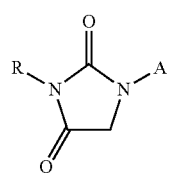 | $Q_{65}$ |
| 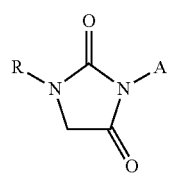 | $Q_{66}$ |
| 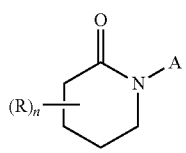 | $Q_{67}$ |
| 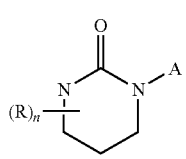 | $Q_{68}$ |
| 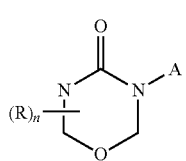 | $Q_{69}$ |
| 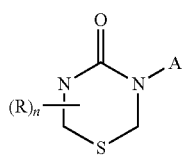 | $Q_{70}$ |
| 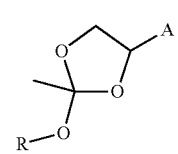 | $Q_{71}$ |
| 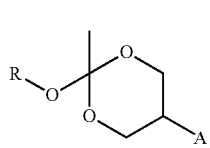 | $Q_{72}$ |
| 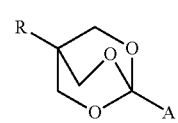 | $Q_{73}$ |
-continued
| | |
|---|---|
| 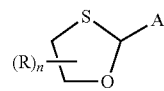 | $Q_{74}$ |
| 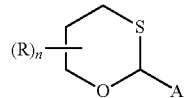 | $Q_{75}$ |
| 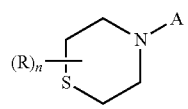 | $Q_{76}$ |
| 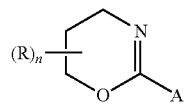 | $Q_{77}$ |
| 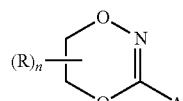 | $Q_{78}$ |
| 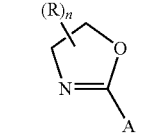 | $Q_{79}$ |
| 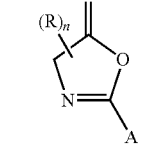 | $Q_{80}$ |
| 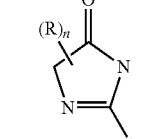 | $Q_{81}$ |
| 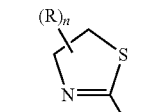 | $Q_{82}$ |
| 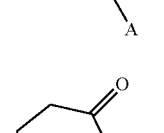 | $Q_{83}$ |
| 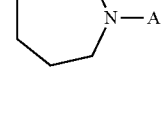 | $Q_{84}$ |

-continued
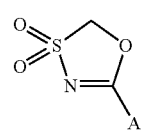 Q85
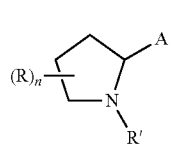 Q86
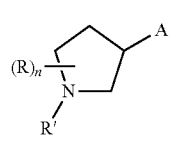 Q87
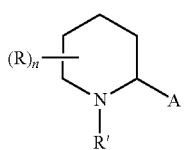 Q88
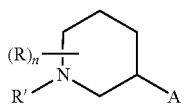 Q89
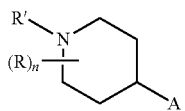 Q90
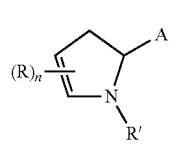 Q91
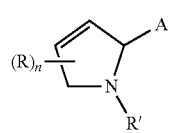 Q92
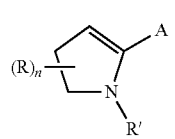 Q93
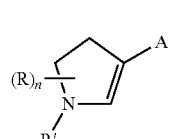 Q94
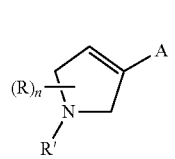 Q95
-continued
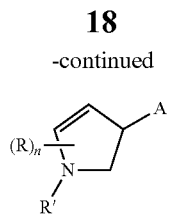 Q96
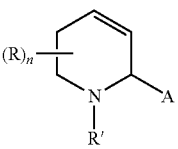 Q97
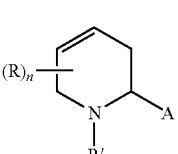 Q98
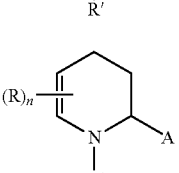 Q99
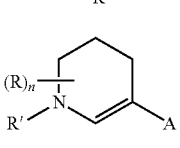 Q100
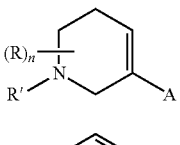 Q101
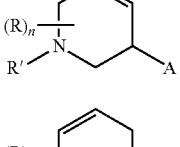 Q102
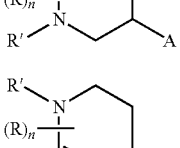 Q103
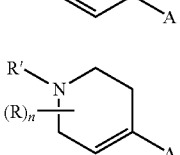 Q104
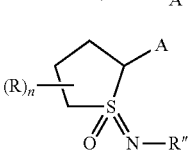 Q105
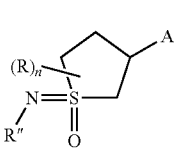 Q106
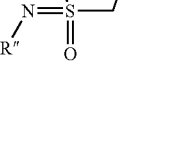 Q107

-continued

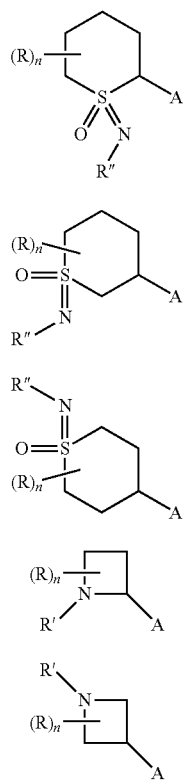

Q108

Q109

Q110

Q106

Q107 wherein

R is hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_2$-$C_6$haloalkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, R' is hydrogen, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_6$-$C_{10}$arylsulfonyl, $C_6$-$C_{10}$arylcarbonyl, $C_6$-$C_{10}$arylaminocarbonyl, $C_7$-$C_{16}$arylalkylaminocarbonyl, $C_1$-$C_9$hetarylsulfonyl, $C_1$-$C_9$hetarylcarbonyl, $C_1$-$C_9$hetarylaminocarbonyl, $C_2$-$C_{15}$hetarylalkylaminocarbonyl, R" is hydrogen, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_1$-$C_6$haloalkylsulfinyl or $C_1$-$C_6$haloalkylsulfonyl, n is 0, 1, 2, 3 or 4 and A denotes the position of attachment to the —$(CR^6R^7)_m$— moiety.

Groups $Q_1$, $Q_2$, $Q_3$, $Q_4$, $Q_5$, $Q_6$, $Q_7$, $Q_{25}$, $Q_{26}$, $Q_{27}$, $Q_{28}$, $Q_{29}$, $Q_{86}$, $Q_{87}$, $Q_{88}$, $Q_{89}$, $Q_{90}$ are more preferred, and groups $Q_1$ to $Q_7$ are particularly preferred.

Preferably, R and R' are independently hydrogen, $C_1$-$C_4$alkyl, $C_1$-$C_4$haloalkyl, $C_1$-$C_4$alkoxy or $C_1$-$C_4$haloalkoxy, and R" is hydrogen, $C_1$-$C_4$alkyl, $C_1$-$C_4$haloalkyl, $C_1$-$C_4$alkoxy, $C_1$-$C_4$haloalkoxy or $C_1$-$C_6$haloalkylcarbonyl.

Preferably, n is 0, 1 and 2.

Preferably, in the compounds of the formula (I), m is 1 or 2 and most preferably m is 1.

Certain compounds of formula (I) are alkenes, and as such undergo further reactions typical of alkenes to give additional compounds of formula (I) according to known procedures. Example of such reaction include, but are not restricted to, halogenation or hydrogenation

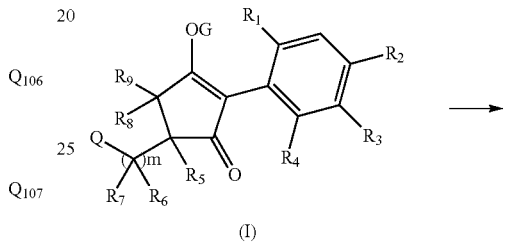

(I)

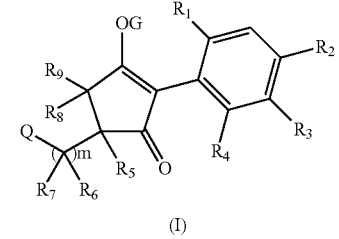

(I)

wherein $R^5$ and $R^6$ form a bond

Compounds of formula (I) wherein $R^5$ and $R^6$ form a bond and $R^7$ is halogen (preferably chloride or bromide) or $R^7$ is $C_1$-$C_6$alkylsulfonate (preferably mesylate) or $C_1$-$C_6$haloalkylsulfonate (preferably triflate) or an arylsulfonate (preferable tosylate) may undergo a cross-coupling reaction with a suitable coupling partner under conditions described in the literature for Suzuki-Miyaura, Sonogashira and related cross-coupling reactions to give additional compounds of formula (I) (see, for example, O'Brien, C. J. and Organ, M. G. Angew. Chem. Int. Ed. (2007), 46, 2768-2813; Suzuki, A. Journal of Organometallic Chemistry (2002), 653, 83; Miyaura N. and Suzuki, A. Chem. Rev. (1995), 95, 2457-2483).

Those skilled in the art will appreciate that compounds of formula (I) may contain a aromatic moiety bearing one or more substituents capable of being transformed into alternative substituents under known conditions, and that these compounds may themselves serve as intermediates in the preparation of additional compounds of formula (I).

For example, compounds of formula (I) wherein $R^1$, $R^2$, $R^3$ or $R^4$ is alkenyl or alkynyl, may be reduced to compounds of formula (I) wherein $R^1$, $R^2$, $R^3$ or $R^4$ is alkyl under known conditions and compounds of formula (I) wherein $R^1$, $R^2$, $R^3$ or $R^4$ is halogen, preferably bromide or iodine, may undergo a cross-coupling reaction with a suitable coupling partner under conditions described in the literature for Suzuki-Miyaura, Sonogashira and related cross-coupling reactions to give additional compounds of formula (I) (see, for example, O'Brien, C. J. and Organ, M. G. Angew. Chem. Int. Ed. (2007), 46, 2768-2813; Suzuki, A. Journal of Organometallic Chemistry (2002), 653, 83; Miyaura N. and Suzuki, A. Chem. Rev. (1995), 95, 2457-2483).

Compounds of formula (I) wherein G is $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$ alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating compounds of formula (A), which are compounds of formula (I) wherein G is H, with a reagent G-Z, wherein G-Z is alkylating agent such as an alkyl halide (the definition of alkyl halides includes simple $C_1$-$C_8$alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di-$C_1$-$C_8$alkyl sulfate, or with a $C_3$-$C_8$alkenyl halide, or with a $C_3$-$C_8$alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$, wherein $X^a$ is oxygen, or an isocyanate, $R^cN{=}C{=}O$, or a carbamoyl chloride, Cl—$C(X^d)$—$N(R^c)$—$R^d$ (wherein $X^d$ is oxygen and with the proviso that neither $R^c$ nor $R^d$ is hydrogen), or a thiocarbamoyl chloride Cl—$C(X^d)$—$N(R^c)$—$R^d$ (wherein $X^d$ is sulfur and with the proviso that neither $R^c$ nor $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^cN{=}C{=}S$, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base.

Isomeric compounds of formula (I) may be formed. For example, compounds of formula (A) may give rise to two isomeric compounds of formula (I), or to isomeric mixtures of compounds of formula (I). This invention covers both isomeric compounds of formula (I), together with mixtures of these compounds in any ratio.

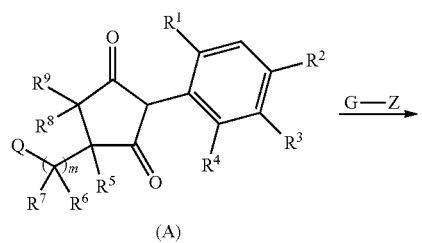

(A)

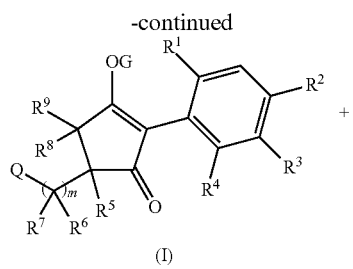

(I)

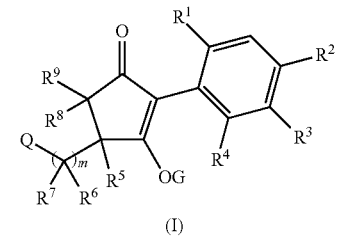

(I)

The O-alkylation of cyclic 1,3-diones is known; suitable methods are described, for example, in U.S. Pat. No. 4,436,666. Alternative procedures have been reported by Pizzorno, M. T. and Albonico, S. M. Chem. Ind. (London) (1972), 425; Born, H. et al. J. Chem. Soc. (1953), 1779; Constantino, M. G. et al. Synth. Commun. (1992), 22 (19), 2859; Tian, Y. et al. Synth. Commun. (1997), 27 (9), 1577; Chandra Roy, S. et al., Chem. Lett. (2006), 35 (1), 16; Zubaidha, P. K. et al. Tetrahedron Lett. (2004), 45, 7187 and by Zwanenburg, B. et al. Tetrahedron (2005), 45 (22), 7109.

The acylation of cyclic 1,3-diones may be effected by procedures similar to those described, for example, in U.S. Pat. No. 4,551,547, U.S. Pat. No. 4,175,135, U.S. Pat. No. 4,422,870, U.S. Pat. No. 4,659,372 and U.S. Pat. No. 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally a base such as triethylamine or pyridine in a suitable solvent such as tetrahydrofuran, dichloromethane or acetonitrile. Suitable procedures are described, for example, by Zhang, W. and Pugh, G. Tetrahedron Lett. (1999), 40 (43), 7595 and Isobe, T. and Ishikawa, T. J. Org. Chem. (1999), 64 (19) 6984.

Phosphorylation of cyclic-1,3-diones may be effected using a phosphoryl halide or thiophosphoryl halide and a base by procedures analogous to those described in U.S. Pat. No. 4,409,153. Sulfonylation of compounds of formula (A) may be achieved using an alkyl or aryl sulfonyl halide, preferably in the presence of at least one equivalent of base, for example by the procedure of Kowalski, C. J. and Fields, K. W. J. Org. Chem. (1981), 46, 197.

Compounds of formula (A) may be prepared from a compounds of formula (I) by hydrolysis, preferably in the presence of an acid catalyst such as hydrochloric acid and optionally in the presence of a suitable solvent such as tetrahydrofuran or acetone preferably between 25° C. and 150° C. under conventional heating or under microwave irradiation.

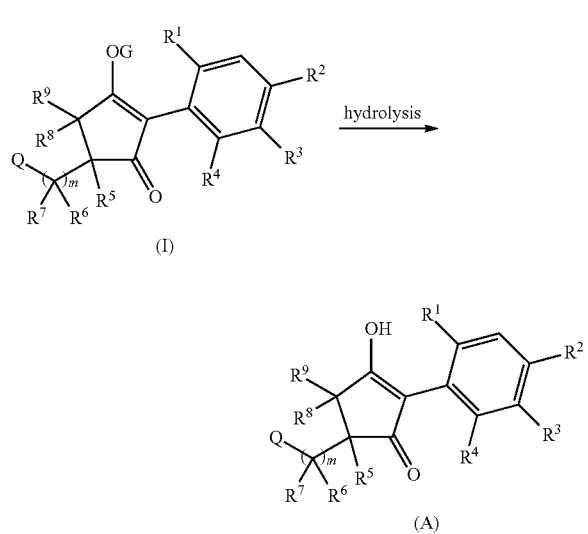

In a further approach, compounds of formula (A) may be prepared by the cyclisation of a compound of formula (B) or a compound of formula (C), wherein R''' is hydrogen or an alkyl group, preferably in the presence of an acid or base, and optionally in the presence of a suitable solvent, by analogous methods to those described by T. N. Wheeler, U.S. Pat. No. 4,209,532. Compounds of formula (B) or compounds of formula (C) wherein R''' is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

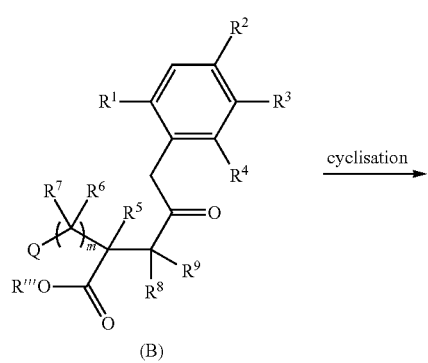

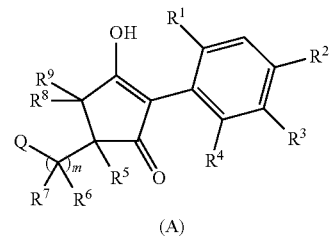

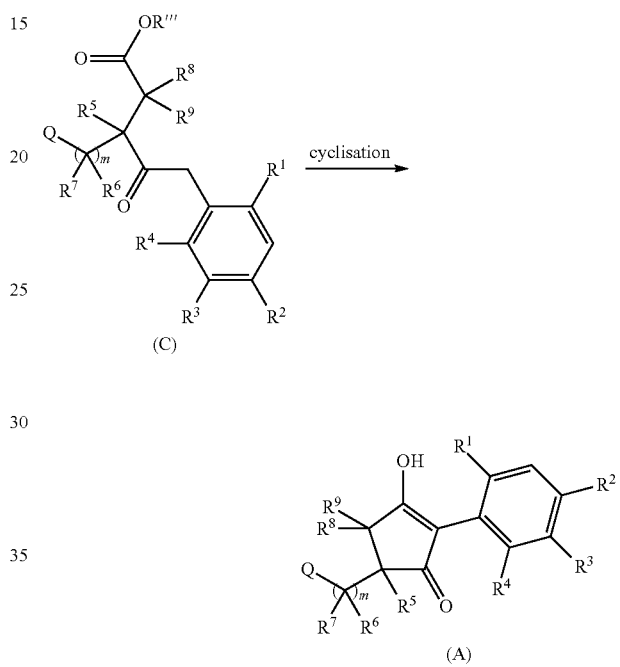

Compounds of formula (B) or compounds of formula (C) wherein R''' is alkyl (preferably methyl or ethyl), may be cyclised under acidic or basic conditions, preferably in the presence of at least one equivalent of a strong base such as potassium tert-butoxide, lithium diisopropylamide or sodium hydride and in a solvent such as tetrahydrofuran, toluene, dimethylsulfoxide or N,N-dimethylformamide.

Compounds of formula (B) and compounds of formula (C), wherein R''' is H, may be esterified to, respectively, compounds of formula (B) and compounds of formula (C), wherein R''' is alkyl, under standard conditions, for example by heating with an alkyl alcohol, ROH, in the presence of an acid catalyst.

Compounds of formula (B) and compounds of formula (C), wherein R''' is H, may be prepared, respectively, by saponification of a compounds of formula (D) and compounds of formula (E) wherein R'''' is alkyl (preferably methyl or ethyl), under standard conditions, followed by acidification of the reaction mixture to effect decarboxylation, by similar processes to those described, for example, by T. N. Wheeler, U.S. Pat. No. 4,209,532.

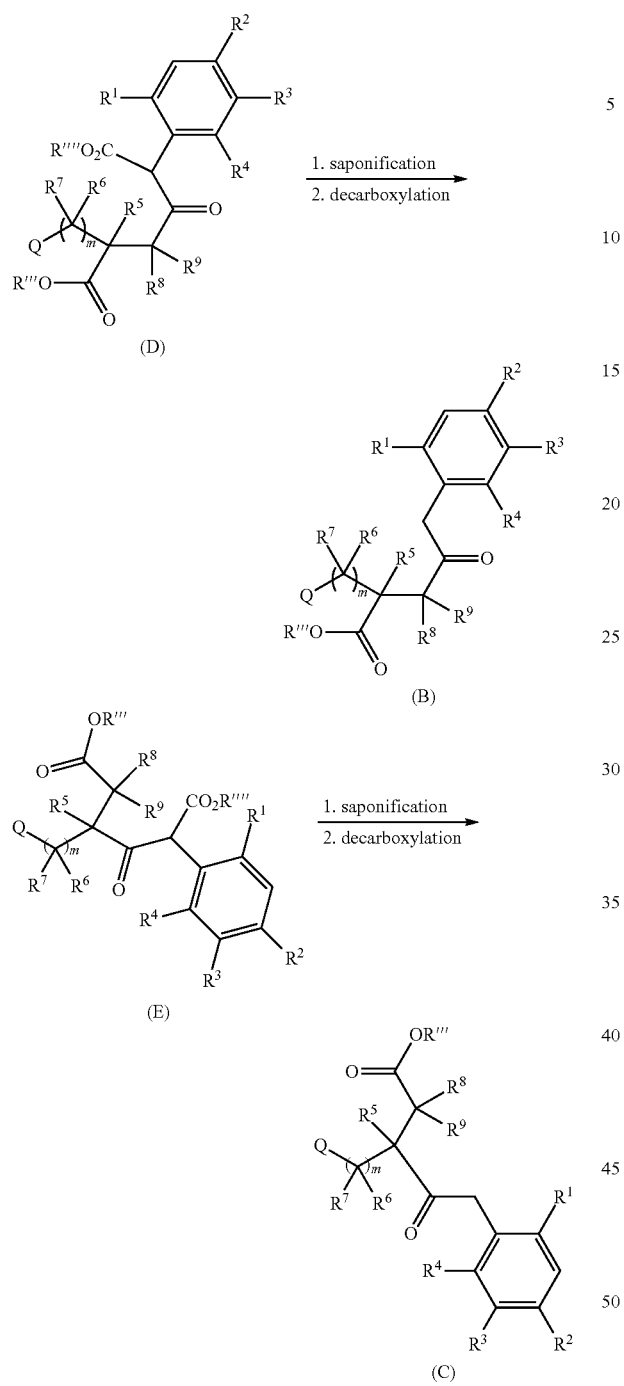

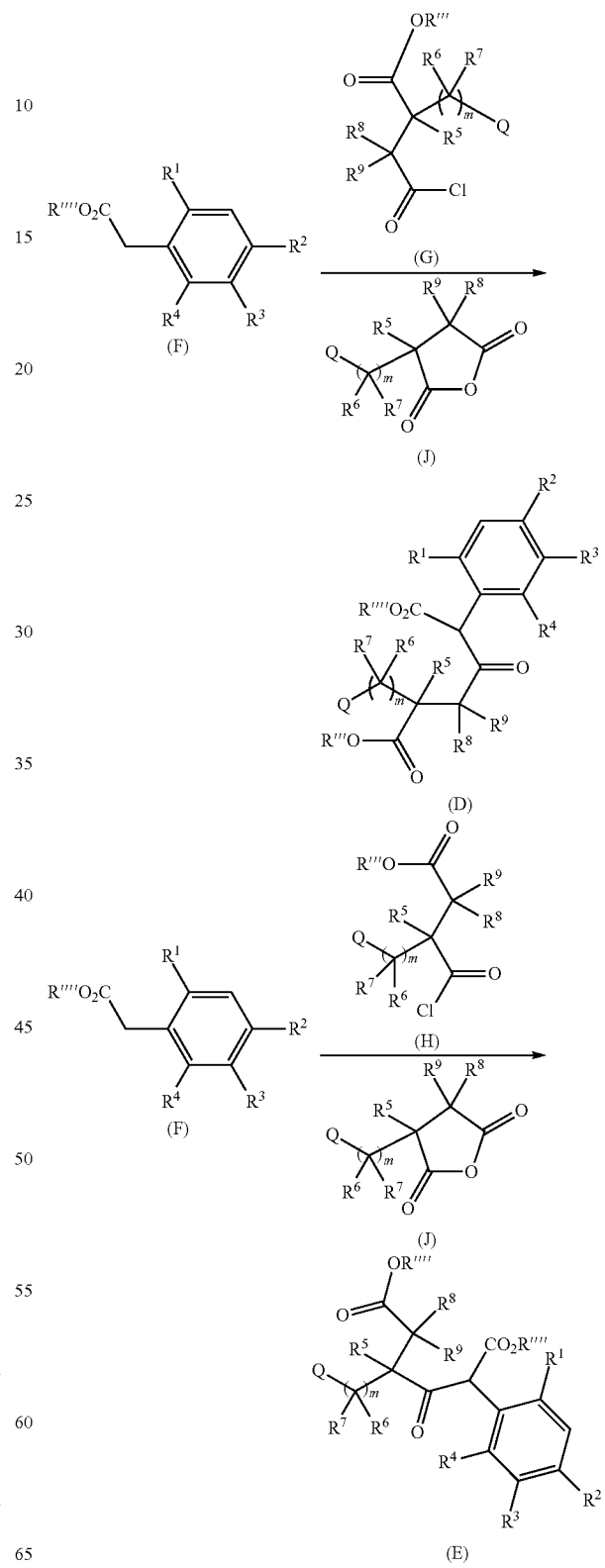

Compounds of formula (D) and compounds of formula (E), wherein R"" is alkyl, may be prepared by treating, respectively, compounds of formula (F) with suitable carboxylic acid chlorides of formula (G) or suitable carboxylic acid chlorides of formula (H) under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C. Alternatively, compounds of formula (D) and compounds of formula (E), wherein R"" is H, may be prepared by treating a compound of formula (F) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (J):

Compounds of formula (F) are known compounds, or may be prepared from known compounds by known methods.

Compounds of formula (J) may be prepared, for example, by analogous methods to those described by Ballini, R. et al. Synthesis (2002), (5), 681-685; Bergmeier, S. C. and Ismail, K. A. Synthesis (2000), (10), 1369-1371; Groutas, W. C. et al. J. Med. Chem. (1989), 32 (7), 1607-11 and Bernhard, K. and Lincke, H. Helv. Chim. Acta (1946), 29, 1457-1466.

Compounds of formula (G) or compounds of formula (H) may be prepared from a compound of formula (J) by treatment with an alkyl alcohol, R'''—OH, in the presence of a base, such as dimethylaminopyridine or an alkaline metal alkoxide (see, for example, Buser, S, and Vasella, A. Helv. Chim. Acta, (2005), 88, 3151 and M. Hart et al. Bioorg. Med. Chem. Letters, (2004), 14, 1969), followed by treatment of the resulting acid with a chlorinating reagent such as oxalyl chloride or thionyl chloride under known conditions (see, for example, Santelli-Rouvier. C. Tetrahedron Lett. (1984), 25 (39), 4371; Walba D. and Wand, M. Tetrahedron Lett. (1982), 23 (48), 4995; Cason, J. Org. Synth. Coll. Vol. III, (169), 1955).

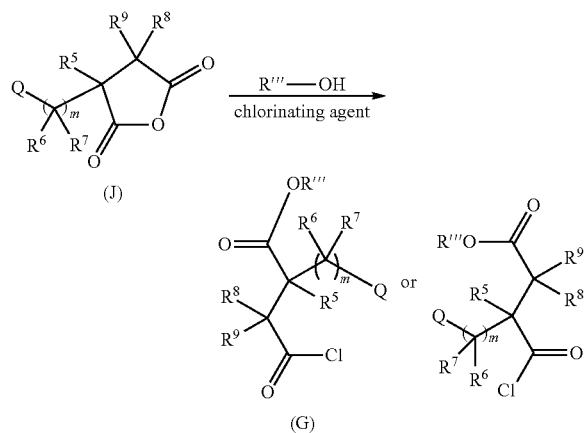

Compounds of formula (G) and compounds of formula (H) may be made from known compounds by known methods. For example, analogous methods to obtain compounds of formula (G) and compounds of formula (H) are described by Bergmeier, S. C. and Ismail, K. A. Synthesis (2000), (10), 1369-1371.

In an further approach to compounds of formula (I) may be prepared by treating compounds of formula (K) with compounds of formula (L) wherein LG is a leaving group such as halogen (preferably iodide or bromide) or an activated alcohol (preferably mesylate or tosylate) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C.

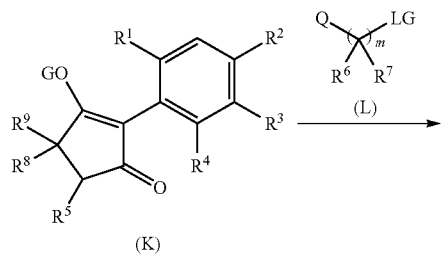

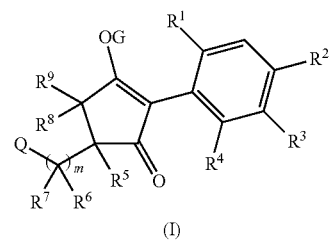

Compounds of formula (L) are known, or may be made known compounds by known methods (see for example: WO2006016178; Ueno, H. et al. J. Med. Chem. (2005), 48(10), 3586-3604; Kanoh, S. et al. Tetrahedron (2002), 58(35), 7049-7064; Strachan, J.-P. et al. J. Org. Chem. (2006), 71(26), 9909-9911).

Compounds of formula (K) are known compounds or may be made from known compounds by known methods (see, for example, Song, Y. S. S. et al. Tetrahedron Lett. (2005), 46 (46), 5987-5990; Kuethe, J. T. et al. J. Org. Chem. (2002), 67(17), 5993-6000).

Alternatively, compounds of formula (K) wherein G is $C_1$-$C_6$alkyl may be prepared by alkylation of compounds of formula (K), wherein G is hydrogen under known conditions or by known methods (see, for example, Eberhardt, U. et al. Chem. Ber. (1983), 116 (1), 119-135).

Compounds of formula (K), wherein G is hydrogen, are known, or may be prepared from known compounds by known methods (see, for example, Nguyen, H. N. et al. J. Am. Chem. Soc. (2003), 125 (39), 11818-11819; Bonjoch, J. et al. Tetrahedron (2001), 57(28), 6011-6017; Fox, J. M. et al. J. Am. Chem. Soc. (2000), 122(7), 1360-1370; U.S. Pat. No. 4,338,122; U.S. Pat. No. 4,283,348).

Alternatively, compounds of formula (I) where $R^5$ and $R^6$ form a bond can be prepared from compounds of formula (M) by known methods (see for example Nagaoka, H. et al. Tetrahedron Letters (1985), 26 (41), 5053-5056; Nagaoka, H. et al. J. Am. Chem. Soc. (1986), 108 (16), 5019-5021; Zuki, M. et al. Bull. Chem. Soc. Japan (1988), 61(4), 1299-1312; Enholm, E. J. et al. J. Org. Chem. (1996), 61 (16), 5384-5390; Clive, D. L. J. et al. Tetrahedron (2001), 57 (18), 3845-3858; Bartoli, G. et al. J. Org. Chem. (2002), 67 (25), 9111-9114. Jung, M. E. et al. Chem. Comm. (2003), (2), 196-197; EP1433772; JP2004203844; IN194295)

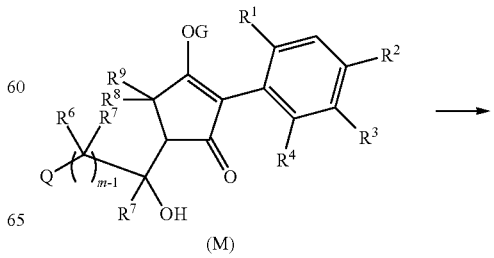

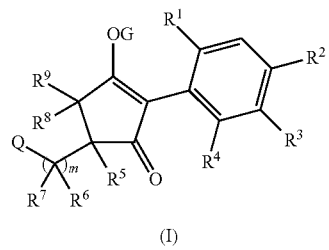

(I)

wherein $R^5$ and $R^6$ form a bond

Compounds of formula (M) may be prepared by treating compounds of formula (K) (in which $R^5$ is hydrogen) with compounds of formula (N) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C.

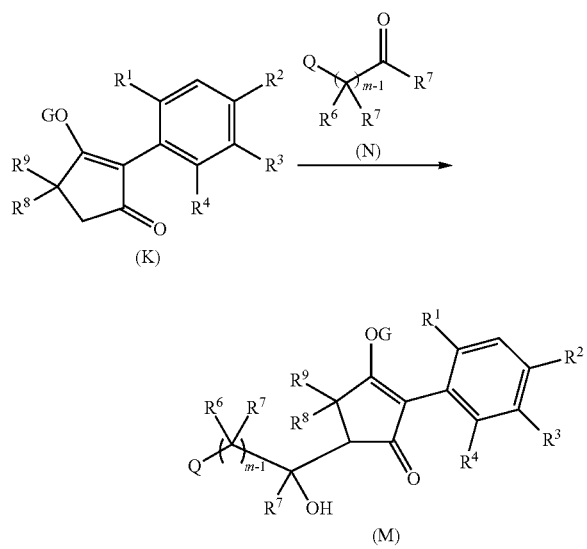

Compounds of formula (N) are known, or may be made from known compounds by known methods.

Compounds of formula (I) (wherein G is $C_1$-$C_4$alkyl) may be prepared by reacting a compounds of formula (O) (wherein G is $C_1$-$C_4$alkyl, and Hal is a halogen, preferably bromine or iodine), with aryl boronic acids, Ar—B(OH)$_2$ of formula (P) or aryl boronate esters in the presence of a suitable palladium catalyst (for example 0.001-50% palladium (II) acetate with respect to compound (O)) and a base (for example 1 to 10 equivalents potassium phosphate with respect to compound (O)) and preferably in the presence of a suitable ligand (for example 0.001-50% (2-dicyclohexylphosphino)-2',6'-dimethoxybiphenyl with respect to compound (O)), and in a suitable solvent (for example toluene or 1,2-dimethoxyethane), preferably between 25° C. and 200° C. under conventional heating or under microwave irradiation (see, for example, Song, Y. S. S. et al. Tetrahedron Lett. (2005), 46 (46), 5987-5990; Kuethe, J. T. et al. J. Org. Chem. (2002), 67(17), 5993-6000).

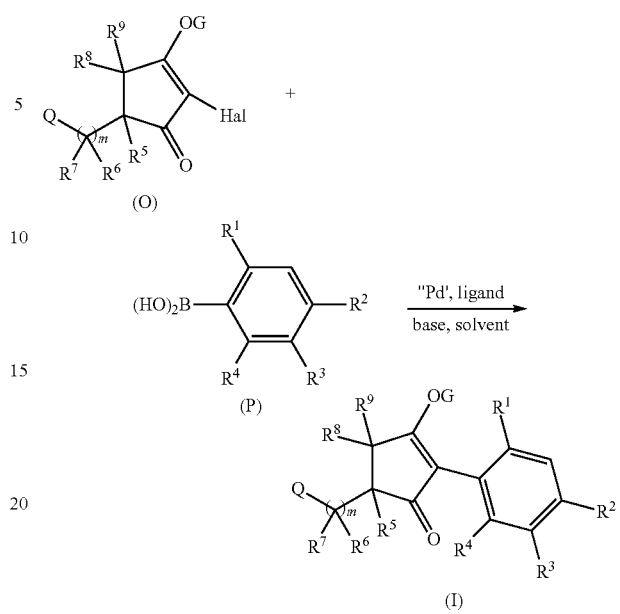

Compounds of formula (O) may be prepared by halogenating compounds of formula (Q), followed by alkylation of the resulting halide of formula (R) with a $C_1$-$C_4$alkyl halide or tri-$C_1$-$C_4$alkylorthoformate under known conditions, for example by the procedures of Shepherd R. G. et al. J. Chem. Soc. Perkin Trans. 1 (1987), 2153-2155 and Lin Y.-L. et al. Bioorg. Med. Chem. (2002), 10, 685-690. Alternatively, compounds of formula (O) may be prepared by alkylating a compound of formula (Q) with a $C_{1-4}$ alkyl halide or a tri-$C_{1-4}$-alkylorthoformate, and halogenating the resulting enone of formula (S) under known conditions (see for example Song, Y. S. et al. Tetrahedron Lett. (2005), 46 (36), 5987-5990; Kuethe, J. T. et al. J. Org. Chem. (2002), 67(17), 5993-6000; Belmont, D. T. et al. J. Org. Chem. 1985, 50 (21), 4102-4107).

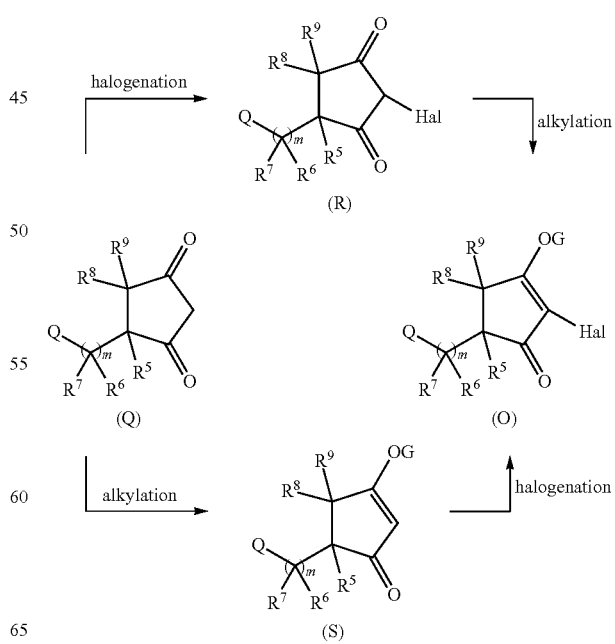

Compounds of formula (S) may be prepared by treating compounds of formula (T) with compounds of formula (L) wherein LG is a leaving group such as halogen (preferably iodide or bromide) or an activated alcohol (preferably mesylate or tosylate) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C. (see, for example, Gulias, M. et al. Org. Lett. (2003), 5(11), 1975-1977; Altenbach, R. J. et al. J. Med. Chem. (2006), 49 (23), 6869-6887; Snowden, R. L. Tetrahedron (1986), 42 (12), 3277-90; Oppolzer, W. et al. Helv. Chim. Acta (1980), 63 (4), 788-92; Mellor, M. et al. Synth. Commun. 1979, 9 (1), 1-4).

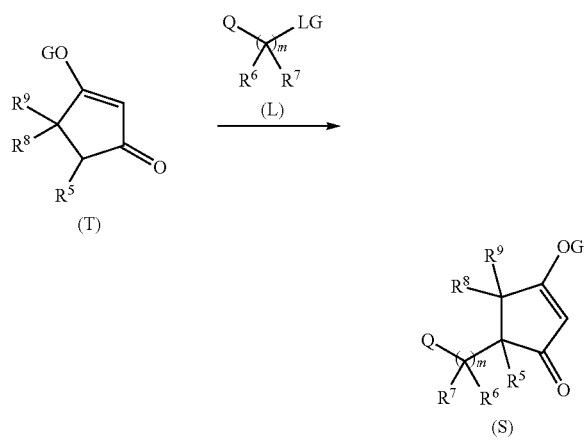

Compounds of formula (T) are known, or may be made from known compounds by known methods.

Alternatively compounds of formula (S) where $R^5$ and $R^6$ from a bond can be prepared from compounds of formula (U) by known methods (see, for example, Nagaoka, H. et al. Tetrahedron Letters (1985), 26 (41), 5053-5056; Nagaoka, H. et al. J. Am. Chem. Soc. (1986), 108 (16), 5019-5021; Zuki, M. et al. Bull. Chem. Soc. Japan (1988), 61(4), 1299-1312; Enholm, E. J. et al. J. Org. Chem. (1996), 61 (16), 5384-5390; Clive, D. L. J. et al. Tetrahedron (2001), 57 (18), 3845-3858; Bartoli, G. et al. J. Org. Chem. (2002), 67 (25), 9111-9114. Jung, M. E. et al. Chem. Comm. (2003), (2), 196-197; EP1433772; JP2004203844; IN194295).

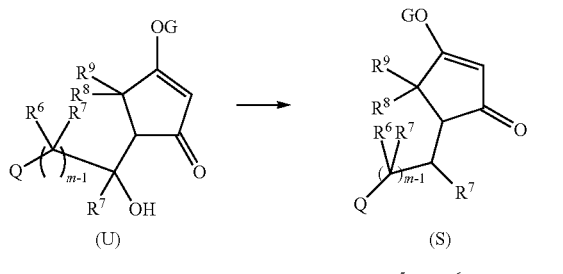

wherein $R^5$ and $R^6$ form a bond

Compounds of formula (U) may be prepared by treating compounds of formula (T) with compounds of formula (N) under basic conditions. Suitable bases include lithium diisopropylamide, sodium hexamethyldisilazide, potassium tert-butoxide and the reaction is preferably conducted in a suitable solvent (such as tetrahydrofuran) at a temperature between −80° C. and 30° C. (see, for example, Aleman, J. et al. Chem. Comm. (2007), (38), 3921-3923).

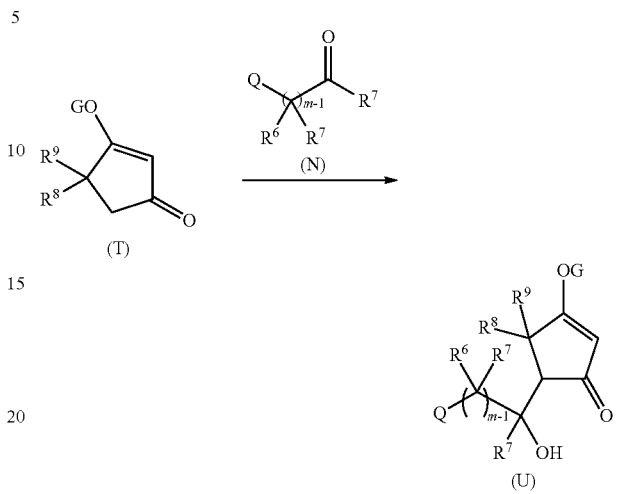

Compounds of formula (P) may be prepared from an aryl halide of formula (V), wherein Hal is bromine or iodine, by known methods (see, for example, Thompson W. et al. J. Org. Chem. (1984), 49, 5237 and R. Hawkins et al. J. Am. Chem. Soc. (1960), 82, 3053). For example, an aryl halide of formula (V) may be treated with an alkyl lithium or alkyl magnesium halide in a suitable solvent, preferably diethyl ether or tetrahydrofuran, at a temperature of between −80° C. and 30° C., and the aryl magnesium or aryl lithium reagent obtained may then be reacted with a trialkyl borate (preferably trimethylborate) to give an aryl dialkylboronate which may be hydrolysed to provide a boronic acid of formula (P) under acidic conditions.

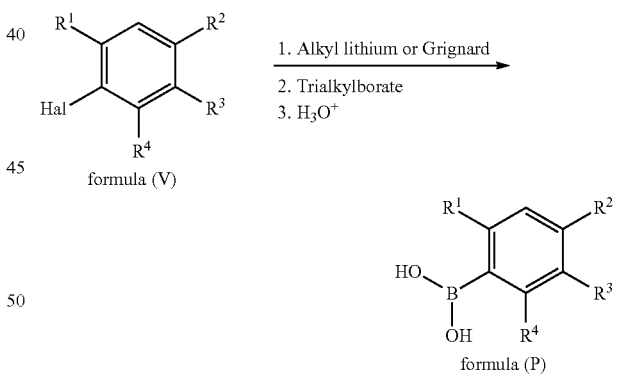

Alternatively a compound of formula (V) may be reacted with a cyclic boronate ester derived from a 1,2- or a 1,3-alkanediol such as pinacol, 2,2-dimethyl-1,3-propanediol and 2-methyl-2,4-pentanediol under known conditions (see, for example, Miyaura N. et al. J. Org. Chem. (1995), 60, 7508, and Zhu W. et al. Org. Lett. (2006), 8 (2), 261), and the resulting boronate ester may be hydrolysed under acidic conditions to give a boronic acid of formula (P).

Aryl halides of formula (V) are known, or may be prepared from known compounds by known methods. For example, aryl halides of formula (V) may be prepared from anilines of formula (W) by known methods, for example the Sandmeyer reaction, via the corresponding diazonium salts.

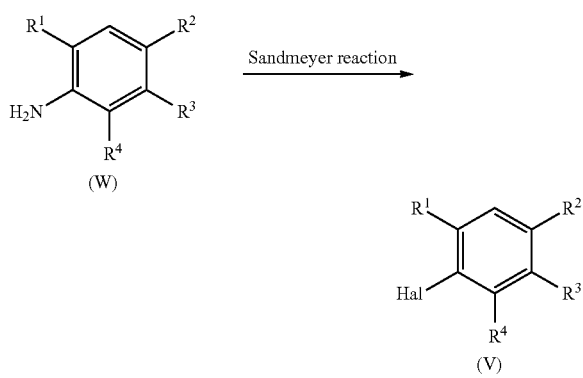

Anilines of formula (W) are known compounds, or may be made from known compounds, by known methods.

Alternatively compounds of formula (V) can be made by halogenations of the corresponding known compounds, by known methods.

Compounds of formula (Q) may be prepared from compounds of formula (S) by hydrolysis, preferably in the presence of an acid catalyst such as hydrochloric acid and optionally in the presence of a suitable solvent such as tetrahydrofuran or acetone preferably between 25° C. and 150° C. under conventional heating or under microwave irradiation.

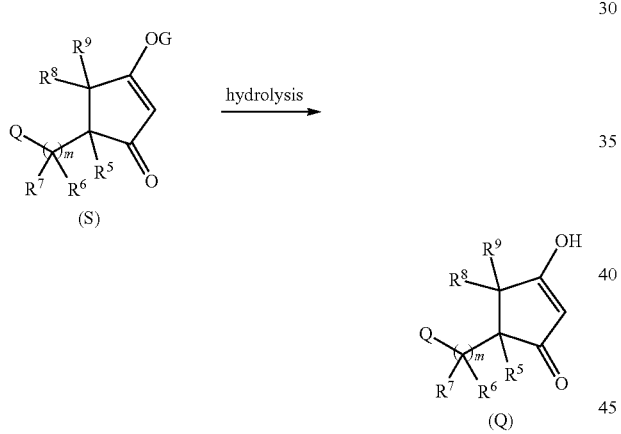

Alternatively, compounds of formula (Q) can be made from known compounds by known methods (see for example Manukina, T. A. et al. Zhurnal Organicheskoi Khimii (1986), 22(4), 873-4; Mellor, M. et al. Synth. Commun. 1979, 9 (1), 1-4).

In a further approach, compounds of formula (A) may be prepared by reacting compounds of formula (Q) with suitable aryl halides (such as aryl-iodides, aryl-bromides or aryl-chlorides), Ar—Hal of formula (V), or suitable $C_1$-$C_6$alkylsulfonates (preferably mesylate) or $C_1$-$C_6$haloalkylsulfonates (preferably triflate) or an arylsulfonates (preferable tosylate) in the presence of a suitable palladium catalyst (for example 0.001-50% palladium(II) acetate with respect to compounds of formula (Q)) and a base (for example 1 to 10 equivalents potassium phosphate with respect to compounds of formula (Q)) and preferably in the presence of a suitable ligand (for example 0.001-50% (2-dicyclohexylphosphino)-2',4',6'-triisopropylbiphenyl with respect to compounds of formula (Q)), and in a suitable solvent (for example dioxane or 1,2-dimethoxyethane), preferably between 25° C. and 200° C. Similar couplings are known in the literature (see for example, Belmont, D. T. et al. J. Org. Chem. 1985, 50 (21), 4102-4107; Fox, J. M. et al. J. Am. Chem. Soc. (2000), 122 (7), 1360-1370; B. Hong et al. WO 2005/000233). Alternatively, compounds of formula (A) may be prepared by reacting compounds of formula (Q) with suitable aryl halides (such as an aryl-iodides), Ar—Hal of formula (V), in the presence of a suitable copper catalyst (for example 0.001-50% copper(I) iodide with respect to compounds of formula (Q)) and a base (for example 1 to 10 equivalents potassium carbonate with respect to compounds of formula (Q)) and preferably in the presence of a suitable ligand (for example 0.001-50% L-proline with respect to compounds of formula (Q)), and in a suitable solvent (for example dimethylsulfoxide), preferably between 25° C. and 200° C. Similar couplings are known in the literature for aryl halides (see, for example, Jiang, Y. et al. Synlett (2005), 18, 2731-2734).

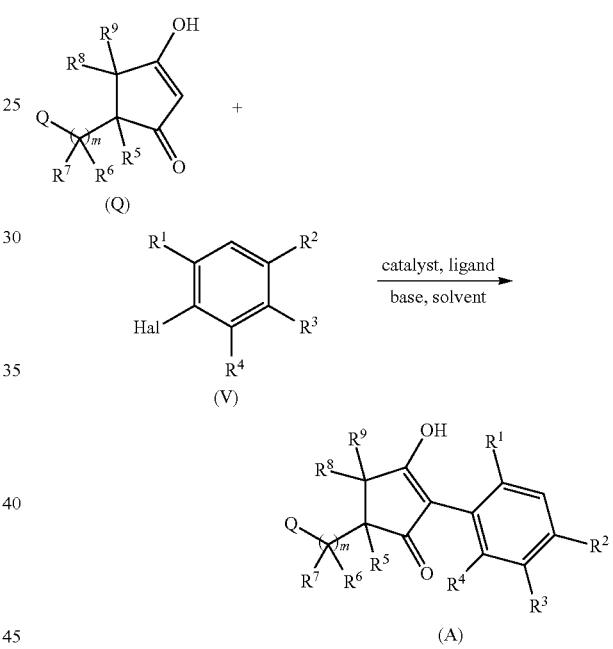

Additional compounds of formula (A) may be prepared by reacting compounds of formula (Q) with organolead reagents of formula (X) under conditions described, for example, by Pinhey, J. Pure and Appl. Chem. (1996), 68 (4), 819 and by Moloney M. et al. Tetrahedron Lett. (2002), 43, 3407.

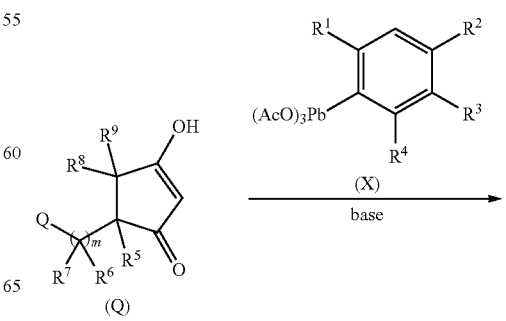

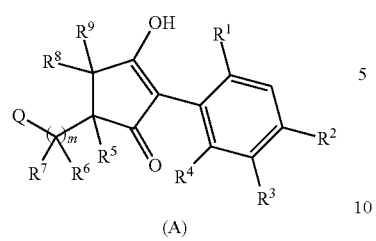

(A)

The organolead reagent of formula (X) may be prepared from a boronic acid of formula (P), a stannane of formula (Y), wherein R'''' is $C_1$-$C_4$ alkyl or by direct plumbation of a compound of formula (Z) with lead tetraacetate according to known procedures.

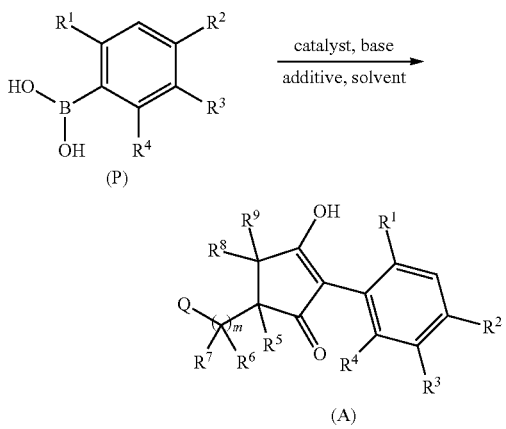

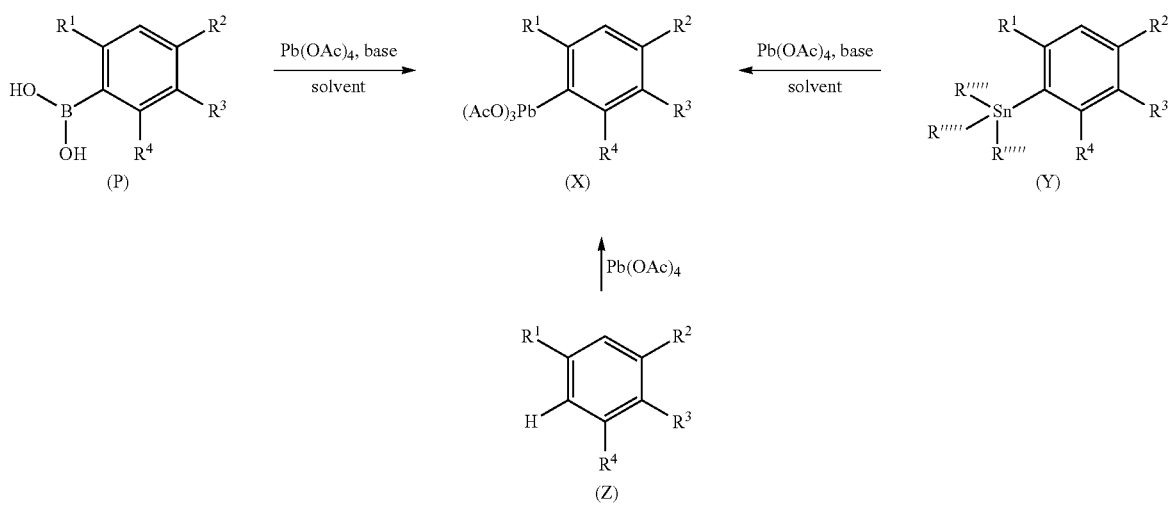

Further compounds of formula (A) may be prepared by reacting compounds of formula (Q) with suitable triarylbismuth compounds under conditions described, for example, by Fedorov, A. U. et al. Russ. Chem. Bull. Int. Ed. (2005), 54 (11), 2602 and by Koech P. et al. J. Am. Chem. Soc. (2004), 126 (17), 5350 and references therein.

Additional compounds of formula (A) may be prepared by reacting an iodonium ylide of formula (AA), wherein Ar is an optionally substituted phenyl group, and an aryl boronic acid of formula (P), in the presence of a suitable palladium catalyst, a base and in a suitable solvent.

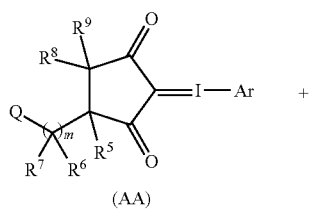

(AA)

Suitable palladium catalysts are generally palladium(II) or palladium(0) complexes, for example palladium(II) dihalides, palladium(II) acetate, palladium(II) sulfate, bis(triphenylphosphine)-palladium(II) dichloride, bis(tricyclopentylphosphine)palladium(II) dichloride, bis(tricyclohexylphosphine)palladium(II) dichloride, bis (dibenzylideneacetone)palladium(0) or tetrakis-(triphenylphosphine)palladium(0). The palladium catalyst can also be prepared in situ from palladium(II) or palladium (0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine, tricyclohexylphosphine, 2-dicyclohexylphosphino-2',6'-dimethoxybiphenyl or 2-dicyclohexylphosphino-2',4',6'-triisopropylbiphenyl and the selected solvent, with a compound of formula (AA), the arylboronic acid of formula (P), and a base. Also suitable are bidendate ligands, for example 1,1'-bis(diphenylphosphino)ferrocene or 1,2-bis (diphenylphosphino)ethane. By heating the reaction medium, the palladium(II) complex or palladium(0) complex desired for the C—C coupling reaction is thus formed in situ, and then initiates the C—C coupling reaction.

The palladium catalysts are used in an amount of from 0.001 to 50 mol %, preferably in an amount of from 0.1 to 15 mol %, based on the compound of formula (AA). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of formula (AA) may be prepared from a compound of formula (Q) by treatment with a hypervalent iodine reagent such as a (diacetoxy)iodobenzene or an iodosylbenzene and a base such as aqueous sodium carbonate, lithium hydroxide or sodium hydroxide in a solvent such as water or an aqueous alcohol such as aqueous ethanol according to the procedures of Schank K. et al. Synthesis (1983), 392, Moriarty R. M. et al. J. Am. Chem. Soc. (1985), 107, 1375 or of Yang Z. et al. Org. Lett. (2002), 4 (19), 3333.

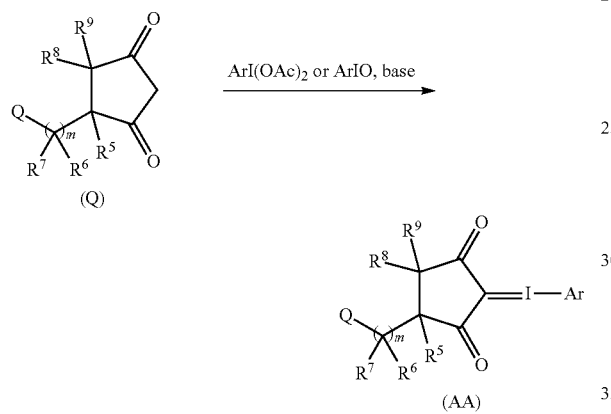

Additional compounds of formula (A) may be prepared by the pinacol rearrangement of compounds of formula (AB) or compounds of formula (AC) wherein R'''''' is $C_1$-$C_4$ alkyl (preferably methyl) under acidic conditions (see, for example, Eberhardt, U. et. al. Chem. Ber. (1983), 116(1), 119-35 and Wheeler, T. N. U.S. Pat. No. 4,283,348)

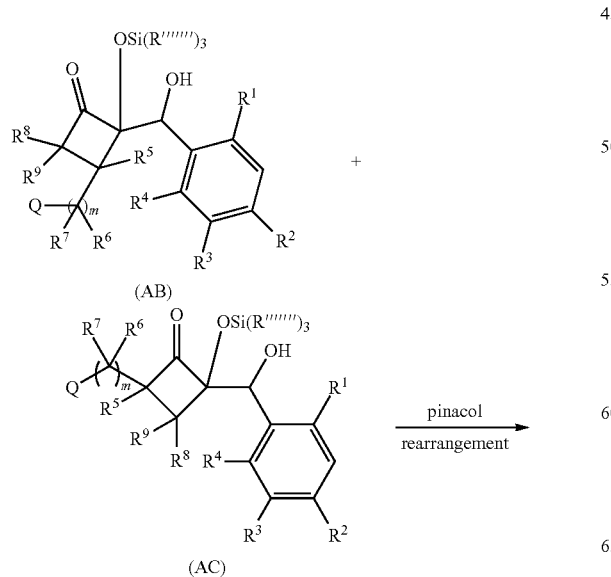

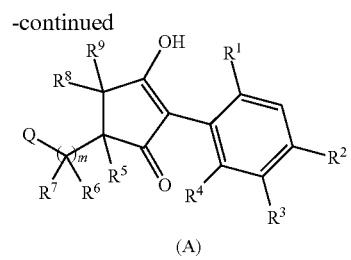

Compounds of formula (AB) and compounds of formula (AC) may be prepared by treating compounds of formula (AD) with compounds of formula (AE) in the presence of an acid (such as titanium tetrachloride or magnesium iodide) optionally in a suitable solvent (such as dichloromethane) at a temperature between −80° C. and 30° C. (see, for example, Li, W.-D. Z. and Zhang, X.-X. Org. Lett. (2002), 4(20), 3485-3488; Shimada, J. et al. J. Am. Chem. Soc. (1984), 106(6), 1759-73; Eberhardt, U. et. al. Chem. Ber. (1983), 116(1), 119-35 and Wheeler, T. N. U.S. Pat. No. 4,283,348).

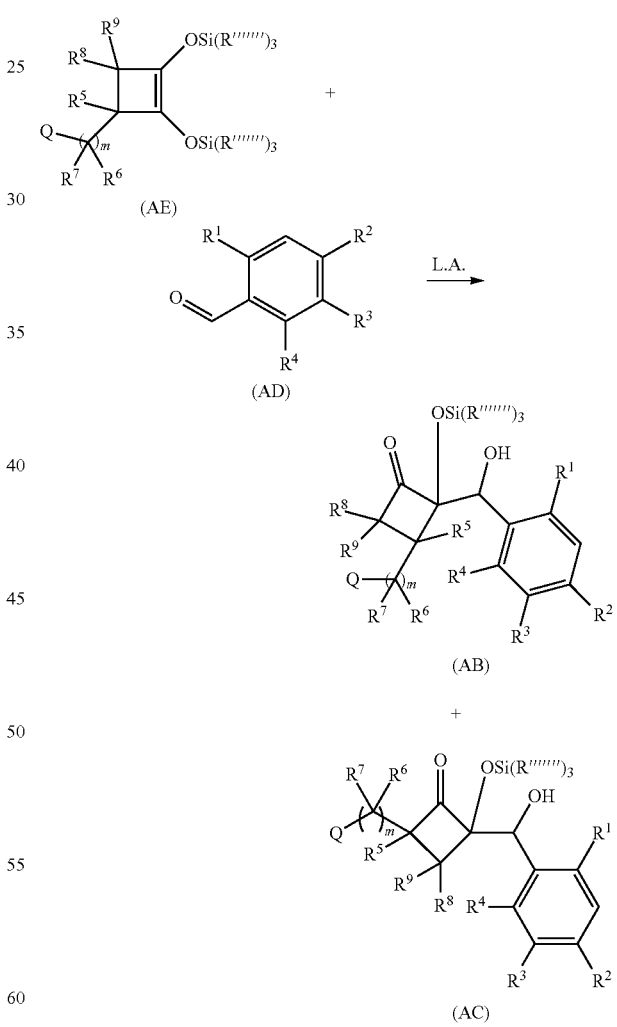

Compounds of formula (AD) are known or may be made by known methods from compounds of formula (V) or compounds of formula (Z).

Compounds of formula (AE) may be prepared from compounds of formula (AF) where in R''' is an alkyl group (preferably methyl) in the presence of chloro tri-$C_1$-$C_4$alkyl silyl and a metal (preferably sodium) in a suitable solvent (such as toluene or diethyl ether) at a temperature between 20° C. and 150° C. (see, for example, Blanchard, A. N. and Burnell, D. J. Tetrahedron Lett. (2001), 42(29), 4779-4781 and Salaun, J. et al. Tetrahedron (1989), 45(10), 3151-62).

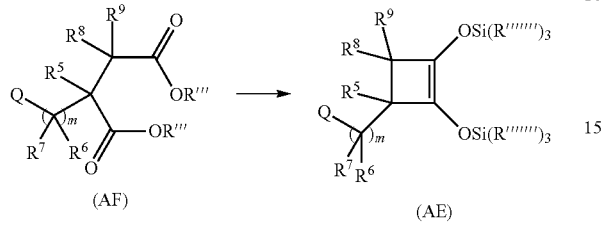

Compounds of formula (AF) are analogous to compounds of formula (H) and compounds of formula (G) and may be prepared by know methods analogous to those describe for compounds of formula (H) and compounds of formula (G).

Additional compounds of formula (I) may be prepared wherein $R^5$ and $R^6$ form a bond and $R^7R^7$ is $C_1$-$C_6$alkylsulfonate (preferably mesylate) or $C_1$-$C_6$haloalkylsulfonate (preferably triflate) or an arylsulfonate (preferable tosylate) may be prepared from compounds of formula (AG) following known procedures (Specklin et al. J. Org. Chem. 2008, 73(19), 7845-7848).

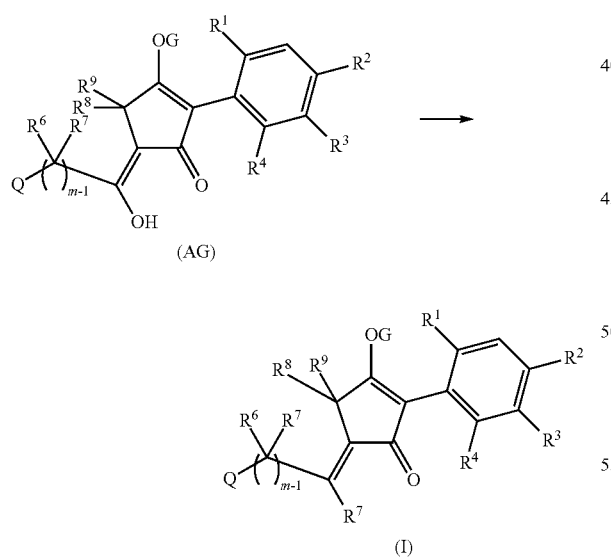

wherein $R^5$ and $R^6$ form a bond

Compounds of formula (AG) may be prepared from compounds of formula (AH) under basic or acidic conditions. For example of a procedure see G. Quinkert et al. Helv. Chim. Acta, 1986, 69(3), 469-537.

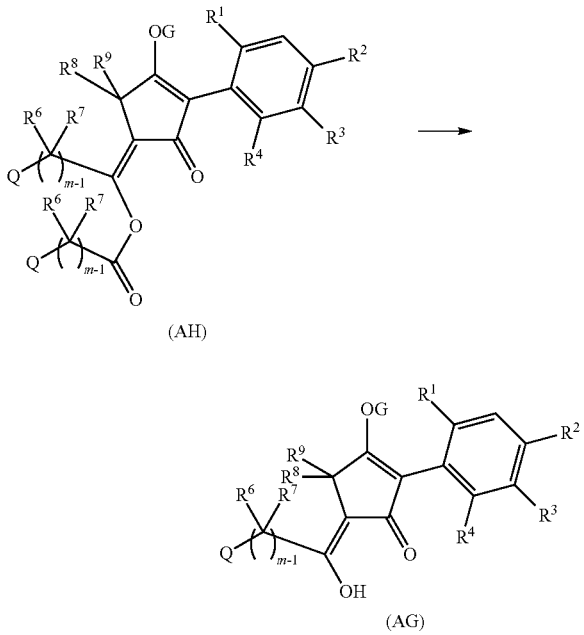

Compounds of formula (AH) may be prepared by reaction of compounds of formula (K) wherein $R^5$ is hydrogen with acids chloride of formula (AJ) in the presence of a base.

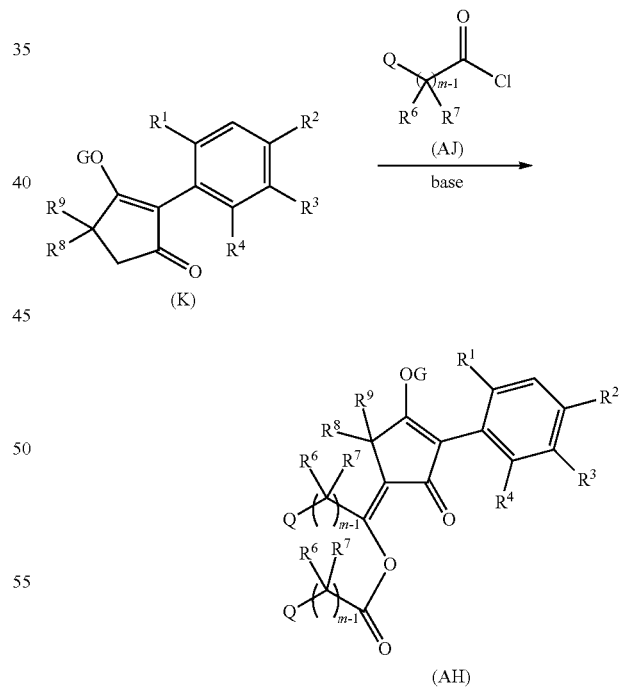

Compounds of formula (AJ) are known or may be made by known methods from known compounds.

Alternatively, compounds of formula (AG) can be prepared from compounds of formula (M) using known oxidative procedures (see for example D. B. Dess and J. C. Martin J. Org. Chem. 1983, 48 (22), 4155-4156).

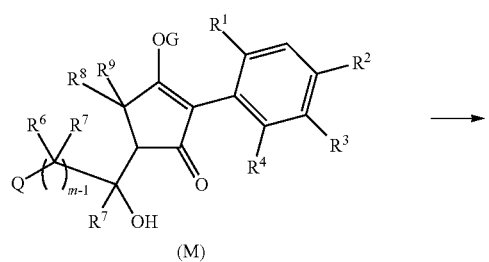

(M)

wherein R⁷ is hydrogen

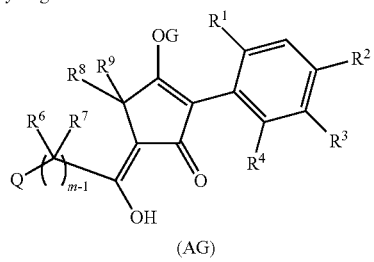

(AG)

The compounds of formula (I) according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecyl-benzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). Further oil additives that are preferred according to the invention are SCORE® (Syngenta Crop Protection Canada) and Adigor® (Syngenta Crop Protection Canada).

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pen-e-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations have especially the following compositions:
(%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, and for non-selective weed control, which comprises treating the useful plants or the area under cultivation or the locus thereof with a compound of formula I. Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular

*Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with further herbicides. Preferably, in these mixtures, the compound of the formula I is one of those compounds listed in Tables 1 to 102 below. The following mixtures of the compound of formula I are especially important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The mixing partners for the compound of formula I may also be in the form of esters or salts, as mentioned e.g. in The Pesticide Manual, 12th Edition (BCPC) 2000.

The compounds of formula I according to the invention can also be used in combination with safeners. Preferably, in these mixtures, the compound of the formula I is one of those compounds listed in Tables 1 to 102 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecoprop and compound of the formula I+mecoprop-P. The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Benoxacor, cloquintocet-mexyl, cyprosulfamide, mefenpyr-diethyl and N-(2-methoxybenzoyl)-4-[(methylaminocarbonyl)amino]benzenesulfonamide are especially preferred, where cloquintocet-mexyl is particularly valuable.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the other herbicide together with one of the safeners mentioned above.

The following examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds are shown in Table T1 as a single enol tautomer, but it should be inferred that this description covers both the diketone form and any possible enols which could arise through tautomerism. Furthermore, some of the compounds in Table T1 and Table P1 are drawn as single enantiomers for the purposes of simplicity, but unless specified as single enantiomers these structures should be construed as representing a mixture of enantiomers. Within the detailed experimental section the diketone tautomer is chosen for naming purposes, even if the predominant tautomer is the enol form.

Step 1

Preparation of 2-(2,4,6-trimethylphenyl)-3-methoxy-cyclopent-2-enone

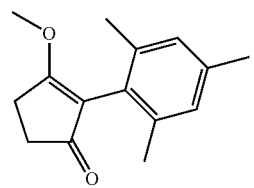

To a suspension of 2-bromo-3-methoxy-cyclopent-2-enone (6.75 g, 35.3 mmol), 2,4,6-trimethylphenyl boronic acid (6.99 g, 42.6 mmol) and freshly ground potassium phosphate (15 g, 70.6 mmol) in degassed toluene (180 ml) under nitrogen are added Pd(OAc)₂ (159 mg, 0.71 mmol) and S-Phos (579 mg, 1.41 mmol), and the reaction heated to 90° C. with stirring under N₂ for 4 hours. The reaction mixture is partitioned between ethyl acetate (150 ml) and water (150 ml), and the organic layer is removed, Silica gel is added to the organic layer, the solvent is evaporated under reduced pressure and the residue is purified by flash chromatography on silica gel to give 2-(2,4,6-trimethylphenyl)-3-methoxy-cyclopent-2-enone (6.2 g).

Step 2

Preparation of 5-[hydroxy-(tetrahydro-pyran-4-yl)-methyl]-3-methoxy-2-(2,4,6-trimethyl-phenyl)-cyclopent-2-enone

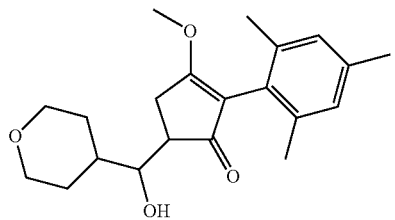 [SMILES: COC1=C(c2c(C)cc(C)cc2C)C(=O)C(C(O)C2CCOCC2)C1]

To a solution of N-ethyl-N,N-diisopropylamine (527 µl, 3.76 mmol) in THF (5 ml) under N₂ at −78° C. is added, dropwise, a 2.5M solution of butyllithium in hexane (1.32 ml, 3.3 mmol) and the reaction allowed to stir at −78° C. for 20 minutes. This pale yellow solution is then added dropwise, over a period of 10 minutes, to a solution of 2-(2,4,6-trimethylphenyl)-3-methoxy-cyclopent-2-enone (691 ml, 3 mmol) in THF (5 ml) under N₂, which is pre-cooled to −78° C. The resulting solution is allowed to stir at −78° C. for 40 minutes. A solution of tetrahydropyran-4-carbaldehyde (377 mg, 3.3 mmol) in THF (1 ml) is then added in one portion, the reaction mixture is stirred at −78° C. for 30 minutes before being allowed to warm to room temperature over a period of 60 minutes. The reaction was quenched by the addition of saturated aqueous ammonium chloride (50 ml) and extracted with ethyl acetate (2×50 ml). The combined organics were purified by flash chromatography to give 5-[hydroxy-(tetrahydro-pyran-4-yl)-methyl]-3-methoxy-2-(2,4,6-trimethyl-phenyl)-cyclopent-2-enone (648 mg).

Step 3

Preparation of 4-[1-(tetrahydro-pyran-4-yl)-meth-(E)-ylidene]-2-(2,4,6-trimethyl-phenyl)-cyclopentane-1,3-dione

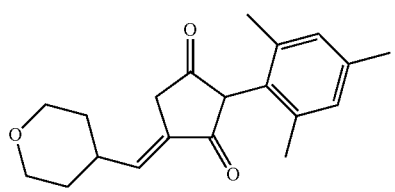 [SMILES: Cc1cc(C)c(C2C(=O)C/C(=C\C3CCOCC3)C2=O)c(C)c1]

To a solution of 5-[hydroxy-(tetrahydro-pyran-4-yl)-methyl]-3-methoxy-2-(2,4,6-trimethyl-phenyl)-cyclopent-2-enone (408 mg, 1.18 mmol) in acetone (2 ml) is added a 2N solution of hydrochloric acid (2 ml) and the resulting solution is heated to 130° C. by microwave irradiation for 90 minutes. The reaction mixture was diluted with 2N hydrochloric acid (25 ml), and extracted with ethyl acetate (2×25 ml). The combined organics are washed with brine (25 ml), dried over magnesium sulphate, filtered and concentrated in vacuuo to give 4-[1-(tetrahydro-pyran-4-yl)-meth-(E)-ylidene]-2-(2,4,6-trimethyl-phenyl)-cyclopentane-1,3-dione (302 mg).

Step 4

Preparation of 4-(tetrahydro-pyran-4-ylmethyl)-2-(2,4,6-trimethyl-phenyl)-cyclopentane-1,3-dione

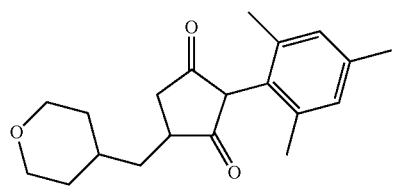 [SMILES: Cc1cc(C)c(C2C(=O)CC(CC3CCOCC3)C2=O)c(C)c1]

To a solution of 4-[1-(tetrahydro-pyran-4-yl)-meth-(E)-ylidene]-2-(2,4,6-trimethyl-phenyl)-cyclopentane-1,3-dione (270 mg, 0.86 mmol) in ethanol (10 ml) was added 10% palladium on charcoal (27 mg) and the resulting solution stirred under hydrogen (3 bar) for 5 hours at room temperature. The reaction mixture was then filtered through a pad of celite, which was washed with methanol, and the filtrated concentrated in vacuuo to give 4-(tetrahydro-pyran-4-ylmethyl)-2-(2,4,6-trimethyl-phenyl)-cyclopentane-1,3-dione (258 mg).

Step 5

Preparation of 2,2-dimethyl-propionic acid 3-oxo-4-(tetrahydro-pyran-4-ylmethyl)-2-(2,4,6-trimethyl-phenyl)-cyclopent-1-enyl ester

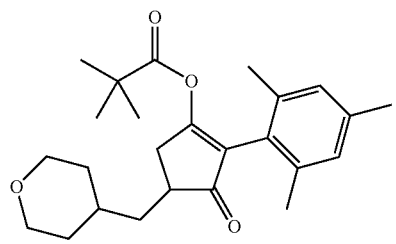 [SMILES: Cc1cc(C)c(C2=C(OC(=O)C(C)(C)C)CC(CC3CCOCC3)C2=O)c(C)c1]

To a solution of 4-(tetrahydro-pyran-4-ylmethyl)-2-(2,4,6-trimethyl-phenyl)-cyclopentane-1,3-dione (100 mg, 0.25 mmol) in dichloromethane (5 ml) and triethylamine (140 µl, 1 mmol) is added the pivaloyl chloride (91 µl, 1 mmol) at room temperature. The reaction mixture is stirred overnight at room temperature. Silica gel is added to the crude reaction mixture, the solvent is evaporated under reduced pressure and the residue is purified by flash chromatography on silica gel to give 2,2-dimethyl-propionic acid 3-oxo-4-(tetrahydro-pyran-4-ylmethyl)-2-(2,4,6-trimethyl-phenyl)-cyclopent-1-enyl ester (102 mg).

Example 2

Preparation of 2-(3,5-dimethylbiphenyl-4-yl)-4-(tetrahydrofuran-3-ylmethyl)cyclopentane-1,3-dione

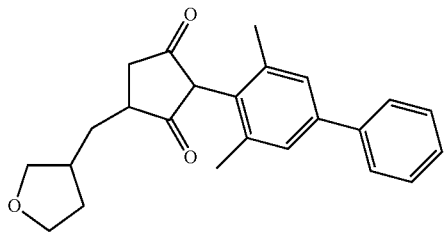 [SMILES: Cc1cc(-c2ccccc2)cc(C)c1C1C(=O)CC(CC2CCOC2)C1=O]

Step 1

Preparation of 2-(3,5-dimethylbiphenyl-4-yl)-3-methoxy cyclopent-2-enone

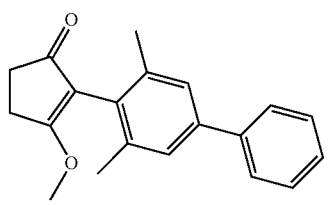 [SMILES: COC1=C(c2c(C)cc(-c3ccccc3)cc2C)C(=O)CC1]

To a mixture of 2-(4-bromo-2,6-dimethylphenyl)-3-methoxy-cyclopent-2-enone (1 g, 3.4 mmol), cesium fluoride (1.5 g, 9.87 mmol), phenylboronic acid (0.5 g, 4.1 mmol) and [1,1'-bis(diphenylphosphino)ferrocene]dichloro-palladium (II) (0.44 g, 0.54 mmol) is added degassed dimethoxyethane (10 ml) and the resulting suspension is stirred under nitrogen for 45 minutes then heated at 80° C. for 4 hrs. After cooling to room temperature the reaction mixture is acidified with 1N aqueous hydrochloric acid. The aqueous phase is further extracted with ethyl acetate (3×100 ml) and then all organic fractions are combined, dried over anhydrous sodium sulphate and concentrated in vacuo. The resulting material is purified by column chromatography on silica gel to afford 2-(3,5-dimethylbiphenyl-4-yl)-3-methoxy cyclopent-2-enone (0.7 g) as a white solid.

Step 2

Preparation of 2-(3,5-dimethylbiphenyl-4-yl)-5-[hydroxyl-(tetrahydrofuran-3-yl)-methyl]-3-methoxy-cyclopent-2-enone

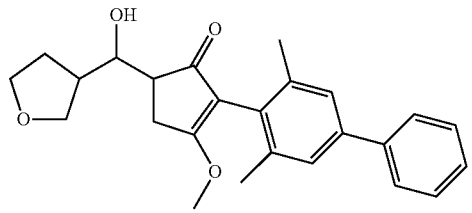 [SMILES: COC1=C(c2c(C)cc(-c3ccccc3)cc2C)C(=O)C(C(O)C2CCOC2)C1]

To a solution of 2-(3,5-Dimethylbiphenyl-4-yl)-3-methoxy cyclopent-2-enone (0.6 g, 2.05 mmol) in tetrahydrofuran (12 ml) is added 1 molar solution of lithium bis(trimethylsilyl)amide in THF (2.5 ml, 2.5 mmol) under nitrogen atmosphere at −75° C. The resulting solution is stirred at −75° C. for 40 minutes and to this mixture, a solution of 3-tetrahydrofurancarboxaldehyde (0.42 g, 4.1 mmol) in THF is added over 20 minutes. The resulting solution is stirred at −75° C. for 2 hours. The cooling bath is removed and the mixture is allowed to reach room temperature, then stirred for 2 hours. The reaction mixture is quenched with ice cold water (100 ml) and extracted with ethyl acetate (3×75 ml, dried over anhydrous sodium sulphate, filtered and the filtrate is concentrated in vacuo to give a residue (1.1 g) which is used as such for the next step.

Step 3

Preparation of 2-(3,5-dimethylbiphenyl-4-yl)-4-[1-(tetrahydrofuran-3-yl)methylidene]-cyclopentane-1,3-dione

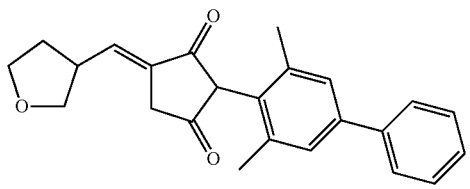 [SMILES: Cc1cc(-c2ccccc2)cc(C)c1C1C(=O)C/C(=C\C2CCOC2)C1=O]

A mixture of 2-(3,5-Dimethylbiphenyl-4-yl)-5-[hydroxyl-(tetrahydrofuran-3-yl)-methyl]-3-methoxy-cyclopent-2-enone (1.1 g, 2.8 mmol), acetone (21 ml) and 2N hydrochloric acid (10 ml) is heated under microwave conditions at 130° C. for 40 minutes. The organic solvent is evaporated under vacuo, diluted with water (100 ml) and extracted with ethyl acetate (3×100 ml). The combined organic extracts are combined, washed with water and brine, dried over anhydrous sodium sulphate, filtered and the filtrate is concentrated in vacuo. The residue is purified by column chromatography on silica gel to give 2-(3,5-dimethylbiphenyl-4-yl)-4-[1-(tetrahydrofuran-3-yl)methylidene]-cyclopentane-1,3-dione (0.29 g).

Step 4

Preparation of 2-(3,5-dimethylbiphenyl-4-yl)-4-(tetrahydrofuran-3ylmethyl)-cyclopentane-1,3-dione

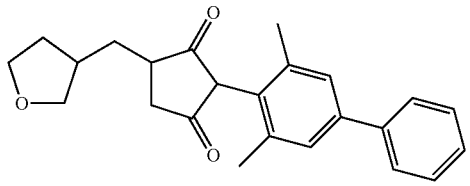 [SMILES: Cc1cc(-c2ccccc2)cc(C)c1C1C(=O)CC(CC2CCOC2)C1=O]

To a solution of 2-(3,5-dimethylbiphenyl-4-yl)-4-[1-(tetrahydrofuran-3-yl)methylidene]-cyclopentane-1,3-dione (0.29 g, 0.8 mmol) in methanol (10 ml) is added 10% palladium on carbon (0.06 g), followed by stirring under a 1 bar hydrogen atmosphere for 8 hours. The reaction mixture is then filtered through diatomaceous earth and concentrated to give a crude product which is purified by flash chromatography (hexane/ethyl acetate) to afford 2-(3,5-dimethylbiphenyl-4-yl)-4-(tetrahydrofuran-3ylmethyl)-cyclopentane-1,3-dione (0.12 g).

Example 3

Preparation of 2-((4-fluoro-2,6-dimethylphenyl)-4-(tetrahydropyran-4-ylmethyl)cyclopentane-1,3-dione

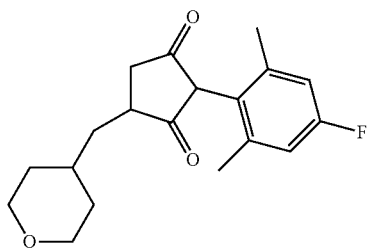 [SMILES: Cc1cc(F)cc(C)c1C1C(=O)CC(CC2CCOCC2)C1=O]

Step 1

Preparation of (4-Fluoro-2,6-dimethylphenyl)furan-2-ylmethanol

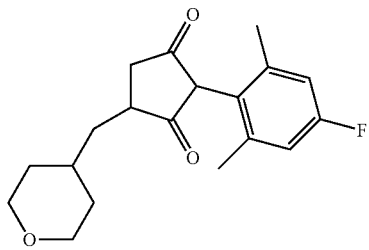 [SMILES: Cc1cc(F)cc(C)c1C1C(=O)CC(CC2CCOCC2)C1=O]

To a solution of 5-fluoro-2-iodo-1,3-xylene (11 g, 44 mmol) in tetrahydrofuran (110 ml) is added 1.6 molar solution of n-butyl lithium in hexane (33 ml, 52 mmol) under nitrogen atmosphere at −75° C. The resulting solution is stirred at −75° C. for 60 minutes and to this mixture, a solution of furfural (6.3 g, 65.6 mmol) in THF (20 ml) is added over 20 minutes. The resulting solution is stirred at −75° C. for 2 hours. The cooling bath is removed and the mixture is allowed to reach room temperature, and then stirred for 5 hours. The reaction mixture is quenched with ice cold water (1000 ml) and extracted with ethyl acetate (3×250 ml), dried over anhydrous sodium sulphate, filtered and the filtrate is concentrated in vacuo to give a residue which is purified by flash chromatography (hexane/ethyl acetate) to afford (4-Fluoro-2,6-dimethylphenyl)furan-2-ylmethanol (6 g).

Step 2

Preparation of 5-(4-Fluoro-2,6-dimethylphenyl)-4-hydroxy cyclopent-2-enone

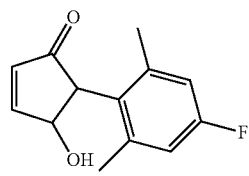 [SMILES: Cc1cc(F)cc(C)c1C1C(=O)C=CC1O]

A mixture of (4-fluoro-2,6-dimethylphenyl)furan-2-ylmethanol (6 g, 27 mmol), acetone (150 ml), water (24 ml) and orthophosphoric acid (0.6 ml) is heated under microwave conditions at 120° C. for 50 minutes. The organic solvent is evaporated under vacuo, diluted with water (150 ml) and extracted with ethylacetate (3×100 ml). The combined organic extracts are combined, washed with water and brine, dried over anhydrous sodium sulphate, filtered and the filtrate is concentrated in vacuo. The residue is purified by column chromatography on silica gel to give 5-(4-fluoro-2,6-dimethylphenyl)-4-hydroxy cyclopent-2-enone (3 g).

Step 3

Preparation of 2-(4-Fluoro-2,6-dimethylphenyl)cyclopent-4-ene-1,3-dione

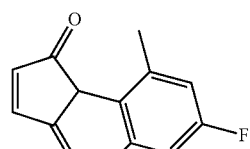

To a solution of 5-(4-fluoro-2,6-dimethylphenyl)-4-hydroxy cyclopent-2-enone (3 g, 13.6 mmol) in acetone (36 ml) is added freshly prepared Jones reagent (24 ml) at 0° C. The resulting solution is stirred at 0° C. for 60 minutes. The reaction mixture is quenched with ice cold isopropyl alcohol (25 ml) and stirred for one hour. The organics evaporated under vacuo and extracted with ethyl acetate, dried over anhydrous sodium sulphate, filtered and the filtrate is concentrated in vacuo to give a residue which is purified by flash chromatography (hexane/ethyl acetate) to afford 2-(4-fluoro-2,6-dimethylphenyl)cyclopent-4-ene-1,3-dione (2.9 g).

Step 4

Preparation of 2-(4-fluoro-2,6-dimethylphenyl)-cyclopentane-1,3-dione

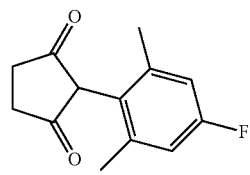 [SMILES: Cc1cc(F)cc(C)c1C1C(=O)CCC1=O]

To a solution of 2-(4-fluoro-2,6-dimethylphenyl)cyclopent-4-ene-1,3-dione (2.9 g, 13.3 mmol) in acetic acid (116 ml) is added zinc powder (6 g, 91.7 mmol) at 25-30° C. The resulting solution is stirred at 25-30° C. for 16 hours. The reaction mixture is then filtered through diatomaceous earth and concentrated to give a crude product (2.9 g) which is used for the next step.

Step 5

Preparation of 2-(4-fluoro-2,6-dimethylphenyl)-3-methoxy-cyclopent-2-enone

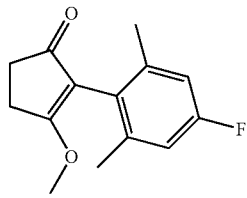 [SMILES: COC1=C(c2c(C)cc(F)cc2C)C(=O)CC1]

To a solution of 2-(4-fluoro-2,6-dimethylphenyl)-cyclopentane-1,3-dione (2.9 g, 13.3 mmol) in tetrahydrofuran (290 ml) is added anhydrous potassium carbonate (22 g, 159 mmol) and iodomethane (22.6 g, 159 mmol. The resulting mixture is stirred at 25-30° C. for 16 hours. The organic layer is evaporated, reaction mixture is quenched with water (150 ml) and extracted with ethylacetate (3×100 ml). The combined organic extracts are combined, washed with water and brine, dried over anhydrous sodium sulphate, filtered and the filtrate is concentrated in vacuo. The residue is purified by column chromatography on silica gel to give 2-(4-fluoro-2, 6-dimethylphenyl)-3-methoxy-cyclopent-2-enone (2 g).

Step 6

Preparation of 2-(4-fluoro-2,6-dimethylphenyl)-3-methoxy-5-[1-tetrahydropyran-4-yl)-ethyl]-cyclopent-2-enone

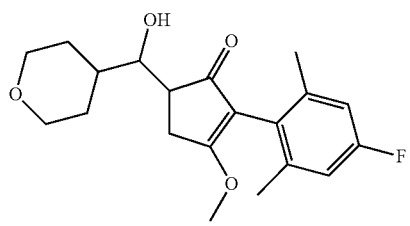 [SMILES: COC1=C(c2c(C)cc(F)cc2C)C(=O)C(C(O)C2CCOCC2)C1]

To a solution of 2-(4-fluoro-2,6-dimethylphenyl)-3-methoxy-cyclopent-2-enone (0.5 g, 2.1 mmol) in tetrahydrofuran (10 ml) is added 1 molar solution of lithium bis(trimethylsilyl)amide in THF (2.7 ml) under nitrogen atmosphere at −75° C. The resulting solution is stirred at −75° C. for 40 minutes and to this mixture, a solution of 3-tetrahydrofurancarboxaldehyde (0.5 g, 4.38 mmol) in THF is added over 20 minutes. The resulting solution is stirred at −75° C. for 2 hours. The cooling bath is removed and the mixture is allowed to reach room temperature and then stirred for 2 hours. The reaction mixture is quenched with ice cold water (100 ml) and extracted with ethyl acetate (3×75 ml), dried over anhydrous sodium sulphate, filtered and the filtrate is concentrated in vacuo to give a residue (0.7 g) which is used as such for the next step.

Step 7

Preparation of 2-(4-fluoro-2,6-dimethylphenyl)-4-[1-(tetrahydropyran-4-yl)-methylidene]-cyclopentane-1,3-dione

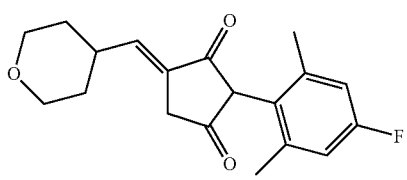 [SMILES: Cc1cc(F)cc(C)c1C1C(=O)C/C(=C\C2CCOCC2)C1=O]

A mixture of 2-(4-fluoro-2,6-dimethylphenyl)-3-methoxy-5-[1-tetrahydropyran-4-yl)-ethyl]-cyclopent-2-enone (0.7 g, 2 mmol), acetone (10 ml) and 2N hydrochloric acid (10 ml) is heated under microwave conditions at 130° C. for 40 minutes. The organic solvent is evaporated under vacuo, diluted with water (100 ml) and extracted with ethylacetate (3×75 ml). The combined organic extracts are combined, washed with water and brine, dried over anhydrous sodium sulphate, filtered and the filtrate is concentrated in vacuo. The residue is purified by column chromatography on silica gel to give 2-(4-fluoro-2,6-dimethylphenyl)-4-[1-(tetrahydropyran-4-yl)-methylidene]-cyclopentane-1,3-dione (0.23 g).

Step 8

Preparation of 2-(4-fluoro-2,6-dimethylphenyl)-4-[tetrahydropyran-4-ylmethyl)-cyclopentane-1,3-dione

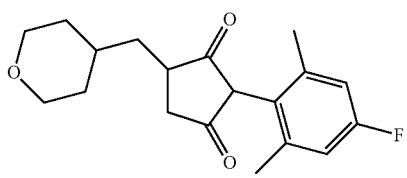 [SMILES: Cc1cc(F)cc(C)c1C1C(=O)CC(CC2CCOCC2)C1=O]

To a solution of 2-(4-fluoro-2,6-dimethylphenyl)-4-[1-(tetrahydropyran-4-yl)-methylidene]-cyclopentane-1,3-dione (0.14 g, 0.44 mmol) in methanol (3 ml) is added 10% palladium on carbon (1.5 mg), followed by stirring under a 1 bar hydrogen atmosphere for 8 hours. The reaction mixture is then filtered through diatomaceous earth and concentrated to give a crude product which is purified by flash chromatography (hexane/ethyl acetate) to afford 2-(4-fluoro-2,6-dimethylphenyl)-4-[tetrahydropyran-4-ylmethyl)-cyclopentane-1,3-dione (0.13 g).

Example 3

Preparation of 2-(4-bromo-2,6-dimethylphenyl)-4-(tetrahydropyran-4-ylmethyl)cyclopentane-1,3-dione

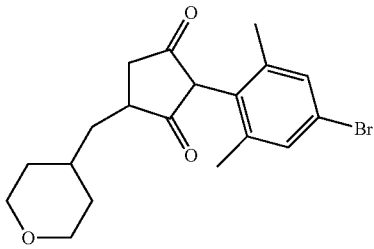 [SMILES: Cc1cc(Br)cc(C)c1C1C(=O)CC(CC2CCOCC2)C1=O]

To a solution of 2-(4-bromo-2,6-dimethylphenyl)-4-[1-(tetrahydropyran-4-yl)-methylidene]-cyclopentane-1,3-dione (0.1 g, 0.26 mmol) in methanol (100 ml) is subjected to hydrogenation under H-Cube conditions using 10% platinum carbon under a 20 bar hydrogen atmosphere. The reaction mixture is then concentrated to give a crude product which is purified by flash chromatography (hexane/ethyl acetate) to afford 2-(4-bromo-2,6-dimethylphenyl)-4-(tetrahydropyran-4-ylmethyl)cyclopentane-1,3-dione (0.09 g).

Example 4

Preparation of 2-(2,6-dimethylphenyl)-4-(tetrahydropyran-4-ylmethyl)cyclopentane-1,3-dione

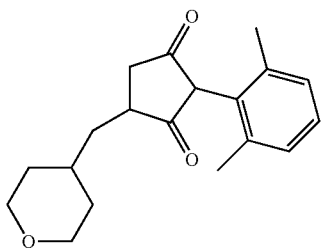 [SMILES: Cc1cccc(C)c1C1C(=O)CC(CC2CCOCC2)C1=O]

To a solution of 2-(4-bromo-2,6-dimethylphenyl)-4-[1-(tetrahydropyran-4-yl)-methylidene]-cyclopentane-1,3-dione (0.3 g, 0.8 mmol) in methanol (5 ml) is added 10% palladium on carbon (0.06 g), followed by stirring under a 1 bar hydrogen atmosphere for 8 hours. The reaction mixture is then filtered through diatomaceous earth and concentrated to give a crude product which is purified by flash chromatography (hexane/ethyl acetate) to afford 2-(2,6-dimethylphenyl)-4-(tetrahydropyran-4-ylmethyl)cyclopentane-1,3-dione (0.12 g).

Example 5

Preparation of 2-(4-cyclopropyl-2,6-dimethyl-phenyl)-4-(tetrahydropyran-4-ylmethyl)-cyclopentane-1,3-dione

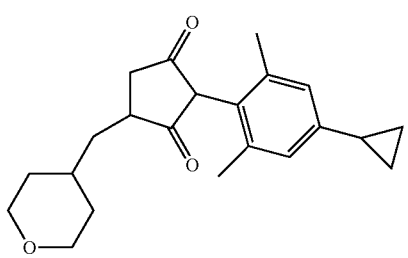 [SMILES: Cc1cc(C2CC2)cc(C)c1C1C(=O)CC(CC2CCOCC2)C1=O]

A mixture of 2-(4-bromo-2,6-dimethylphenyl)-4-(tetrahydropyran-4-ylmethyl)cyclopentane-1,3-dione (0.1 g, 0.26 mmol), potassium phosphate (0.11 g, 0.53 mmol), cyclopropyl boronic acid (0.09 g, 1.05 mmol) and tetrakis(triphenylphosphine)palladium (0) (0.06 g, 0.053 mmol), toluene (2 ml), dimethoxyethane (0.5 ml) and water (0.5 ml) is heated under microwave conditions at 130° C. for 22 minutes. The organic solvent is evaporated under vacuo, diluted with water and extracted with ethylacetate (3×25 ml). The combined organic extracts are combined, washed with water and brine, dried over anhydrous sodium sulphate, filtered and the filtrate is concentrated in vacuo. The residue is purified by column chromatography on silica gel followed by preparative HPLC to give 2-(4-cyclopropyl-2,6-dimethyl-phenyl)-4-(tetrahydropyran-4-ylmethyl)-cyclopentane-1,3-dione (0.012 g).

Example 6

Preparation of (4-(1-cyclopropanecarbonyl-piperidin-4-ylmethyl)-2-(2,4,6-trimethyl-phenyl)-cyclopentane-1,3-dione

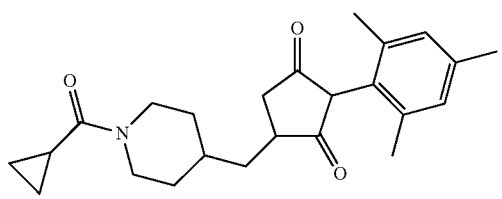 [SMILES: Cc1cc(C)c(C2C(=O)CC(CC3CCN(C(=O)C4CC4)CC3)C2=O)c(C)c1]

Step 1

Preparation of 4-[4-methoxy-2-oxo-3-(2,4,6-trimethyl-phenyl)-cyclopent-3-en-(E)-ylidenemethyl]-piperidine-1-carboxylic acid tert-butyl ester

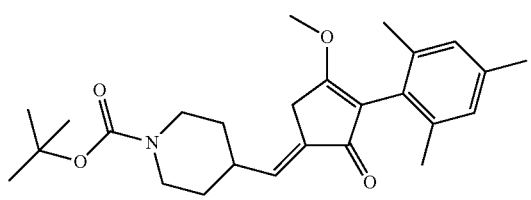 [SMILES: COC1=C(c2c(C)cc(C)cc2C)C(=O)/C(=C/C2CCN(C(=O)OC(C)(C)C)CC2)C1]

To a solution of 2-(2,4,6-trimethylphenyl)-3-methoxy-cyclopent-2-enone (9.05 g, 39.21 mmol) in THF (150 ml) under $N_2$ at −78° C. is added, dropwise over a period of 30 minutes, lithium diisopropylamide solution (24 ml, 43.24 mmol, 1.8 M in hexane/THF/ethylbenzene), and the reaction allowed to stir at this temperature for a further 30 minutes. 4-Formyl-piperidine-1-carboxylic acid tert-butyl ester (10 g, 43.24 mmol) is then added in one portion and the reaction kept at −78° C. for 30 minutes, before being allowed to warm gradually to room temperature over a period of 60 minutes. Potassium tert-butoxide (7.28 g, 64.86 mmol) is then added in one portion and the reaction stirred at room temperature for a further 2 hours.

63

The reaction is quenched by the addition of saturated aqueous ammonium chloride solution (500 ml), and extracted with ethyl acetate (500 ml). The organic layer is removed, silica gel is added to the organic layer, the solvent is evaporated under reduced pressure and the residue is purified by flash chromatography on silica gel to give 4-[4-methoxy-2-oxo-3-(2,4,6-trimethyl-phenyl)-cyclopent-3-en-(E)-ylidenemethyl]-piperidine-1-carboxylic acid tert-butyl ester (15.33 g)

Step 2

Preparation of 4-[4-methoxy-2-oxo-3-(2,4,6-trimethyl-phenyl)-cyclopent-3-enylmethyl]-piperidine-1-carboxylic acid tert-butyl ester

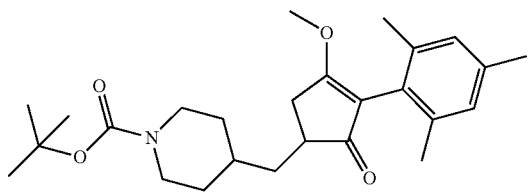 [SMILES: COC1=C(c2c(C)cc(C)cc2C)C(=O)C(CC2CCN(C(=O)OC(C)(C)C)CC2)C1]

To a solution of 4-[4-methoxy-2-oxo-3-(2,4,6-trimethyl-phenyl)-cyclopent-3-en-(E)-ylidenemethyl]-piperidine-1-carboxylic acid tert-butyl ester (15.33 g, 36.02 mmol) in ethanol (150 ml) is added 10% palladium on activated charcoal (1.53 g) and the reaction stirred under hydrogen (4 bar) for hours. The reaction is filtered through a pad of Celite and the solvent removed under reduced pressure to give 4-[4-methoxy-2-oxo-3-(2,4,6-trimethyl-phenyl)-cyclopent-3-enylmethyl]-piperidine-1-carboxylic acid tert-butyl ester (15.4 g)

Step 3

Preparation of 4-[2,4-dioxo-3-(2,4,6-trimethyl-phenyl)-cyclopentylmethyl]-piperidinium hydrochloride

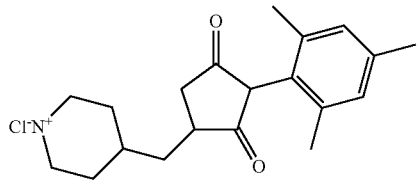

To a solution of 4-[4-methoxy-2-oxo-3-(2,4,6-trimethyl-phenyl)-cyclopent-3-enylmethyl]-piperidine-1-carboxylic acid tert-butyl ester (15.4 g, 36 mmol) in acetone (100 ml) is added 2N HCl (100 ml) and the reaction heated to reflux for 4 hours. The solvent is removed under reduced pressure to give 4-[2,4-dioxo-3-(2,4,6-trimethyl-phenyl)-cyclopentylmethyl]-piperidinium hydrochloride (12.58 g)

64

Step 4

Preparation of cyclopropanecarboxylic acid 4-(1-cyclopropanecarbonyl-piperidin-4-ylmethyl)-3-oxo-2-(2,4,6-trimethyl-phenyl)-cyclopent-1-enyl ester

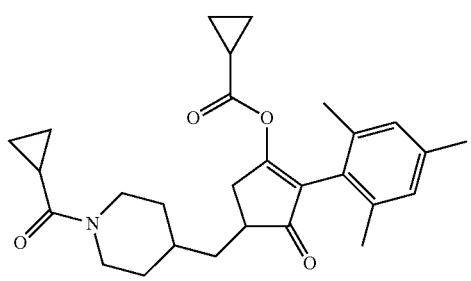 [SMILES: Cc1cc(C)c(C2=C(OC(=O)C3CC3)CC(CC3CCN(C(=O)C4CC4)CC3)C2=O)c(C)c1]

To a suspension of 4-[2,4-dioxo-3-(2,4,6-trimethyl-phenyl)-cyclopentylmethyl]-piperidinium hydrochloride (175 mg, 0.5 mmol) in DCM (5 ml) is added triethylamine (697 µl, 5 mmol), followed by cyclopropyl carbonyl chloride (608 µl, 4.5 mmol) and the reaction stirred at room temperature for 5 hours. Silica gel is added to the crude reaction, the solvent is evaporated under reduced pressure and the residue is purified by flash chromatography on silica gel to give cyclopropanecarboxylic acid 4-(1-cyclopropanecarbonyl-piperidin-4-ylmethyl)-3-oxo-2-(2,4,6-trimethyl-phenyl)-cyclopent-1-enyl ester (162 mg)

Step 5

Preparation of 4-(1-cyclopropanecarbonyl-piperidin-4-ylmethyl)-2-(2,4,6-trimethyl-phenyl)-cyclopentane-1,3-dione

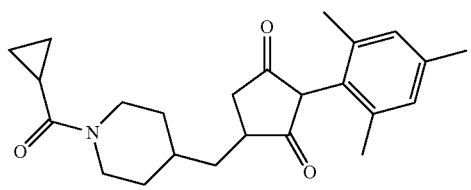 [SMILES: Cc1cc(C)c(C2C(=O)CC(CC3CCN(C(=O)C4CC4)CC3)C2=O)c(C)c1]

To a suspension of 4-(1-cyclopropanecarbonyl-piperidin-4-ylmethyl)-3-oxo-2-(2,4,6-trimethyl-phenyl)-cyclopent-1-enyl ester (162 mg, 0.36 mmol) in methanol is added potassium carbonate (149 mg, 1.08 mmol) and the reaction stirred at room temperature for 4 hours. The solvent is removed under reduced pressure and the residue dissolved in water (2 ml). 2N HCl (3 ml) is then added, and the resulting precipitate is filtered off, washed with hexane and air dried to give 4-(1- cyclopropanecarbonyl-piperidin-4-ylmethyl)-2-(2,4,6-trimethyl-phenyl)-cyclopentane-1,3-dione (72 mg).

Example 7

Preparation of the sodium salt of the 4-(tetrahydro-pyran-4-ylmethyl)-2-(2,4,6-trimethyl-phenyl)-cyclopentane-1,3-dione

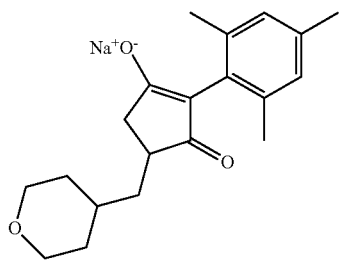

A 0.5 M solution of sodium methoxide in methanol (2 ml, 1 mmol) is added to the 4-(tetrahydro-pyran-4-ylmethyl)-2-(2,4,6-trimethyl-phenyl)-cyclopentane-1,3-dione (314 mg, 1 mmol) at room temperature under nitrogen. The reaction mixture was stirred at room temperature for 15 minutes. The reaction mixture was evaporated under reduced pressure to give the sodium salt of the 4-(tetrahydro-pyran-4-ylmethyl)-2-(2,4,6-trimethyl-phenyl)-cyclopentane-1,3-dione (336 mg).

Where more than one tautomer or rotational conformer is observed in the proton NMR spectrum, the data shown below are for the mixture of isomers and conformers.

Unless otherwise stated, proton NMR spectra were recorded at ambient temperature.

Compounds characterised by HPLC-MS were analysed using one of three methods described below.

Method A

Compounds characterised by HPLC-MS were analysed using a Waters 2795 HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minutes run time, according to the following gradient table:

| Time (mins) | Solvent A (%) | Solvent B (%) | Flow (ml/mn) |
|---|---|---|---|
| 0.00 | 90.0 | 10.0 | 2.00 |
| 0.25 | 90.0 | 10.0 | 2.00 |
| 2.00 | 10.0 | 90.0 | 2.00 |
| 2.50 | 10.0 | 90.0 | 2.00 |
| 2.60 | 90.0 | 10.0 | 2.00 |
| 3.0 | 90.0 | 10.0 | 2.00 |

Solvent A: $H_2O$ containing 0.1% HCOOH
Solvent B: $CH_3CN$ containing 0.1% HCOOH Method B Compounds characterised by HPLC-MS were analysed using an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minutes run time, according to the following gradient table:

| Time (mins) | Solvent A (%) | Solvent B (%) | Flow (ml/mn) |
|---|---|---|---|
| 0.00 | 95.0 | 5 | 1.300 |
| 2.50 | 0.00 | 100 | 1.300 |
| 2.80 | 0.00 | 100 | 1.300 |
| 2.90 | 95.0 | 5 | 1.300 |

Solvent A: $H_2O$ with 0.05% TFA
Solvent B: $CH_3CN$ with 0.05% TFA

Method C:

Compounds characterised by HPLC-MS were analysed using a Finnigan Surveyor MSQ Plus equipped with a Waters Xterra column (column length 50 mm, internal diameter of column 4.6 mm, particle size 3.5 micron, temperature 40° C.), Waters photodiode array and Micromass ZQ2000. The analysis was conducted using a six minutes run time, according to the following gradient table:

| Time (mins) | Solvent A (%) | Solvent B (%) | Flow (ml/mn) |
|---|---|---|---|
| 0.00 | 90.0 | 10.0 | 1.30 |
| 3.80 | 0.00 | 100 | 1.30 |
| 4.80 | 0.00 | 100 | 1.30 |
| 5.00 | 90.0 | 10.0 | 1.30 |
| 6.00 | 90.0 | 10.0 | 1.30 |

Solvent A: $H_2O$ containing 0.05% HCOOH
Solvent B: $CH_3CN$ containing 0.05% HCOOH

TABLE T1

| Compound Number | Structure | $^1H$ nmr ($CDCl_3$ unless stated), LC/MS or other physical data |
|---|---|---|
| T1 | 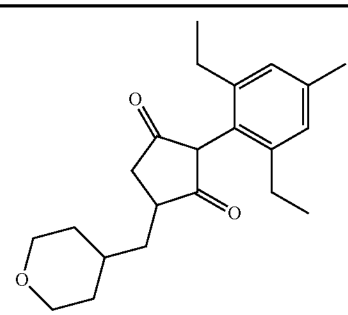 | δ ppm 1.05-1.10 (m, 6H), 1.29-1.45 (m, 3H), 1.49-1.57 (m, 1H), 1.62-1.72 (m, 3H), 1.90-1.96 (m, 2H), 2.32-2.39 (m, 8H), 3.36-3.43 (m, 2H), 3.93-3.99 (m, 2H) |

TABLE T1-continued

| Compound Number | Structure | ¹H nmr (CDCl₃ unless stated), LC/MS or other physical data |
|---|---|---|
| T2 | 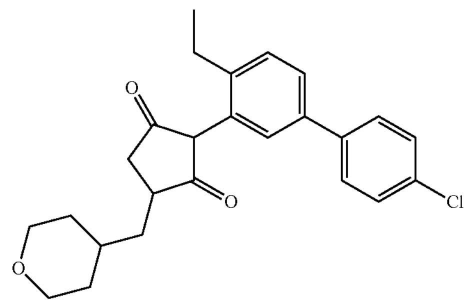 [SMILES: CCc1ccc(-c2ccc(Cl)cc2)cc1C1C(=O)CC(CC2CCOCC2)C1=O] | δ ppm 1.14 (t, 3H), 1.28-1.43 (m, 3H), 1.58-1.74 (m, 3H), 1.85-1.97 (m, 1H), 2.50 (q, 2H), 2.61-3.10 (m, 3 H), 3.30-3.47 (m, 2H), 3.89-4.02 (m, 2H), 7.24 (d, 1H), 7.38-7.41 (m, 2H), 7.42 (d, 1H), 7.45-7.49 (m, 2H). 7.55 (dd, 1H) |
| T3 | 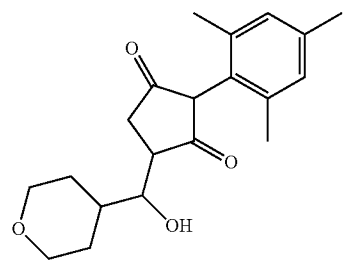 [SMILES: Cc1cc(C)c(C2C(=O)CC(C(O)C3CCOCC3)C2=O)c(C)c1] | δ ppm 1.50-1.58 (m, 2H), 1.66-1.82 (m, 3H), 2.09 (s, 6H), 2.27 (s, 3H), 2.32-2.43 (m, 1H), 2.69-2.82 (m, 1H), 2.96 (s, 1H), 3.35-3.48 (m, 2H), 3.67-3.76 (m, 1H), 3.99-4.11 (m, 2H), 6.90 (s, 2H) |
| T4 | 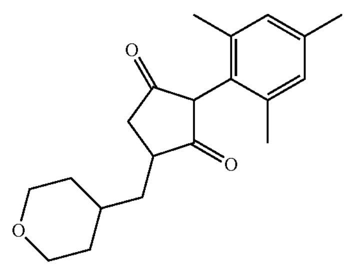 [SMILES: Cc1cc(C)c(C2C(=O)CC(CC3CCOCC3)C2=O)c(C)c1] | δ ppm 1.29-1.46 (m, 3H), 1.61-1.76 (m, 3H), 1.86-1.98 (m, 1H), 2.08 (d, 6H), 2.28 (s, 3H), 2.37 (d (br), 1H), 2.80-2.95 (m, 2H), 3.35-3.47 (m, 2H), 3.92-4.04 (m, 2H), 6.92 (s, 2H) |
| T5 | 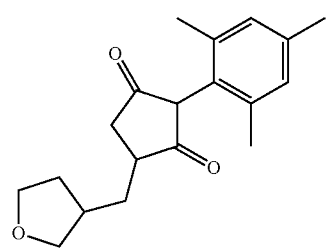 [SMILES: Cc1cc(C)c(C2C(=O)CC(CC3CCOC3)C2=O)c(C)c1] | δ ppm 1.48-1.68 (m, 2H), 2.05-2.13 (m, 8H), 2.28 (s, 3H), 2.33-2.46 (m, 2H), 2.80-2.98 (m (br), 2H), 3.36-3.47 (m, 1H), 3.78 (dd, 1H), 3.86-3.92 (m, 1H), 3.95 (dd, 1H), 6.92 (s, 2H) |
| T6 | 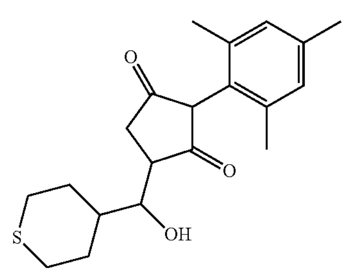 [SMILES: Cc1cc(C)c(C2C(=O)CC(C(O)C3CCSCC3)C2=O)c(C)c1] | δ ppm 1.46-1.61 (m, 2H), 1.66-1.86 (m, 1H), 1.93-2.05 (m, 2H), 2.07-2.09 (m, 6H), 2.27 (s, 3H), 2.65-2.83 (m, 6H), 2.91-3.05 (m, 1H), 3.67 (d, 1H), 6.90 (s, 2H) |

TABLE T1-continued

| Compound Number | Structure | $^1$H nmr (CDCl$_3$ unless stated), LC/MS or other physical data |
|---|---|---|
| T7 | 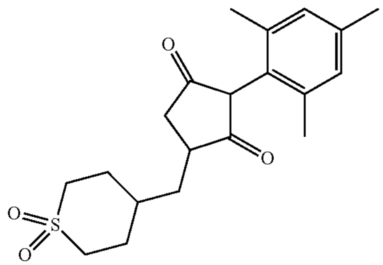 [SMILES: Cc1cc(C)c(C2C(=O)CC(CC3CCS(=O)(=O)CC3)C2=O)c(C)c1] | δ ppm 1.41-1.53 (m, 1H), 1.85-2.02 (m, 4H), 2.05-2.10 (m, 6H), 2.12-2.25 (m, 2H), 2.28 (s, 3H), 2.30-2.38 (m, 1H), 2.83-3.14 (m, 6H), 6.93 (s, 2H) |
| T8 | 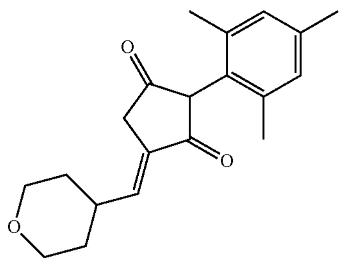 [SMILES: Cc1cc(C)c(C2C(=O)C/C(=C\C3CCOCC3)C2=O)c(C)c1] | δ ppm 1.51-1.73 (m, 4H), 2.10 (s, 6H), 2.29 (s, 3H), 2.40-2.55 (m, 1H), 3.13 (s, 2H), 3.48 (td, 2H), 3.92-4.06 (m, 2H), 6.01 (s, 1H), 6.94 (s, 2H) |
| T9 | 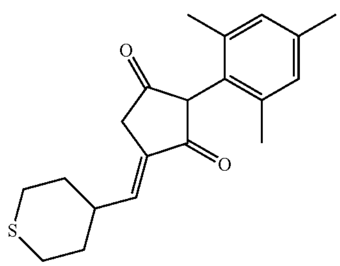 [SMILES: Cc1cc(C)c(C2C(=O)C/C(=C\C3CCSCC3)C2=O)c(C)c1] | δ ppm 1.67 (m, 2H), 1.98-2.08 (m, 2H), 2.10 (s, 6H), 2.27-2.30 (m, 4H), 2.63-2.83 (m, 4H), 3.09 (s, 2H), 6.00 (d, 1H), 6.94 (s, 2H) |
| T10 | 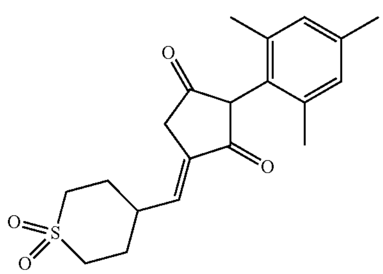 [SMILES: Cc1cc(C)c(C2C(=O)C/C(=C\C3CCS(=O)(=O)CC3)C2=O)c(C)c1] | δ ppm 2.10 (s, 6H), 2.13-2.25 (m, 5H), 2.29 (s, 3H), 2.44-2.62 (m, 1H), 2.99-3.27 (m, 6H), 6.02 (d, 1H), 6.94 (s, 2H) |
| T11 | 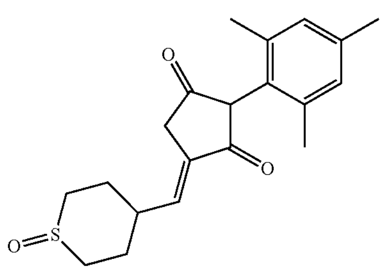 [SMILES: Cc1cc(C)c(C2C(=O)C/C(=C\C3CCS(=O)CC3)C2=O)c(C)c1] | LC-MS (Method A) ES$^+$: MH$^+$ = 345 rt = 1.17 min |

TABLE T1-continued

| Compound Number | Structure | ¹H nmr (CDCl₃ unless stated), LC/MS or other physical data |
|---|---|---|
| T12 | 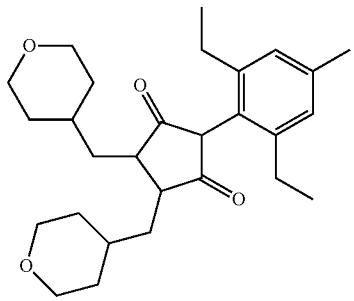 [SMILES: CCc1cc(C)cc(CC)c1C1C(=O)C(CC2CCOCC2)C(CC2CCOCC2)C1=O] | LC-MS (Method A) ES⁺: MH⁺ = 441 |
| T13 | 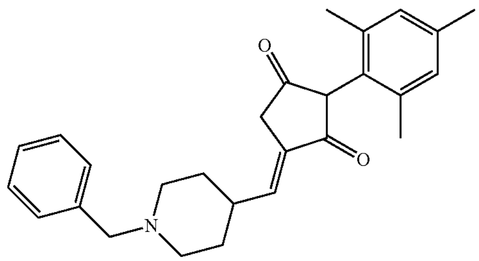 [SMILES: Cc1cc(C)c(C2C(=O)C/C(=C\C3CCN(Cc4ccccc4)CC3)C2=O)c(C)c1] | LC-MS (Method A) ES⁺: MH⁺ = 402<br>rt = 1.31 min |
| T14 | 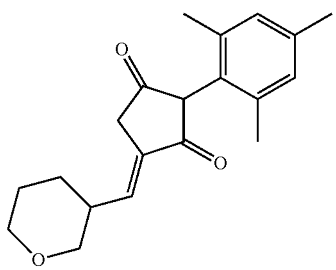 [SMILES: Cc1cc(C)c(C2C(=O)C/C(=C\C3CCCOC3)C2=O)c(C)c1] | LC-MS (Method A) ES⁺: MH⁺ = 313<br>rt = 1.39 min |
| T15 | 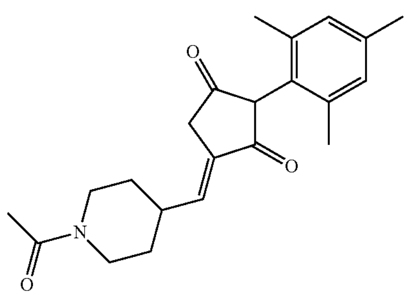 [SMILES: CC(=O)N1CCC(/C=C2\CC(=O)C(c3c(C)cc(C)cc3C)C2=O)CC1] | LC-MS (Method A) ES⁺: MH⁺ = 354<br>rt = 1.27 min |
| T16 | 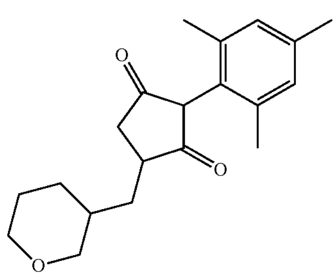 [SMILES: Cc1cc(C)c(C2C(=O)CC(CC3CCCOC3)C2=O)c(C)c1] | LC-MS (Method A) ES⁺: MH⁺ = 315<br>rt = 1.34 min |

TABLE T1-continued

| Compound Number | Structure | ¹H nmr (CDCl₃ unless stated), LC/MS or other physical data |
|---|---|---|
| T17 | 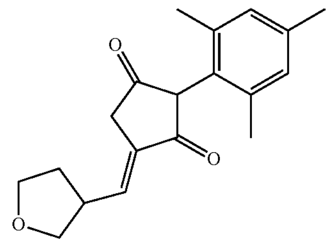 [SMILES: Cc1cc(C)c(C2C(=O)C/C(=C\C3CCOC3)C2=O)c(C)c1] | LC-MS (Method A) ES⁺: MH⁺ = 299<br>rt = 1.27 min |
| T18 | 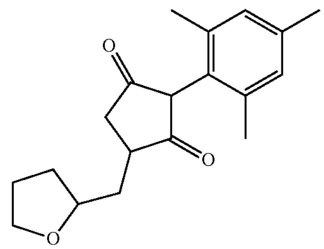 [SMILES: Cc1cc(C)c(C2C(=O)CC(CC3CCCO3)C2=O)c(C)c1] | LC-MS (Method A) ES⁺: MH⁺ = 301<br>rt = 1.36 min |
| T19 | 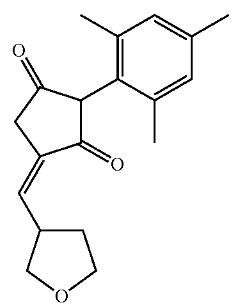 [SMILES: Cc1cc(C)c(C2C(=O)C/C(=C/C3CCOC3)C2=O)c(C)c1] | LC-MS (Method A) ES⁺: MH⁺ = 299<br>rt = 1.32 min |
| T20 | 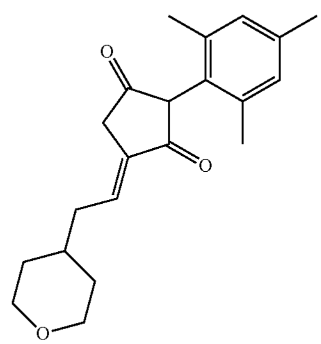 [SMILES: Cc1cc(C)c(C2C(=O)C/C(=C\CC3CCOCC3)C2=O)c(C)c1] | δ ppm 1.19-1.38 (m, 2H), 1.52-1.72 (m, 3H), 2.05 (s, 6H), 2.03-2.07 (m, 2H), 2.25 (s, 3H), 2.94 (s, 2H), 3.24-3.30 (m, 2H), 3.79-2.83 (m, 2H), 6.21 (t, 1H), 6.87 (s, 2H) |
| T21 | 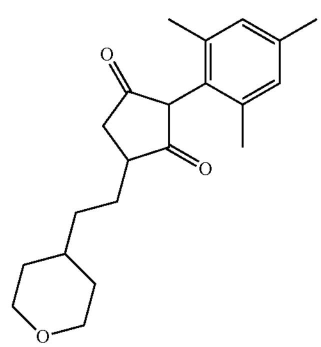 [SMILES: Cc1cc(C)c(C2C(=O)CC(CCC3CCOCC3)C2=O)c(C)c1] | LC-MS (Method B) ES⁺: MH⁺ = 329<br>rt = 1.34 min |

TABLE T1-continued

| Compound Number | Structure | ¹H nmr (CDCl₃ unless stated), LC/MS or other physical data |
|---|---|---|
| T22 | 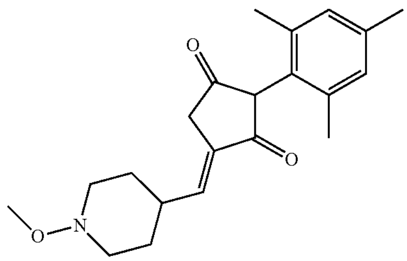 | LC-MS (Method A) ES⁺: MH⁺ = 344<br>rt = 1.27 min |
| T23 | 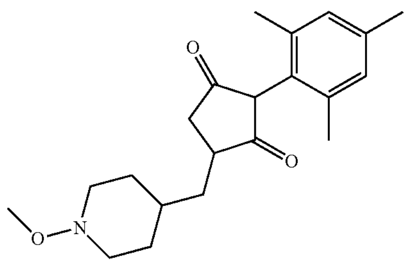 | LC-MS (Method A) ES⁺: MH⁺ = 344<br>rt = 1.19 min |
| T24 | 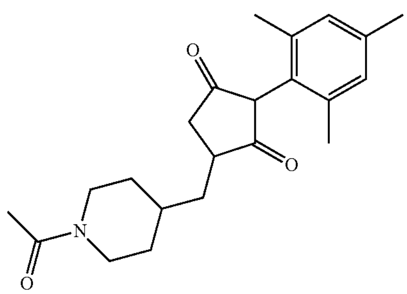 [SMILES: CC(=O)N1CCC(CC2CC(=O)C(c3c(C)cc(C)cc3C)C2=O)CC1] | LC-MS (Method A) ES⁺: MH⁺ = 356<br>rt = 1.29 min |
| T25 | 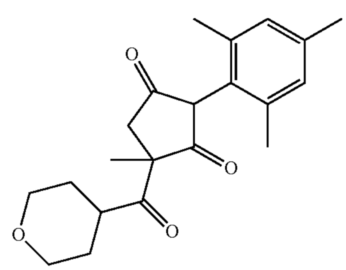 [SMILES: Cc1cc(C)c(C2C(=O)CC(C)(C(=O)C3CCOCC3)C2=O)c(C)c1] | LC-MS (Method B) ES⁺: MH⁺ = 343<br>rt = 1.33 min |
| T26 | 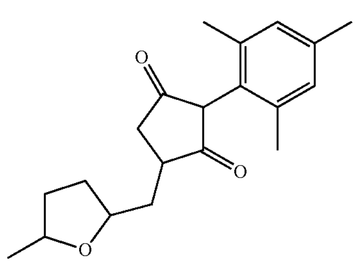 | LC-MS (Method A) ES⁺: MH⁺ = 315<br>rt = 1.46 min |

TABLE T1-continued

| Compound Number | Structure | $^1$H nmr (CDCl$_3$ unless stated), LC/MS or other physical data |
|---|---|---|
| T27 | 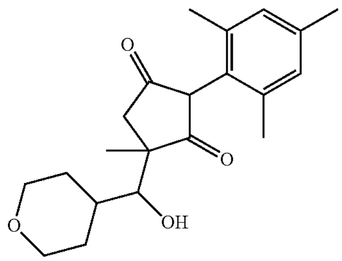 [SMILES: Cc1cc(C)c(C2C(=O)CC(C)(C(O)C3CCOCC3)C2=O)c(C)c1] | LC-MS (Method B) ES$^+$: MH$^+$ = 345<br>rt = 1.10 min |
| T28 | 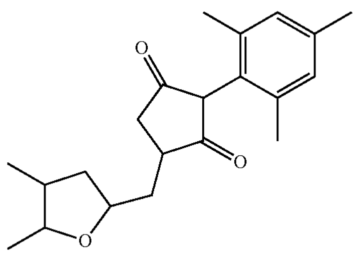 | LC-MS (Method A) ES$^+$: MH$^+$ = 329<br>rt = 1.52 min |
| T29 | 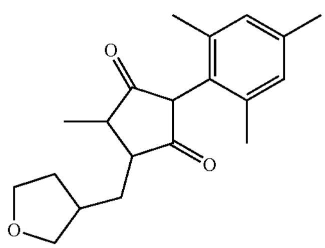 [SMILES: Cc1cc(C)c(C2C(=O)C(C)C(CC3CCOC3)C2=O)c(C)c1] | LC-MS (Method B) ES$^+$: MH$^+$ = 315<br>rt = 1.24 min |
| T30 | 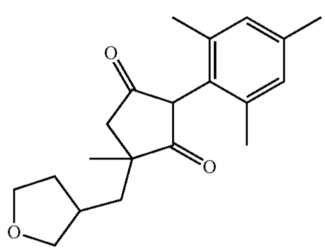 [SMILES: Cc1cc(C)c(C2C(=O)CC(C)(CC3CCOC3)C2=O)c(C)c1] | LC-MS (Method B) ES$^+$: MH$^+$ = 315<br>rt = 1.21 min |
| T31 | 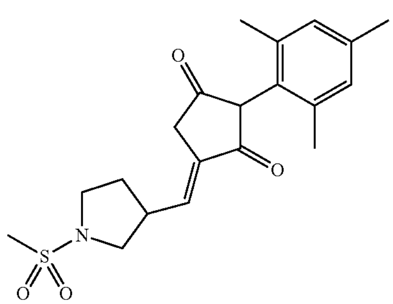 | LC-MS (Method A) ES$^+$: MH$^+$ = 376<br>rt = 1.29 min |

TABLE T1-continued

| Compound Number | Structure | ¹H nmr (CDCl₃ unless stated), LC/MS or other physical data |
|---|---|---|
| T32 | 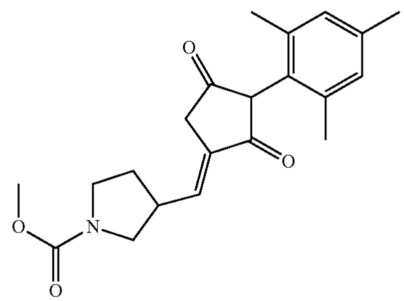 [SMILES: COC(=O)N1CCC(/C=C2\CC(=O)C(c3c(C)cc(C)cc3C)C2=O)C1] | LC-MS (Method A) ES⁺: MH⁺ = 356<br>rt = 1.36 min |
| T33 | 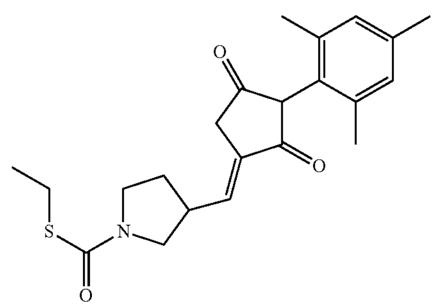 [SMILES: CCSC(=O)N1CCC(/C=C2\CC(=O)C(c3c(C)cc(C)cc3C)C2=O)C1] | LC-MS (Method A) ES⁺: MH⁺ = 386<br>rt = 1.51 min |
| T34 | 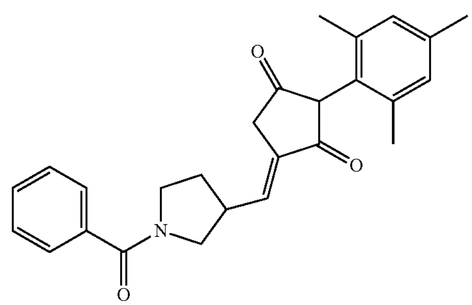 [SMILES: Cc1cc(C)c(C2C(=O)C/C(=C\C3CCN(C(=O)c4ccccc4)C3)C2=O)c(C)c1] | LC-MS (Method A) ES⁺: MH⁺ = 402<br>rt = 1.42 min |
| T35 | 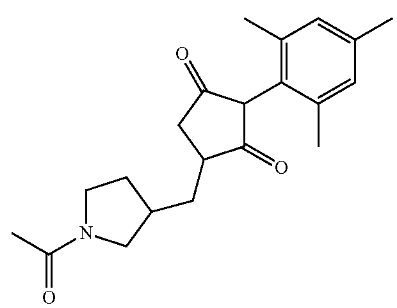 [SMILES: CC(=O)N1CCC(CC2CC(=O)C(c3c(C)cc(C)cc3C)C2=O)C1] | LC-MS (Method A) ES⁺: MH⁺ = 342<br>rt = 1.21 min |
| T36 | 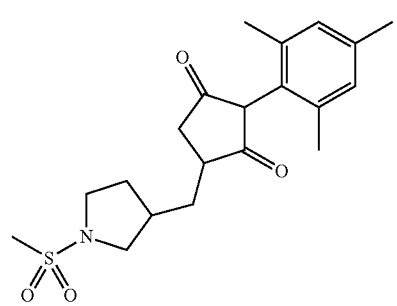 | LC-MS (Method A) ES⁺: MH⁺ = 378<br>rt = 1.29 min |

TABLE T1-continued

| Compound Number | Structure | $^1$H nmr (CDCl$_3$ unless stated), LC/MS or other physical data |
|---|---|---|
| T37 | 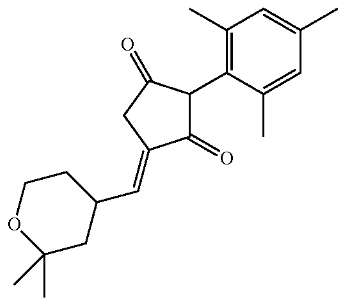 [SMILES: Cc1cc(C)c(C2C(=O)C/C(=C\C3CCOC(C)(C)C3)C2=O)c(C)c1] | LC-MS (Method A) ES$^+$: MH$^+$ = 341<br>rt = 1.44 min |
| T38 | 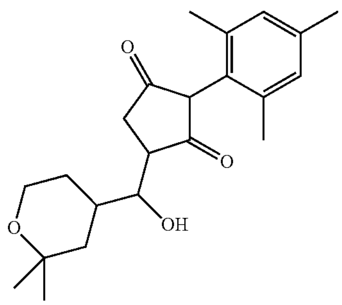 [SMILES: Cc1cc(C)c(C2C(=O)CC(C(O)C3CCOC(C)(C)C3)C2=O)c(C)c1] | LC-MS (Method A) ES$^+$: MH$^+$ = 359<br>rt = 1.22 min |
| T39 | 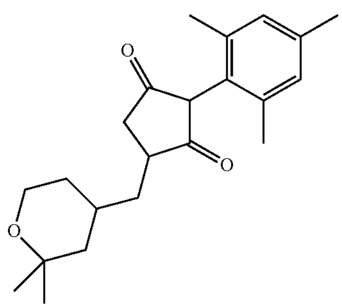 [SMILES: Cc1cc(C)c(C2C(=O)CC(CC3CCOC(C)(C)C3)C2=O)c(C)c1] | LC-MS (Method A) ES$^+$: MH$^+$ = 343<br>rt = 1.42 min |
| T40 | 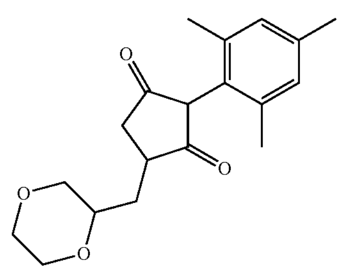 [SMILES: Cc1cc(C)c(C2C(=O)CC(CC3COCCO3)C2=O)c(C)c1] | LC-MS (Method A) ES$^+$: MH$^+$ = 317<br>rt = 1.22 min |
| T41 | 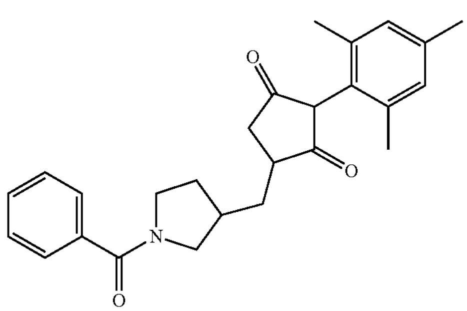 [SMILES: Cc1cc(C)c(C2C(=O)CC(CC3CCN(C(=O)c4ccccc4)C3)C2=O)c(C)c1] | LC-MS (Method A) ES$^+$: MH$^+$ = 404<br>rt = 1.41 min |

TABLE T1-continued

| Compound Number | Structure | $^1$H nmr (CDCl$_3$ unless stated), LC/MS or other physical data |
|---|---|---|
| T42 | 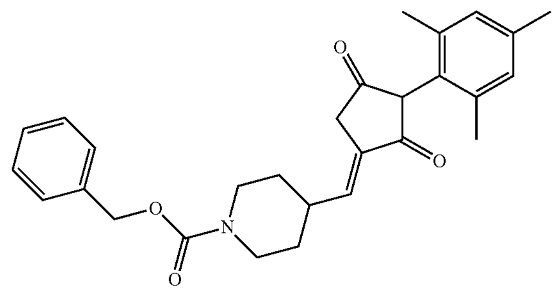 [SMILES: Cc1cc(C)c(C2C(=O)C/C(=C\C3CCN(C(=O)OCc4ccccc4)CC3)C2=O)c(C)c1] | LC-MS (Method A) ES$^+$: MH$^+$ = 446<br>rt = 1.66 min |
| T43 | 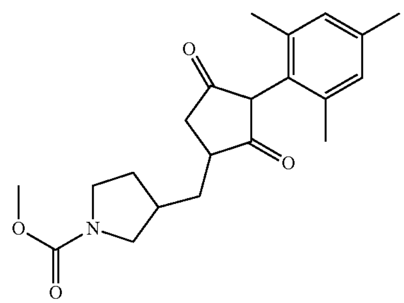 | LC-MS (Method A) ES$^+$: MH$^+$ = 358<br>rt = 1.34 min |
| T44 | 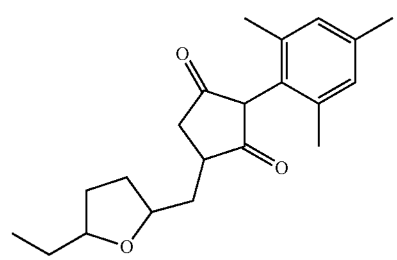 [SMILES: CCC1CCC(CC2CC(=O)C(c3c(C)cc(C)cc3C)C2=O)O1] | LC-MS (Method A) ES$^+$: MH$^+$ = 329<br>rt = 1.59 min |
| T45 | 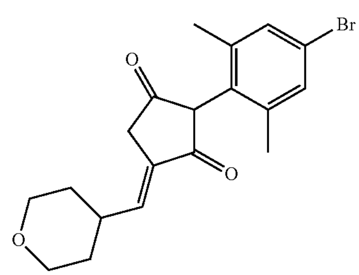 [SMILES: Cc1cc(Br)cc(C)c1C1C(=O)C/C(=C\C2CCOCC2)C1=O] | δ (DMSO-d6) ppm 1.45 (m, 2H), 1.59 (m, 2H), 2.01 (s, 6H), 3.08 (br, s), 3.37 (m, 2H), 3.87 (m, 2H), 5.75 (s, 1H), 6.04 (br s, 1H), 7.27 (s, 2H). |
| T46 | 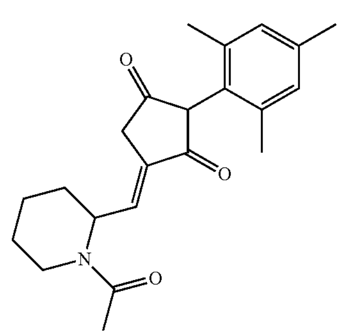 [SMILES: CC(=O)N1CCCCC1/C=C1\CC(=O)C(c2c(C)cc(C)cc2C)C1=O] | LC-MS (Method A) ES$^+$: MH$^+$ = 354<br>rt = 1.32 min |

TABLE T1-continued

| Compound Number | Structure | $^1$H nmr (CDCl$_3$ unless stated), LC/MS or other physical data |
| --- | --- | --- |
| T47 | 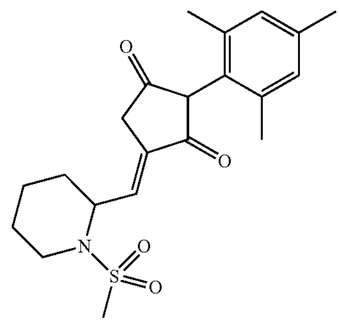 [SMILES: Cc1cc(C)c(C2C(=O)C/C(=C\C3CCCCN3S(C)(=O)=O)C2=O)c(C)c1] | LC-MS (Method A) ES$^+$: MH$^+$ = 390<br>rt = 1.38 min |
| T48 | 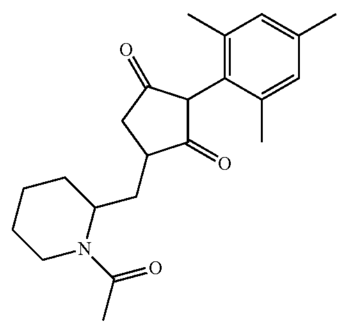 [SMILES: CC(=O)N1CCCCC1CC1CC(=O)C(c2c(C)cc(C)cc2C)C1=O] | LC-MS (Method A) ES$^+$: MH$^+$ = 356<br>rt = 1.38 min |
| T49 | 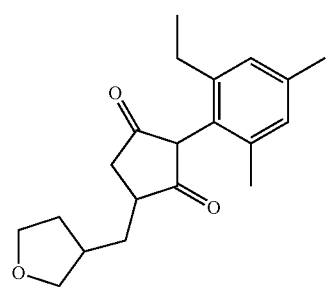 [SMILES: CCc1cc(C)cc(C)c1C1C(=O)CC(CC2CCOC2)C1=O] | LC-MS (Method B) ES$^+$: MH$^+$ = 315<br>rt = 1.34 min |
| T50 | 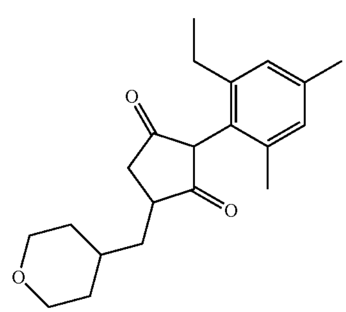 [SMILES: CCc1cc(C)cc(C)c1C1C(=O)CC(CC2CCOCC2)C1=O] | LC-MS (Method B) ES$^+$: MH$^+$ = 329<br>rt = 1.29 min |
| T51 | 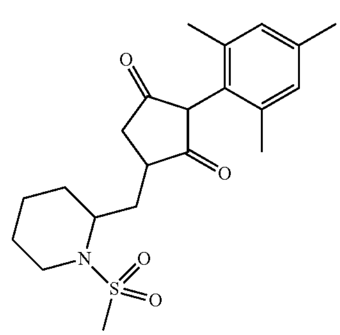 [SMILES: Cc1cc(C)c(C2C(=O)CC(CC3CCCCN3S(C)(=O)=O)C2=O)c(C)c1] | LC-MS (Method A) ES$^+$: MH$^+$ = 392<br>rt = 1.36 min |

TABLE T1-continued

| Compound Number | Structure | $^1$H nmr (CDCl$_3$ unless stated), LC/MS or other physical data |
|---|---|---|
| T52 | 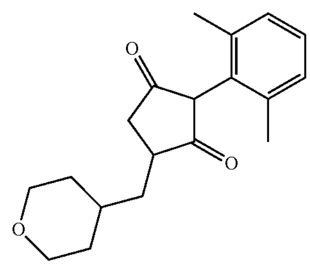 [SMILES: Cc1cccc(C)c1C1C(=O)CC(CC2CCOCC2)C1=O] | LC-MS (Method C) ES−: M − H$^+$ = 299<br>Rt = 4.75 mins<br>Melting point: 165-167° C. |
| T53 | 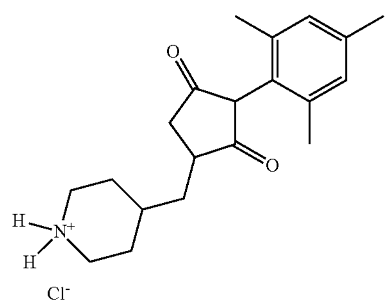 [SMILES: Cc1cc(C)c(C2C(=O)CC(CC3CC[NH2+]CC3)C2=O)c(C)c1 ; [Cl-]] | LC-MS (Method A) ES$^+$: MH$^+$ = 314<br>rt = 1.09 min |
| T54 | 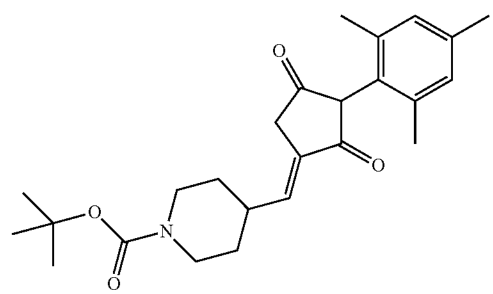 [SMILES: Cc1cc(C)c(C2C(=O)C/C(=C\C3CCN(C(=O)OC(C)(C)C)CC3)C2=O)c(C)c1] | LC-MS (Method A) ES$^+$: MH$^+$ = 412<br>rt = 1.63 min |
| T55 | 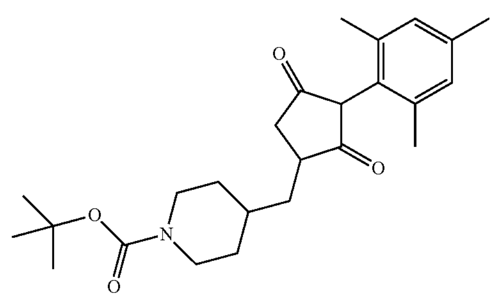 [SMILES: Cc1cc(C)c(C2C(=O)CC(CC3CCN(C(=O)OC(C)(C)C)CC3)C2=O)c(C)c1] | LC-MS (Method A) ES$^+$: MH$^+$ = 414<br>rt = 1.61 min |
| T56 | 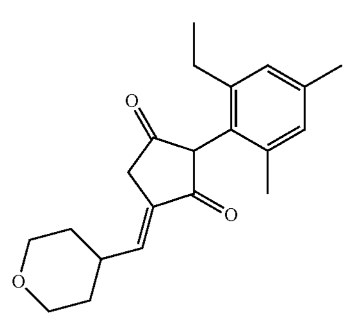 [SMILES: CCc1cc(C)cc(C)c1C1C(=O)C/C(=C\C2CCOCC2)C1=O] | LC-MS (Method B) ES$^+$: MH$^+$ = 327<br>rt = 1.39 min |

TABLE T1-continued

| Compound Number | Structure | ¹H nmr (CDCl₃ unless stated), LC/MS or other physical data |
|---|---|---|
| T57 | 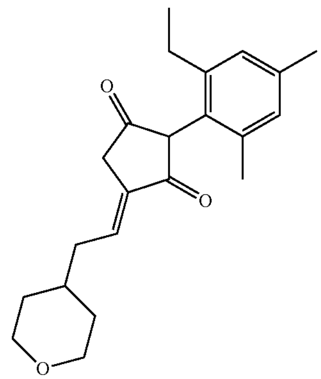 [SMILES: CCc1cc(C)cc(C)c1C1C(=O)C/C(=C\CC2CCOCC2)C1=O] | LC-MS (Method B) ES⁺: MH⁺ = 341<br>rt = 1.39 min |
| T58 | 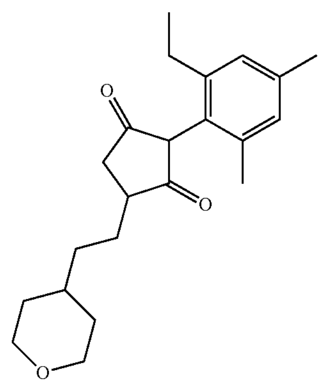 [SMILES: CCc1cc(C)cc(C)c1C1C(=O)CC(CCC2CCOCC2)C1=O] | LC-MS (Method B) ES⁺: MH⁺ = 343<br>rt = 1.34 min |
| T59 | 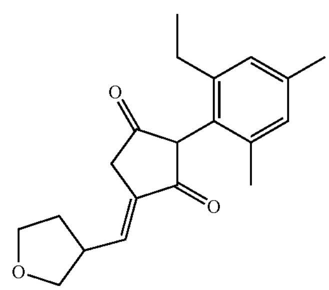 [SMILES: CCc1cc(C)cc(C)c1C1C(=O)C/C(=C\C2CCOC2)C1=O] | LC-MS (Method B) ES⁺: MH⁺ = 313<br>rt = 1.29 min |
| T60 | 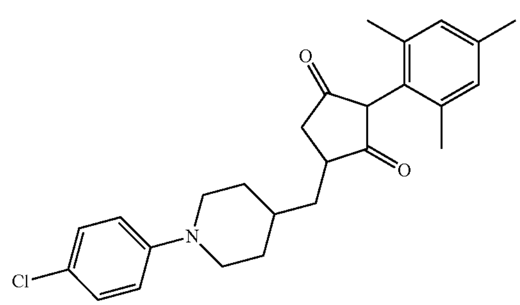 [SMILES: Cc1cc(C)c(C2C(=O)CC(CC3CCN(c4ccc(Cl)cc4)CC3)C2=O)c(C)c1] | LC-MS (Method A) ES⁺: MH⁺ = 426, 424<br>rt = 1.56 min |

TABLE T1-continued

| Compound Number | Structure | ¹H nmr (CDCl₃ unless stated), LC/MS or other physical data |
|---|---|---|
| T61 | 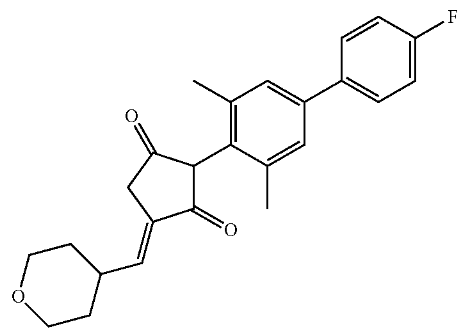 [SMILES: Cc1cc(-c2ccc(F)cc2)cc(C)c1C1C(=O)C/C(=C\C2CCOCC2)C1=O] | Melting point: 230-232° C. |
| T62 | 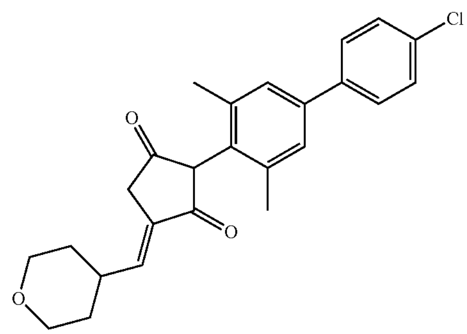 [SMILES: Cc1cc(-c2ccc(Cl)cc2)cc(C)c1C1C(=O)C/C(=C\C2CCOCC2)C1=O] | LC-MS (Method C) ES−: M − H⁺ = 407, 409<br>rt = 5.77 min<br>Melting point: 242-244° C. |
| T63 | 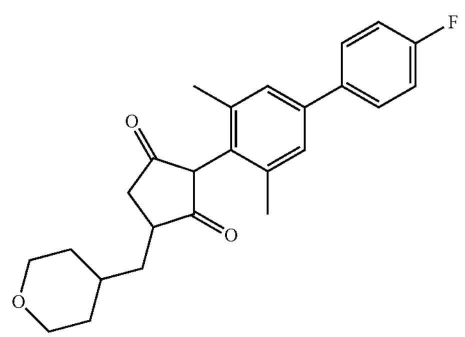 [SMILES: Cc1cc(-c2ccc(F)cc2)cc(C)c1C1C(=O)CC(CC2CCOCC2)C1=O] | Melting point: 115-117° C. |
| T64 | 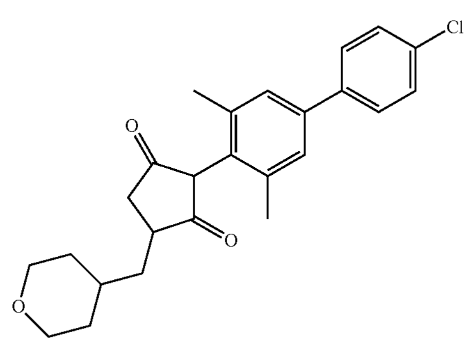 [SMILES: Cc1cc(-c2ccc(Cl)cc2)cc(C)c1C1C(=O)CC(CC2CCOCC2)C1=O] | Melting point: 232-233° C. |

TABLE T1-continued

| Compound Number | Structure | ¹H nmr (CDCl₃ unless stated), LC/MS or other physical data |
|---|---|---|
| T65 | 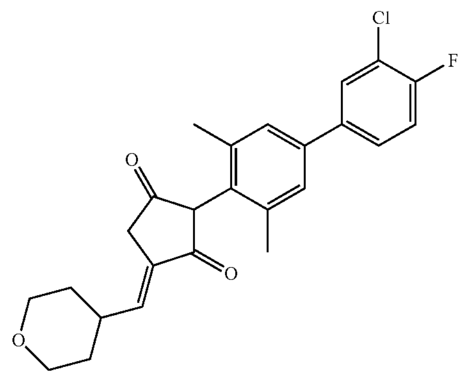 [SMILES: Cc1cc(-c2ccc(F)c(Cl)c2)cc(C)c1C1C(=O)C/C(=C\C2CCOCC2)C1=O] | Melting point: 225-227° C. |
| T66 | 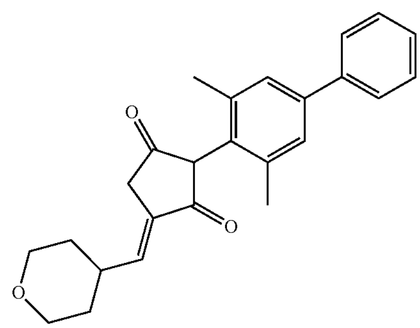 [SMILES: Cc1cc(-c2ccccc2)cc(C)c1C1C(=O)C/C(=C\C2CCOCC2)C1=O] | LC-MS (Method C) ES⁺: MH⁺ = 375<br>rt = 4.93 min |
| T67 | 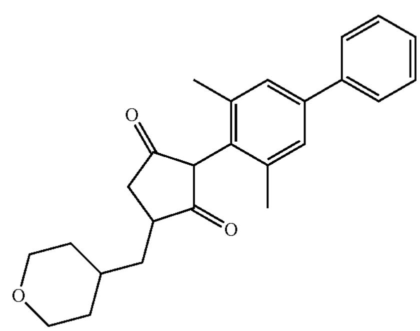 [SMILES: Cc1cc(-c2ccccc2)cc(C)c1C1C(=O)CC(CC2CCOCC2)C1=O] | LC-MS (Method C) ES⁺: MH⁺ = 377<br>rt = 4.05 min |
| T68 | 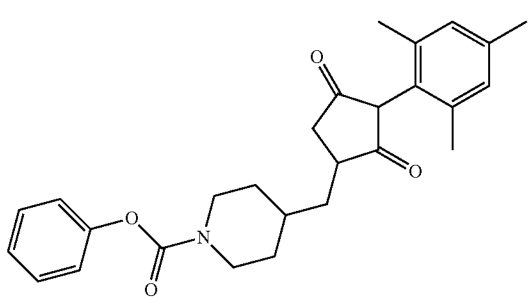 [SMILES: Cc1cc(C)c(C2C(=O)CC(CC3CCN(C(=O)Oc4ccccc4)CC3)C2=O)c(C)c1] | LC-MS (Method B) ES⁺: MH⁺ = 434<br>rt = 1.61 min |

TABLE T1-continued

| Compound Number | Structure | $^1$H nmr (CDCl$_3$ unless stated), LC/MS or other physical data |
|---|---|---|
| T69 | 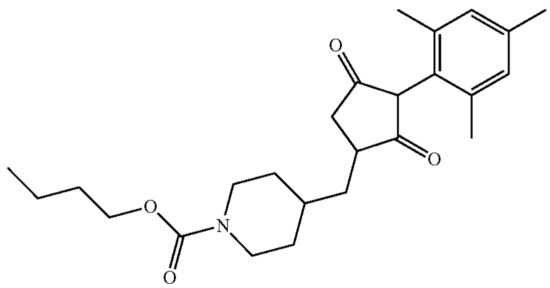 [SMILES: CCCCOC(=O)N1CCC(CC2CC(=O)C(c3c(C)cc(C)cc3C)C2=O)CC1] | LC-MS (Method B) ES$^+$: MH$^+$ = 414<br>rt = 1.64 min |
| T70 | 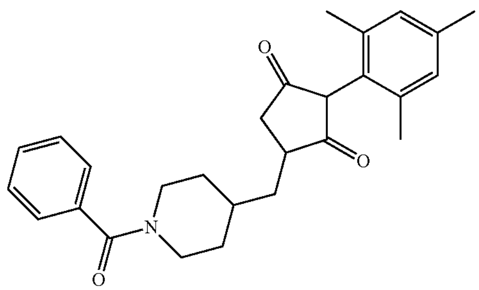 [SMILES: Cc1cc(C)c(C2C(=O)CC(CC3CCN(C(=O)c4ccccc4)CC3)C2=O)c(C)c1] | LC-MS (Method B) ES$^+$: MH$^+$ = 418<br>rt = 1.44 min |
| T71 | 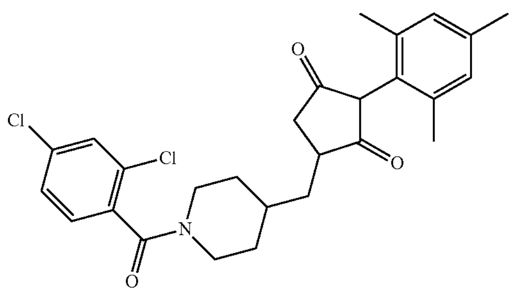 [SMILES: Cc1cc(C)c(C2C(=O)CC(CC3CCN(C(=O)c4ccc(Cl)cc4Cl)CC3)C2=O)c(C)c1] | LC-MS (Method B) ES$^+$: MH$^+$ = 490, 488, 486<br>rt = 1.61 min |
| T72 | 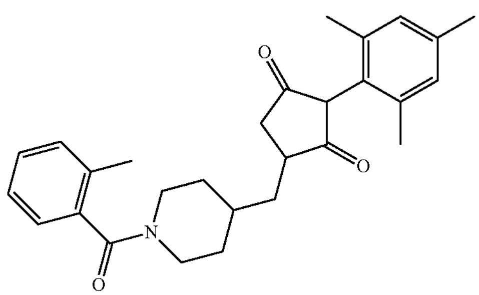 [SMILES: Cc1cc(C)c(C2C(=O)CC(CC3CCN(C(=O)c4ccccc4C)CC3)C2=O)c(C)c1] | LC-MS (Method B) ES$^+$: MH$^+$ = 432<br>rt = 1.49 min |
| T73 | 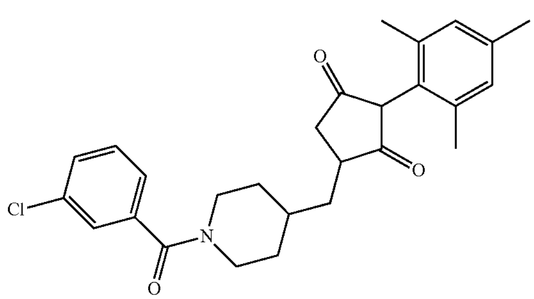 [SMILES: Cc1cc(C)c(C2C(=O)CC(CC3CCN(C(=O)c4cccc(Cl)c4)CC3)C2=O)c(C)c1] | LC-MS (Method B) ES$^+$: MH$^+$ = 454, 452<br>rt = 1.55 min |

TABLE T1-continued

| Compound Number | Structure | ¹H nmr (CDCl₃ unless stated), LC/MS or other physical data |
|---|---|---|
| T74 | 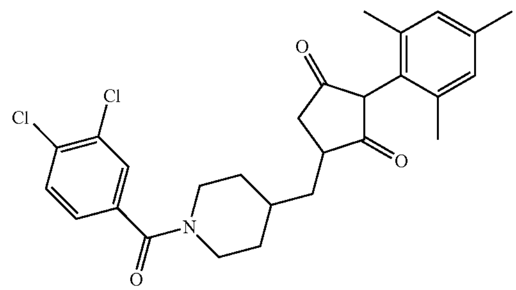 [SMILES: Cc1cc(C)c(C2C(=O)CC(CC3CCN(C(=O)c4ccc(Cl)c(Cl)c4)CC3)C2=O)c(C)c1] | LC-MS (Method B) ES⁺: MH⁺ = 490, 488, 486<br>rt = 1.64 min |
| T75 | 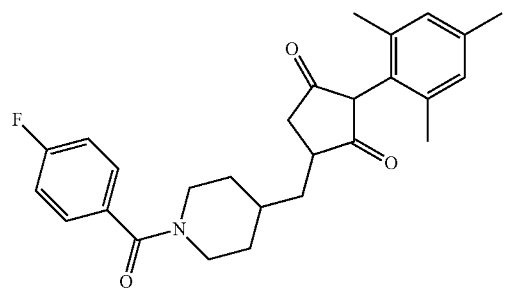 [SMILES: Cc1cc(C)c(C2C(=O)CC(CC3CCN(C(=O)c4ccc(F)cc4)CC3)C2=O)c(C)c1] | LC-MS (Method B) ES⁺: MH⁺ = 436<br>rt = 1.48 min |
| T76 | 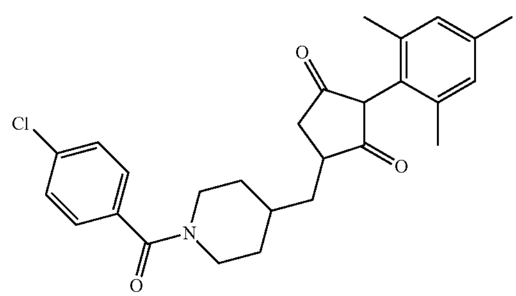 [SMILES: Cc1cc(C)c(C2C(=O)CC(CC3CCN(C(=O)c4ccc(Cl)cc4)CC3)C2=O)c(C)c1] | LC-MS (Method B) ES⁺: MH⁺ = 454, 452<br>rt = 1.56 min |
| T77 | 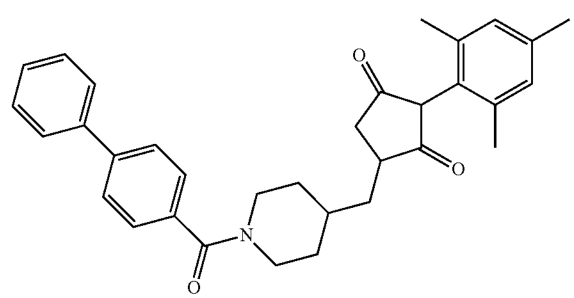 [SMILES: Cc1cc(C)c(C2C(=O)CC(CC3CCN(C(=O)c4ccc(-c5ccccc5)cc4)CC3)C2=O)c(C)c1] | LC-MS (Method B) ES⁺: MH⁺ = 494<br>rt = 1.70 min |
| T78 | 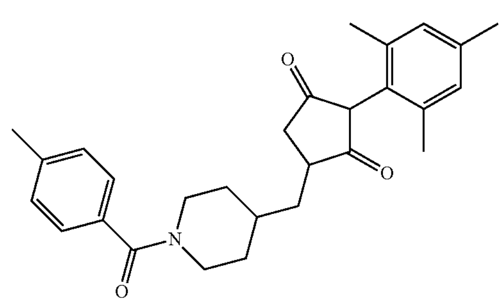 | LC-MS (Method B) ES⁺: MH⁺ = 432<br>rt = 1.52 min |

TABLE T1-continued
| Compound Number | Structure | ¹H nmr (CDCl₃ unless stated), LC/MS or other physical data |
|---|---|---|
| T79 | 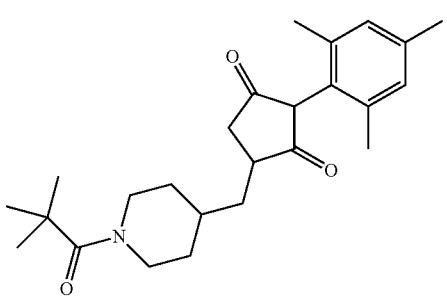 [SMILES: Cc1cc(C)c(C2C(=O)CC(CC3CCN(C(=O)C(C)(C)C)CC3)C2=O)c(C)c1] | LC-MS (Method B) ES⁺: MH⁺ = 398<br>rt = 1.47 min |
| T80 | 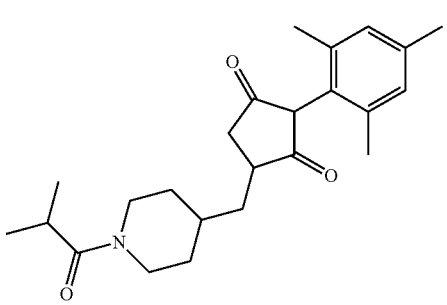 [SMILES: Cc1cc(C)c(C2C(=O)CC(CC3CCN(C(=O)C(C)C)CC3)C2=O)c(C)c1] | LC-MS (Method B) ES⁺: MH⁺ = 384<br>rt = 1.38 min |
| T81 | 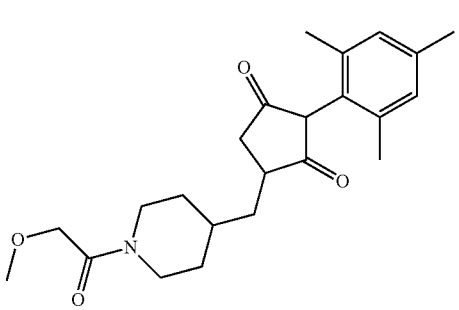 | LC-MS (Method B) ES⁺: MH⁺ = 386<br>rt = 1.25 min |
| T82 | 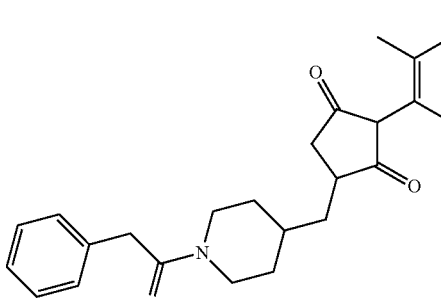 | LC-MS (Method B) ES⁺: MH⁺ = 432<br>rt = 1.49 min |
| T83 | 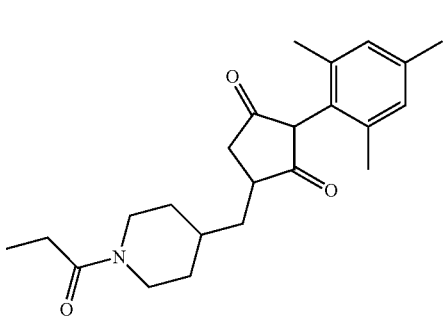 [SMILES: CCC(=O)N1CCC(CC2CC(=O)C(c3c(C)cc(C)cc3C)C2=O)CC1] | LC-MS (Method B) ES⁺: MH⁺ = 370<br>rt = 1.32 min |

TABLE T1-continued
| Compound Number | Structure | ¹H nmr (CDCl₃ unless stated), LC/MS or other physical data |
|---|---|---|
| T84 | 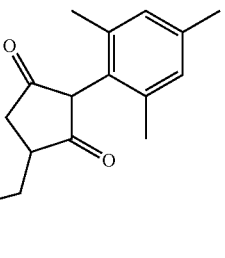 | LC-MS (Method B) ES⁺: MH⁺ = 384<br>rt = 1.39 min |
| T85 | 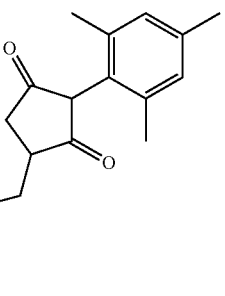 | LC-MS (Method B) ES⁺: MH⁺ = 398<br>rt = 1.48 min |
| T86 | 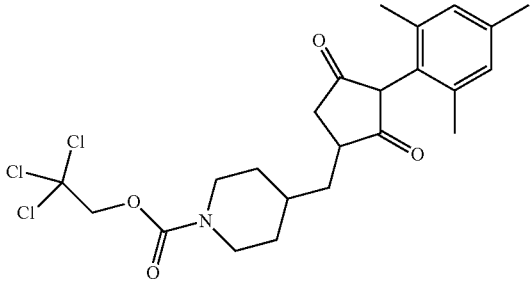 [SMILES: Cc1cc(C)c(C2C(=O)CC(CC3CCN(C(=O)OCC(Cl)(Cl)Cl)CC3)C2=O)c(C)c1] | LC-MS (Method B) ES⁺: MH⁺ = 492, 490, 488<br>rt = 1.71 min |
| T87 | 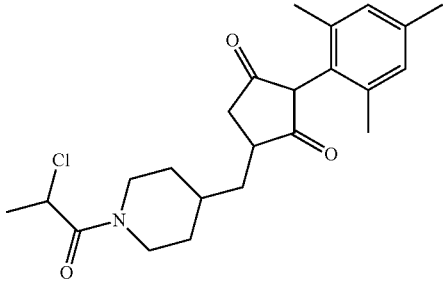 [SMILES: Cc1cc(C)c(C2C(=O)CC(CC3CCN(C(=O)C(C)Cl)CC3)C2=O)c(C)c1] | LC-MS (Method B) ES⁺: MH⁺ = 406, 404<br>rt = 1.42 min |
| T88 | 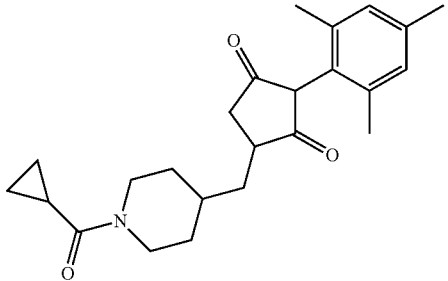 [SMILES: Cc1cc(C)c(C2C(=O)CC(CC3CCN(C(=O)C4CC4)CC3)C2=O)c(C)c1] | LC-MS (Method B) ES⁺: MH⁺ = 382<br>rt = 1.36 min |

TABLE T1-continued
| Compound Number | Structure | $^1$H nmr (CDCl$_3$ unless stated), LC/MS or other physical data |
|---|---|---|
| T89 | 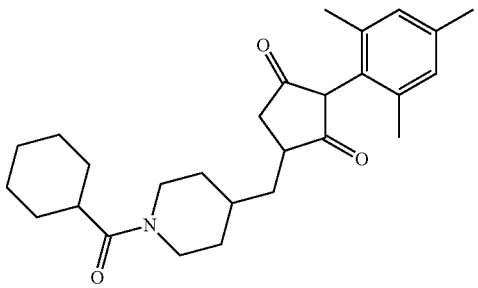 [SMILES: Cc1cc(C)c(C2C(=O)CC(CC3CCN(C(=O)C4CCCCC4)CC3)C2=O)c(C)c1] | LC-MS (Method B) ES$^+$: MH$^+$ = 424<br>rt = 1.55 min |
| T90 | 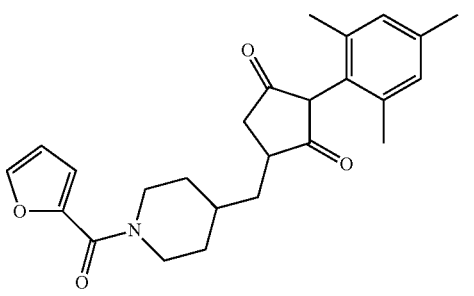 [SMILES: Cc1cc(C)c(C2C(=O)CC(CC3CCN(C(=O)c4ccco4)CC3)C2=O)c(C)c1] | LC-MS (Method B) ES$^+$: MH$^+$ = 408<br>rt = 1.38 min |
| T91 | 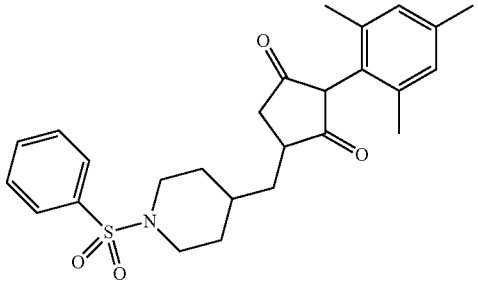 [SMILES: Cc1cc(C)c(C2C(=O)CC(CC3CCN(S(=O)(=O)c4ccccc4)CC3)C2=O)c(C)c1] | LC-MS (Method B) ES$^+$: MH$^+$ = 454<br>rt = 1.60 min |
| T92 | 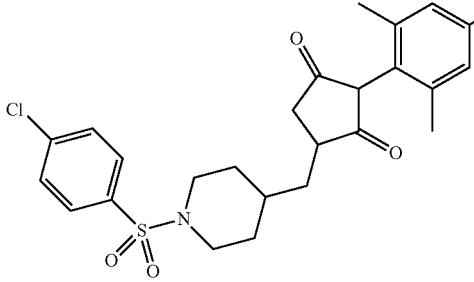 | LC-MS (Method B) ES$^+$: MH$^+$ = 490, 488<br>rt = 1.70 min |
| T93 | 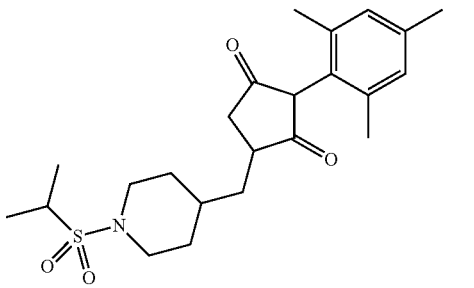 [SMILES: Cc1cc(C)c(C2C(=O)CC(CC3CCN(S(=O)(=O)C(C)C)CC3)C2=O)c(C)c1] | |

TABLE T1-continued

| Compound Number | Structure | ¹H nmr (CDCl₃ unless stated), LC/MS or other physical data |
|---|---|---|
| T94 | 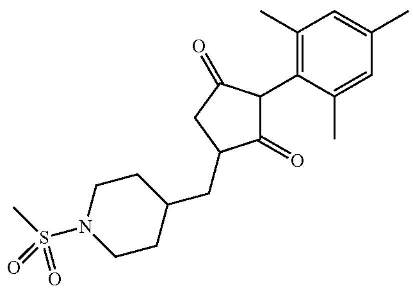 | LC-MS (Method B) ES⁺: MH⁺ = 392<br>rt = 1.34 min |
| T95 | 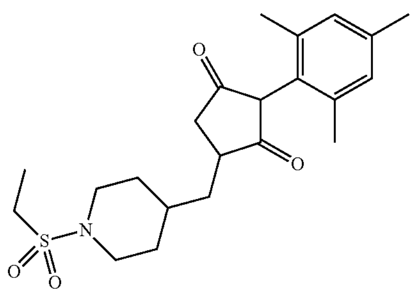 [SMILES: CCS(=O)(=O)N1CCC(CC2CC(=O)C(c3c(C)cc(C)cc3C)C2=O)CC1] | LC-MS (Method B) ES⁺: MH⁺ = 406<br>rt = 1.39 min |
| T96 | 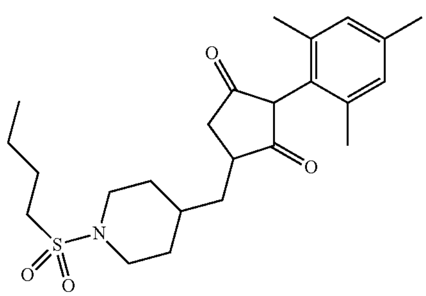 [SMILES: CCCCS(=O)(=O)N1CCC(CC2CC(=O)C(c3c(C)cc(C)cc3C)C2=O)CC1] | LC-MS (Method B) ES⁺: MH⁺ = 434<br>rt = 1.60 min |
| T97 | 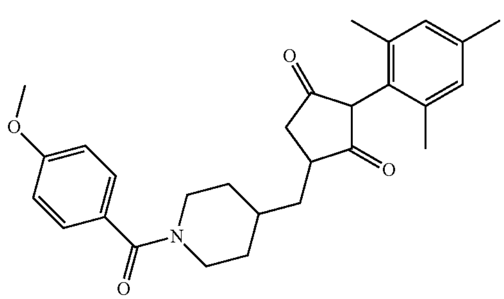 [SMILES: COc1ccc(C(=O)N2CCC(CC3CC(=O)C(c4c(C)cc(C)cc4C)C3=O)CC2)cc1] | LC-MS (Method B) ES⁺: MH⁺ = 448<br>rt = 1.47 min |
| T98 | 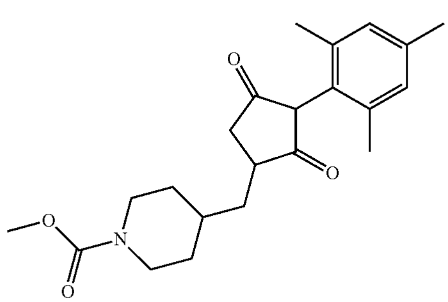 | LC-MS (Method B) ES⁺: MH⁺ = 372<br>rt = 1.40 min |

TABLE T1-continued
| Compound Number | Structure | ¹H nmr (CDCl₃ unless stated), LC/MS or other physical data |
|---|---|---|
| T99 | 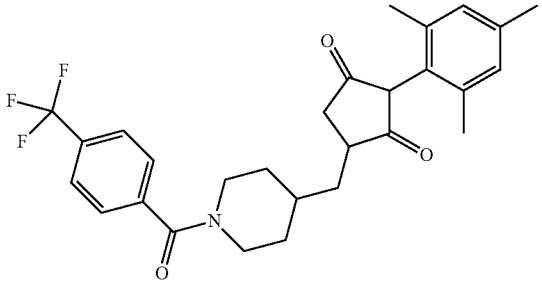 [SMILES: Cc1cc(C)c(C2C(=O)CC(CC3CCN(C(=O)c4ccc(C(F)(F)F)cc4)CC3)C2=O)c(C)c1] | LC-MS (Method B) ES⁺: MH⁺ = 486<br>rt = 1.60 min |
| T100 | 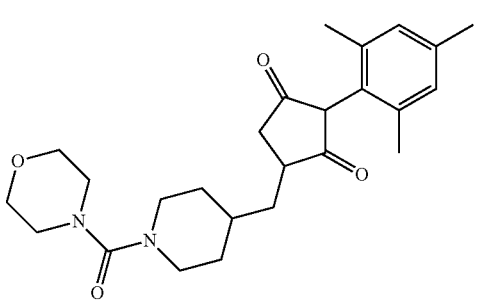 | LC-MS (Method B) ES⁺: MH⁺ = 427<br>rt = 1.31 min |
| T101 | 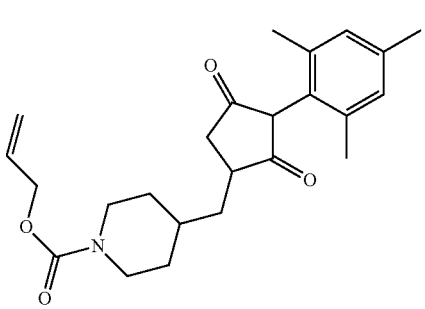 [SMILES: C=CCOC(=O)N1CCC(CC2CC(=O)C(c3c(C)cc(C)cc3C)C2=O)CC1] | LC-MS (Method B) ES⁺: MH⁺ = 398<br>rt = 1.51 min |
| T102 | 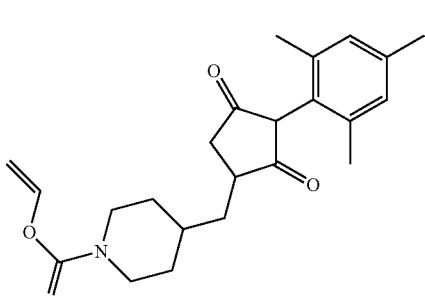 | LC-MS (Method B) ES⁺: MH⁺ = 384<br>rt = 1.51 min |
| T103 | 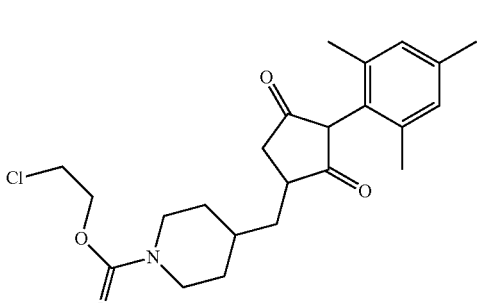 | LC-MS (Method B) ES⁺: MH⁺ = 422, 420<br>rt = 1.52 min |

TABLE T1-continued

| Compound Number | Structure | ¹H nmr (CDCl₃ unless stated), LC/MS or other physical data |
|---|---|---|
| T104 | 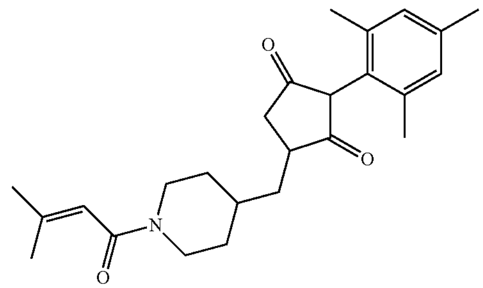 [SMILES: CC(C)=CC(=O)N1CCC(CC2CC(=O)C(c3c(C)cc(C)cc3C)C2=O)CC1] | LC-MS (Method B) ES⁺: MH⁺ = 396<br>rt = 1.41 min |
| T105 | 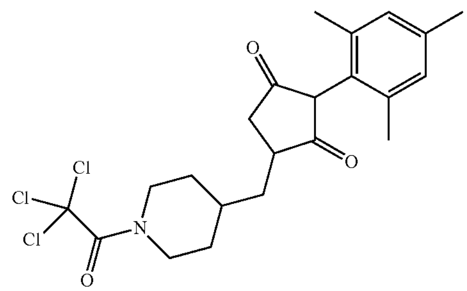 [SMILES: Cc1cc(C)c(C2C(=O)CC(CC3CCN(C(=O)C(Cl)(Cl)Cl)CC3)C2=O)c(C)c1] | LC-MS (Method B) ES⁺: MH⁺ = 462, 460, 458<br>rt = 1.64 min |
| T106 | 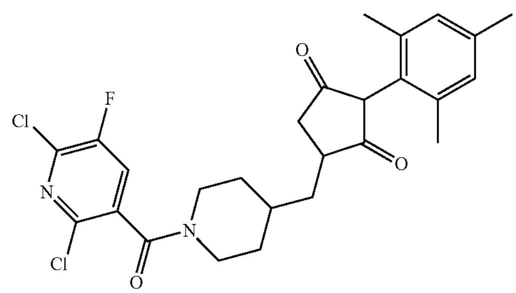 [SMILES: Cc1cc(C)c(C2C(=O)CC(CC3CCN(C(=O)c4cc(F)c(Cl)nc4Cl)CC3)C2=O)c(C)c1] | LC-MS (Method B) ES⁺: MH⁺ = 509, 507, 505<br>rt = 1.58 min |
| T107 | 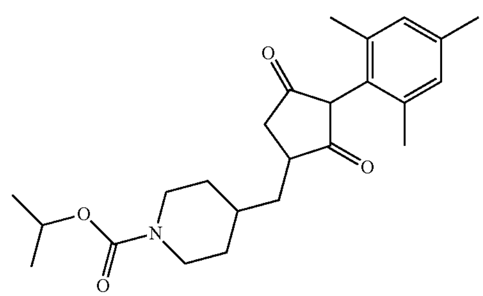 | LC-MS (Method B) ES⁺: MH⁺ = 400<br>rt = 1.54 min |
| T108 | 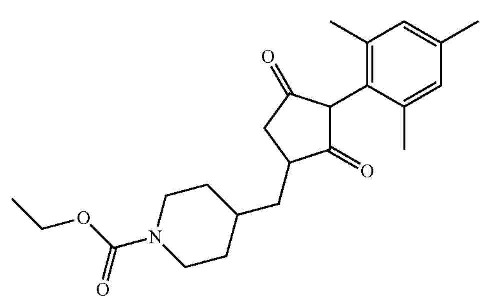 [SMILES: CCOC(=O)N1CCC(CC2CC(=O)C(c3c(C)cc(C)cc3C)C2=O)CC1] | LC-MS (Method B) ES⁺: MH⁺ = 386<br>rt = 1.46 min |

TABLE T1-continued
| Compound Number | Structure | $^1$H nmr (CDCl$_3$ unless stated), LC/MS or other physical data |
|---|---|---|
| T109 | 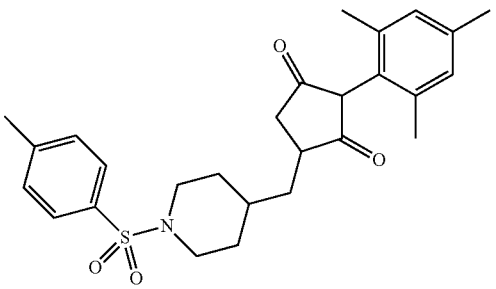 | LC-MS (Method B) ES$^+$: MH$^+$ = 468<br>rt = 1.65 min |
| T110 | 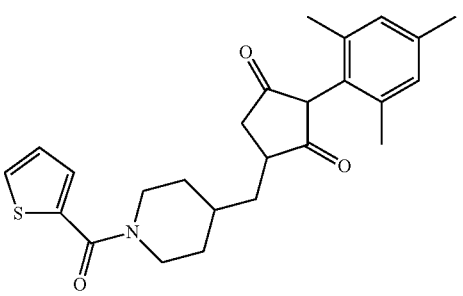 | LC-MS (Method B) ES$^+$: MH$^+$ = 424<br>rt = 1.44 min |
| T111 | 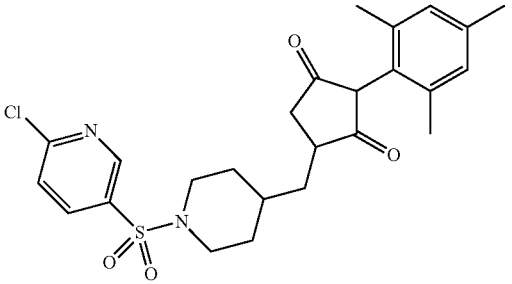 | LC-MS (Method B) ES$^+$: MH$^+$ = 455, 453<br>rt = 1.42 min |
| T112 | 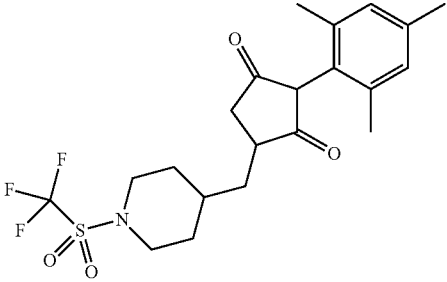 [SMILES: Cc1cc(C)c(C2C(=O)CC(CC3CCN(S(=O)(=O)C(F)(F)F)CC3)C2=O)c(C)c1] | LC-MS (Method B) ES$^+$: MH$^+$ = 446<br>rt = 1.66 min |
| T113 | 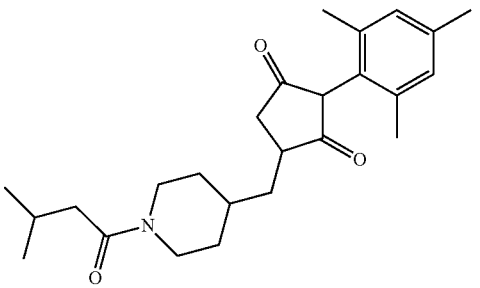 [SMILES: Cc1cc(C)c(C2C(=O)CC(CC3CCN(C(=O)CC(C)C)CC3)C2=O)c(C)c1] | LC-MS (Method B) ES$^+$: MH$^+$ = 398<br>rt = 1.44 min |

TABLE T1-continued

| Compound Number | Structure | ¹H nmr (CDCl₃ unless stated), LC/MS or other physical data |
|---|---|---|
| T114 | 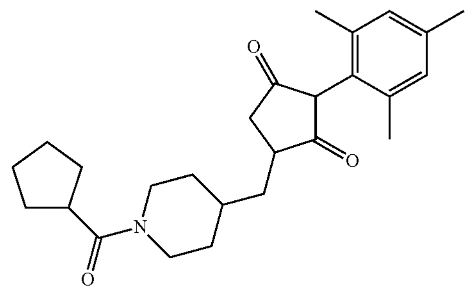 [SMILES: Cc1cc(C)c(C2C(=O)CC(CC3CCN(C(=O)C4CCCC4)CC3)C2=O)c(C)c1] | LC-MS (Method B) ES⁺: MH⁺ = 410<br>rt = 1.50 min |
| T115 | 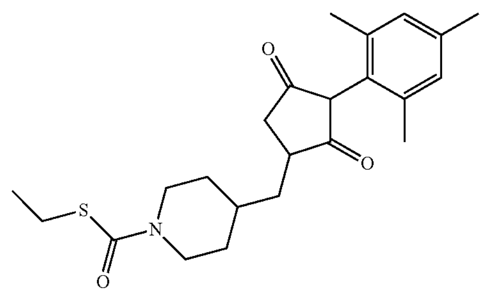 | LC-MS (Method B) ES⁺: MH⁺ = 402<br>rt = 1.56 min |
| T116 | 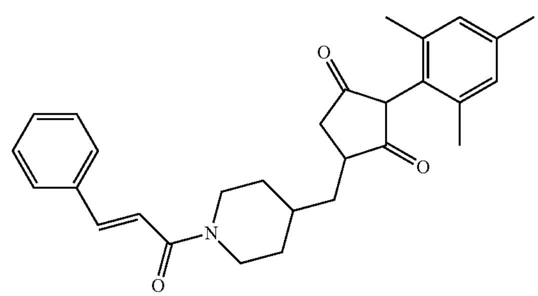 [SMILES: Cc1cc(C)c(C2C(=O)CC(CC3CCN(C(=O)/C=C/c4ccccc4)CC3)C2=O)c(C)c1] | LC-MS (Method B) ES⁺: MH⁺ = 444<br>rt = 1.55 min |
| T117 | 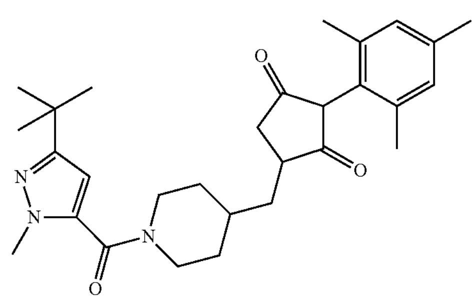 | LC-MS (Method B) ES⁺: MH⁺ = 478<br>rt = 1.54 min |
| T118 | 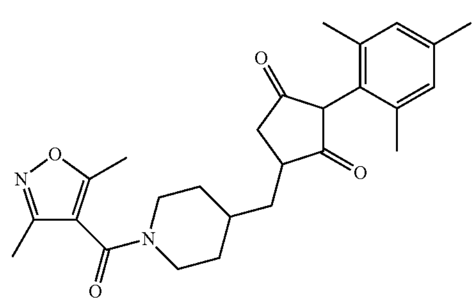 | LC-MS (Method B) ES⁺: MH⁺ = 437<br>rt = 1.35 min |

TABLE T1-continued

| Compound Number | Structure | ¹H nmr (CDCl₃ unless stated), LC/MS or other physical data |
|---|---|---|
| T119 | 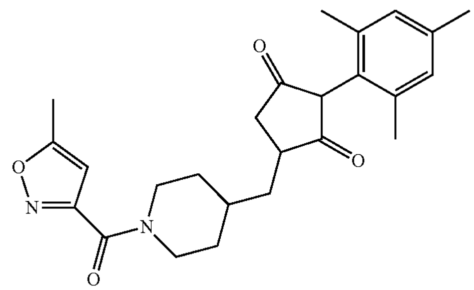 [SMILES: Cc1cc(C)c(C2C(=O)CC(CC3CCN(C(=O)c4cc(C)on4)CC3)C2=O)c(C)c1] | LC-MS (Method B) ES⁺: MH⁺ = 423<br>rt = 1.42 min |
| T120 | 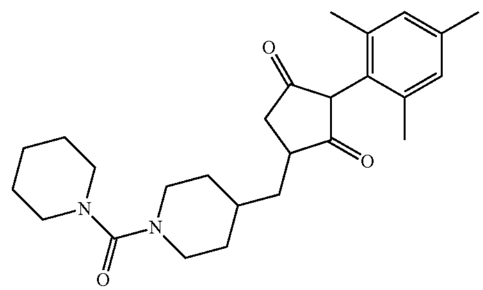 [SMILES: Cc1cc(C)c(C2C(=O)CC(CC3CCN(C(=O)N4CCCCC4)CC3)C2=O)c(C)c1] | LC-MS (Method B) ES⁺: MH⁺ = 425<br>rt = 1.51 min |
| T121 | 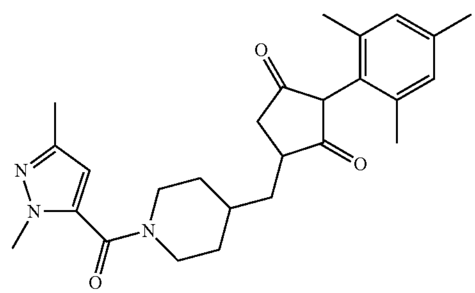 | LC-MS (Method B) ES⁺: MH⁺ = 436<br>rt = 1.36 min |
| T122 | 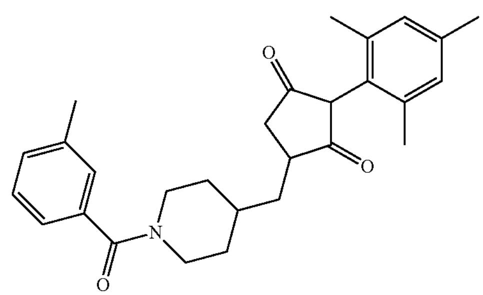 [SMILES: Cc1cccc(C(=O)N2CCC(CC3CC(=O)C(c4c(C)cc(C)cc4C)C3=O)CC2)c1] | LC-MS (Method B) ES⁺: MH⁺ = 432<br>rt = 1.52 min |
| T123 | 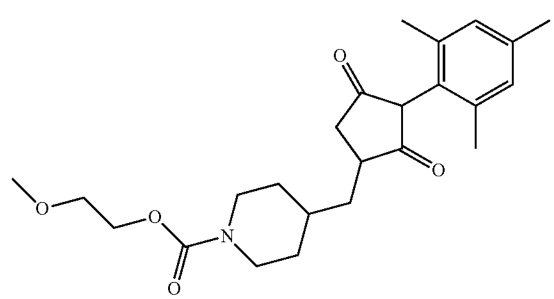 | LC-MS (Method B) ES⁺: MH⁺ = 416<br>rt = 1.38 min |

TABLE T1-continued

| Compound Number | Structure | $^1$H nmr (CDCl$_3$ unless stated), LC/MS or other physical data |
|---|---|---|
| T124 | 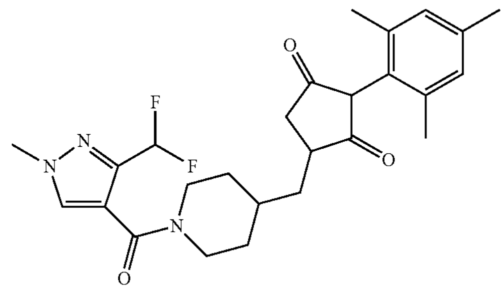 | LC-MS (Method B) ES$^+$: MH$^+$ = 472 rt = 1.35 min |
| T125 | 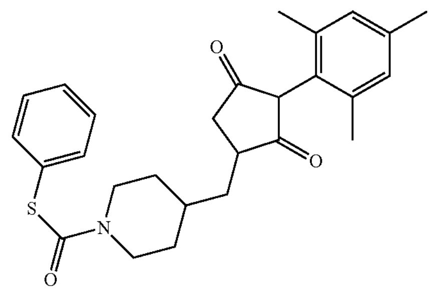 [SMILES: Cc1cc(C)c(C2C(=O)CC(CC3CCN(C(=O)Sc4ccccc4)CC3)C2=O)c(C)c1] | LC-MS (Method B) ES$^+$: MH$^+$ = 450 rt = 1.67 min |
| T126 | 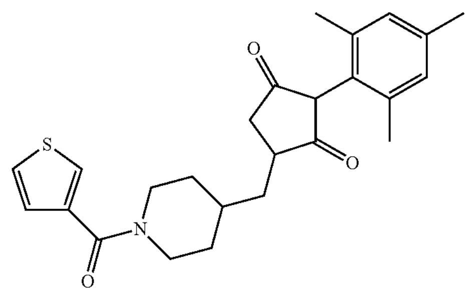 [SMILES: Cc1cc(C)c(C2C(=O)CC(CC3CCN(C(=O)c4ccsc4)CC3)C2=O)c(C)c1] | |
| T127 | 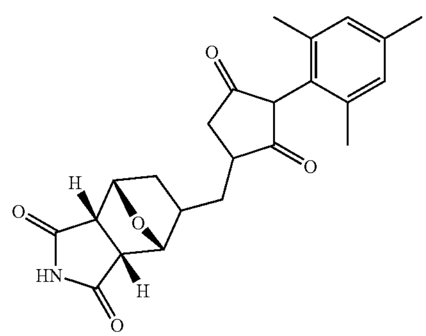 [SMILES: Cc1cc(C)c(C2C(=O)CC(CC3C[C@@H]4O[C@H]3[C@@H]3C(=O)NC(=O)[C@@H]34)C2=O)c(C)c1] | LC-MS (Method A) ES$^+$: MH$^+$ = 396 rt = 1.12 min |
| T128 | 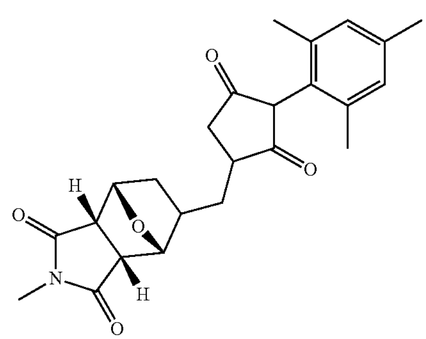 [SMILES: Cc1cc(C)c(C2C(=O)CC(CC3C[C@@H]4O[C@H]3[C@@H]3C(=O)N(C)C(=O)[C@@H]34)C2=O)c(C)c1] | LC-MS (Method A) ES$^+$: MH$^+$ = 410 rt = 1.21 min |

TABLE T1-continued

| Compound Number | Structure | $^1$H nmr (CDCl$_3$ unless stated), LC/MS or other physical data |
| --- | --- | --- |
| T129 | 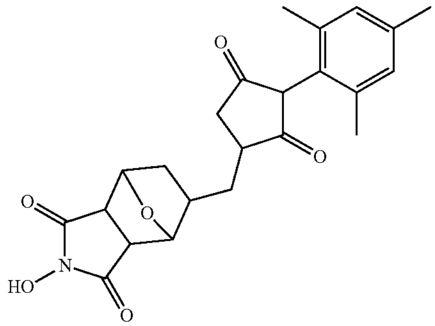 [SMILES: Cc1cc(C)c(C2C(=O)CC(CC3CC4OC3C3C(=O)N(O)C(=O)C43)C2=O)c(C)c1] | LC-MS (Method A) ES$^+$: MH$^+$ = 412<br>rt = 1.14 min |
| T130 | 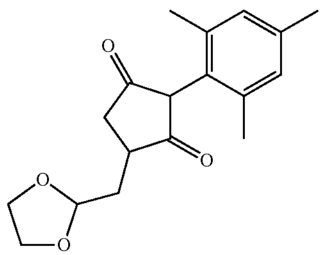 [SMILES: Cc1cc(C)c(C2C(=O)CC(CC3OCCO3)C2=O)c(C)c1] | LC-MS (Method A) ES$^+$: MH$^+$ = 303<br>rt = 1.26 min |
| T131 | 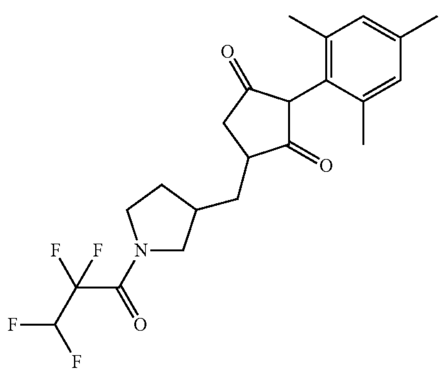 [SMILES: Cc1cc(C)c(C2C(=O)CC(CC3CCN(C(=O)C(F)(F)C(F)F)C3)C2=O)c(C)c1] | LC-MS (Method A) ES$^+$: MH$^+$ = 428<br>rt = 1.46 min |
| T132 | 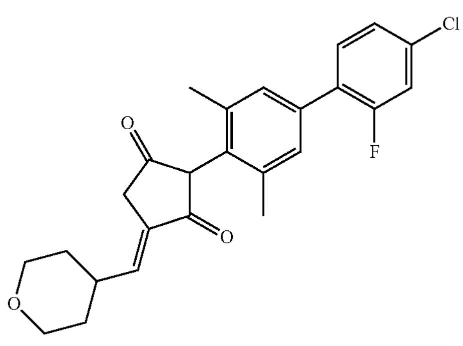 [SMILES: Cc1cc(-c2ccc(Cl)cc2F)cc(C)c1C1C(=O)C/C(=C\C2CCOCC2)C1=O] | LC-MS (Method C) ES$^-$: M − H$^+$ = 425, 427<br>rt = 4.50 mins |

TABLE T1-continued

| Compound Number | Structure | $^1$H nmr (CDCl$_3$ unless stated), LC/MS or other physical data |
| --- | --- | --- |
| T133 | 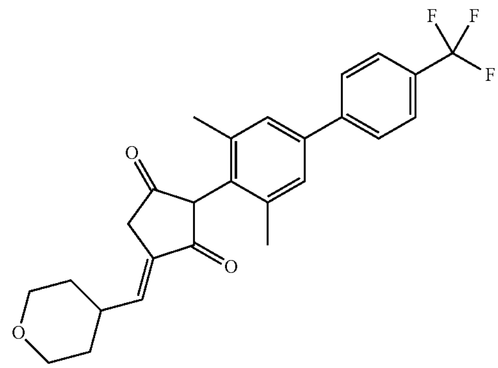 [SMILES: Cc1cc(-c2ccc(C(F)(F)F)cc2)cc(C)c1C1C(=O)C/C(=C\C2CCOCC2)C1=O] | LC-MS (Method C) ES$^-$: M − H$^+$ = 441 rt = 4.47 mins |
| T134 | 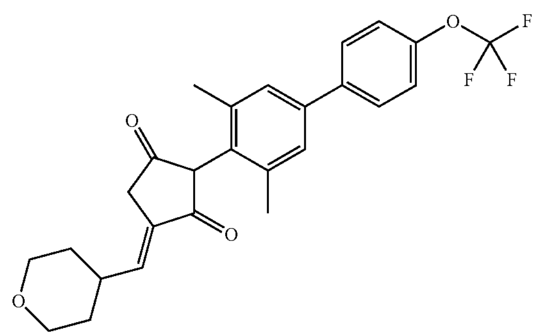 [SMILES: Cc1cc(-c2ccc(OC(F)(F)F)cc2)cc(C)c1C1C(=O)C/C(=C\C2CCOCC2)C1=O] | δ ppm 1.64-1.62 (m, 4H), 2.5 (m, 1H), 3.16 (s, 2H), 3.52-3.46 (m, 2H), 4.02-3.98 (m, 2H), 6.03 (d, 1H), 6.26 (s, 1H), 7.29-7.25 (m, 4H), 7.56 (d, 2H). |
| T135 | 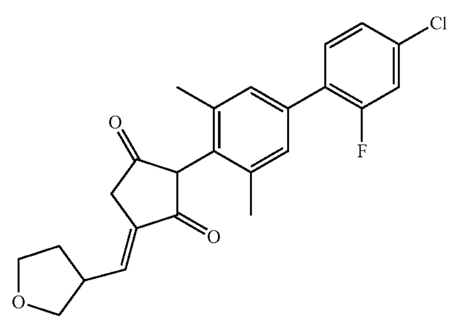 [SMILES: Cc1cc(-c2ccc(Cl)cc2F)cc(C)c1C1C(=O)C/C(=C\C2CCOC2)C1=O] | Melting point: 135-137° C. |
| T136 | 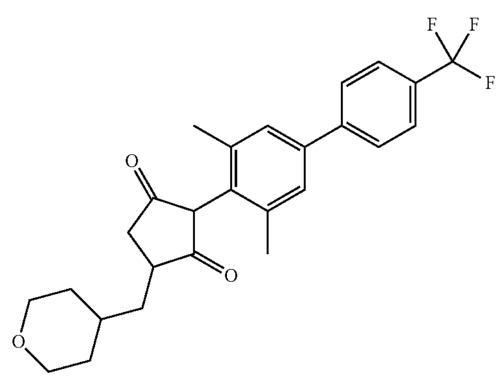 [SMILES: Cc1cc(-c2ccc(C(F)(F)F)cc2)cc(C)c1C1C(=O)CC(CC2CCOCC2)C1=O] | LC-MS (Method C) ES$^+$: MH$^+$ = 445 rt = 4.43 mins |

TABLE T1-continued

| Compound Number | Structure | ¹H nmr (CDCl₃ unless stated), LC/MS or other physical data |
|---|---|---|
| T137 | 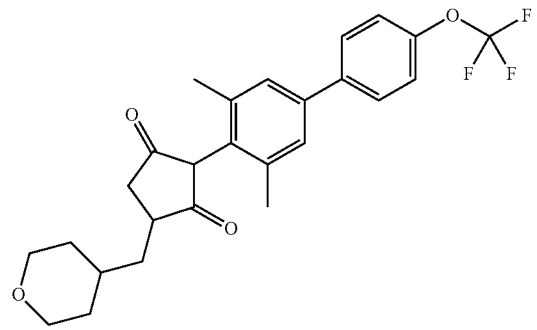 [SMILES: Cc1cc(-c2ccc(OC(F)(F)F)cc2)cc(C)c1C1C(=O)CC(CC2CCOCC2)C1=O] | δ (CD₃OD) ppm 1.8-1.5 (m, 6H), 2.07 (s, 3H), 2.08 (s, 3H), 2.67-2.59 (m, 2H), 3.2 (m, 2H), 3.35 (m, 2H), 3.9 (m, 2H), 7.22 (s, 2H), 7.58 (d, 2H), 7.67 (d, 2H). |
| T138 | 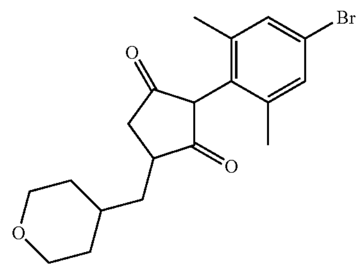 [SMILES: Cc1cc(Br)cc(C)c1C1C(=O)CC(CC2CCOCC2)C1=O] | δ ppm 1.33 (m, 3H), 1.66 (m, 3H), 1.88 (m, 1H), 2.05 (s, 6H), 2.29 (m, 1H), 2.78 (m, 2H), 3.38 (m, 2H), 3.9 (m, 2H), 7.21 (s, 2H). |
| T139 | 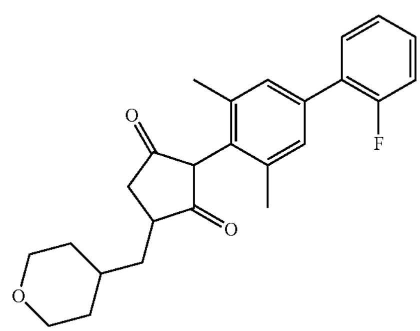 [SMILES: Cc1cc(-c2ccccc2F)cc(C)c1C1C(=O)CC(CC2CCOCC2)C1=O] | δ ppm 1.4 (m, 4H), 1.7 (m, 2H), 1.9 (m, 1H), 2.18 (2 × s, 6H), 2.4 (br, 1H), 2.9 (br, 2H), 3.4 (m, 2H), 3.97 (m, 2H), 7.14 (m, 1H), 7.2 (m, 1H), 7.28 (s, 2H), 7.32 (d, 1H), 7.4 (m, 1H). |
| T140 | 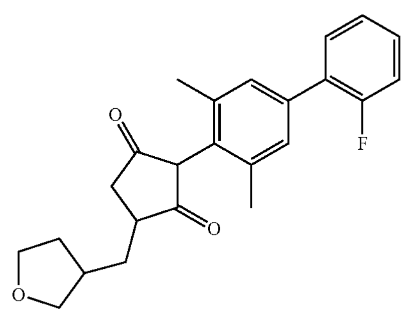 [SMILES: Cc1cc(-c2ccccc2F)cc(C)c1C1C(=O)CC(CC2CCOC2)C1=O] | LC-MS (Method C) ES⁺: MH⁺ = 380 rt = 3.98 min |
| T141 | 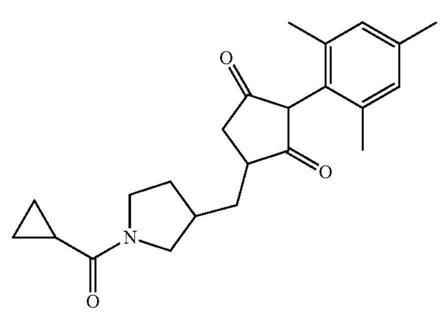 [SMILES: Cc1cc(C)c(C2C(=O)CC(CC3CCN(C(=O)C4CC4)C3)C2=O)c(C)c1] | LC-MS (Method A) ES⁺: MH⁺ = 368 rt = 1.29 min |

TABLE T1-continued

| Compound Number | Structure | $^1$H nmr (CDCl$_3$ unless stated), LC/MS or other physical data |
|---|---|---|
| T142 | 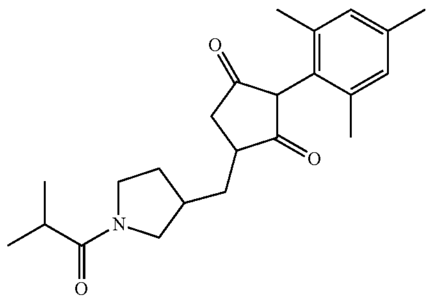 [SMILES: Cc1cc(C)c(C2C(=O)CC(CC3CCN(C(=O)C(C)C)C3)C2=O)c(C)c1] | LC-MS (Method A) ES$^+$: MH$^+$ = 370<br>rt = 1.39 min |
| T143 | 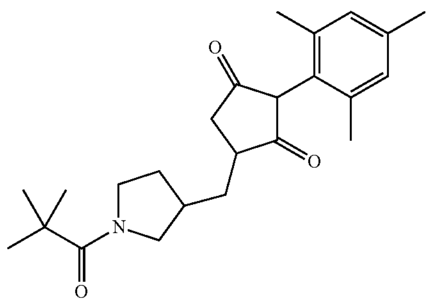 [SMILES: Cc1cc(C)c(C2C(=O)CC(CC3CCN(C(=O)C(C)(C)C)C3)C2=O)c(C)c1] | LC-MS (Method A) ES$^+$: MH$^+$ = 384<br>rt = 1.39 min |
| T144 | 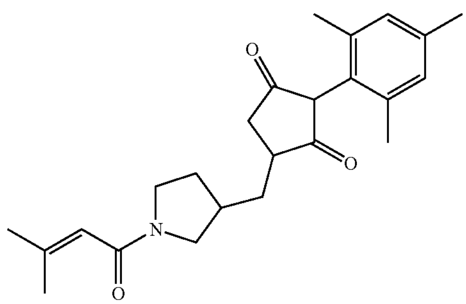 [SMILES: CC(C)=CC(=O)N1CCC(CC2CC(=O)C(c3c(C)cc(C)cc3C)C2=O)C1] | LC-MS (Method A) ES$^+$: MH$^+$ = 382<br>rt = 1.36 min |
| T145 | 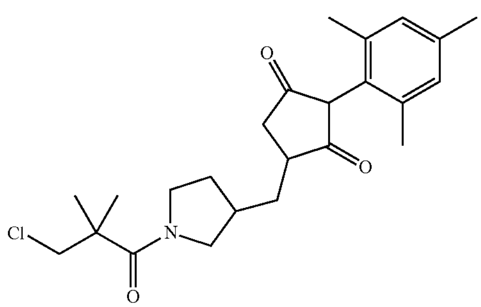 [SMILES: Cc1cc(C)c(C2C(=O)CC(CC3CCN(C(=O)C(C)(C)CCl)C3)C2=O)c(C)c1] | LC-MS (Method A) ES$^+$: MH$^+$ = 420, 418<br>rt = 1.41 min |
| T146 | 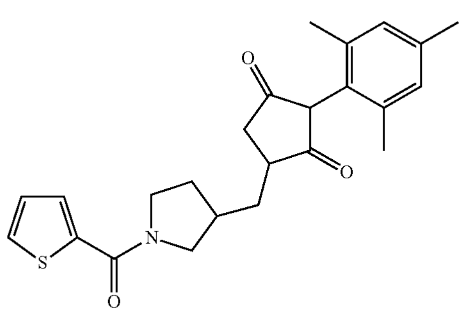 | LC-MS (Method A) ES$^+$: MH$^+$ = 410<br>rt = 1.38 min |

TABLE T1-continued

| Compound Number | Structure | ¹H nmr (CDCl₃ unless stated), LC/MS or other physical data |
|---|---|---|
| T147 | 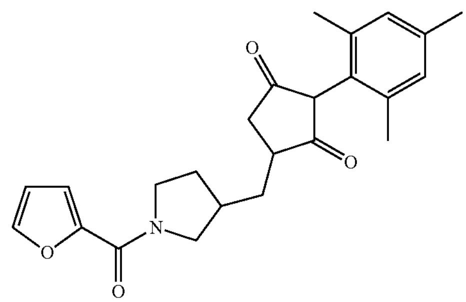 [SMILES: Cc1cc(C)c(C2C(=O)CC(CC3CCN(C(=O)c4ccco4)C3)C2=O)c(C)c1] | LC-MS (Method A) ES⁺: MH⁺ = 394<br>rt = 1.31 min |
| T148 | 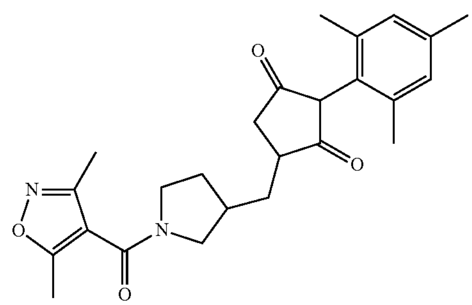 [SMILES: Cc1cc(C)c(C2C(=O)CC(CC3CCN(C(=O)c4c(C)noc4C)C3)C2=O)c(C)c1] | LC-MS (Method A) ES⁺: MH⁺ = 423<br>rt = 1.27 min |
| T149 | 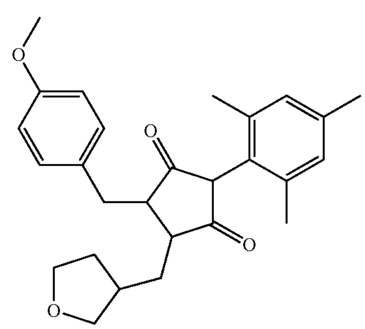 [SMILES: COc1ccc(CC2C(=O)C(c3c(C)cc(C)cc3C)C(=O)C2CC2CCOC2)cc1] | LC-MS (Method A) ES⁺: MH⁺ = 421<br>rt = 1.65 min |
| T150 | 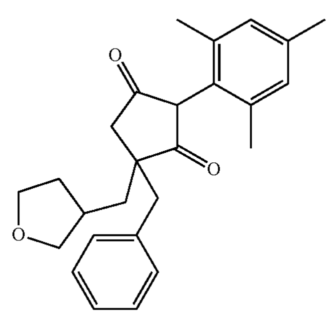 [SMILES: Cc1cc(C)c(C2C(=O)CC(Cc3ccccc3)(CC3CCOC3)C2=O)c(C)c1] | LC-MS (Method A) ES⁺: MH⁺ = 391<br>rt = 1.62 min |
| T151 | 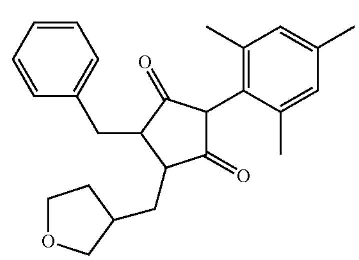 [SMILES: Cc1cc(C)c(C2C(=O)C(Cc3ccccc3)C(CC3CCOC3)C2=O)c(C)c1] | LC-MS (Method A) ES⁺: MH⁺ = 391<br>rt = 1.65 min |

TABLE T1-continued

| Compound Number | Structure | ¹H nmr (CDCl₃ unless stated), LC/MS or other physical data |
|---|---|---|
| T152 | 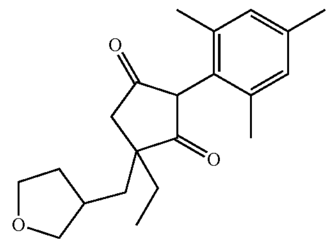 [SMILES: CCC1(CC2CCOC2)CC(=O)C(c2c(C)cc(C)cc2C)C1=O] | LC-MS (Method A) ES⁺: MH⁺ = 329<br>rt = 1.45 min |
| T153 | 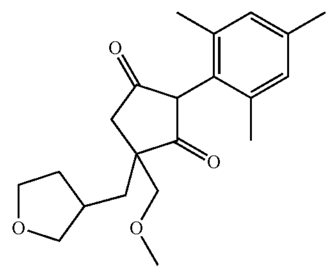 [SMILES: COCC1(CC2CCOC2)CC(=O)C(c2c(C)cc(C)cc2C)C1=O] | LC-MS (Method A) ES⁺: MH⁺ = 345<br>rt = 1.38 min |
| T154 | 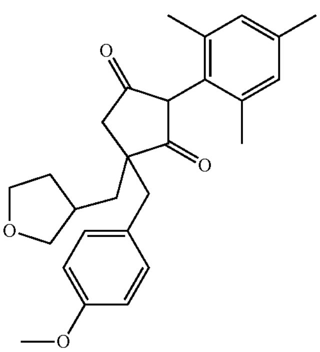 [SMILES: COc1ccc(CC2(CC3CCOC3)CC(=O)C(c3c(C)cc(C)cc3C)C2=O)cc1] | LC-MS (Method A) ES⁺: MH⁺ = 421<br>rt = 1.60 min |
| T155 | 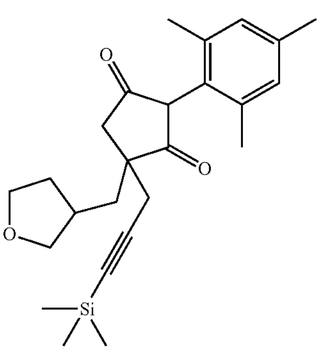 [SMILES: Cc1cc(C)c(C2C(=O)CC(CC#C[Si](C)(C)C)(CC3CCOC3)C2=O)c(C)c1] | LC-MS (Method A) ES⁺: MH⁺ = 411<br>rt = 1.81 min |
| T156 | 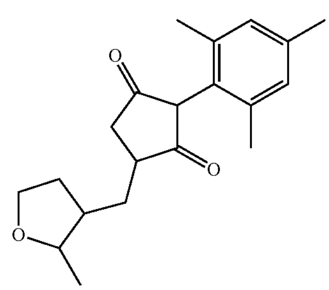 [SMILES: Cc1cc(C)c(C2C(=O)CC(CC3CCOC3C)C2=O)c(C)c1] | LC-MS (Method A) ES⁺: MH⁺ = 315<br>rt = 1.37 min |

TABLE T1-continued
| Compound Number | Structure | ¹H nmr (CDCl₃ unless stated), LC/MS or other physical data |
|---|---|---|
| T157 | 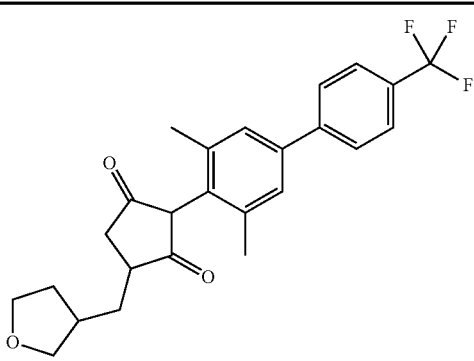 | δ ppm 1.6 (m, 2H), 2.10 (m, 2H), 2.20 (s, 6H), 2.40 (m, 2H), 2.90 (br, 2H), 3.40 (m, 1H), 3.76 (m, 1H), 3.90 (m, 2H), 7.31 (s, 2H), 7.66 (m, 4H). |
| T158 | 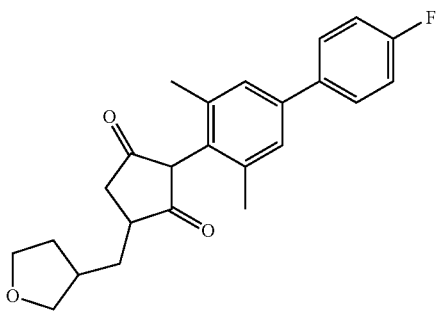 [SMILES: Cc1cc(-c2ccc(F)cc2)cc(C)c1C1C(=O)CC(CC2CCOC2)C1=O] | δ ppm 1.60 (m, 2H), 2.05 (m, 2H), 2.10 (s, 6H), 2.40 (m, 2H), 2.90 (m, 2H), 3.40 (m, 1H), 3.78 (m, 1H), 3.9 (m, 2H), 7.10 (t, 2H), 7.25 (s, 2H), 7.5 (m, 2H). |
| T159 | 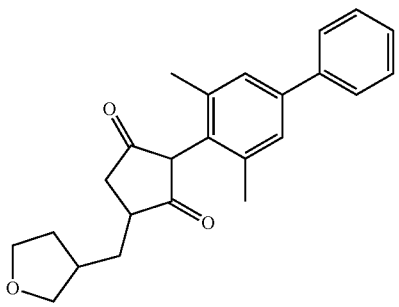 [SMILES: Cc1cc(-c2ccccc2)cc(C)c1C1C(=O)CC(CC2CCOC2)C1=O] | δ ppm 1.4 (br, 2H), 1.9 (br, 2H), 2.09 (s, 3H), 2.1 (s, 3H), 2.22 (d, 2H), 2.6 (m, 2H), 3.2 (m, 1H), 3.62 (m, 1H), 3.76 (m, 2H), 7.25 (s, 2H), 7.32 (d, 1H), 7.39 (t, 2H), 7.52 (d, 2H). |
| T160 | 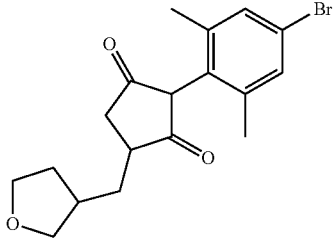 [SMILES: Cc1cc(Br)cc(C)c1C1C(=O)CC(CC2CCOC2)C1=O] | δ ppm 1.33 (m, 3H), 1.4 (m, 1H), 1.55 (m, 1H), 1.95 (m, 1H), 2.01 (s, 3H), 2.03 (s, 3H), 2.10 (m, 1H), 2.29-2.17 (m, 2H), 2.75-2.57 (m, 2H), 3.3 (m, 1H), 3.69 (m, 1H), 3.82 (m, 2H), 7.17 (s, 2H), |
| T161 | 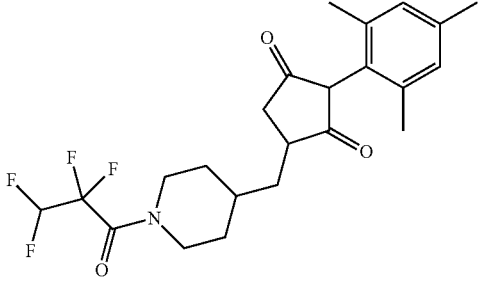 [SMILES: Cc1cc(C)c(C2C(=O)CC(CC3CCN(C(=O)C(F)(F)C(F)F)CC3)C2=O)c(C)c1] | LC-MS (Method A) ES⁺: MH⁺ = 442 rt = 1.66 min |

TABLE T1-continued
| Compound Number | Structure | $^1$H nmr (CDCl$_3$ unless stated), LC/MS or other physical data |
|---|---|---|
| T162 | 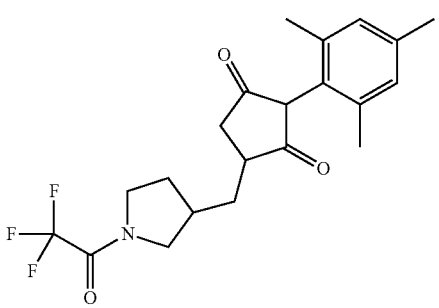 [SMILES: Cc1cc(C)c(C2C(=O)CC(CC3CCN(C(=O)C(F)(F)F)C3)C2=O)c(C)c1] | LC-MS (Method A) ES$^+$: MH$^+$ = 396<br>rt = 1.51 min |
| T163 | 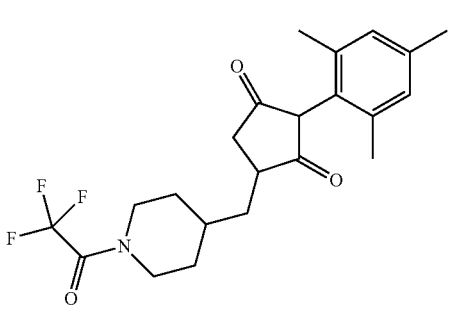 [SMILES: Cc1cc(C)c(C2C(=O)CC(CC3CCN(C(=O)C(F)(F)F)CC3)C2=O)c(C)c1] | LC-MS (Method A) ES$^+$: MH$^+$ = 410<br>rt = 1.59 min |
| T164 | 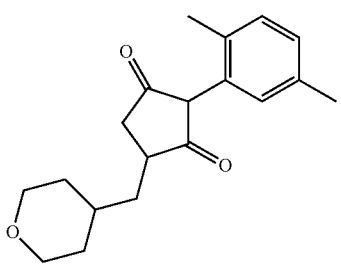 [SMILES: Cc1ccc(C)c(C2C(=O)CC(CC3CCOCC3)C2=O)c1] | LC-MS (Method A) ES$^+$: MH$^+$ = 301<br>rt = 1.31 min |
| T165 | 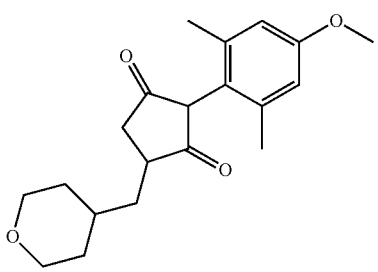 [SMILES: COc1cc(C)c(C2C(=O)CC(CC3CCOCC3)C2=O)c(C)c1] | LC-MS (Method A) ES$^+$: MH$^+$ = 331<br>rt = 1.27 min |
| T166 | 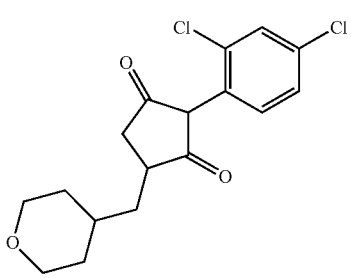 [SMILES: O=C1CC(CC2CCOCC2)C(=O)C1c1ccc(Cl)cc1Cl] | LC-MS (Method A) ES$^+$: MH$^+$ = 341, 343, 345<br>rt = 1.39 min |

TABLE T1-continued

| Compound Number | Structure | $^1$H nmr (CDCl$_3$ unless stated), LC/MS or other physical data |
|---|---|---|
| T167 | 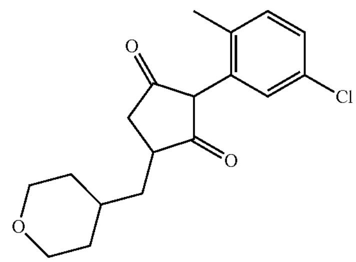 [SMILES: Cc1ccc(Cl)cc1C1C(=O)CC(CC2CCOCC2)C1=O] | LC-MS (Method A) ES$^+$: MH$^+$ = 321, 323 rt = 1.39 min |
| T168 | 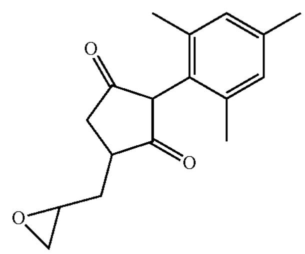 [SMILES: Cc1cc(C)c(C2C(=O)CC(CC3CO3)C2=O)c(C)c1] | LC-MS (Method A) ES$^+$: MH$^+$ = 273 rt = 1.26 min |
| T169 | 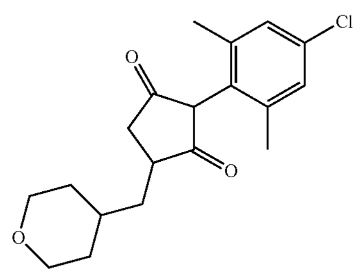 [SMILES: Cc1cc(Cl)cc(C)c1C1C(=O)CC(CC2CCOCC2)C1=O] | δ ppm 1.33 (m, 3H), 1.65 (m, 3H), 1.9 (m, 1H), 2.08 (s, 3H), 2.09 (s, 3H), 2.35 (d, 1H), 2.85 (d, 2H), 3.39 (m, 2H), 3.97 (m, 2H), 7.09 (s, 2H). |
| T170 | 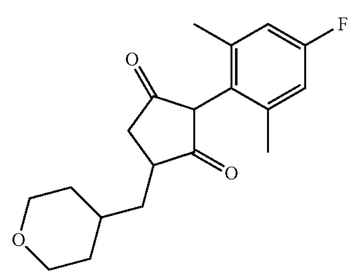 [SMILES: Cc1cc(F)cc(C)c1C1C(=O)CC(CC2CCOCC2)C1=O] | δ ppm 1.42 (m, 3H), 1.70 (m, 3H), 1.89 (m, 1H), 2.08 (s, 3H), 2.10 (s, 3H), 2.34 (d, 1H), 2.85 (d, 2H), 3.39 (m, 2H), 3.97 (m, 2H), 6.8 (d, 2H). |
| T171 | 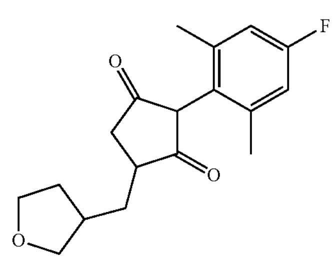 [SMILES: Cc1cc(F)cc(C)c1C1C(=O)CC(CC2CCOC2)C1=O] | LC-MS (Method C) ES$^+$: MH$^+$ = 305 rt = 3.37 min |

TABLE T1-continued
| Compound Number | Structure | ¹H nmr (CDCl₃ unless stated), LC/MS or other physical data |
|---|---|---|
| T172 | 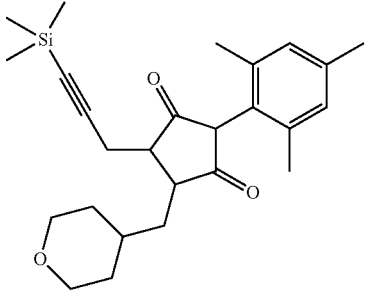 | LC-MS (Method A) ES⁺: MH⁺ = 425<br>rt = 1.83 min |
| T173 | 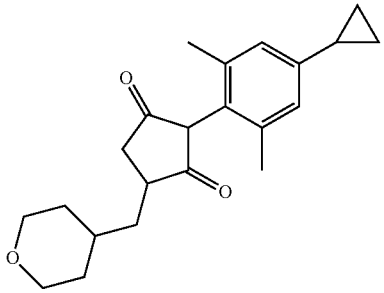 [SMILES: Cc1cc(C2CC2)cc(C)c1C1C(=O)CC(CC2CCOCC2)C1=O] | δ ppm 0.65 (m, 2H), 0.9 (m, 2H), 1.41 (m, 3H), 1.68 (m, 3H), 1.80 (m, 1H), 1.90 (m, 1H), 2.07 (s, 6H), 2.35 (br, 1H), 2.8 (br, 2H), 3.38 (m, 2H), 3.96 (m, 2H), 6.78 (s, 2H) |
| T174 | 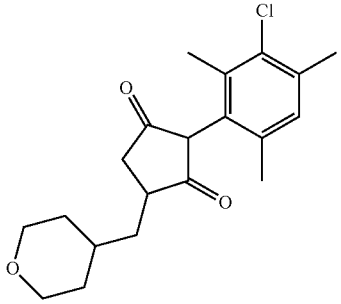 [SMILES: Cc1cc(C)c(C2C(=O)CC(CC3CCOCC3)C2=O)c(C)c1Cl] | LC-MS (Method A) ES⁺: MH⁺ = 349, 351<br>rt = 1.48 min |
| T175 | 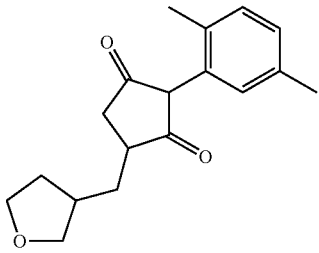 [SMILES: Cc1ccc(C)c(C2C(=O)CC(CC3CCOC3)C2=O)c1] | LC-MS (Method A) ES⁺: MH⁺ = 287<br>rt = 1.24 min |
| T176 | 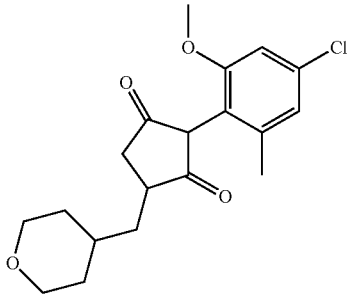 [SMILES: COc1cc(Cl)cc(C)c1C1C(=O)CC(CC2CCOCC2)C1=O] | LC-MS (Method A) ES⁺: MH⁺ = 351, 353<br>rt = 1.35 min |

TABLE T1-continued

| Compound Number | Structure | $^1$H nmr (CDCl$_3$ unless stated), LC/MS or other physical data |
|---|---|---|
| T177 | 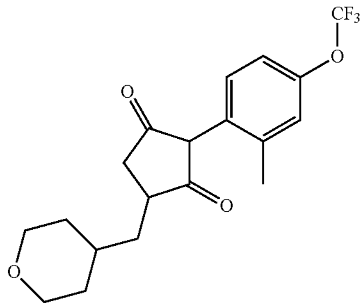 [SMILES: Cc1cc(OC(F)(F)F)ccc1C1C(=O)CC(CC2CCOCC2)C1=O] | LC-MS (Method A) ES$^+$: MH$^+$ = 371. rt = 1.51 min |
| T178 | 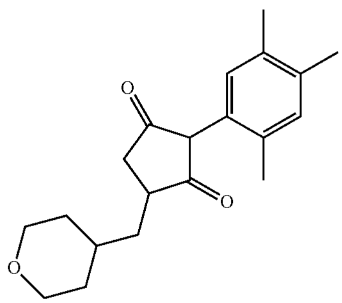 [SMILES: Cc1cc(C)c(C2C(=O)CC(CC3CCOCC3)C2=O)cc1C] | LC-MS (Method A) ES$^+$: MH$^+$ = 315. rt = 1.31 min |

TABLE P1

| Compound Number | Structure | $^1$H nmr (CDCl$_3$ unless stated), or other physical data |
|---|---|---|
| P1 | 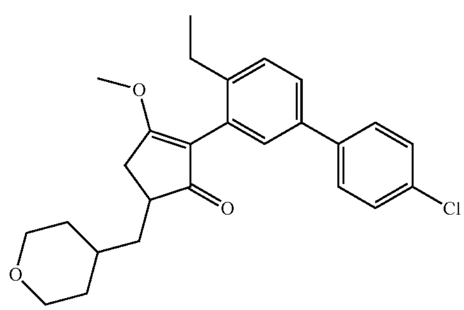 [SMILES: CCc1ccc(-c2ccc(Cl)cc2)cc1C1=C(OC)CC(CC2CCOCC2)C1=O] | δ ppm 1.21 (t, 3H), 1.32-1.47 (m, 3H), 1.61-1.70 (m, 2H), 1.72-1.82 (m, 1H), 1.91-2.02 (m, 1H), 2.42-2.58 (m, 3H), 2.65-2.77 (m, 1H), 3.00 (dd, 1H), 3.35-3.45 (m, 2H), 3.84 (s, 3H), 3.95-4.04 (m, 2H), 7.24 (d, 1H), 7.38-7.41 (m, 2H), 7.42 (d, 1H), 7.45-7.49 (m, 2H). 7.55 (dd, 1H) |
| P2 | 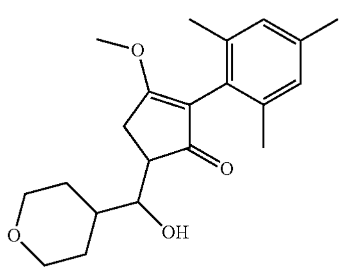 [SMILES: COC1=C(c2c(C)cc(C)cc2C)C(=O)C(C(O)C2CCOCC2)C1] | δ ppm 1.53 (d, 2H), 1.70-1.79 (m, 2H), 1.85 (td, 1H), 2.09 (d, 6H), 2.26 (s, 3H), 2.50 (dd, 1H), 2.73-2.81 (m, 1H), 2.83-2.94 (m, 1H), 3.33-3.48 (m, 2H), 3.61 (d, 1H), 3.74 (s, 3H), 4.01-4.10 (m, 2H), 4.58 (s, 1H), 6.87 (s, 2H) |

TABLE P1-continued

| Compound Number | Structure | ¹H nmr (CDCl₃ unless stated), or other physical data |
|---|---|---|
| P3 | 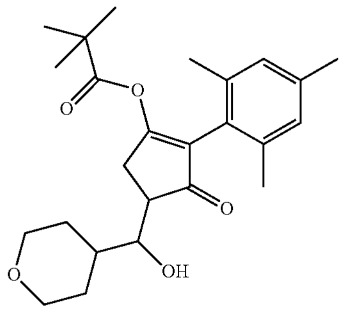 [SMILES: Cc1cc(C)c(C2=C(OC(=O)C(C)(C)C)CC(C(O)C3CCOCC3)C2=O)c(C)c1] | δ ppm 1.11 (s, 9H), 1.53 (d, 2H), 1.69-1.91 (m, 3H), 2.06 (d, 6H), 2.26 (s, 3H), 2.78-2.86 (m, 3H), 2.89 (ddd, 1H), 3.13 (dd, 1H), 3.33-3.47 (m, 2H), 3.69 (d, 1H), 4.05 (td, 2H), 4.13 (s, 3H), 6.85 (s, 2H) |
| P4 | 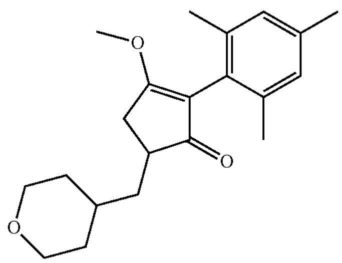 | δ ppm 1.28-1.46 (m, 3H), 1.61-1.70 (m, 2H), 1.70-1.79 (m, 1H), 1.94 (ddd, 1H), 2.08 (d, 6H), 2.26 (s, 3H), 2.44 (dd, 1H), 2.66-2.77 (m, 1H), 2.97 (dd, 1H), 3.35-3.48 (m, 2H), 3.73 (s, 3H), 3.95-4.05 (m, 2H), 6.87 (s, 2H) |
| P5 | 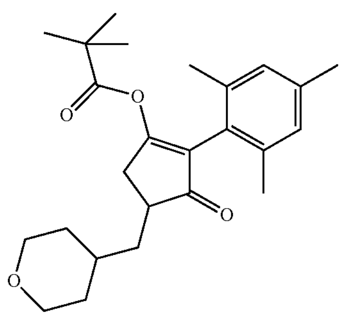 [SMILES: Cc1cc(C)c(C2=C(OC(=O)C(C)(C)C)CC(CC3CCOCC3)C2=O)c(C)c1] | δ ppm 1.09 (s, 9H), 1.28-1.46 (m, 3H), 1.59-1.69 (m, 2H), 1.70-1.77 (m, 1H), 1.94 (ddd, 1H), 2.05 (d, 6H), 2.25 (s, 3H), 2.70 (dd, 1H), 2.76-2.86 (m, 1H), 3.16 (dd, 1H), 3.33-3.45 (m, 2H), 3.91-4.07 (m, 2H), 6.84 (s, 2H) |
| P6 | 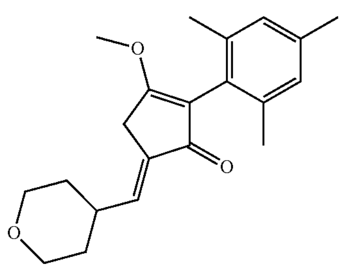 [SMILES: COC1=C(c2c(C)cc(C)cc2C)C(=O)/C(=C/C2CCOCC2)C1] | δ ppm 1.58-1.68 (m, 4H), 2.12 (s, 6H), 2.27 (s, 3H), 2.37-2.54 (m, 1H), 3.09 (d, 2H), 3.49 (td, 2H), 3.55 (s, 3H), 3.96-4.07 (m, 2H), 5.92 (d, 1H), 6.88 (s, 2H) |
| P7 | 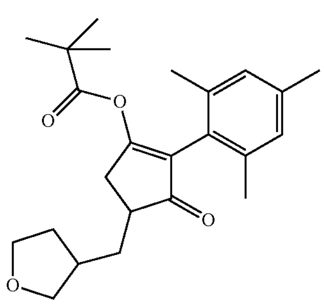 [SMILES: Cc1cc(C)c(C2=C(OC(=O)C(C)(C)C)CC(CC3CCOC3)C2=O)c(C)c1] | δ ppm 1.09 (s, 9H), 1.58-1.66 (m, 2H), 2.05 (d, 6H), 2.07-2.15 (m, 2H), 2.25 (s, 3H), 2.35-2.45 (m, 1H), 2.64-2.79 (m, 2H), 3.17 (dd, 1H), 3.40 (dt, 1H), 3.79 (ddd, 1H), 3.89 (ddd, 1H), 3.97 (t, 1H), 6.84 (s, 2H) |

TABLE P1-continued

| Compound Number | Structure | ¹H nmr (CDCl₃ unless stated), or other physical data |
|---|---|---|
| P8 | 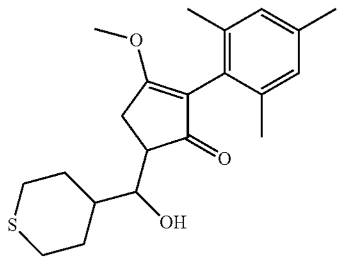 [SMILES: COC1=C(c2c(C)cc(C)cc2C)C(=O)C(C(O)C2CCSCC2)C1] | δ ppm 1.44-1.52 (m, 1H), 1.79 (ddd, 1H), 1.88-1.95 (m, 1H), 1.96-2.03 (m, 2H), 2.08 (d, 6H), 2.26 (s, 3H), 2.44 (dd, 1H), 2.66-2.74 (m, 4H), 2.75-2.81 (m, 1H), 2.82-2.92 (m, 1H), 3.59 (dd, 1H), 3.74 (s, 3H), 4.75 (s, 1H), 6.87 (s, 2H) |
| P9 | 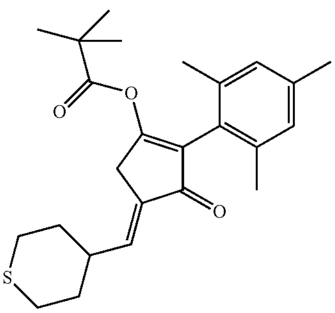 [SMILES: Cc1cc(C)c(C2=C(OC(=O)C(C)(C)C)C/C(=C\C3CCSCC3)C2=O)c(C)c1] | δ ppm 1.11 (s, 9H), 1.70 (ddd, 2H), 1.97-2.06 (m, 2H), 2.07 (s, 6H), 2.26 (s, 3H), 2.28-2.40 (m, 1H), 2.62-2.80 (m, 4H), 3.59 (d, 2H), 6.57 (d, 1H), 6.85 (s, 2H) |
| P10 | 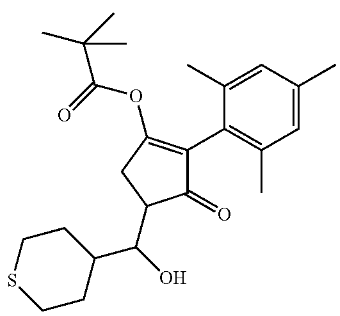 [SMILES: Cc1cc(C)c(C2=C(OC(=O)C(C)(C)C)CC(C(O)C3CCSCC3)C2=O)c(C)c1] | δ ppm 1.11 (s, 9H), 1.48-1.53 (m, 1H), 1.74-1.84 (m, 1H), 1.88-1.95 (m, 1H), 1.96-2.02 (m, 2H), 2.05 (d, 6H), 2.26 (s, 3H), 2.63-2.73 (m, 4H), 2.74-2.82 (m, 1H), 2.90 (ddd, 1H), 3.10 (dd, 1H), 3.67 (dd, 1H), 4.32 (s, 1H), 6.85 (s, 2H) |
| P11 | 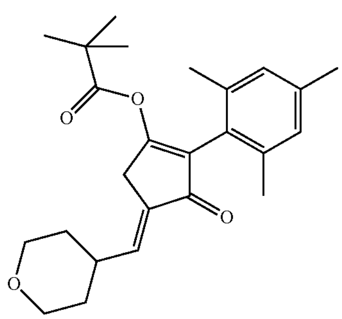 [SMILES: Cc1cc(C)c(C2=C(OC(=O)C(C)(C)C)C/C(=C\C3CCOCC3)C2=O)c(C)c1] | LC-MS (Method A) ES⁺: MH⁺ = 397 rt = 1.95 min |
| P12 | 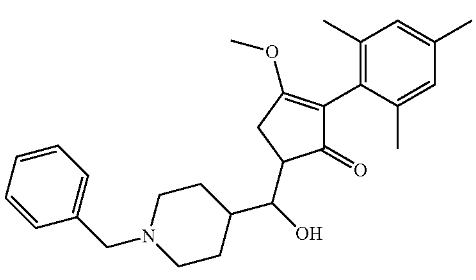 | LC-MS (Method A) ES⁺: MH⁺ = 315 rt = 1.37 min |

TABLE P1-continued
| Compound Number | Structure | $^1$H nmr (CDCl$_3$ unless stated), or other physical data |
|---|---|---|
| P13 | 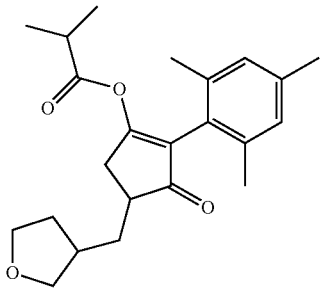 [SMILES: Cc1cc(C)c(C2=C(OC(=O)C(C)C)CC(CC3CCOC3)C2=O)c(C)c1] | LC-MS (Method A) ES$^+$: MH$^+$ = 371<br>rt = 1.83 min |
| P14 | 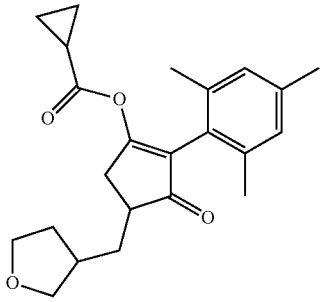 [SMILES: Cc1cc(C)c(C2=C(OC(=O)C3CC3)CC(CC3CCOC3)C2=O)c(C)c1] | LC-MS (Method A) ES$^+$: MH$^+$ = 369<br>rt = 1.73 min |
| P15 | 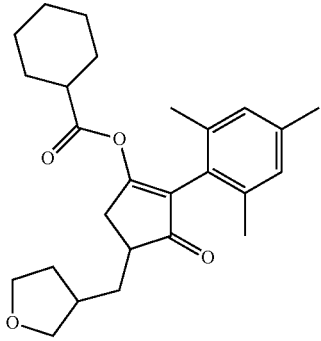 [SMILES: Cc1cc(C)c(C2=C(OC(=O)C3CCCCC3)CC(CC3CCOC3)C2=O)c(C)c1] | LC-MS (Method A) ES$^+$: MH$^+$ = 411<br>rt = 1.95 min |
| P16 | 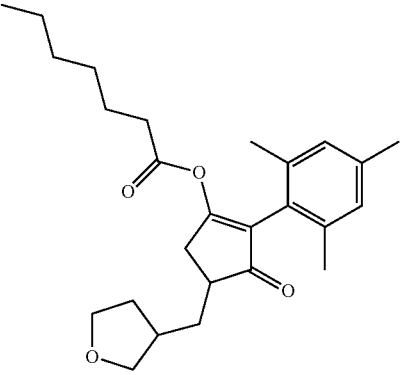 [SMILES: CCCCCCC(=O)OC1=C(c2c(C)cc(C)cc2C)C(=O)C(CC2CCOC2)C1] | LC-MS (Method A) ES$^+$: MH$^+$ = 413<br>rt = 2.00 min |

TABLE P1-continued

| Compound Number | Structure | $^1$H nmr (CDCl$_3$ unless stated), or other physical data |
|---|---|---|
| P17 | 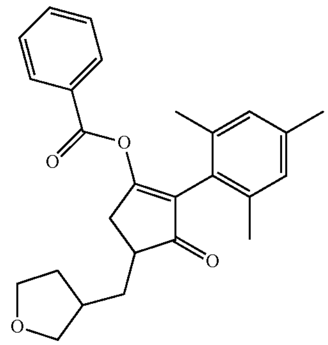 [SMILES: Cc1cc(C)c(C2=C(OC(=O)c3ccccc3)CC(CC3CCOC3)C2=O)c(C)c1] | LC-MS (Method A) ES$^+$: MH$^+$ = 405<br>rt = 1.81 min |
| P18 | 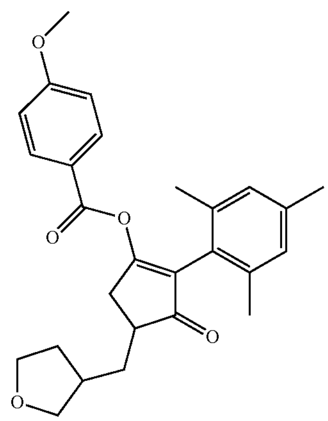 [SMILES: COc1ccc(C(=O)OC2=C(c3c(C)cc(C)cc3C)C(=O)C(CC3CCOC3)C2)cc1] | LC-MS (Method A) ES$^+$: MH$^+$ = 435<br>rt = 1.81 min |
| P19 | 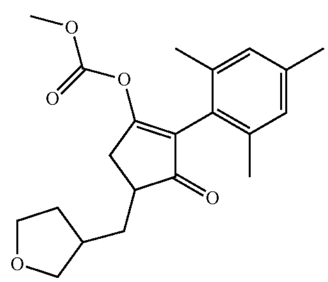 [SMILES: COC(=O)OC1=C(c2c(C)cc(C)cc2C)C(=O)C(CC2CCOC2)C1] | LC-MS (Method A) ES$^+$: MH$^+$ = 359<br>rt = 1.56 min |
| P20 | 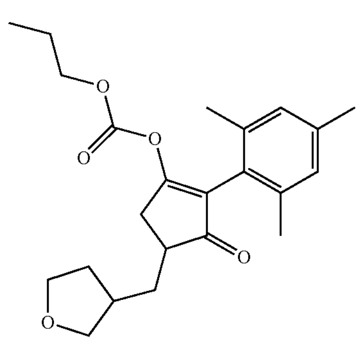 [SMILES: CCCOC(=O)OC1=C(c2c(C)cc(C)cc2C)C(=O)C(CC2CCOC2)C1] | LC-MS (Method A) ES$^+$: MH$^+$ = 387 |

TABLE P1-continued
| Compound Number | Structure | $^1$H nmr (CDCl$_3$ unless stated), or other physical data |
|---|---|---|
| P21 | 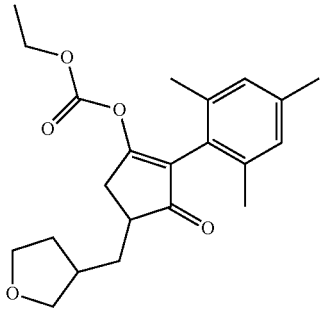 [SMILES: CCOC(=O)OC1=C(c2c(C)cc(C)cc2C)C(=O)C(CC2CCOC2)C1] | LC-MS (Method A) ES$^+$: MH$^+$ = 373 |
| P22 | 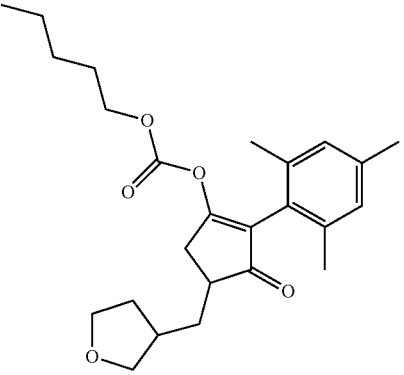 [SMILES: CCCCCOC(=O)OC1=C(c2c(C)cc(C)cc2C)C(=O)C(CC2CCOC2)C1] | LC-MS (Method A) ES$^+$: MH$^+$ = 415 |
| P23 | 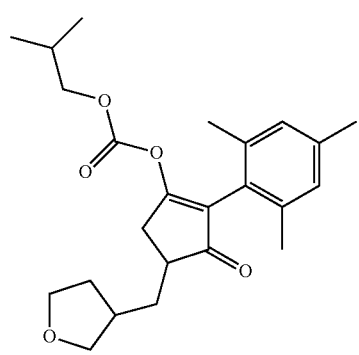 [SMILES: Cc1cc(C)c(C2=C(OC(=O)OCC(C)C)CC(CC3CCOC3)C2=O)c(C)c1] | LC-MS (Method A) ES$^+$: MH$^+$ = 401 |
| P24 | 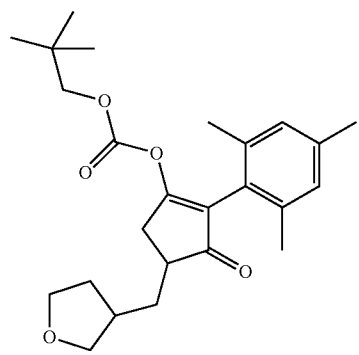 [SMILES: Cc1cc(C)c(C2=C(OC(=O)OCC(C)(C)C)CC(CC3CCOC3)C2=O)c(C)c1] | LC-MS (Method A) ES$^+$: MH$^+$ = 415 |

TABLE P1-continued

| Compound Number | Structure | ¹H nmr (CDCl₃ unless stated), or other physical data |
|---|---|---|
| P25 | 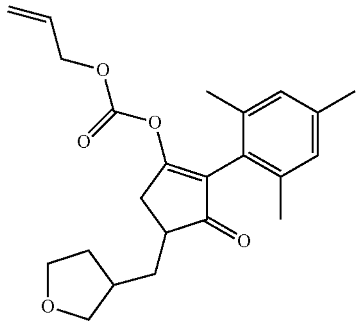 [SMILES: C=CCOC(=O)OC1=C(c2c(C)cc(C)cc2C)C(=O)C(CC2CCOC2)C1] | LC-MS (Method A) ES⁺: MH⁺ = 385 |
| P26 | 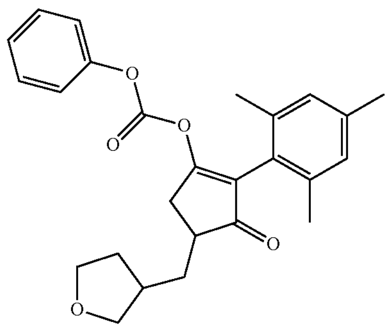 [SMILES: Cc1cc(C)c(C2=C(OC(=O)Oc3ccccc3)CC(CC3CCOC3)C2=O)c(C)c1] | LC-MS (Method A) ES⁺: MH⁺ = 421 rt = 1.83 min |
| P27 | 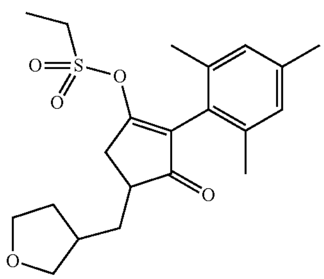 [SMILES: CCS(=O)(=O)OC1=C(c2c(C)cc(C)cc2C)C(=O)C(CC2CCOC2)C1] | LC-MS (Method A) ES⁺: MH⁺ = 393 rt = 1.64 min |
| P28 | 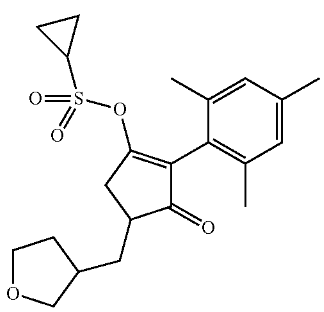 [SMILES: Cc1cc(C)c(C2=C(OS(=O)(=O)C3CC3)CC(CC3CCOC3)C2=O)c(C)c1] | LC-MS (Method A) ES⁺: MH⁺ = 405 rt = 1.66 min |
| P29 | 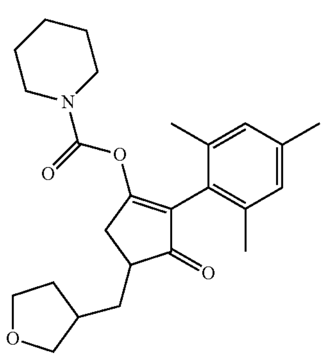 [SMILES: Cc1cc(C)c(C2=C(OC(=O)N3CCCCC3)CC(CC3CCOC3)C2=O)c(C)c1] | LC-MS (Method A) ES⁺: MH⁺ = 412 rt = 1.73 min |

TABLE P1-continued

| Compound Number | Structure | ¹H nmr (CDCl₃ unless stated), or other physical data |
|---|---|---|
| P30 | 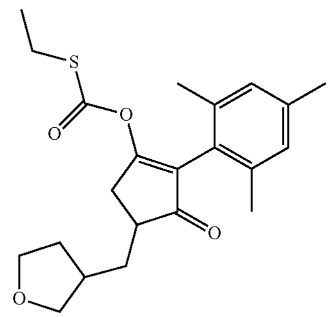 [SMILES: CCSC(=O)OC1=C(c2c(C)cc(C)cc2C)C(=O)C(CC2CCOC2)C1] | LC-MS (Method A) ES⁺: MH⁺ = 389<br>rt = 1.83 min |
| P31 | 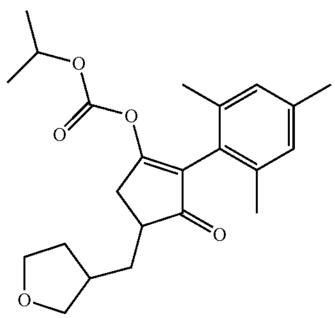 [SMILES: Cc1cc(C)c(C2=C(OC(=O)OC(C)C)CC(CC3CCOC3)C2=O)c(C)c1] | LC-MS (Method A) ES⁺: MH⁺ = 387<br>rt = 1.78 min |
| P32 | 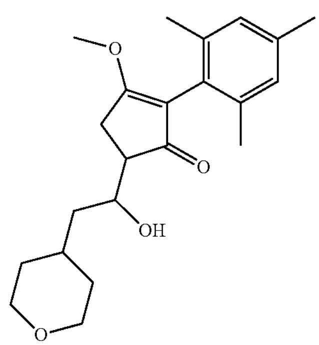 [SMILES: COC1=C(c2c(C)cc(C)cc2C)C(=O)C(C(O)CC2CCOCC2)C1] | LC-MS (Method B) ES⁺: MH⁺ = 359<br>rt = 1.26 min |
| P33 | 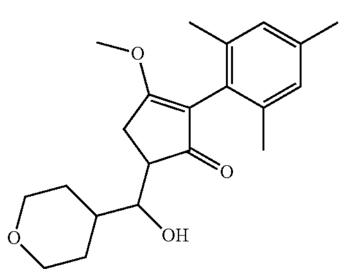 [SMILES: COC1=C(c2c(C)cc(C)cc2C)C(=O)C(C(O)C2CCOCC2)C1] | LC-MS (Method A) ES⁺: MH⁺ = 345 |

TABLE P1-continued

| Compound Number | Structure | ¹H nmr (CDCl₃ unless stated), or other physical data |
|---|---|---|
| P34 | 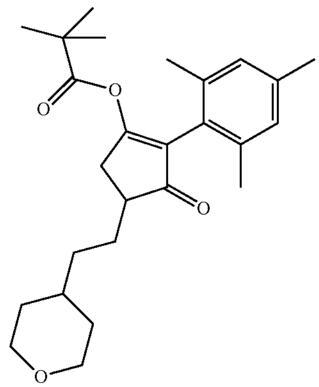 [SMILES: Cc1cc(C)c(C2=C(OC(=O)C(C)(C)C)CC(CCC3CCOCC3)C2=O)c(C)c1] | LC-MS (Method A) ES⁺: MH⁺ = 413<br>rt = 2.03 min |
| P35 | 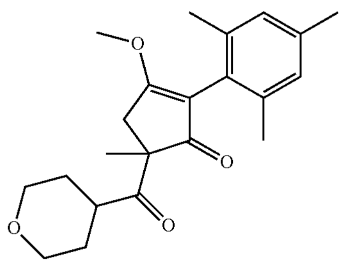 [SMILES: COC1=C(c2c(C)cc(C)cc2C)C(=O)C(C)(C(=O)C2CCOCC2)C1] | LC-MS (Method B) ES⁺: MH⁺ = 357<br>rt = 1.44 min |
| P36 | 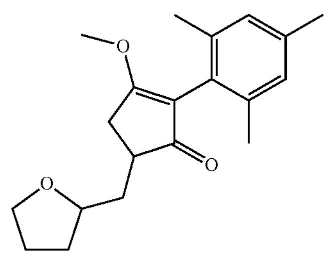 [SMILES: COC1=C(c2c(C)cc(C)cc2C)C(=O)C(CC2CCCO2)C1] | LC-MS (Method A) ES⁺: MH⁺ = 315 |
| P37 | 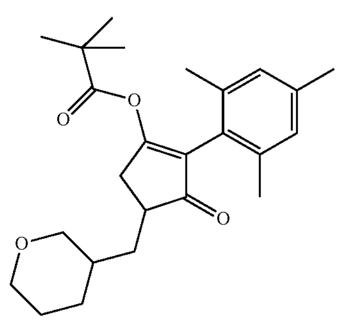 [SMILES: Cc1cc(C)c(C2=C(OC(=O)C(C)(C)C)CC(CC3CCCOC3)C2=O)c(C)c1] | LC-MS (Method A) ES+: M + H⁺ = 399<br>rt = 1.98 min |
| P38 | 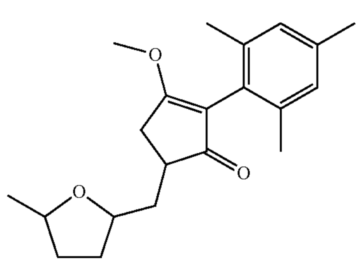 | LC-MS (Method A) ES⁺: MH⁺ = 329 |

TABLE P1-continued

| Compound Number | Structure | $^1$H nmr (CDCl$_3$ unless stated), or other physical data |
|---|---|---|
| P39 | 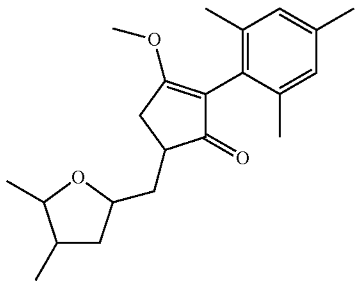 | LC-MS (Method A) ES$^+$: MH$^+$ = 342 |
| P40 | 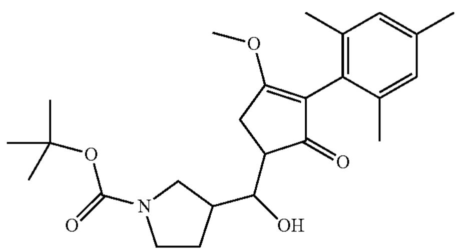 [SMILES: COC1=C(c2c(C)cc(C)cc2C)C(=O)C(C(O)C2CCN(C(=O)OC(C)(C)C)C2)C1] | LC-MS (Method A) ES$^+$: MH$^+$ = 430 |
| P41 | 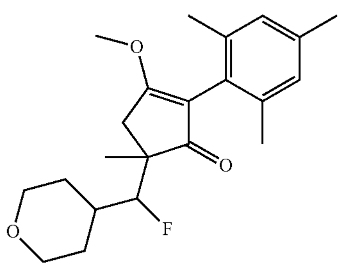 [SMILES: COC1=C(c2c(C)cc(C)cc2C)C(=O)C(C)(C(F)C2CCOCC2)C1] | LC-MS (Method A) ES$^+$: MH$^+$ = 361<br>rt = 1.54 min |
| P42 | 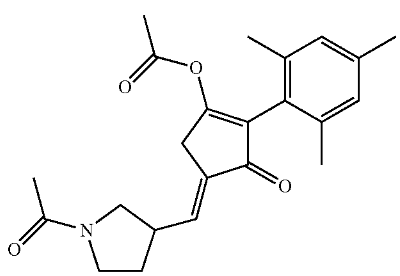 [SMILES: CC(=O)OC1=C(c2c(C)cc(C)cc2C)C(=O)/C(=C/C2CCN(C(C)=O)C2)C1] | LC-MS (Method A) ES$^+$: MH$^+$ = 382 |
| P43 | 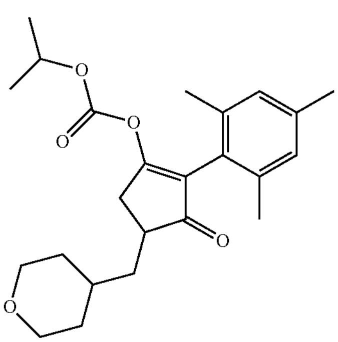 [SMILES: Cc1cc(C)c(C2=C(OC(=O)OC(C)C)CC(CC3CCOCC3)C2=O)c(C)c1] | LC-MS (Method A) ES$^+$: MH$^+$ = 401<br>rt = 1.77 min |

TABLE P1-continued

| Compound Number | Structure | ¹H nmr (CDCl₃ unless stated), or other physical data |
|---|---|---|
| P44 | 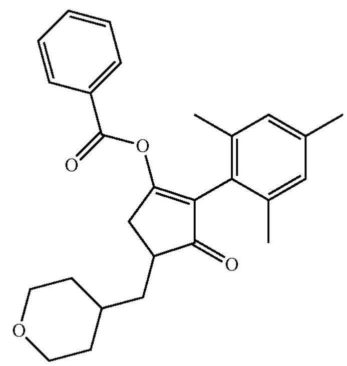 [SMILES: Cc1cc(C)c(C2=C(OC(=O)c3ccccc3)CC(CC3CCOCC3)C2=O)c(C)c1] | LC-MS (Method B) ES⁺: MH⁺ = 419<br>rt = 1.84 min |
| P45 | 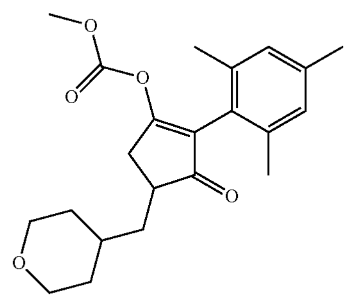 [SMILES: COC(=O)OC1=C(c2c(C)cc(C)cc2C)C(=O)C(CC2CCOCC2)C1] | LC-MS (Method A) ES⁺: MH⁺ = 373<br>rt = 1.64 min |
| P46 | 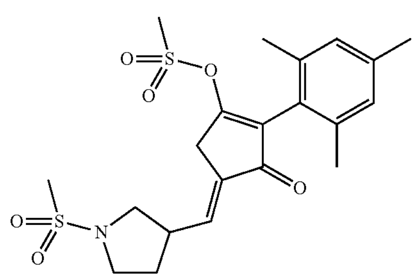 [SMILES: Cc1cc(C)c(C2=C(OS(C)(=O)=O)C/C(=C\C3CCN(S(C)(=O)=O)C3)C2=O)c(C)c1] | LC-MS (Method A) ES⁺: MH⁺ = 454<br>rt = 1.51 min |
| P47 | 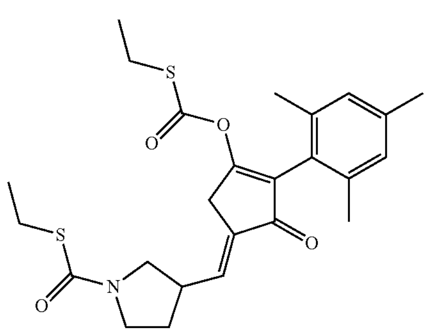 [SMILES: CCSC(=O)OC1=C(c2c(C)cc(C)cc2C)C(=O)/C(=C/C2CCN(C(=O)SCC)C2)C1] | LC-MS (Method A) ES⁺: MH⁺ = 474<br>rt = 1.91 min |

TABLE P1-continued

| Compound Number | Structure | $^1$H nmr (CDCl$_3$ unless stated), or other physical data |
|---|---|---|
| P48 | 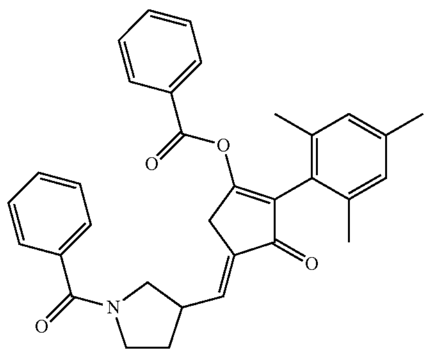 [SMILES: Cc1cc(C)c(C2=C(OC(=O)c3ccccc3)C/C(=C\C3CCN(C(=O)c4ccccc4)C3)C2=O)c(C)c1] | LC-MS (Method A) ES$^+$: MH$^+$ = 506<br>rt = 1.85 min |
| P49 | 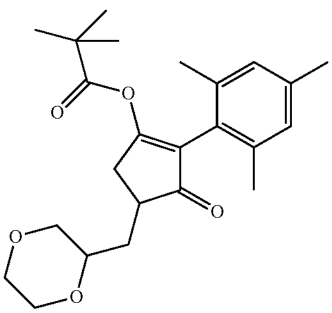 | LC-MS (Method A) ES$^+$: MH$^+$ = 401<br>rt = 1.81 min |
| P50 | 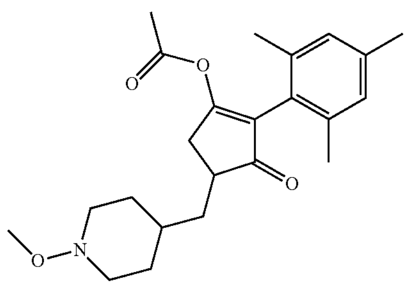 | LC-MS (Method A) ES$^+$: MH$^+$ = 386<br>rt = 1.53 min |
| P51 | 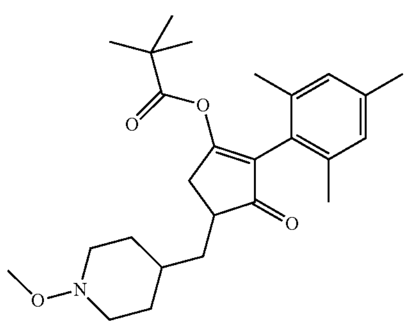 | LC-MS (Method A) ES$^+$: MH$^+$ = 428<br>rt = 1.88 min |
| P52 | 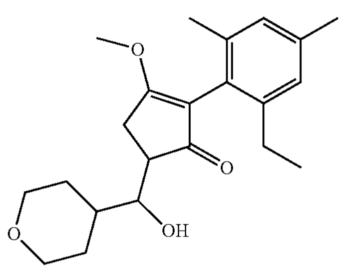 [SMILES: CCc1cc(C)cc(C)c1C1=C(OC)CC(C(O)C2CCOCC2)C1=O] | LC-MS (Method A) ES$^+$: MH$^+$ = 359<br>rt = 1.46 min |

TABLE P1-continued

| Compound Number | Structure | $^{1}$H nmr (CDCl$_3$ unless stated), or other physical data |
|---|---|---|
| P53 | 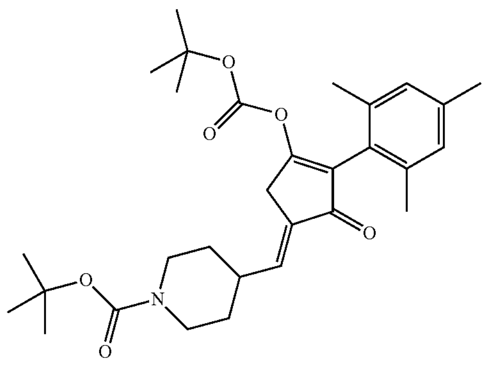 [SMILES: Cc1cc(C)c(C2=C(OC(=O)OC(C)(C)C)C/C(=C\C3CCN(C(=O)OC(C)(C)C)CC3)C2=O)c(C)c1] | LC-MS (Method A) ES$^+$: MH$^+$ = 512<br>rt = 2.03 min |
| P54 | 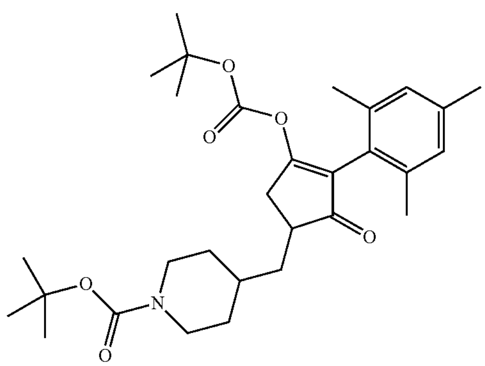 [SMILES: Cc1cc(C)c(C2=C(OC(=O)OC(C)(C)C)CC(CC3CCN(C(=O)OC(C)(C)C)CC3)C2=O)c(C)c1] | LC-MS (Method A) ES$^+$: MH$^+$ = 514<br>rt = 2.03 min |
| P55 | 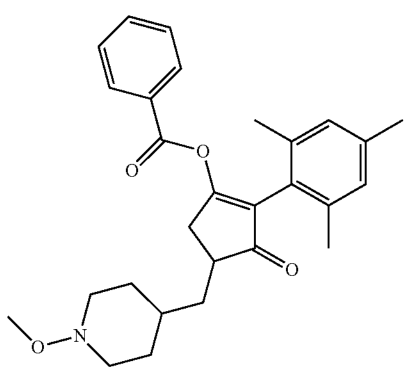 | LC-MS (Method A) ES$^+$: MH$^+$ = 448<br>rt = 1.78 min |
| P56 | 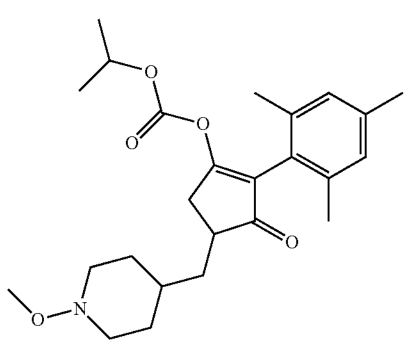 | LC-MS (Method A) ES$^+$: MH$^+$ = 430<br>rt = 1.64 min |

TABLE P1-continued
| Compound Number | Structure | 1H nmr (CDCl3 unless stated), or other physical data |
|---|---|---|
| P57 | 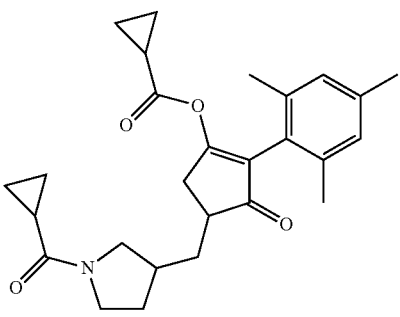 [SMILES: Cc1cc(C)c(C2=C(OC(=O)C3CC3)CC(CC3CCN(C(=O)C4CC4)C3)C2=O)c(C)c1] | LC-MS (Method A) ES+: MH+ = 436<br>rt = 1.56 mins |
| P58 | 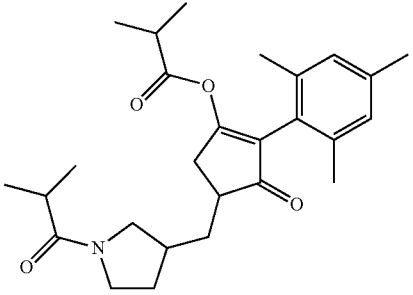 [SMILES: Cc1cc(C)c(C2=C(OC(=O)C(C)C)CC(CC3CCN(C(=O)C(C)C)C3)C2=O)c(C)c1] | LC-MS (Method A) ES+: MH+ = 440<br>rt = 1.71 mins |
| P59 | 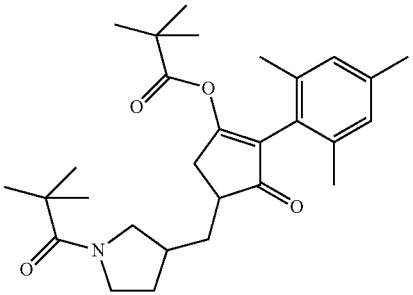 [SMILES: Cc1cc(C)c(C2=C(OC(=O)C(C)(C)C)CC(CC3CCN(C(=O)C(C)(C)C)C3)C2=O)c(C)c1] | LC-MS (Method A) ES+: MH+ = 468<br>rt = 1.85 mins |
| P60 | 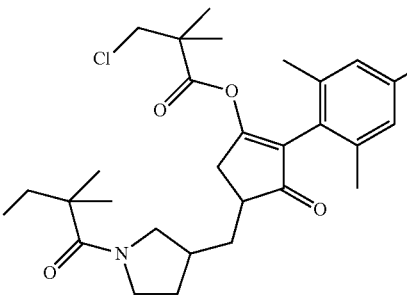 | LC-MS (Method A) ES+: MH+ = 540, 538, 536<br>rt = 1.85 mins |
| P61 | 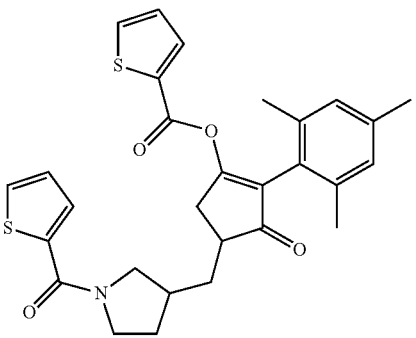 [SMILES: Cc1cc(C)c(C2=C(OC(=O)c3cccs3)CC(CC3CCN(C(=O)c4cccs4)C3)C2=O)c(C)c1] | LC-MS (Method A) ES+: MH+ = 520<br>rt = 1.76 mins |

TABLE P1-continued

| Compound Number | Structure | ¹H nmr (CDCl₃ unless stated), or other physical data |
|---|---|---|
| P62 | 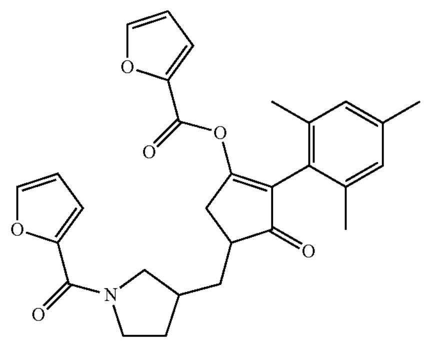 [SMILES: Cc1cc(C)c(C2=C(OC(=O)c3ccco3)CC(CC3CCN(C(=O)c4ccco4)C3)C2=O)c(C)c1] | LC-MS (Method A) ES⁺: MH⁺ = 488<br>rt = 1.63 mins |
| P63 | 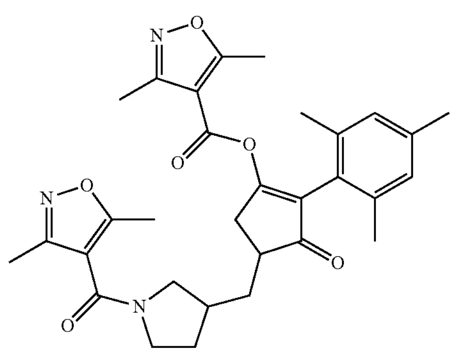 | LC-MS (Method A) ES⁺: MH⁺ = 546<br>rt = 1.66 mins |
| P64 | 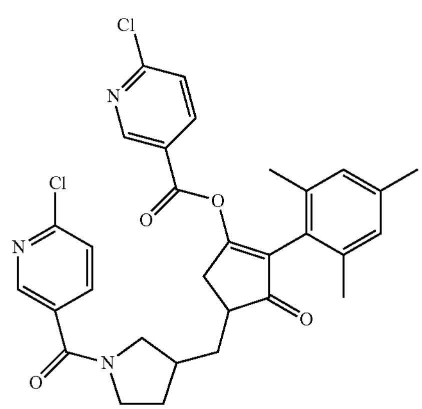 [SMILES: Cc1cc(C)c(C2=C(OC(=O)c3ccc(Cl)nc3)CC(CC3CCN(C(=O)c4ccc(Cl)nc4)C3)C2=O)c(C)c1] | LC-MS (Method A) ES⁺: MH⁺ = 582, 580, 578<br>rt = 1.86 mins |
| P65 | 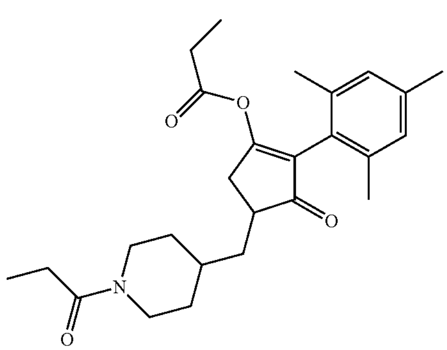 [SMILES: CCC(=O)OC1=C(c2c(C)cc(C)cc2C)C(=O)C(CC2CCN(C(=O)CC)CC2)C1] | LC-MS (Method A) ES⁺: MH⁺ = 426<br>rt = 1.78 mins |

TABLE P1-continued

| Compound Number | Structure | ¹H nmr (CDCl₃ unless stated), or other physical data |
|---|---|---|
| P66 | 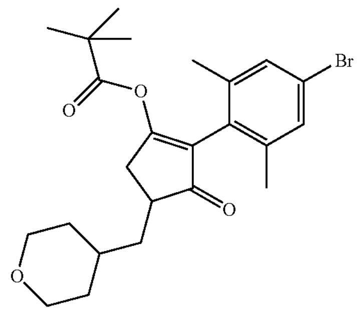 [SMILES: Cc1cc(Br)cc(C)c1C1=C(OC(=O)C(C)(C)C)CC(CC2CCOCC2)C1=O] | Melting point: 82-84° C. |
| P67 | 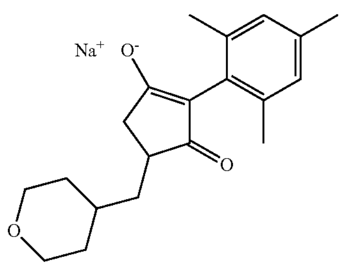 [SMILES: Cc1cc(C)c(C2=C([O-])CC(CC3CCOCC3)C2=O)c(C)c1 ; [Na+]] | δ ppm (D₂O) 1.20-1.40 (m, 3H), 1.60-1.85 (m, 4H), 2.01 (s, 6H), 2.15-2.25 (m, 4H), 2.60-2.70 (m, 2H), 3.40-3.55 (m, 2H), 3.90-4.05 (m, 2H), 6.91 (s, 2H) |
| P68 | 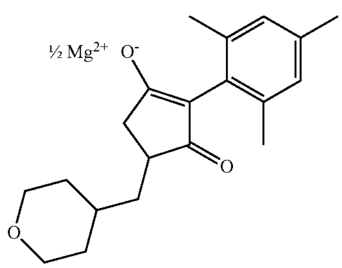 | δ ppm (D₂O) 1.20-1.40 (m, 3H), 1.60-1.85 (m, 4H), 2.01 (s, 6H), 2.15-2.25 (m, 4H), 2.60-2.70 (m, 2H), 3.40-3.55 (m, 2H), 3.90-4.05 (m, 2H), 6.91 (s, 2H) |
| P69 | 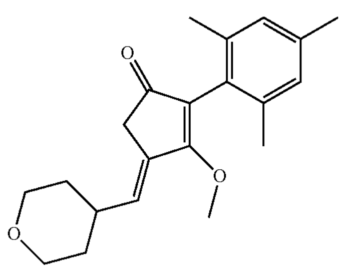 [SMILES: COC1=C(c2c(C)cc(C)cc2C)C(=O)C/C1=C\C1CCOCC1] | LC-MS (Method A) ES⁺: MH⁺ = 327 rt = 1.54 mins |
| P70 | 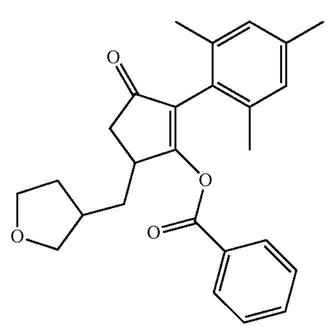 [SMILES: Cc1cc(C)c(C2=C(OC(=O)c3ccccc3)C(CC3CCOC3)CC2=O)c(C)c1] | LC-MS (Method A) ES⁺: MH⁺ = 405 rt = 1.75 mins |

TABLE P1-continued

| Compound Number | Structure | $^1$H nmr (CDCl$_3$ unless stated), or other physical data |
|---|---|---|
| P71 | 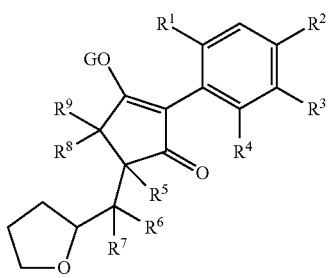 | LC-MS (Method A) ES$^+$: MH$^+$ = 435 rt = 1.81 mins |

The compounds of the following Tables 1 to 102 can be obtained in an analogous manner.

TABLE 1 covers 262 compounds of the following type:

where G, R$^5$, R$^6$, R$^7$, R$^8$ and R$^9$ are all hydrogen, and R$^1$, R$^2$, R$^3$ and R$^4$ are as described in Table 1 below:

| Compound Number | R$^1$ | R$^2$ | R$^3$ | R$^4$ |
|---|---|---|---|---|
| 1.001 | CH$_3$ | H | H | H |
| 1.002 | CH$_3$ | CH$_3$ | H | H |
| 1.003 | CH$_3$ | H | CH$_3$ | H |
| 1.004 | CH$_3$ | H | H | CH$_3$ |
| 1.005 | CH$_3$ | CH$_3$ | CH$_3$ | H |
| 1.006 | CH$_3$ | CH$_3$ | H | CH$_3$ |
| 1.007 | CH$_3$ | CH$_3$ | CH$_3$ | CH$_3$ |
| 1.008 | CH$_3$ | Cl | H | H |
| 1.009 | CH$_3$ | Cl | H | CH$_3$ |
| 1.010 | CH$_3$ | Cl | H | OCH$_3$ |
| 1.011 | CH$_3$ | H | Cl | H |
| 1.012 | CH$_3$ | H | H | Cl |
| 1.013 | CH$_3$ | CH$_3$ | Cl | H |
| 1.014 | CH$_3$ | CH$_3$ | H | Cl |
| 1.015 | CH$_3$ | H | Cl | CH$_3$ |
| 1.016 | CH$_3$ | CH$_3$ | Cl | CH$_3$ |
| 1.017 | CH$_3$ | Br | H | H |
| 1.018 | CH$_3$ | Br | H | CH$_3$ |
| 1.019 | CH$_3$ | Br | H | OCH$_3$ |
| 1.020 | CH$_3$ | H | Br | H |
| 1.021 | CH$_3$ | H | H | Br |
| 1.022 | CH$_3$ | CH$_3$ | Br | H |
| 1.023 | CH$_3$ | CH$_3$ | H | Br |
| 1.024 | CH$_3$ | H | Br | CH$_3$ |
| 1.025 | CH$_3$ | CH$_3$ | Br | CH$_3$ |
| 1.026 | CH$_3$ | CH$_3$O | H | H |
| 1.027 | CH$_3$ | CH$_3$O | H | CH$_3$ |
| 1.028 | CH$_3$ | CH$_3$O | H | Cl |
| 1.029 | CH$_3$ | CH$_3$O | H | Br |
| 1.030 | CH$_3$ | CH$_3$CH$_2$O | H | H |

TABLE 1-continued covers 262 compounds of the following type:

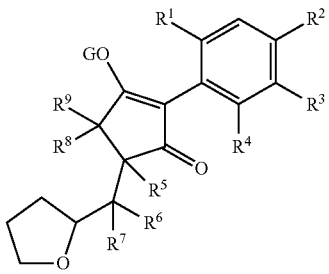

where G, $R^5$, $R^6$, $R^7$, $R^8$ and $R^9$ are all hydrogen, and $R^1$, $R^2$, $R^3$ and $R^4$ are as described in Table 1 below:

| Compound Number | $R^1$ | $R^2$ | $R^3$ | $R^4$ |
| --- | --- | --- | --- | --- |
| 1.031 | $CH_3$ | $CH_3CH_2O$ | H | $CH_3$ |
| 1.032 | $CH_3$ | $CH_3CH_2O$ | H | Cl |
| 1.033 | $CH_3$ | $CH_3CH_2O$ | H | Br |
| 1.034 | $CH_3$ | H | $CH_3O$ | H |
| 1.035 | $CH_3$ | H | H | $CH_3O$ |
| 1.036 | $CH_3$ | $CH_3$ | $CH_3O$ | H |
| 1.037 | $CH_3$ | $CH_3$ | H | $CH_3O$ |
| 1.038 | $CH_3$ | H | $CH_3O$ | $CH_3$ |
| 1.039 | $CH_3$ | $CH_3$ | $CH_3O$ | $CH_3$ |
| 1.040 | $CH_3$ | —CH=$CH_2$ | H | $CH_3$ |
| 1.041 | $CH_3$ | $CH_3$ | H | —CH=$CH_2$ |
| 1.042 | $CH_3$ | —C•CH | H | $CH_3$ |
| 1.043 | $CH_3$ | $CH_3$ | H | —C•CH |
| 1.044 | $CH_3$ | —CH=$CH_2$ | H | —CH=$CH_2$ |
| 1.045 | $CH_3$ | $CH_2CH_3$ | H | $CH_3$ |
| 1.046 | $CH_3$ | phenyl | H | $CH_3$ |
| 1.047 | $CH_3$ | 2-fluorophenyl | H | $CH_3$ |
| 1.048 | $CH_3$ | 2-chlorophenyl | H | $CH_3$ |
| 1.049 | $CH_3$ | 2-trifluoromethylphenyl | H | $CH_3$ |
| 1.050 | $CH_3$ | 2-nitrophenyl | H | $CH_3$ |
| 1.051 | $CH_3$ | 2-nnethylphenyl | H | $CH_3$ |
| 1.052 | $CH_3$ | 2-nnethanesulfonylphenyl | H | $CH_3$ |
| 1.053 | $CH_3$ | 2-cyanophenyl | H | $CH_3$ |
| 1.054 | $CH_3$ | 3-fluorophenyl | H | $CH_3$ |
| 1.055 | $CH_3$ | 3-chlorophenyl | H | $CH_3$ |
| 1.056 | $CH_3$ | 3-trifluoronnethylphenyl | H | $CH_3$ |
| 1.057 | $CH_3$ | 3-nitrophenyl | H | $CH_3$ |
| 1.058 | $CH_3$ | 3-methylphenyl | H | $CH_3$ |
| 1.059 | $CH_3$ | 3-methanesulfonylphenyl | H | $CH_3$ |
| 1.060 | $CH_3$ | 3-cyanophenyl | H | $CH_3$ |
| 1.061 | $CH_3$ | 4-fluorophenyl | H | $CH_3$ |
| 1.062 | $CH_3$ | 4-chlorophenyl | H | $CH_3$ |
| 1.063 | $CH_3$ | 4-bromophenyl | H | $CH_3$ |
| 1.064 | $CH_3$ | 4-difluoromethoxyphenyl | H | $CH_3$ |
| 1.065 | $CH_3$ | 2-fluoro-4-chlorophenyl | H | $CH_3$ |
| 1.066 | $CH_3$ | 2-chloro-4-chlorophenyl | H | $CH_3$ |
| 1.067 | $CH_3$ | 2-methyl-4-chlorophenyl | H | $CH_3$ |
| 1.068 | $CH_3$ | 4-trifluoromethylphenyl | H | $CH_3$ |
| 1.069 | $CH_3$ | 4-nitrophenyl | H | $CH_3$ |
| 1.070 | $CH_3$ | 4-methylphenyl | H | $CH_3$ |
| 1.071 | $CH_3$ | 4-methanesulfonylphenyl | H | $CH_3$ |
| 1.072 | $CH_3$ | 4-cyanophenyl | H | $CH_3$ |
| 1.073 | $CH_3$ | H | phenyl | H |
| 1.074 | $CH_3$ | H | 2-fluorophenyl | H |
| 1.075 | $CH_3$ | H | 2-chlorophenyl | H |
| 1.076 | $CH_3$ | H | 2-trifluoromethylphenyl | H |
| 1.077 | $CH_3$ | H | 2-nitrophenyl | H |
| 1.078 | $CH_3$ | H | 2-methylphenyl | H |
| 1.079 | $CH_3$ | H | 2-methylsulfonylphenyl | H |
| 1.080 | $CH_3$ | H | 2-cyanophenyl | H |
| 1.081 | $CH_3$ | H | 3-fluorophenyl | H |
| 1.082 | $CH_3$ | H | 3-chlorophenyl | H |
| 1.083 | $CH_3$ | H | 3-trifluoromethylphenyl | H |
| 1.084 | $CH_3$ | H | 3-nitrophenyl | H |
| 1.085 | $CH_3$ | H | 3-nnethylphenyl | H |
| 1.086 | $CH_3$ | H | 3-methylsulfonylphenyl | H |
| 1.087 | $CH_3$ | H | 3-cyanophenyl | H |
| 1.088 | $CH_3$ | H | 4-fluorophenyl | H |
| 1.089 | $CH_3$ | H | 4-chlorophenyl | H |

TABLE 1-continued covers 262 compounds of the following type:

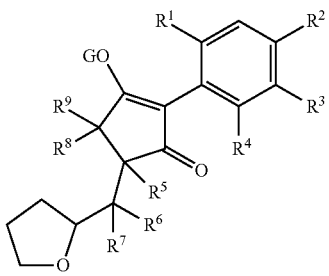

where G, $R^5$, $R^6$, $R^7$, $R^8$ and $R^9$ are all hydrogen, and $R^1$, $R^2$, $R^3$ and $R^4$ are as described in Table 1 below:

| Compound Number | $R^1$ | $R^2$ | $R^3$ | $R^4$ |
|---|---|---|---|---|
| 1.090 | $CH_3$ | H | 4-bromophenyl | H |
| 1.091 | $CH_3$ | H | 4-difluoromethoxyphenyl | H |
| 1.092 | $CH_3$ | H | 2-fluoro-4-chlorophenyl | H |
| 1.093 | $CH_3$ | H | 2-chloro-4-chlorophenyl | H |
| 1.094 | $CH_3$ | H | 2-methyl-4-chlorophenyl | H |
| 1.095 | $CH_3$ | H | 4-trifluoromethylphenyl | H |
| 1.096 | $CH_3$ | H | 4-nitrophenyl | H |
| 1.097 | $CH_3$ | H | 4-methylphenyl | H |
| 1.098 | $CH_3$ | H | 4-methylsulfonylphenyl | H |
| 1.099 | $CH_3$ | H | 4-cyanophenyl | H |
| 1.100 | $CH_2CH_3$ | H | H | H |
| 1.101 | $CH_2CH_3$ | $CH_3$ | H | H |
| 1.102 | $CH_2CH_3$ | H | $CH_3$ | H |
| 1.103 | $CH_2CH_3$ | H | H | $CH_3$ |
| 1.104 | $CH_2CH_3$ | $CH_3$ | $CH_3$ | H |
| 1.105 | $CH_2CH_3$ | $CH_3$ | H | $CH_3$ |
| 1.106 | $CH_2CH_3$ | $CH_3$ | $CH_3$ | $CH_3$ |
| 1.107 | $CH_2CH_3$ | Cl | H | H |
| 1.108 | $CH_2CH_3$ | Cl | H | $CH_3$ |
| 1.109 | $CH_2CH_3$ | Cl | H | $OCH_3$ |
| 1.110 | $CH_2CH_3$ | H | Cl | H |
| 1.111 | $CH_2CH_3$ | H | H | Cl |
| 1.112 | $CH_2CH_3$ | $CH_3$ | Cl | H |
| 1.113 | $CH_2CH_3$ | $CH_3$ | H | Cl |
| 1.114 | $CH_2CH_3$ | H | Cl | $CH_3$ |
| 1.115 | $CH_2CH_3$ | $CH_3$ | Cl | $CH_3$ |
| 1.116 | $CH_2CH_3$ | Br | H | H |
| 1.117 | $CH_2CH_3$ | Br | H | $CH_3$ |
| 1.118 | $CH_2CH_3$ | Br | H | $OCH_3$ |
| 1.119 | $CH_2CH_3$ | H | Br | H |
| 1.120 | $CH_2CH_3$ | H | H | Br |
| 1.121 | $CH_2CH_3$ | $CH_3$ | Br | H |
| 1.122 | $CH_2CH_3$ | $CH_3$ | H | Br |
| 1.123 | $CH_2CH_3$ | H | Br | $CH_3$ |
| 1.124 | $CH_2CH_3$ | $CH_3$ | Br | $CH_3$ |
| 1.125 | $CH_2CH_3$ | $CH_3O$ | H | H |
| 1.126 | $CH_2CH_3$ | $CH_3O$ | H | $CH_3$ |
| 1.127 | $CH_2CH_3$ | $CH_3O$ | H | Cl |
| 1.128 | $CH_2CH_3$ | $CH_3O$ | H | Br |
| 1.129 | $CH_2CH_3$ | $CH_3CH_2O$ | H | H |
| 1.130 | $CH_2CH_3$ | $CH_3CH_2O$ | H | $CH_3$ |
| 1.131 | $CH_2CH_3$ | $CH_3CH_2O$ | H | Cl |
| 1.132 | $CH_2CH_3$ | $CH_3CH_2O$ | H | Br |
| 1.133 | $CH_2CH_3$ | H | $CH_3O$ | H |
| 1.134 | $CH_2CH_3$ | H | H | $CH_3O$ |
| 1.135 | $CH_2CH_3$ | $CH_3$ | $CH_3O$ | H |
| 1.136 | $CH_2CH_3$ | $CH_3$ | H | $CH_3O$ |
| 1.137 | $CH_2CH_3$ | H | $CH_3O$ | $CH_3$ |
| 1.138 | $CH_2CH_3$ | $CH_3$ | $CH_3O$ | $CH_3$ |
| 1.139 | $CH_2CH_3$ | —CH=$CH_2$ | H | $CH_3$ |
| 1.140 | $CH_2CH_3$ | $CH_3$ | H | —CH=$CH_2$ |
| 1.141 | $CH_2CH_3$ | —C•CH | H | $CH_3$ |
| 1.142 | $CH_2CH_3$ | $CH_3$ | H | —C•CH |
| 1.143 | $CH_2CH_3$ | —CH=$CH_2$ | H | —CH=$CH_2$ |
| 1.144 | $CH_2CH_3$ | $CH_2CH_3$ | H | $CH_3$ |
| 1.145 | $CH_2CH_3$ | phenyl | H | $CH_3$ |
| 1.146 | $CH_2CH_3$ | 2-fluorophenyl | H | $CH_3$ |
| 1.147 | $CH_2CH_3$ | 2-chlorophenyl | H | $CH_3$ |
| 1.148 | $CH_2CH_3$ | 2-trifluoromethylphenyl | H | $CH_3$ |

TABLE 1-continued covers 262 compounds of the following type:

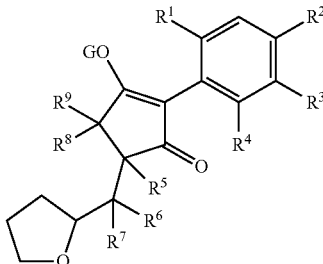

where G, $R^5$, $R^6$, $R^7$, $R^8$ and $R^9$ are all hydrogen, and $R^1$, $R^2$, $R^3$ and $R^4$ are as described in Table 1 below:

| Compound Number | $R^1$ | $R^2$ | $R^3$ | $R^4$ |
|---|---|---|---|---|
| 1.149 | $CH_2CH_3$ | 2-nitrophenyl | H | $CH_3$ |
| 1.150 | $CH_2CH_3$ | 2-nnethylphenyl | H | $CH_3$ |
| 1.151 | $CH_2CH_3$ | 2-methylsulfonylphenyl | H | $CH_3$ |
| 1.152 | $CH_2CH_3$ | 2-cyanophenyl | H | $CH_3$ |
| 1.153 | $CH_2CH_3$ | 3-fluorophenyl | H | $CH_3$ |
| 1.154 | $CH_2CH_3$ | 3-chlorophenyl | H | $CH_3$ |
| 1.155 | $CH_2CH_3$ | 3-trifluoromethylphenyl | H | $CH_3$ |
| 1.156 | $CH_2CH_3$ | 3-nitrophenyl | H | $CH_3$ |
| 1.157 | $CH_2CH_3$ | 3-methylphenyl | H | $CH_3$ |
| 1.158 | $CH_2CH_3$ | 3-nnethylsulfonylphenyl | H | $CH_3$ |
| 1.159 | $CH_2CH_3$ | 3-cyanophenyl | H | $CH_3$ |
| 1.160 | $CH_2CH_3$ | 4-fluorophenyl | H | $CH_3$ |
| 1.161 | $CH_2CH_3$ | 4-chlorophenyl | H | $CH_3$ |
| 1.162 | $CH_2CH_3$ | 4-bromophenyl | H | $CH_3$ |
| 1.163 | $CH_2CH_3$ | 4-difluoromethoxyphenyl | H | $CH_3$ |
| 1.164 | $CH_2CH_3$ | 2-fluoro-4-chlorophenyl | H | $CH_3$ |
| 1.165 | $CH_2CH_3$ | 2-chloro-4-chlorophenyl | H | $CH_3$ |
| 1.166 | $CH_2CH_3$ | 2-methyl-4-chlorophenyl | H | $CH_3$ |
| 1.167 | $CH_2CH_3$ | 4-trifluoromethylphenyl | H | $CH_3$ |
| 1.168 | $CH_2CH_3$ | 4-nitrophenyl | H | $CH_3$ |
| 1.169 | $CH_2CH_3$ | 4-methylphenyl | H | $CH_3$ |
| 1.170 | $CH_2CH_3$ | 4-methylsulfonylphenyl | H | $CH_3$ |
| 1.171 | $CH_2CH_3$ | 4-cyanophenyl | H | $CH_3$ |
| 1.172 | $CH_2CH_3$ | H | phenyl | H |
| 1.173 | $CH_2CH_3$ | H | 2-fluorophenyl | H |
| 1.174 | $CH_2CH_3$ | H | 2-chlorophenyl | H |
| 1.175 | $CH_2CH_3$ | H | 2-trifluoromethylphenyl | H |
| 1.176 | $CH_2CH_3$ | H | 2-nitrophenyl | H |
| 1.177 | $CH_2CH_3$ | H | 2-methylphenyl | H |
| 1.178 | $CH_2CH_3$ | H | 2-methylsulfonylphenyl | H |
| 1.179 | $CH_2CH_3$ | H | 2-cyanophenyl | H |
| 1.180 | $CH_2CH_3$ | H | 3-fluorophenyl | H |
| 1.181 | $CH_2CH_3$ | H | 3-chlorophenyl | H |
| 1.182 | $CH_2CH_3$ | H | 3-trifluoromethylphenyl | H |
| 1.183 | $CH_2CH_3$ | H | 3-nitrophenyl | H |
| 1.184 | $CH_2CH_3$ | H | 3-nnethylphenyl | H |
| 1.185 | $CH_2CH_3$ | H | 3-nnethylsulfonylphenyl | H |
| 1.186 | $CH_2CH_3$ | H | 3-cyanophenyl | H |
| 1.187 | $CH_2CH_3$ | H | 4-fluorophenyl | H |
| 1.188 | $CH_2CH_3$ | H | 4-chlorophenyl | H |
| 1.189 | $CH_2CH_3$ | H | 4-bromophenyl | H |
| 1.190 | $CH_2CH_3$ | H | 4-difluoromethoxyphenyl | H |
| 1.191 | $CH_2CH_3$ | H | 2-fluoro-4-chlorophenyl | H |
| 1.192 | $CH_2CH_3$ | H | 2-chloro-4-chlorophenyl | H |
| 1.193 | $CH_2CH_3$ | H | 2-methyl-4-chlorophenyl | H |
| 1.194 | $CH_2CH_3$ | H | 4-trifluoromethylphenyl | H |
| 1.195 | $CH_2CH_3$ | H | 4-nitrophenyl | H |
| 1.196 | $CH_2CH_3$ | H | 4-nnethylphenyl | H |
| 1.197 | $CH_2CH_3$ | H | 4-methylsulfonylphenyl | H |
| 1.198 | $CH_2CH_3$ | H | 4-cyanophenyl | H |
| 1.199 | $CH_2CH_3$ | $CH_3$ | H | $CH_2CH_3$ |
| 1.200 | $CH_2CH_3$ | $CH_2CH_3$ | H | $CH_2CH_3$ |
| 1.201 | $CH_2CH_3$ | Cl | H | $CH_2CH_3$ |
| 1.202 | $CH_2CH_3$ | Br | H | $CH_2CH_3$ |
| 1.203 | $CH_2CH_3$ | $NO_2$ | H | $CH_2CH_3$ |
| 1.204 | $CH_2CH_3$ | $CH_3O$ | H | $CH_2CH_3$ |
| 1.205 | $CH_2CH_3$ | $CH_3S$ | H | $CH_2CH_3$ |
| 1.206 | $CH_2CH_3$ | $CH_3SO_2$ | H | $CH_2CH_3$ |
| 1.207 | $CH_2CH_3$ | $CH_2=CH$ | H | $CH_2CH_3$ |

TABLE 1-continued covers 262 compounds of the following type:

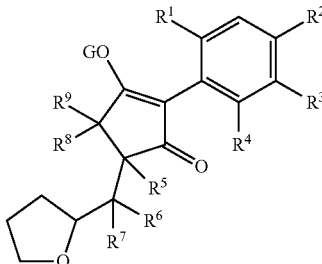

where G, $R^5$, $R^6$, $R^7$, $R^8$ and $R^9$ are all hydrogen, and $R^1$, $R^2$, $R^3$ and $R^4$ are as described in Table 1 below:

| Compound Number | $R^1$ | $R^2$ | $R^3$ | $R^4$ |
| --- | --- | --- | --- | --- |
| 1.208 | $CH_2CH_3$ | —C•CH | H | $CH_2CH_3$ |
| 1.209 | $CH_2CH_3$ | phenyl | H | $CH_2CH_3$ |
| 1.210 | $CH_2CH_3$ | 2-fluorophenyl | H | $CH_2CH_3$ |
| 1.211 | $CH_2CH_3$ | 2-chlorophenyl | H | $CH_2CH_3$ |
| 1.212 | $CH_2CH_3$ | 2-trifluoromethylphenyl | H | $CH_2CH_3$ |
| 1.213 | $CH_2CH_3$ | 2-nitrophenyl | H | $CH_2CH_3$ |
| 1.214 | $CH_2CH_3$ | 2-methylphenyl | H | $CH_2CH_3$ |
| 1.215 | $CH_2CH_3$ | 2-methylsulfonylphenyl | H | $CH_2CH_3$ |
| 1.216 | $CH_2CH_3$ | 2-cyanophenyl | H | $CH_2CH_3$ |
| 1.217 | $CH_2CH_3$ | 3-fluorophenyl | H | $CH_2CH_3$ |
| 1.218 | $CH_2CH_3$ | 3-chlorophenyl | H | $CH_2CH_3$ |
| 1.219 | $CH_2CH_3$ | 3-trifluoromethylphenyl | H | $CH_2CH_3$ |
| 1.220 | $CH_2CH_3$ | 3-nitrophenyl | H | $CH_2CH_3$ |
| 1.221 | $CH_2CH_3$ | 3-methylphenyl | H | $CH_2CH_3$ |
| 1.222 | $CH_2CH_3$ | 3-methylsulfonylphenyl | H | $CH_2CH_3$ |
| 1.223 | $CH_2CH_3$ | 3-cyanophenyl | H | $CH_2CH_3$ |
| 1.224 | $CH_2CH_3$ | 4-fluorophenyl | H | $CH_2CH_3$ |
| 1.225 | $CH_2CH_3$ | 4-chlorophenyl | H | $CH_2CH_3$ |
| 1.226 | $CH_2CH_3$ | 4-bromophenyl | H | $CH_2CH_3$ |
| 1.227 | $CH_2CH_3$ | 4-difluoromethoxyphenyl | H | $CH_2CH_3$ |
| 1.228 | $CH_2CH_3$ | 2-fluoro-4-chlorophenyl | H | $CH_2CH_3$ |
| 1.229 | $CH_2CH_3$ | 2-chloro-4-chlorophenyl | H | $CH_2CH_3$ |
| 1.230 | $CH_2CH_3$ | 2-methyl-4-chlorophenyl | H | $CH_2CH_3$ |
| 1.231 | $CH_2CH_3$ | 4-trifluoromethylphenyl | H | $CH_2CH_3$ |
| 1.232 | $CH_2CH_3$ | 4-nitrophenyl | H | $CH_2CH_3$ |
| 1.233 | $CH_2CH_3$ | 4-nnethylphenyl | H | $CH_2CH_3$ |
| 1.234 | $CH_2CH_3$ | 4-methylsulfonylphenyl | H | $CH_2CH_3$ |
| 1.235 | $CH_2CH_3$ | 4-cyanophenyl | H | $CH_2CH_3$ |
| 1.236 | $OCH_3$ | H | phenyl | H |
| 1.237 | $OCH_3$ | H | 2-fluorophenyl | H |
| 1.238 | $OCH_3$ | H | 2-chlorophenyl | H |
| 1.239 | $OCH_3$ | H | 2-trifluoromethylphenyl | H |
| 1.240 | $OCH_3$ | H | 2-nitrophenyl | H |
| 1.241 | $OCH_3$ | H | 2-methylphenyl | H |
| 1.242 | $OCH_3$ | H | 2-methylsulfonylphenyl | H |
| 1.243 | $OCH_3$ | H | 2-cyanophenyl | H |
| 1.244 | $OCH_3$ | H | 3-fluorophenyl | H |
| 1.245 | $OCH_3$ | H | 3-chlorophenyl | H |
| 1.246 | $OCH_3$ | H | 3-trifluoromethylphenyl | H |
| 1.247 | $OCH_3$ | H | 3-nitrophenyl | H |
| 1.248 | $OCH_3$ | H | 3-methylphenyl | H |
| 1.249 | $OCH_3$ | H | 3-methylsulfonylphenyl | H |
| 1.250 | $OCH_3$ | H | 3-cyanophenyl | H |
| 1.251 | $OCH_3$ | H | 4-fluorophenyl | H |
| 1.252 | $OCH_3$ | H | 4-chlorophenyl | H |
| 1.253 | $OCH_3$ | H | 4-bromophenyl | H |
| 1.254 | $OCH_3$ | H | 4-difluoromethoxyphenyl | H |
| 1.255 | $OCH_3$ | H | 2-fluoro-4-chlorophenyl | H |
| 1.256 | $OCH_3$ | H | 2-chloro-4-chlorophenyl | H |
| 1.257 | $OCH_3$ | H | 2-methyl-4-chlorophenyl | H |
| 1.258 | $OCH_3$ | H | 4-trifluoromethylphenyl | H |
| 1.259 | $OCH_3$ | H | 4-nitrophenyl | H |
| 1.260 | $OCH_3$ | H | 4-nnethylphenyl | H |
| 1.261 | $OCH_3$ | H | 4-methylsulfonylphenyl | H |
| 1.262 | $OCH_3$ | H | 4-cyanophenyl | H |

TABLE 2 covers 262 compounds of the following type

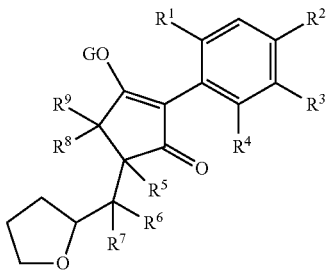

where G, $R^5$, $R^6$, $R^8$ and $R^9$ are hydrogen, $R^7$ is methyl and $R^1$, $R^2$, $R^3$ and $R^4$ are as described in Table 1.

TABLE 3 covers 262 comopunds of the following type

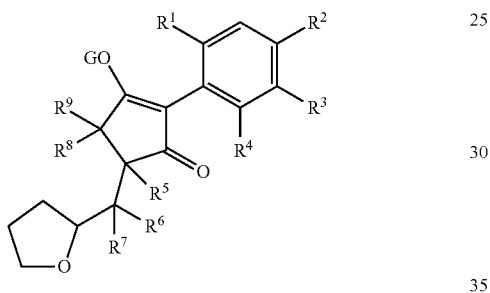

where G and $R^5$, $R^8$ and $R^9$ are hydrogen, $R^6$ and $R^7$ are methyl and $R^1$, $R^2$, $R^3$ and $R^4$ are as described in Table 1.

TABLE 4 covers 262 compounds of the following type:

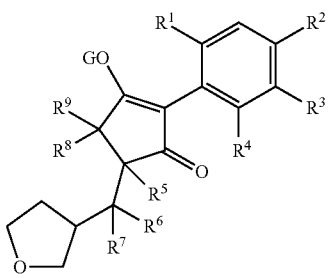

where G, $R^5$, $R^6$, $R^7$, $R^8$ and $R^9$ are all hydrogen, and $R^1$, $R^2$, $R^3$ and $R^4$ are as described in Table 1.

TABLE 5 covers 262 compounds of the following type

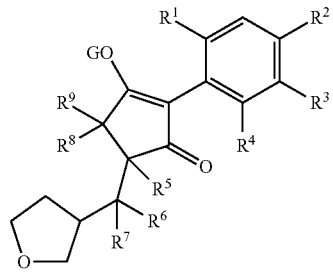

where G, R⁵, R⁶, R⁸ and R⁹ are hydrogen, R⁷ is methyl and R¹, R², R³ and R⁴ are as described in Table 1.

TABLE 6 covers 262 compounds of the following type

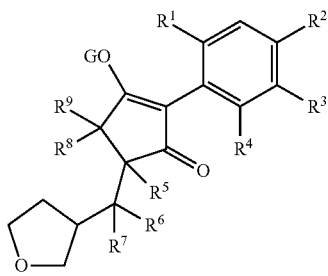

where G and R⁵, R⁸ and R⁹ are hydrogen, R⁶ and R⁷ are methyl and R¹, R², R³ and R⁴ are as described in Table 1.

TABLE 7 covers 262 compounds of the following type:

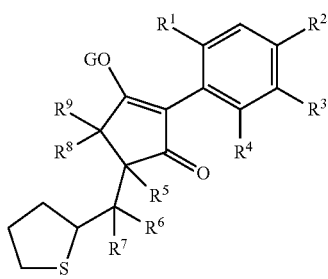

where G, R⁵, R⁶, R⁷, R⁸ and R⁹ are all hydrogen, and R¹, R², R³ and R⁴ are as described in Table 1.

TABLE 8 covers 262 compounds of the following type

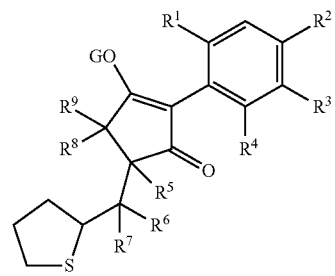

where G, R⁵, R⁶, R⁸ and R⁹ are hydrogen, R⁷ is methyl and R¹, R², R³ and R⁴ are as described in Table 1.

TABLE 9 covers 262 compounds of the following type

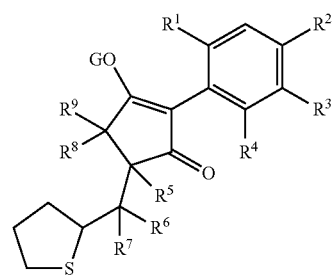

where G and R⁵, R⁸ and R⁹ are hydrogen, R⁶ and R⁷ are methyl and R¹, R², R³ and R⁴ are as described in Table 1.

TABLE 10 covers 262 compounds of the following type:

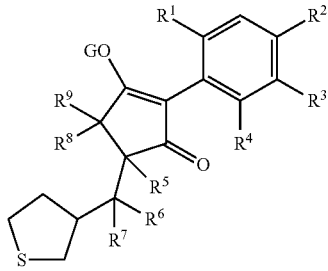

where G, R$^5$, R$^6$, R$^7$, R$^8$ and R$^9$ are all hydrogen, and R$^1$, R$^2$, R$^3$ and R$^4$ are as described in Table 1.

TABLE 11 covers 262 compounds of the following type

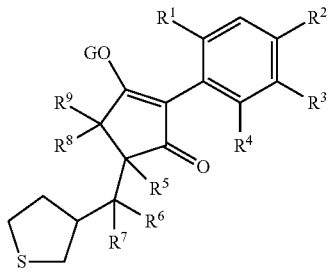

where G, R$^5$, R$^6$, R$^8$ and R$^9$ are hydrogen, R$^7$ is methyl and R$^1$, R$^2$, R$^3$ and R$^4$ are as described in Table 1.

TABLE 12 covers 262 compounds of the following type

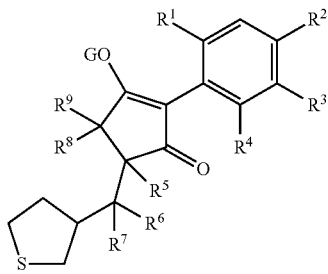

where G and R$^5$, R$^8$ and R$^9$ are hydrogen, R$^6$ and R$^7$ are methyl and R$^1$, R$^2$, R$^3$ and R$^4$ are as described in Table 1.

TABLE 13 covers 262 compounds of the following type:

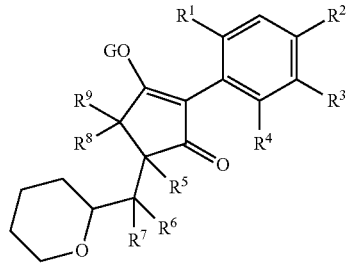

where G, R$^5$, R$^6$, R$^7$, R$^8$ and R$^9$ are all hydrogen, and R$^1$, R$^2$, R$^3$ and R$^4$ are as described in Table 1.

TABLE 14 covers 262 compounds of the following type

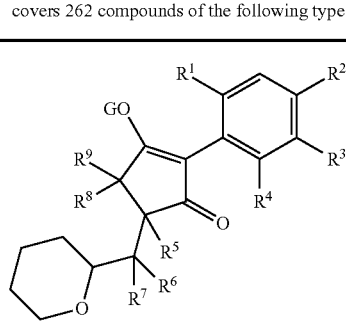

where G, R$^5$, R$^6$, R$^8$ and R$^9$ are hydrogen, R$^7$ is methyl and R$^1$, R$^2$, R$^3$ and R$^4$ are as described in Table 1.

TABLE 15 covers 262 compounds of the following type

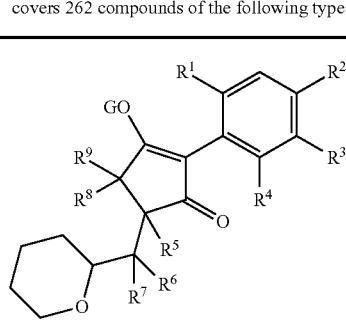

where G and R$^5$, R$^8$ and R$^9$ are hydrogen, R$^6$ and R$^7$ are methyl and R$^1$, R$^2$, R$^3$ and R$^4$ are as described in Table 1.

TABLE 16 covers 262 compounds of the following type:

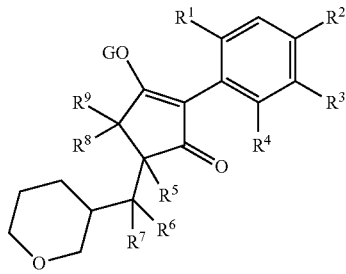

where G, $R^5$, $R^6$, $R^7$, $R^8$ and $R^9$ are all hydrogen, and $R^1$, $R^2$, $R^3$ and $R^4$ are as described in Table 1.

TABLE 17 covers 262 compounds of the following type

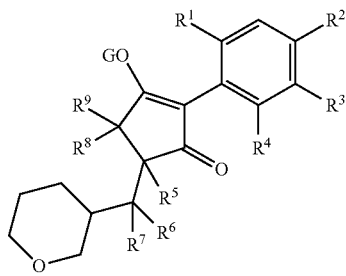

where G, $R^5$, $R^6$, $R^8$ and $R^9$ are hydrogen, $R^7$ is methyl and $R^1$, $R^2$, $R^3$ and $R^4$ are as described in Table 1.

TABLE 18 covers 262 compounds of the following type

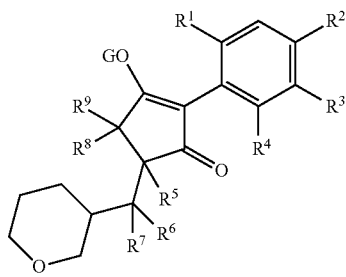

where G and $R^5$, $R^8$ and $R^9$ are hydrogen, $R^6$ and $R^7$ are methyl and $R^1$, $R^2$, $R^3$ and $R^4$ are as described in Table 1.

TABLE 19 covers 262 compounds of the following type:

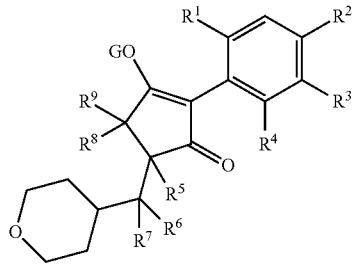

where G, $R^5$, $R^6$, $R^7$, $R^8$ and $R^9$ are all hydrogen, and $R^1$, $R^2$, $R^3$ and $R^4$ are as described in Table 1.

TABLE 20 covers 262 compounds of the following type

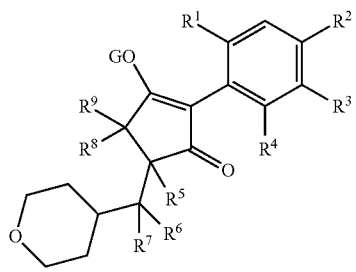

where G, $R^5$, $R^6$, $R^8$ and $R^9$ are hydrogen, $R^7$ is methyl and $R^1$, $R^2$, $R^3$ and $R^4$ are as described in Table 1.

TABLE 21 covers 262 compounds of the following type

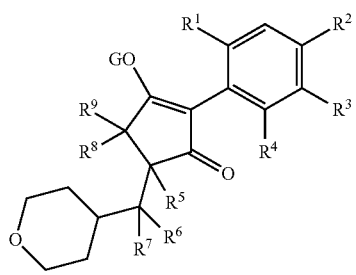

where G and $R^5$, $R^8$ and $R^9$ are hydrogen, $R^6$ and $R^7$ are methyl and $R^1$, $R^2$, $R^3$ and $R^4$ are as described in Table 1.

TABLE 22 covers 262 compounds of the following type:

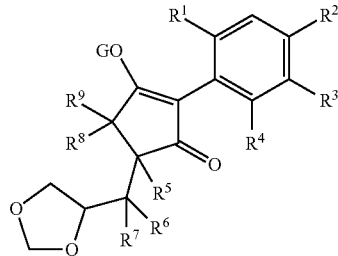

where G, $R^5$, $R^6$, $R^7$, $R^8$ and $R^9$ are all hydrogen, and $R^1$, $R^2$, $R^3$ and $R^4$ are as described in Table 1.

TABLE 23 covers 262 compounds of the following type

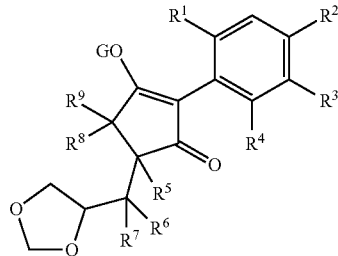

where G, $R^5$, $R^6$, $R^8$ and $R^9$ are hydrogen, $R^7$ is methyl and $R^1$, $R^2$, $R^3$ and $R^4$ are as described in Table 1.

TABLE 24 covers 262 compounds of the following type

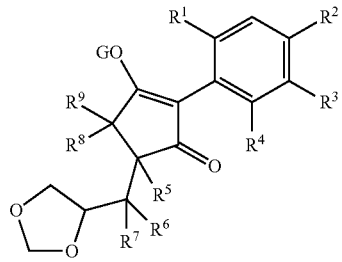

where G and $R^5$, $R^8$ and $R^9$ are hydrogen, $R^6$ and $R^7$ are methyl and $R^1$, $R^2$, $R^3$ and $R^4$ are as described in Table 1.

TABLE 25 covers 262 compounds of the following type:

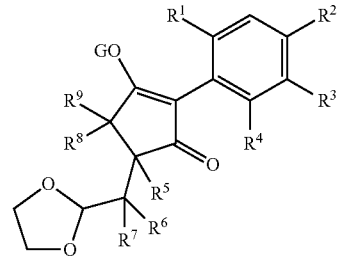

where G, $R^5$, $R^6$, $R^7$, $R^8$ and $R^9$ are all hydrogen, and $R^1$, $R^2$, $R^3$ and $R^4$ are as described in Table 1.

TABLE 26 covers 262 compounds of the following type

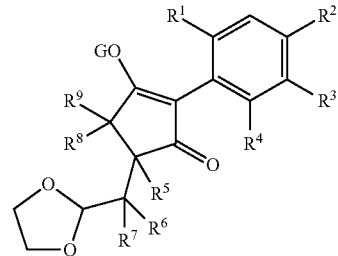

where G, $R^5$, $R^6$, $R^8$ and $R^9$ are hydrogen, $R^7$ is methyl and $R^1$, $R^2$, $R^3$ and $R^4$ are as described in Table 1.

TABLE 27 covers 262 compounds of the following type

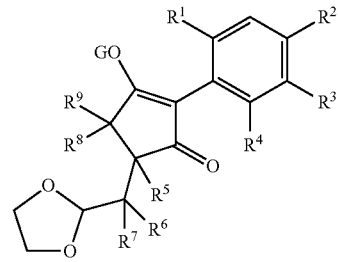

where G and $R^5$, $R^8$ and $R^9$ are hydrogen, $R^6$ and $R^7$ are methyl and $R^1$, $R^2$, $R^3$ and $R^4$ are as described in Table 1.

TABLE 28 covers 262 compounds of the following type:

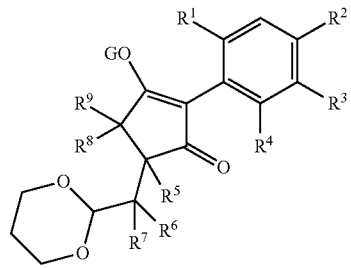

where G, R⁵, R⁶, R⁷, R⁸ and R⁹ are all hydrogen, and R¹, R², R³ and R⁴ are as described in Table 1.

TABLE 29 covers 262 compounds of the following type

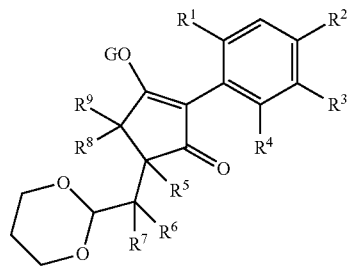

where G, R⁵, R⁶, R⁸ and R⁹ are hydrogen, R⁷ is methyl and R¹, R², R³ and R⁴ are as described in Table 1.

TABLE 30 covers 262 compounds of the following type

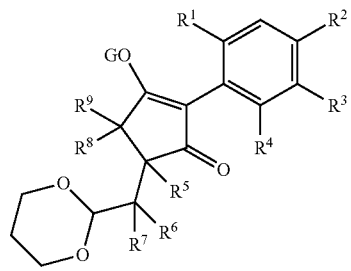

where G and R⁵, R⁸ and R⁹ are hydrogen, R⁶ and R⁷ are methyl and R¹, R², R³ and R⁴ are as described in Table 1.

TABLE 31 covers 262 compounds of the following type:

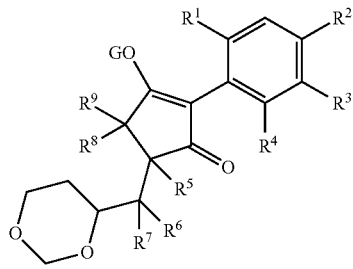

where G, R⁵, R⁶, R⁷, R⁸ and R⁹ are all hydrogen, and R¹, R², R³ and R⁴ are as described in Table 1.

TABLE 32 covers 262 compounds of the following type

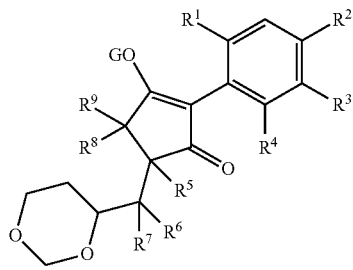

where G, R⁵, R⁶, R⁸ and R⁹ are hydrogen, R⁷ is methyl and R¹, R², R³ and R⁴ are as described in Table 1.

TABLE 33 covers 262 compounds of the following type

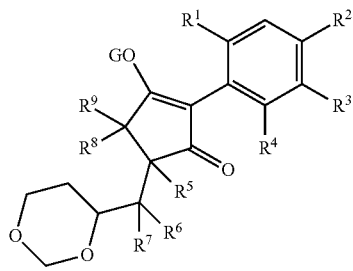

where G and R⁵, R⁸ and R⁹ are hydrogen, R⁶ and R⁷ are methyl and R¹, R², R³ and R⁴ are as described in Table 1.

TABLE 34 covers 262 compounds of the following type:

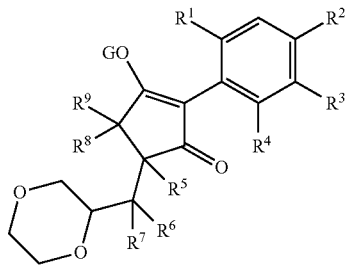

where G, $R^5$, $R^6$, $R^7$, $R^8$ and $R^9$ are all hydrogen, and $R^1$, $R^2$, $R^3$ and $R^4$ are as described in Table 1.

TABLE 35 covers 262 compounds of the following type

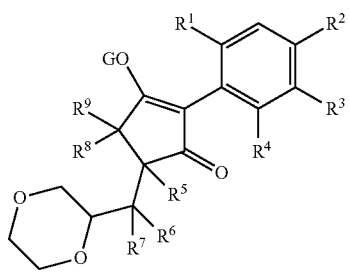

where G, $R^5$, $R^6$, $R^8$ and $R^9$ are hydrogen, $R^7$ is methyl and $R^1$, $R^2$, $R^3$ and $R^4$ are as described in Table 1.

TABLE 36 covers 262 compounds of the following type

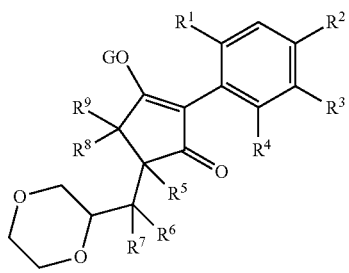

where G and $R^5$, $R^8$ and $R^9$ are hydrogen, $R^6$ and $R^7$ are methyl and $R^1$, $R^2$, $R^3$ and $R^4$ are as described in Table 1.

TABLE 37 covers 262 compounds of the following type:

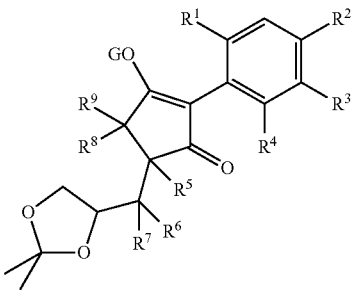

where G, $R^5$, $R^6$, $R^7$, $R^8$ and $R^9$ are all hydrogen, and $R^1$, $R^2$, $R^3$ and $R^4$ are as described in Table 1.

TABLE 38 covers 262 compounds of the following type

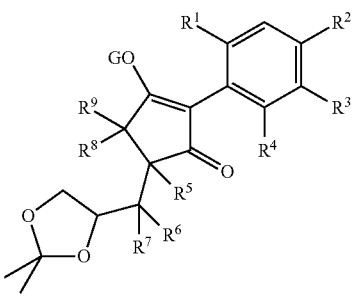

where G, $R^5$, $R^6$, $R^8$ and $R^9$ are hydrogen, $R^7$ is methyl and $R^1$, $R^2$, $R^3$ and $R^4$ are as described in Table 1.

TABLE 39 covers 262 compounds of the following type

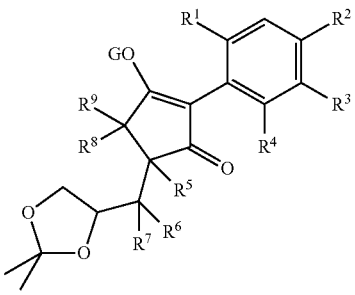

where G and $R^5$, $R^8$ and $R^9$ are hydrogen, $R^6$ and $R^7$ are methyl and $R^1$, $R^2$, $R^3$ and $R^4$ are as described in Table 1.

TABLE 40 covers 262 compounds of the following type:

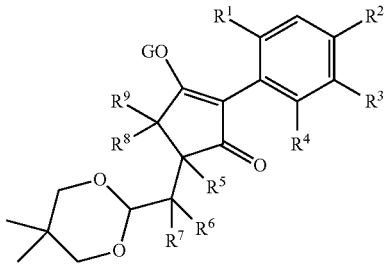

where G, R⁵, R⁶, R⁷, R⁸ and R⁹ are all hydrogen, and R¹, R², R³ and R⁴ are as described in Table 1.

TABLE 41 covers 262 compounds of the following type

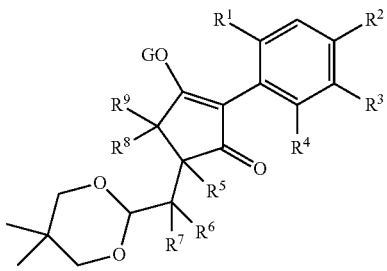

where G, R⁵, R⁶, R⁸ and R⁹ are hydrogen, R⁷ is methyl and R¹, R², R³ and R⁴ are as described in Table 1.

TABLE 42 covers 262 compounds of the following type

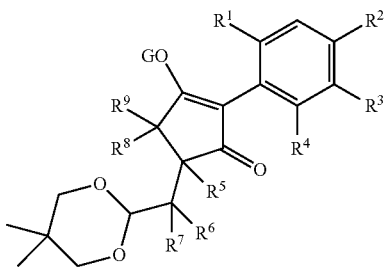

where G and R⁵, R⁸ and R⁹ are hydrogen, R⁶ and R⁷ are methyl and R¹, R², R³ and R⁴ are as described in Table 1.

TABLE 43 covers 262 compounds of the following type:

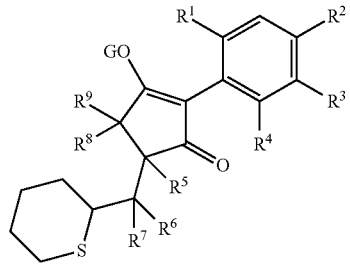

where G, R⁵, R⁶, R⁷, R⁸ and R⁹ are all hydrogen, and R¹, R², R³ and R⁴ are as described in Table 1.

TABLE 44 covers 262 compounds of the following type

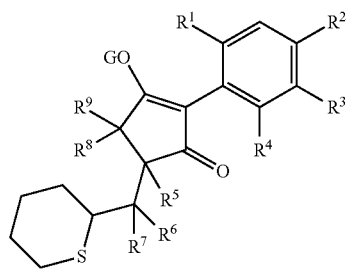

where G, R⁵, R⁶, R⁸ and R⁹ are hydrogen, R⁷ is methyl and R¹, R², R³ and R⁴ are as described in Table 1.

TABLE 45 covers 262 compounds of the following type

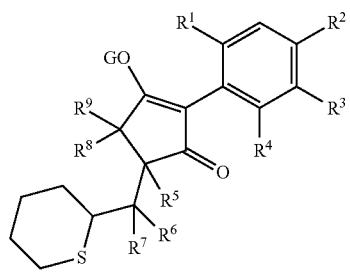

where G and R⁵, R⁸ and R⁹ are hydrogen, R⁶ and R⁷ are methyl and R¹, R², R³ and R⁴ are as described in Table 1.

TABLE 46 covers 262 compounds of the following type:

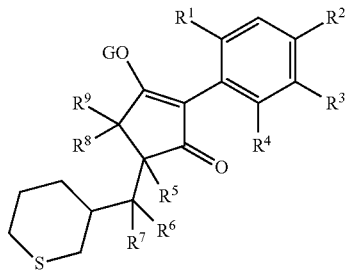

where G, R⁵, R⁶, R⁷, R⁸ and R⁹ are all hydrogen, and R¹, R², R³ and R⁴ are as described in Table 1.

TABLE 47 covers 262 compounds of the following type

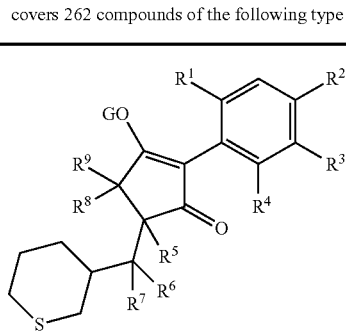

where G, R⁵, R⁶, R⁸ and R⁹ are hydrogen, R⁷ is methyl and R¹, R², R³ and R⁴ are as described in Table 1.

TABLE 48 covers 262 compounds of the following type

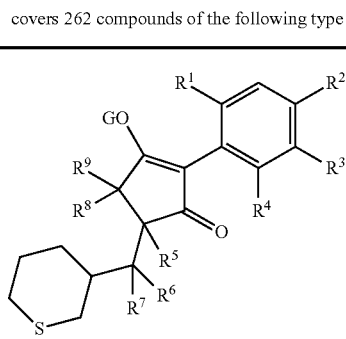

where G and R⁵, R⁸ and R⁹ are hydrogen, R⁶ and R⁷ are methyl and R¹, R², R³ and R⁴ are as described in Table 1.

TABLE 49 covers 262 compounds of the following type:

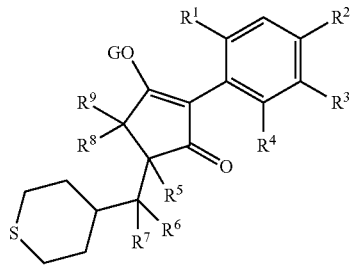

where G, R⁵, R⁶, R⁷, R⁸ and R⁹ are all hydrogen, and R¹, R², R³ and R⁴ are as described in Table 1.

TABLE 50 covers 262 compounds of the following type

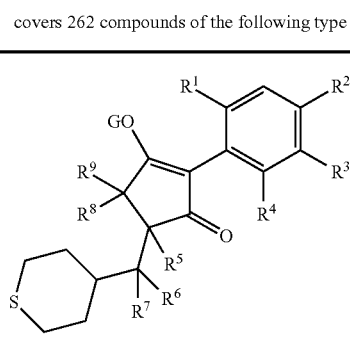

where G, R⁵, R⁶, R⁸ and R⁹ are hydrogen, R⁷ is methyl and R¹, R², R³ and R⁴ are as described in Table 1.

TABLE 51 covers 262 compounds of the following type

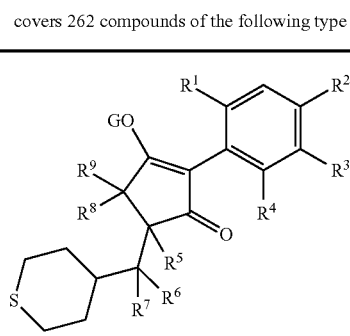

where G and R⁵, R⁸ and R⁹ are hydrogen, R⁶ and R⁷ are methyl and R¹, R², R³ and R⁴ are as described in Table 1.

TABLE 52 covers 262 compounds of the following type:

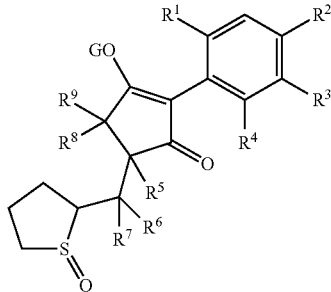

where G, R$^5$, R$^6$, R$^7$, R$^8$ and R$^9$ are all hydrogen, and R$^1$, R$^2$, R$^3$ and R$^4$ are as described in Table 1.

TABLE 53 covers 262 compounds of the following type

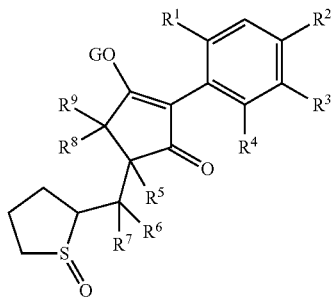

where G, R$^5$, R$^6$, R$^8$ and R$^9$ are hydrogen, R$^7$ is methyl and R$^1$, R$^2$, R$^3$ and R$^4$ are as described in Table 1.

TABLE 54 covers 262 compounds of the following type

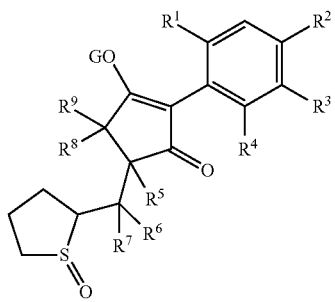

where G and R$^5$, R$^8$ and R$^9$ are hydrogen, R$^6$ and R$^7$ are methyl and R$^1$, R$^2$, R$^3$ and R$^4$ are as described in Table 1.

TABLE 55 covers 262 compounds of the following type:

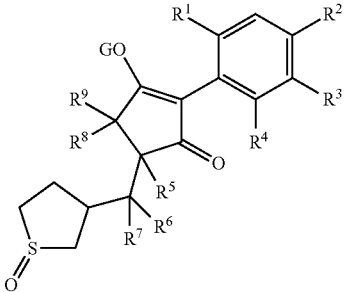

where G, R$^5$, R$^6$, R$^7$, R$^8$ and R$^9$ are all hydrogen, and R$^1$, R$^2$, R$^3$ and R$^4$ are as described in Table 1.

TABLE 56 covers 262 compounds of the following type

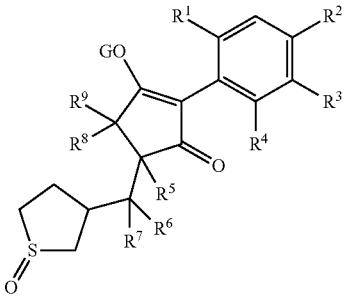

where G, R$^5$, R$^6$, R$^8$ and R$^9$ are hydrogen, R$^7$ is methyl and R$^1$, R$^2$, R$^3$ and R$^4$ are as described in Table 1.

TABLE 57 covers 262 compounds of the following type

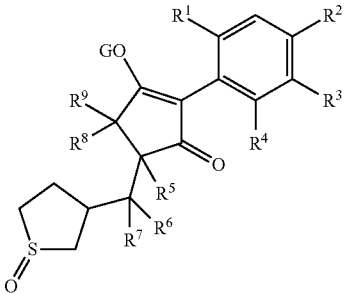

where G and R$^5$, R$^8$ and R$^9$ are hydrogen, R$^6$ and R$^7$ are methyl and R$^1$, R$^2$, R$^3$ and R$^4$ are as described in Table 1.

TABLE 58 covers 262 compounds of the following type:

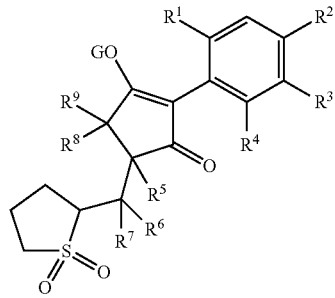

where G, R⁵, R⁶, R⁷, R⁸ and R⁹ are all hydrogen, and R¹, R², R³ and R⁴ are as described in Table 1.

Table 59 covers 262 compounds of the following type

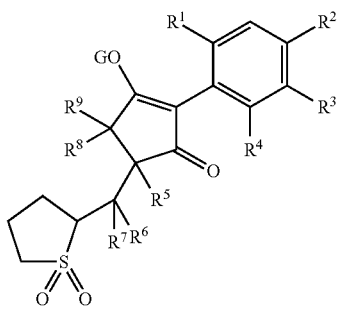

where G, R⁵, R⁶, R⁸ and R⁹ are hydrogen, R⁷ is methyl and R¹, R², R³ and R⁴ are as described in Table 1.

Table 60 covers 262 compounds of the following type

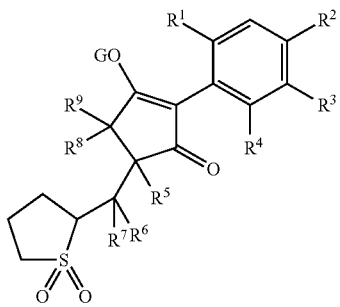

where G and R⁵, R⁸ and R⁹ are hydrogen, R⁶ and R⁷ are methyl and R¹, R², R³ and R⁴ are as described in Table 1.

Table 61 covers 262 compounds of the following type:

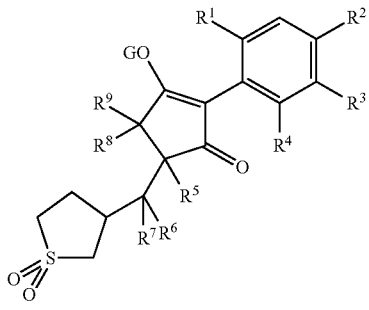

where G, R⁵, R⁶, R⁷, R⁸ and R⁹ are all hydrogen, and R¹, R², R³ and R⁴ are as described in Table 1.

Table 62 covers 262 compounds of the following type

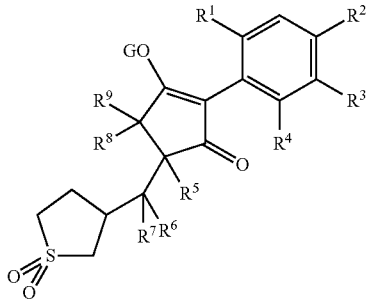

where G, R⁵, R⁶, R⁸ and R⁹ are hydrogen, R⁷ is methyl and R¹, R², R³ and R⁴ are as described in Table 1.

Table 63 covers 262 compounds of the following type

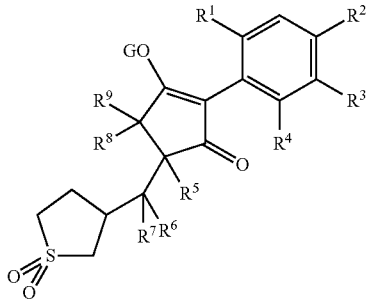

where G and R⁵, R⁸ and R⁹ are hydrogen, R⁶ and R⁷ are methyl and R¹, R², R³ and R⁴ are as described in Table 1.

Table 64 covers 262 compounds of the following type:

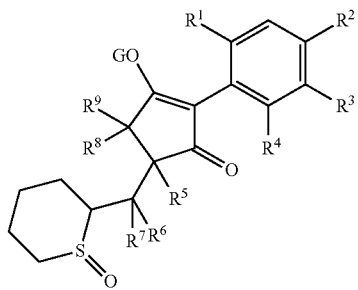

where G, $R^5$, $R^6$, $R^7$, $R^8$ and $R^9$ are all hydrogen, and $R^1$, $R^2$, $R^3$ and $R^4$ are as described in Table 1.

Table 65 covers 262 compounds of the following type

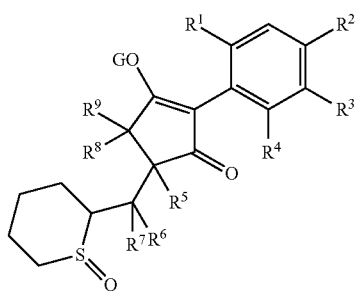

where G, $R^5$, $R^6$, $R^8$ and $R^9$ are hydrogen, $R^7$ is methyl and $R^1$, $R^2$, $R^3$ and $R^4$ are as described in Table 1.

Table 66 covers 262 compounds of the following type

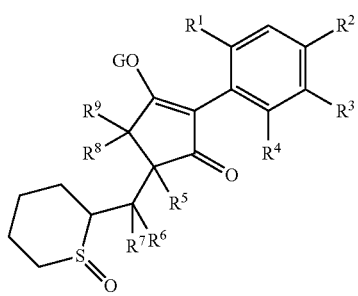

where G and $R^5$, $R^8$ and $R^9$ are hydrogen, $R^6$ and $R^7$ are methyl and $R^1$, $R^2$, $R^3$ and $R^4$ are as described in Table 1.

Table 67 covers 262 compounds of the following type:

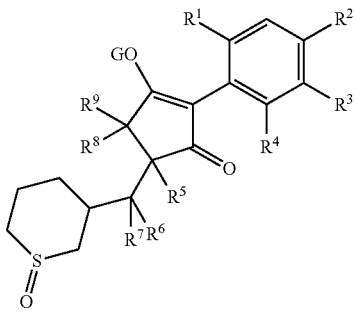

where G, $R^5$, $R^6$, $R^7$, $R^8$ and $R^9$ are all hydrogen, and $R^1$, $R^2$, $R^3$ and $R^4$ are as described in Table 1.

Table 68 covers 262 compounds of the following type

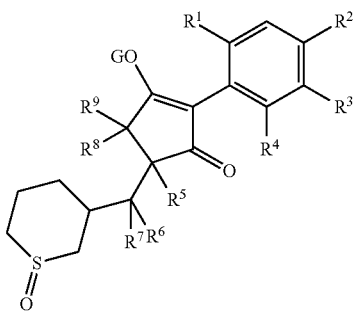

where G, $R^5$, $R^6$, $R^8$ and $R^9$ are hydrogen, $R^7$ is methyl and $R^1$, $R^2$, $R^3$ and $R^4$ are as described in Table 1.

Table 69 covers 262 compounds of the following type

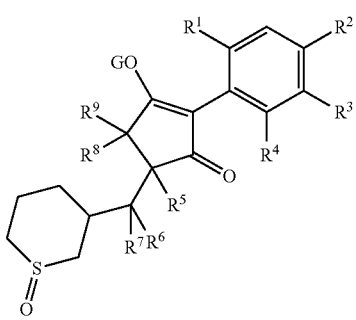

where G and $R^5$, $R^8$ and $R^9$ are hydrogen, $R^6$ and $R^7$ are methyl and $R^1$, $R^2$, $R^3$ and $R^4$ are as described in Table 1.

Table 70 covers 262 compounds of the following type:

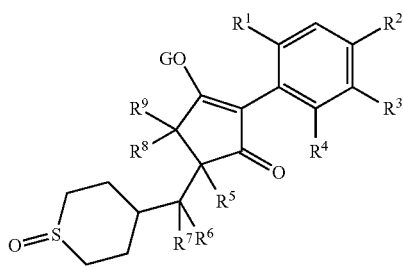

where G, $R^5$, $R^6$, $R^7$, $R^8$ and $R^9$ are all hydrogen, and $R^1$, $R^2$, $R^3$ and $R^4$ are as described in Table 1.

Table 71 covers 262 compounds of the following type

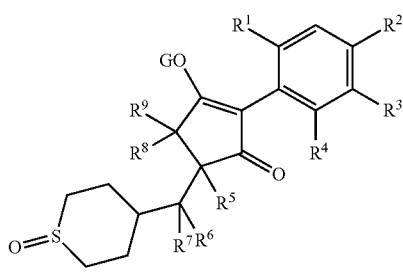

where G, $R^5$, $R^6$, $R^8$ and $R^9$ are hydrogen, $R^7$ is methyl and $R^1$, $R^2$, $R^3$ and $R^4$ are as described in Table 1.

Table 72 covers 262 compounds of the following type

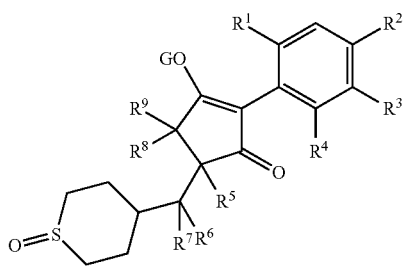

where G and $R^5$, $R^8$ and $R^9$ are hydrogen, $R^6$ and $R^7$ are methyl and $R^1$, $R^2$, $R^3$ and $R^4$ are as described in Table 1.

Table 73 covers 262 compounds of the following type:

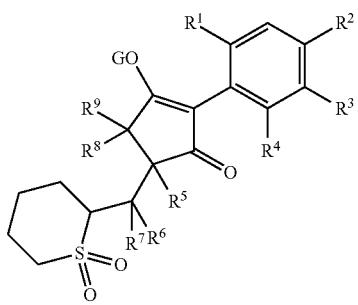

where G, $R^5$, $R^6$, $R^7$, $R^8$ and $R^9$ are all hydrogen, and $R^1$, $R^2$, $R^3$ and $R^4$ are as described in Table 1.

TABLE 74 covers 262 compounds of the following type

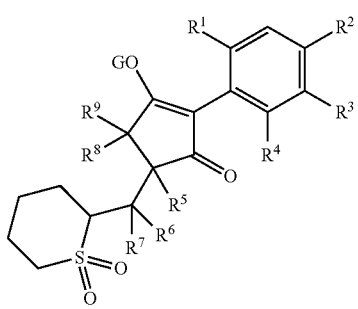

where G, $R^5$, $R^6$, $R^8$ and $R^9$ are hydrogen, $R^7$ is methyl and $R^1$, $R^2$, $R^3$ and $R^4$ are as described in Table 1.

TABLE 75 covers 262 compounds of the following type

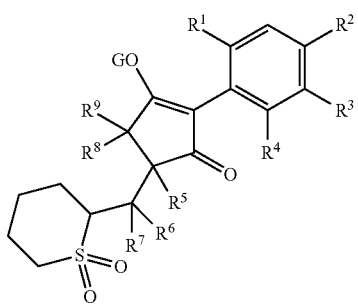

where G and $R^5$, $R^8$ and $R^9$ are hydrogen, $R^6$ and $R^7$ are methyl and $R^1$, $R^2$, $R^3$ and $R^4$ are as described in Table 1.

TABLE 76 covers 262 compounds of the following type:

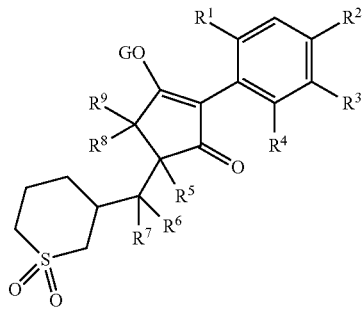

where G, $R^5$, $R^6$, $R^7$, $R^8$ and $R^9$ are all hydrogen, and $R^1$, $R^2$, $R^3$ and $R^4$ are as described in Table 1.

TABLE 77 covers 262 compounds of the following type

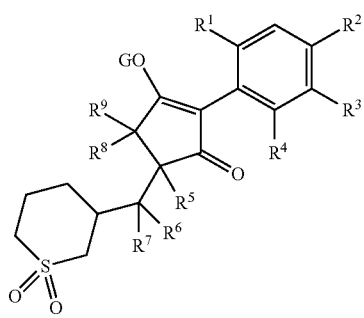

where G, $R^5$, $R^6$, $R^8$ and $R^9$ are hydrogen, $R^7$ is methyl and $R^1$, $R^2$, $R^3$ and $R^4$ are as described in Table 1.

TABLE 78 covers 262 compounds of the following type

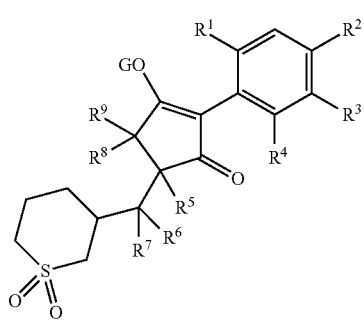

where G and $R^5$, $R^8$ and $R^9$ are hydrogen, $R^6$ and $R^7$ are methyl and $R^1$, $R^2$, $R^3$ and $R^4$ are as described in Table 1.

TABLE 79 covers 262 compounds of the following type:

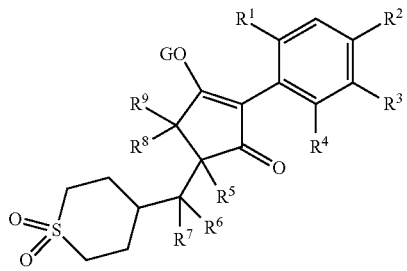

where G, $R^5$, $R^6$, $R^7$, $R^8$ and $R^9$ are all hydrogen, and $R^1$, $R^2$, $R^3$ and $R^4$ are as described in Table 1.

TABLE 80 covers 262 compounds of the following type

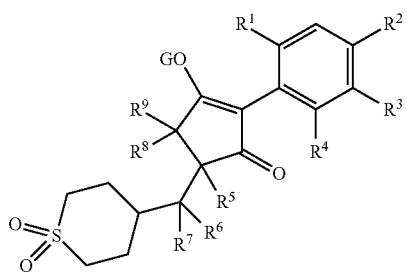

where G, $R^5$, $R^6$, $R^8$ and $R^9$ are hydrogen, $R^7$ is methyl and $R^1$, $R^2$, $R^3$ and $R^4$ are as described in Table 1.

TABLE 81 covers 262 compounds of the following type

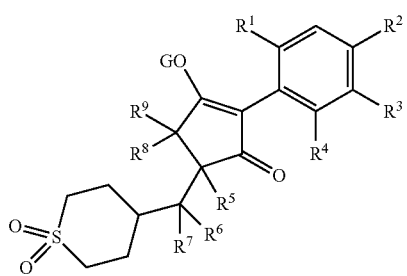

where G and $R^5$, $R^8$ and $R^9$ are hydrogen, $R^6$ and $R^7$ are methyl and $R^1$, $R^2$, $R^3$ and $R^4$ are as described in Table 1.

TABLE 82 covers 262 compounds of the following type:

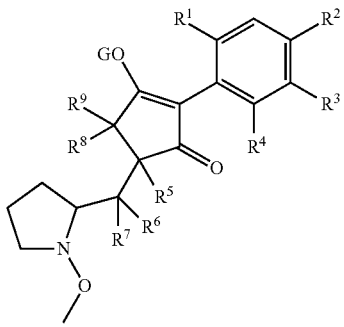

where G, $R^5$, $R^6$, $R^7$, $R^8$ and $R^9$ are all hydrogen,
and $R^1$, $R^2$, $R^3$ and $R^4$ are as described in Table 1.

TABLE 83 covers 262 compounds of the following type

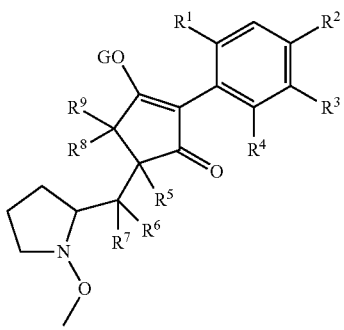

where G, $R^5$, $R^6$, $R^8$ and $R^9$ are hydrogen, $R^7$ is methyl
and $R^1$, $R^2$, $R^3$ and $R^4$ are as described in Table 1.

TABLE 84 covers 262 compounds of the following type

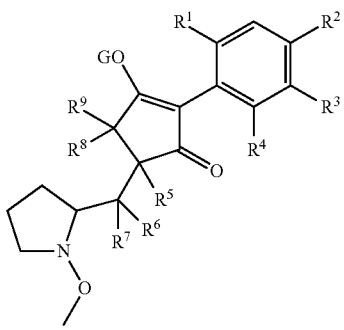

where G and $R^5$, $R^8$ and $R^9$ are hydrogen, $R^6$ and $R^7$ are
methyl and $R^1$, $R^2$, $R^3$ and $R^4$ are as described in Table 1.

TABLE 85 covers 262 compounds of the following type:

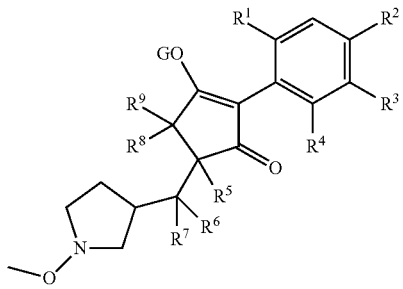

where G, $R^5$, $R^6$, $R^7$, $R^8$ and $R^9$ are all hydrogen,
and $R^1$, $R^2$, $R^3$ and $R^4$ are as described in Table 1.

TABLE 86 covers 262 compounds of the following type

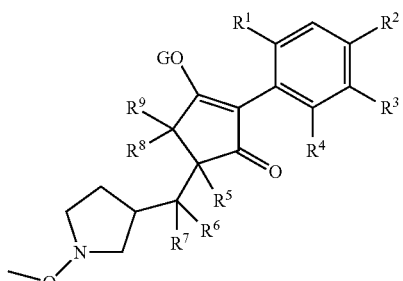

where G, $R^5$, $R^6$, $R^8$ and $R^9$ are hydrogen, $R^7$ is methyl
and $R^1$, $R^2$, $R^3$ and $R^4$ are as described in Table 1.

TABLE 87 covers 262 compounds of the following type

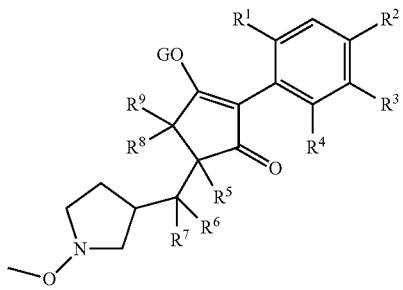

where G and $R^5$, $R^8$ and $R^9$ are hydrogen, $R^6$ and $R^7$ are
methyl and $R^1$, $R^2$, $R^3$ and $R^4$ are as described in Table 1.

TABLE 88 covers 262 compounds of the following type:

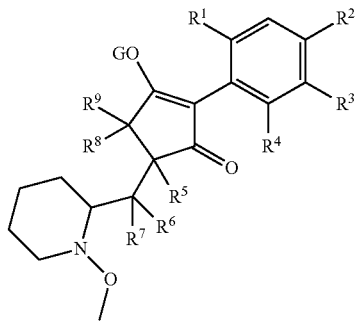

where G, $R^5$, $R^6$, $R^7$, $R^8$ and $R^9$ are all hydrogen, and $R^1$, $R^2$, $R^3$ and $R^4$ are as described in Table 1.

TABLE 89 covers 262 compounds of the following type

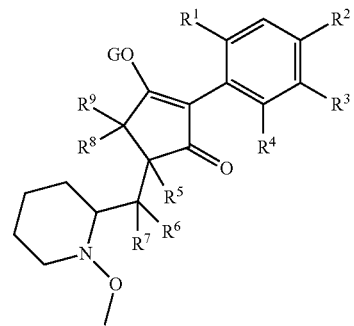

where G, $R^5$, $R^6$, $R^8$ and $R^9$ are hydrogen, $R^7$ is methyl and $R^1$, $R^2$, $R^3$ and $R^4$ are as described in Table 1.

TABLE 90 covers 262 compounds of the following type

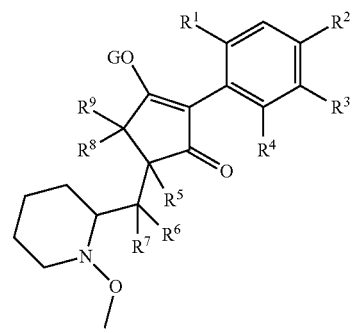

where G and $R^5$, $R^8$ and $R^9$ are hydrogen, $R^6$ and $R^7$ are methyl and $R^1$, $R^2$, $R^3$ and $R^4$ are as described in Table 1.

TABLE 91 covers 262 compounds of the following type:

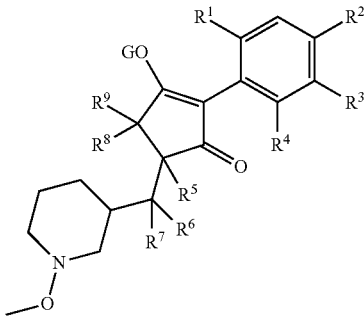

where G, $R^5$, $R^6$, $R^7$, $R^8$ and $R^9$ are all hydrogen, and $R^1$, $R^2$, $R^3$ and $R^4$ are as described in Table 1.

TABLE 92 covers 262 compounds of the following type

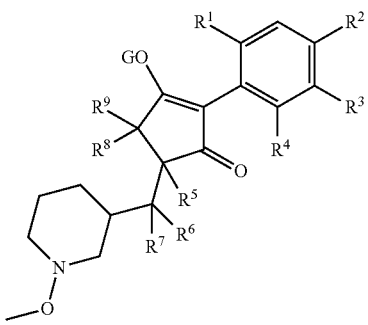

where G, $R^5$, $R^6$, $R^8$ and $R^9$ are hydrogen, $R^7$ is methyl and $R^1$, $R^2$, $R^3$ and $R^4$ are as described in Table 1.

TABLE 93 covers 262 compounds of the following type

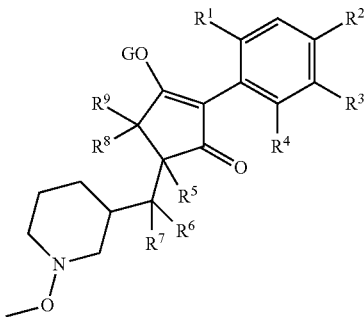

where G and $R^5$, $R^8$ and $R^9$ are hydrogen, $R^6$ and $R^7$ are methyl and $R^1$, $R^2$, $R^3$ and $R^4$ are as described in Table 1.

TABLE 94 covers 262 compounds of the following type:

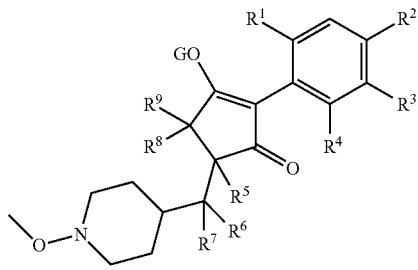

where G, $R^5$, $R^6$, $R^7$, $R^8$ and $R^9$ are all hydrogen, and $R^1$, $R^2$, $R^3$ and $R^4$ are as described in Table 1.

TABLE 95 covers 262 compounds of the following type

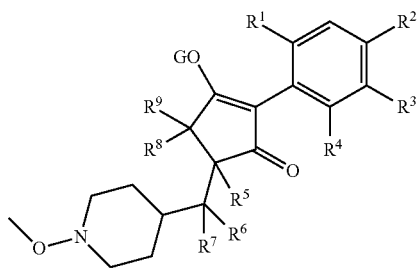

where G, $R^5$, $R^6$, $R^8$ and $R^9$ are hydrogen, $R^7$ is methyl and $R^1$, $R^2$, $R^3$ and $R^4$ are as described in Table 1.

TABLE 96 covers 262 compounds of the following type

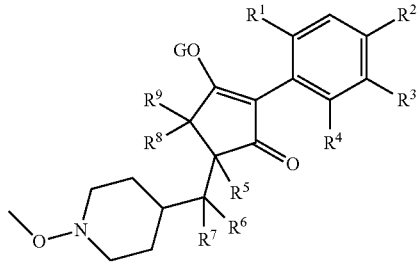

where G and $R^5$, $R^8$ and $R^9$ are hydrogen, $R^6$ and $R^7$ are methyl and $R^1$, $R^2$, $R^3$ and $R^4$ are as described in Table 1.

TABLE 97 covers 262 compounds of the following type:

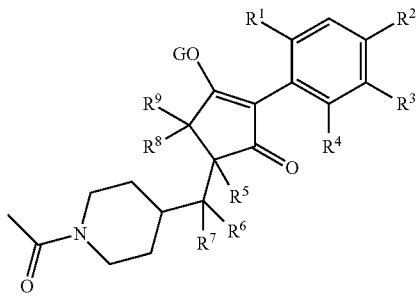

where G, $R^5$, $R^6$, $R^7$, $R^8$ and $R^9$ are all hydrogen, and $R^1$, $R^2$, $R^3$ and $R^4$ are as described in Table 1.

TABLE 98 covers 262 compounds of the following type

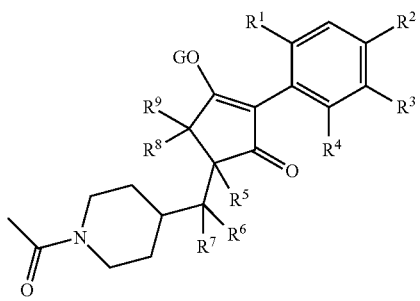

where G, $R^5$, $R^6$, $R^8$ and $R^9$ are hydrogen, $R^7$ is methyl and $R^1$, $R^2$, $R^3$ and $R^4$ are as described in Table 1.

TABLE 99 covers 262 compounds of the following type

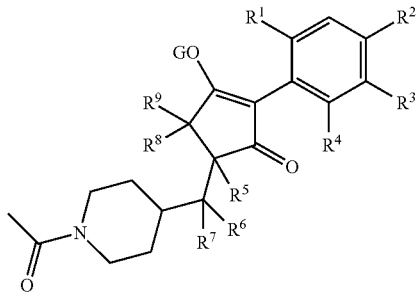

where G and $R^5$, $R^8$ and $R^9$ are hydrogen, $R^6$ and $R^7$ are methyl and $R^1$, $R^2$, $R^3$ and $R^4$ are as described in Table 1.

TABLE 100 covers 262 compounds of the following type:

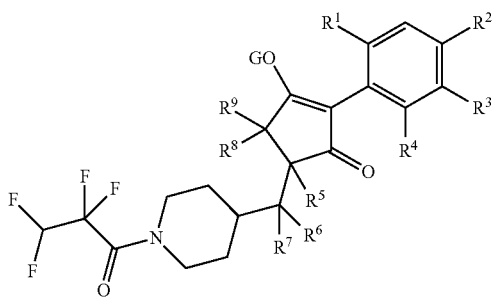

where G, $R^5$, $R^6$, $R^7$, $R^8$ and $R^9$ are all hydrogen, and $R^1$, $R^2$, $R^3$ and $R^4$ are as described in Table 1.

TABLE 101 covers 262 compounds of the following type

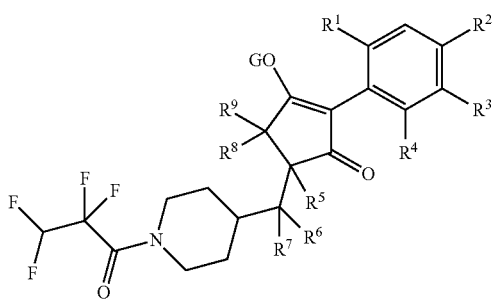

where G, $R^5$, $R^6$, $R^8$ and $R^9$ are hydrogen, $R^7$ is methyl and $R^1$, $R^2$, $R^3$ and $R^4$ are as described in Table 1.

TABLE 102 covers 262 compounds of the following type

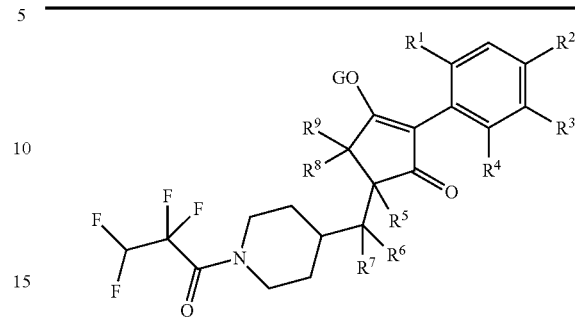

where G and $R^5$, $R^8$ and $R^9$ are hydrogen, $R^6$ and $R^7$ are methyl and $R^1$, $R^2$, $R^3$ and $R^4$ are as described in Table 1.

BIOLOGICAL EXAMPLES

Example A

Seeds of a variety of test species were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 14 or 15 days later for post-emergence and 19 or 20 days for pre-emergence, the test was evaluated (100=total damage to plant; 0=no damage to plant).

Test Plants:

*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG)

Pre-Emergence Activity

| Compound Number | Rate g/ha | ALOMY | AVEFA | LOLPE | SETFA | DIGSA | ECHCG |
|---|---|---|---|---|---|---|---|
| T1 | 500 | 100 | 90 | 100 | 70 | 100 | 80 |
| T2 | 500 | 70 | 10 | 90 | 70 | 80 | 70 |

Post-Emergence Activity

| Compound Number | Rate g/ha | ALOMY | AVEFA | LOLPE | SETFA | DIGSA | ECHCG |
|---|---|---|---|---|---|---|---|
| T1 | 125 | 100 | 90 | 100 | 70 | 100 | 100 |
| T2 | 125 | 80 | 40 | 20 | 100 | 100 | 100 |
| T4 | 250 | 100 | 90 | 100 | 90 | 90 | 100 |

-continued

| Compound Number | Rate g/ha | ALOMY | AVEFA | LOLPE | SETFA | DIGSA | ECHCG |
|---|---|---|---|---|---|---|---|
| T5 | 250 | 100 | 80 | 100 | 30 | 50 | 80 |
| T8 | 250 | 100 | 90 | 100 | 100 | 80 | 100 |
| P5 | 250 | 100 | 100 | 100 | 80 | 70 | 100 |

Example B

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:
*Lolium perenne* (LOLPE), *Alopecurus myosuroides* (ALOMY), *Echinochloa crus-galli* (ECHCG), *Avena fatua* (AVEFA)

Pre-Emergence Activity

| Compound Number | Rate g/ha | LOLPE | ALOMY | ECHCG | AVEFA |
|---|---|---|---|---|---|
| T3 | 250 | 60 | 50 | 20 | 50 |
| T4 | 250 | 100 | 100 | 100 | 90 |
| T5 | 250 | 100 | 100 | 100 | 80 |
| T7 | 250 | 80 | 70 | 100 | 50 |
| T8 | 250 | 100 | 100 | 100 | 100 |
| T9 | 250 | 60 | 20 | 20 | 0 |
| T10 | 250 | 90 | 70 | 70 | 40 |
| T11 | 250 | 70 | 30 | 20 | 0 |
| T12 | 250 | 100 | 100 | 100 | 100 |
| T13 | 250 | 30 | 30 | 10 | 0 |
| T14 | 250 | 100 | 100 | 100 | 100 |
| T15 | 250 | 100 | 70 | 100 | 100 |
| T16 | 250 | 100 | 100 | 100 | 80 |
| T17 | 250 | 100 | 100 | 100 | 100 |
| T18 | 250 | 100 | 100 | 100 | 70 |
| T21 | 250 | 100 | 100 | 90 | 70 |
| T22 | 250 | 100 | 100 | 100 | 90 |
| T23 | 250 | 100 | 100 | 100 | 100 |
| T24 | 250 | 100 | 100 | 100 | 90 |
| T26 | 250 | 100 | 70 | 100 | 60 |
| T27 | 250 | 100 | 90 | 80 | 60 |
| T29 | 250 | 100 | 70 | 90 | 50 |
| T30 | 250 | 90 | 60 | 80 | 30 |
| T31 | 250 | 90 | 80 | 80 | 90 |
| T32 | 250 | 100 | 70 | 100 | 90 |
| T33 | 250 | 90 | 60 | 90 | 50 |
| T34 | 250 | 90 | 70 | 100 | 70 |
| T35 | 250 | 70 | 30 | 40 | 10 |
| T36 | 250 | 90 | 90 | 100 | 90 |
| T37 | 250 | 100 | 100 | 100 | 90 |
| T38 | 250 | 70 | 90 | 100 | 40 |
| T39 | 250 | 100 | 100 | 100 | 100 |
| T40 | 250 | 100 | 100 | 100 | 80 |
| T41 | 250 | 90 | 70 | 100 | 90 |
| T42 | 250 | 0 | 0 | 20 | 0 |
| T43 | 250 | 100 | 80 | 100 | 100 |
| T44 | 250 | 100 | 90 | 60 | 20 |
| T46 | 250 | 10 | 50 | 10 | 10 |
| T47 | 250 | 60 | 20 | 40 | 50 |

-continued

| Compound Number | Rate g/ha | LOLPE | ALOMY | ECHCG | AVEFA |
|---|---|---|---|---|---|
| T48 | 250 | 90 | 90 | 100 | 90 |
| T50 | 250 | 100 | 100 | 100 | 100 |
| T51 | 250 | 100 | 80 | 80 | 90 |
| T52 | 250 | 100 | 100 | 80 | 80 |
| T53 | 250 | 40 | 30 | 0 | 0 |
| T54 | 250 | 100 | 80 | 100 | 50 |
| T55 | 250 | 100 | 80 | 90 | 60 |
| T58 | 250 | 100 | 90 | 100 | 90 |
| T59 | 250 | 100 | 90 | 100 | 90 |
| T60 | 250 | 10 | 10 | 0 | 0 |
| T61 | 250 | 90 | 70 | 90 | 80 |
| T62 | 250 | 100 | 80 | 100 | 70 |
| T63 | 250 | 100 | 70 | 100 | 90 |
| T64 | 250 | 100 | 50 | 100 | 90 |
| T65 | 250 | 80 | 70 | 100 | 80 |
| T66 | 250 | 80 | 90 | 100 | 80 |
| T67 | 250 | 100 | 90 | 100 | 90 |
| T68 | 250 | 90 | 30 | 50 | 40 |
| T69 | 250 | 10 | 0 | 20 | 10 |
| T70 | 250 | 70 | 20 | 60 | 70 |
| T71 | 250 | 30 | 20 | 10 | 20 |
| T72 | 250 | 60 | 30 | 80 | 20 |
| T73 | 250 | 80 | 40 | 80 | 80 |
| T74 | 250 | 30 | 30 | 50 | 20 |
| T75 | 250 | 80 | 30 | 70 | 70 |
| T76 | 250 | 60 | 30 | 60 | 20 |
| T77 | 250 | 0 | 0 | 0 | 0 |
| T78 | 250 | 30 | 20 | 30 | 0 |
| T79 | 250 | 90 | 60 | 60 | 20 |
| T80 | 250 | 100 | 70 | 70 | 70 |
| T81 | 250 | 80 | 80 | 60 | 80 |
| T82 | 250 | 90 | 50 | 60 | 50 |
| T83 | 250 | 90 | 60 | 90 | 70 |
| T84 | 250 | 90 | 50 | 60 | 50 |
| T85 | 250 | 60 | 60 | 30 | 20 |
| T86 | 250 | 100 | 60 | 50 | 30 |
| T87 | 250 | 100 | 90 | 60 | 90 |
| T88 | 250 | 100 | 90 | 80 | 90 |
| T89 | 250 | 70 | 50 | 60 | 10 |
| T90 | 250 | 60 | 40 | 50 | 60 |
| T91 | 250 | 70 | 20 | 60 | 40 |
| T92 | 250 | 30 | 30 | 40 | 10 |
| T93 | 250 | 90 | 60 | 90 | 60 |
| T94 | 250 | 90 | 90 | 80 | 90 |
| T95 | 250 | 100 | 90 | 60 | 90 |
| T96 | 250 | 60 | 20 | 20 | 10 |
| T97 | 250 | 70 | 30 | 60 | 30 |
| T98 | 250 | 90 | 70 | 90 | 80 |
| T99 | 250 | 60 | 20 | 60 | 30 |
| T100 | 250 | 90 | 60 | 70 | 60 |
| T101 | 250 | 50 | 20 | 50 | 30 |
| T102 | 250 | 70 | 50 | 50 | 30 |
| T103 | 250 | 30 | 30 | 10 | 20 |
| T104 | 250 | 70 | 60 | 90 | 60 |
| T105 | 250 | 60 | 20 | 40 | 30 |
| T106 | 250 | 20 | 20 | 20 | 30 |
| T107 | 250 | 70 | 80 | 70 | 60 |
| T108 | 250 | 50 | 10 | 60 | 40 |
| T109 | 250 | 0 | 0 | 0 | 0 |
| T110 | 250 | 50 | 30 | 70 | 30 |
| T111 | 250 | 90 | 40 | 80 | 40 |
| T112 | 250 | 50 | 40 | 30 | 20 |
| T113 | 250 | 70 | 60 | 90 | 70 |
| T114 | 250 | 40 | 50 | 60 | 20 |
| T118 | 250 | 40 | 40 | 30 | 20 |

| Compound Number | Rate g/ha | LOLPE | ALOMY | ECHCG | AVEFA |
|---|---|---|---|---|---|
| T119 | 250 | 80 | 40 | 100 | 30 |
| T120 | 250 | 20 | 30 | 30 | 10 |
| T121 | 250 | 80 | 30 | 90 | 60 |
| T122 | 250 | 50 | 20 | 70 | 20 |
| T123 | 250 | 60 | 60 | 60 | 60 |
| T124 | 250 | 20 | 20 | 30 | 10 |
| T126 | 250 | 60 | 30 | 50 | 40 |
| T128 | 250 | 50 | 70 | 60 | 40 |
| T130 | 250 | 100 | 70 | 30 | 10 |
| T131 | 250 | 90 | 70 | 100 | 70 |
| T132 | 250 | 70 | 20 | 90 | 70 |
| T135 | 250 | 40 | 0 | 60 | 30 |
| T138 | 250 | 90 | 80 | 90 | 70 |
| T139 | 250 | 80 | 70 | 90 | 60 |
| T140 | 250 | 70 | 60 | 90 | 50 |
| T141 | 250 | 80 | 80 | 80 | 80 |
| T142 | 250 | 70 | 90 | 90 | 80 |
| T143 | 250 | 100 | 80 | 100 | 50 |
| T144 | 250 | 70 | 80 | 90 | 70 |
| T145 | 250 | 50 | 60 | 20 | 30 |
| T146 | 250 | 90 | 70 | 70 | 50 |
| T147 | 250 | 30 | 50 | 40 | 10 |
| T148 | 250 | 50 | 70 | 30 | 40 |
| T149 | 250 | 20 | 30 | 30 | 10 |
| T151 | 250 | 30 | 20 | 40 | 10 |
| T156 | 250 | 100 | 80 | 100 | 70 |
| T157 | 250 | 10 | 10 | 40 | 0 |
| T158 | 250 | 90 | 80 | 100 | 70 |
| T159 | 250 | 70 | 50 | 100 | 30 |
| T160 | 250 | 90 | 30 | 70 | 40 |
| T161 | 250 | 90 | 30 | 100 | 60 |
| T162 | 250 | 70 | 40 | 50 | 50 |
| T163 | 250 | 80 | 50 | 60 | 60 |
| P5 | 250 | 100 | 100 | 100 | 80 |
| P7 | 250 | 100 | 100 | 100 | 90 |
| P9 | 250 | 40 | 30 | 20 | 0 |
| P11 | 250 | 100 | 100 | 100 | 100 |
| P13 | 250 | 100 | 100 | 100 | 90 |
| P14 | 250 | 100 | 100 | 100 | 80 |
| P15 | 250 | 100 | 100 | 100 | 90 |
| P16 | 250 | 100 | 100 | 100 | 90 |
| P17 | 250 | 100 | 100 | 90 | 90 |
| P18 | 250 | 100 | 100 | 90 | 80 |
| P20 | 250 | 100 | 100 | 80 | 90 |
| P23 | 250 | 100 | 100 | 100 | 80 |
| P24 | 250 | 100 | 100 | 90 | 90 |
| P25 | 250 | 90 | 100 | 90 | 80 |
| P26 | 250 | 100 | 100 | 90 | 80 |
| P27 | 250 | 100 | 100 | 80 | 80 |
| P28 | 250 | 100 | 70 | 20 | 30 |
| P29 | 250 | 90 | 50 | 0 | 20 |
| P30 | 250 | 100 | 100 | 80 | 90 |
| P31 | 250 | 100 | 100 | 100 | 90 |
| P34 | 250 | 100 | 90 | 100 | 90 |
| P37 | 250 | 100 | 100 | 70 | 70 |
| P42 | 250 | 40 | 30 | 30 | 0 |
| P43 | 250 | 100 | 100 | 100 | 100 |
| P44 | 250 | 100 | 100 | 100 | 90 |
| P45 | 250 | 100 | 100 | 100 | 100 |
| P46 | 250 | 90 | 70 | 100 | 60 |
| P47 | 250 | 60 | 30 | 60 | 50 |
| P48 | 250 | 80 | 70 | 40 | 60 |
| P49 | 250 | 100 | 80 | 100 | 60 |
| P50 | 250 | 100 | 100 | 100 | 100 |
| P51 | 250 | 100 | 100 | 100 | 100 |
| P53 | 250 | 100 | 60 | 90 | 70 |
| P54 | 250 | 100 | 80 | 100 | 70 |
| P55 | 250 | 100 | 100 | 100 | 90 |
| P56 | 250 | 100 | 100 | 100 | 90 |
| P57 | 250 | 60 | 50 | 30 | 70 |
| P58 | 250 | 80 | 70 | 80 | 70 |
| P59 | 250 | 80 | 50 | 70 | 30 |
| P60 | 250 | 80 | 30 | 50 | 0 |
| P61 | 250 | 90 | 50 | 80 | 30 |
| P63 | 250 | 70 | 50 | 70 | 40 |
| P64 | 250 | 80 | 70 | 80 | 70 |
| P65 | 250 | 90 | 60 | 80 | 60 |
| P67 | 250 | 100 | 80 | 90 | 90 |
| P68 | 250 | 100 | 90 | 100 | 90 |
| P71 | 250 | 100 | 90 | 100 | 100 |

Post-Emergence Activity

| Compound Number | Rate g/ha | LOLPE | ALOMY | ECHCG | AVEFA |
|---|---|---|---|---|---|
| T3 | 250 | 70 | 40 | 70 | 70 |
| T4 | 250 | 100 | 100 | 100 | 100 |
| T5 | 250 | 100 | 100 | 100 | 90 |
| T6 | 250 | 10 | 20 | 10 | 0 |
| T7 | 250 | 80 | 100 | 90 | 90 |
| T8 | 250 | 100 | 100 | 100 | 100 |
| T9 | 250 | 80 | 60 | 80 | 30 |
| T10 | 250 | 70 | 70 | 80 | 80 |
| T11 | 250 | 50 | 60 | 70 | 30 |
| T12 | 250 | 100 | 100 | 100 | 100 |
| T13 | 250 | 30 | 10 | 40 | 0 |
| T14 | 250 | 100 | 100 | 100 | 100 |
| T15 | 250 | 100 | 100 | 100 | 100 |
| T16 | 250 | 100 | 100 | 100 | 100 |
| T17 | 250 | 100 | 90 | 100 | 100 |
| T18 | 250 | 100 | 80 | 90 | 70 |
| T21 | 250 | 90 | 90 | 80 | 90 |
| T22 | 250 | 100 | 90 | 100 | 100 |
| T23 | 250 | 100 | 90 | 100 | 100 |
| T24 | 250 | 100 | 90 | 100 | 100 |
| T26 | 250 | 80 | 60 | 60 | 70 |
| T27 | 250 | 80 | 70 | 80 | 70 |
| T29 | 250 | 90 | 70 | 80 | 60 |
| T30 | 250 | 80 | 80 | 80 | 70 |
| T31 | 250 | 70 | 90 | 80 | 90 |
| T32 | 250 | 90 | 90 | 90 | 90 |
| T33 | 250 | 60 | 60 | 60 | 70 |
| T34 | 250 | 90 | 90 | 100 | 100 |
| T35 | 250 | 70 | 70 | 70 | 60 |
| T36 | 250 | 80 | 80 | 90 | 90 |
| T37 | 250 | 100 | 90 | 100 | 100 |
| T38 | 250 | 100 | 100 | 100 | 100 |
| T39 | 250 | 100 | 90 | 100 | 100 |
| T40 | 250 | 100 | 80 | 100 | 90 |
| T41 | 250 | 100 | 100 | 100 | 100 |
| T42 | 250 | 20 | 0 | 30 | 0 |
| T43 | 250 | 100 | 90 | 80 | 90 |
| T44 | 250 | 70 | 60 | 80 | 40 |
| T46 | 250 | 40 | 60 | 60 | 50 |
| T47 | 250 | 30 | 30 | 60 | 50 |
| T48 | 250 | 70 | 90 | 100 | 90 |
| T50 | 250 | 100 | 100 | 100 | 100 |
| T51 | 250 | 60 | 70 | 70 | 80 |
| T52 | 250 | 90 | 90 | 100 | 80 |
| T54 | 250 | 70 | 80 | 80 | 80 |
| T55 | 250 | 60 | 70 | 70 | 50 |
| T58 | 250 | 90 | 100 | 90 | 90 |
| T59 | 250 | 100 | 90 | 90 | 100 |
| T60 | 250 | 20 | 30 | 10 | 10 |
| T61 | 250 | 90 | 90 | 100 | 100 |
| T62 | 250 | 90 | 90 | 100 | 100 |
| T63 | 250 | 90 | 90 | 90 | 100 |
| T64 | 250 | 90 | 90 | 100 | 100 |
| T65 | 250 | 90 | 90 | 100 | 100 |
| T66 | 250 | 60 | 90 | 100 | 90 |
| T67 | 250 | 100 | 90 | 100 | 100 |
| T68 | 250 | 90 | 60 | 90 | 90 |
| T69 | 250 | 30 | 30 | 20 | 30 |
| T70 | 250 | 80 | 70 | 80 | 100 |
| T71 | 250 | 40 | 30 | 70 | 80 |
| T72 | 250 | 80 | 50 | 90 | 80 |
| T73 | 250 | 80 | 90 | 90 | 100 |
| T74 | 250 | 40 | 70 | 100 | 90 |
| T75 | 250 | 100 | 90 | 90 | 100 |

| Compound Number | Rate g/ha | LOLPE | ALOMY | ECHCG | AVEFA |
|---|---|---|---|---|---|
| T76 | 250 | 40 | 90 | 90 | 100 |
| T77 | 250 | 40 | 30 | 20 | 40 |
| T78 | 250 | 50 | 40 | 70 | 40 |
| T79 | 250 | 60 | 60 | 70 | 80 |
| T80 | 250 | 90 | 90 | 80 | 100 |
| T81 | 250 | 90 | 90 | 80 | 100 |
| T82 | 250 | 90 | 90 | 80 | 100 |
| T83 | 250 | 90 | 80 | 70 | 100 |
| T84 | 250 | 100 | 90 | 90 | 100 |
| T85 | 250 | 90 | 90 | 80 | 90 |
| T86 | 250 | 70 | 40 | 80 | 80 |
| T87 | 250 | 90 | 70 | 70 | 90 |
| T88 | 250 | 90 | 90 | 90 | 100 |
| T89 | 250 | 40 | 30 | 40 | 20 |
| T90 | 250 | 80 | 70 | 80 | 100 |
| T91 | 250 | 50 | 40 | 50 | 90 |
| T92 | 250 | 20 | 30 | 40 | 60 |
| T93 | 250 | 70 | 60 | 60 | 70 |
| T94 | 250 | 90 | 100 | 90 | 100 |
| T95 | 250 | 100 | 90 | 70 | 100 |
| T96 | 250 | 60 | 60 | 40 | 40 |
| T97 | 250 | 60 | 70 | 80 | 70 |
| T98 | 250 | 100 | 100 | 90 | 100 |
| T99 | 250 | 50 | 70 | 90 | 90 |
| T100 | 250 | 80 | 90 | 60 | 90 |
| T101 | 250 | 40 | 40 | 20 | 40 |
| T102 | 250 | 80 | 90 | 40 | 90 |
| T103 | 250 | 50 | 50 | 30 | 60 |
| T104 | 250 | 80 | 70 | 70 | 90 |
| T105 | 250 | 50 | 30 | 30 | 40 |
| T106 | 250 | 30 | 40 | 30 | 10 |
| T107 | 250 | 90 | 70 | 60 | 90 |
| T108 | 250 | 70 | 70 | 40 | 70 |
| T110 | 250 | 50 | 30 | 40 | 80 |
| T111 | 250 | 80 | 80 | 70 | 90 |
| T112 | 250 | 30 | 40 | 30 | 30 |
| T113 | 250 | 100 | 90 | 70 | 100 |
| T114 | 250 | 50 | 40 | 30 | 40 |
| T116 | 250 | 90 | 60 | 50 | 90 |
| T118 | 250 | 30 | 60 | 40 | 80 |
| T119 | 250 | 90 | 90 | 90 | 80 |
| T120 | 250 | 30 | 30 | 10 | 20 |
| T121 | 250 | 90 | 80 | 80 | 100 |
| T122 | 250 | 80 | 60 | 70 | 30 |
| T123 | 250 | 70 | 80 | 60 | 90 |
| T124 | 250 | 20 | 30 | 20 | 30 |
| T126 | 250 | 70 | 50 | 60 | 70 |
| T127 | 250 | 20 | 20 | 20 | 10 |
| T128 | 250 | 50 | 40 | 50 | 90 |
| T130 | 250 | 90 | 60 | 60 | 70 |
| T131 | 250 | 100 | 90 | 90 | 90 |
| T132 | 250 | 70 | 70 | 100 | 80 |
| T133 | 250 | 0 | 20 | 90 | 30 |
| T135 | 250 | 70 | 80 | 90 | 80 |
| T136 | 250 | 30 | 50 | 60 | 70 |
| T138 | 250 | 90 | 90 | 70 | 90 |
| T139 | 250 | 90 | 90 | 100 | 90 |
| T140 | 250 | 90 | 90 | 90 | 60 |
| T141 | 250 | 70 | 80 | 60 | 90 |
| T142 | 250 | 70 | 90 | 60 | 90 |
| T143 | 250 | 60 | 60 | 60 | 80 |
| T144 | 250 | 80 | 80 | 80 | 90 |
| T145 | 250 | 40 | 60 | 30 | 50 |
| T146 | 250 | 80 | 80 | 70 | 90 |
| T147 | 250 | 40 | 60 | 50 | 70 |
| T148 | 250 | 70 | 80 | 60 | 100 |
| T149 | 250 | 40 | 30 | 20 | 40 |
| T151 | 250 | 20 | 30 | 40 | 10 |
| T152 | 250 | 30 | 20 | 10 | 10 |
| T153 | 250 | 20 | 10 | 10 | 20 |
| T156 | 250 | 100 | 90 | 70 | 90 |
| T157 | 250 | 30 | 30 | 60 | 50 |
| T158 | 250 | 100 | 100 | 100 | 100 |
| T159 | 250 | 100 | 90 | 100 | 90 |
| T160 | 250 | 100 | 40 | 70 | 60 |
| T161 | 250 | 100 | 70 | 90 | 90 |
| T162 | 250 | 90 | 60 | 70 | 80 |
| T163 | 250 | 100 | 90 | 90 | 100 |
| P4 | 250 | 30 | 60 | 20 | 40 |
| P5 | 250 | 100 | 100 | 100 | 90 |
| P7 | 250 | 100 | 100 | 90 | 80 |
| P9 | 250 | 40 | 30 | 50 | 10 |
| P11 | 250 | 100 | 90 | 100 | 90 |
| P13 | 250 | 100 | 90 | 100 | 90 |
| P14 | 250 | 100 | 90 | 90 | 90 |
| P15 | 250 | 100 | 100 | 100 | 90 |
| P16 | 250 | 100 | 100 | 100 | 100 |
| P17 | 250 | 100 | 100 | 100 | 90 |
| P18 | 250 | 100 | 90 | 90 | 90 |
| P20 | 250 | 100 | 100 | 100 | 90 |
| P23 | 250 | 100 | 90 | 90 | 90 |
| P24 | 250 | 100 | 90 | 90 | 90 |
| P25 | 250 | 100 | 90 | 100 | 90 |
| P26 | 250 | 100 | 100 | 100 | 90 |
| P27 | 250 | 100 | 80 | 90 | 80 |
| P28 | 250 | 100 | 70 | 60 | 70 |
| P29 | 250 | 100 | 80 | 30 | 70 |
| P30 | 250 | 100 | 100 | 90 | 100 |
| P31 | 250 | 100 | 90 | 100 | 90 |
| P34 | 250 | 100 | 80 | 60 | 90 |
| P37 | 250 | 90 | 90 | 90 | 90 |
| P42 | 250 | 40 | 60 | 70 | 70 |
| P43 | 250 | 100 | 100 | 100 | 90 |
| P44 | 250 | 100 | 100 | 100 | 100 |
| P45 | 250 | 100 | 100 | 90 | 100 |
| P46 | 250 | 80 | 90 | 70 | 90 |
| P47 | 250 | 60 | 70 | 50 | 60 |
| P48 | 250 | 90 | 90 | 90 | 100 |
| P49 | 250 | 100 | 80 | 100 | 90 |
| P50 | 250 | 100 | 100 | 100 | 100 |
| P51 | 250 | 100 | 100 | 100 | 100 |
| P53 | 250 | 20 | 60 | 70 | 40 |
| P54 | 250 | 40 | 70 | 80 | 50 |
| P55 | 250 | 100 | 90 | 100 | 100 |
| P56 | 250 | 100 | 90 | 90 | 100 |
| P57 | 250 | 60 | 80 | 70 | 80 |
| P58 | 250 | 90 | 90 | 70 | 90 |
| P59 | 250 | 80 | 90 | 70 | 80 |
| P60 | 250 | 70 | 80 | 40 | 80 |
| P61 | 250 | 90 | 90 | 90 | 90 |
| P62 | 250 | 80 | 70 | 70 | 70 |
| P63 | 250 | 80 | 90 | 70 | 90 |
| P64 | 250 | 90 | 100 | 90 | 100 |
| P65 | 250 | 90 | 90 | 90 | 90 |
| P67 | 250 | 100 | 100 | 100 | 100 |
| P68 | 250 | 100 | 90 | 100 | 90 |
| P69 | 250 | 40 | 0 | 80 | 20 |
| P71 | 250 | 100 | 100 | 100 | 90 |

Example C

Seeds of the Winter Wheat variety 'Hereward' were sown in standard soil in pots. After 8 days cultivation under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

Seeds of the Winter Wheat variety 'Hereward' were seed treated with a wettable powder formulation of the cereal herbicide safener, cloquintocet mexyl, at a rate of 0.5 grams per kilogram of dry seed prior to the initiation of glasshouse testing. One seed was sown per 1.5 inch plastic pot into a sandy loam soil at a depth of 1 cm, 8 days prior to application of the test compounds and was watered and grown under controlled conditions in a glasshouse (at 24/16° C., day/night;

14 hours light; 65% humidity). The plants were sprayed Post-emergence with an aqueous spray solution derived from the formulation of the technical active ingredient in acetone/water (50:50) solution containing 0.5% Tween 20 (polyoxy-ethelyene sorbitan monolaurate, CAS RN 9005-64-5).

The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

| Compound Number | Rate g/ha | Winter Wheat (Hereward) | Winter Wheat (Hereward) + cloquintocet mexyl |
|---|---|---|---|
| T4  | 250 | 70 | 40 |
| T5  | 250 | 80 | 20 |
| T8  | 250 | 90 | 80 |
| T10 | 250 | 60 | 20 |
| T12 | 250 | 70 | 60 |
| T14 | 250 | 80 | 60 |
| T16 | 250 | 80 | 20 |
| T17 | 250 | 70 | 50 |
| T22 | 250 | 80 | 70 |
| T37 | 250 | 80 | 70 |
| T39 | 250 | 80 | 70 |
| T40 | 250 | 60 | 10 |
| T41 | 250 | 90 | 80 |
| T62 | 250 | 80 | 70 |
| T64 | 250 | 80 | 70 |
| T66 | 250 | 50 | 20 |
| T67 | 250 | 70 | 30 |
| T75 | 250 | 60 | 50 |
| T84 | 250 | 70 | 60 |
| T88 | 250 | 70 | 50 |
| T98 | 250 | 90 | 60 |
| P5  | 250 | 60 | 30 |
| P7  | 250 | 70 | 0 |
| P11 | 250 | 80 | 70 |
| P13 | 250 | 70 | 10 |
| P16 | 250 | 70 | 0 |
| P17 | 250 | 70 | 0 |
| P20 | 250 | 40 | 0 |
| P43 | 250 | 50 | 40 |
| P44 | 250 | 70 | 40 |
| P56 | 250 | 90 | 60 |

What is claimed is:

1. A compound of formula I

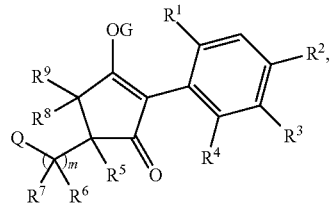

(I)

wherein:

$R^1$ is methyl, ethyl, n-propyl, iso-propyl, halomethyl, haloethyl, halogen, vinyl, ethynyl, methoxy, ethoxy, halomethoxy, haloethoxy, cyclopropyl or halocyclopropyl, $R^2$ and $R^3$ are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_2$-$C_6$haloalkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl; or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl;

$R^4$ is hydrogen, methyl, ethyl, n-propyl, iso-propyl, halomethyl, haloethyl, halogen, vinyl, ethynyl, methoxy, ethoxy, halomethoxy or haloethoxy;

$R^5$ is hydrogen or methyl;

$R^6$ and $R^7$ independently are hydrogen or methyl;

$R^8$ and $R^9$ independently are hydrogen or methyl; and m is 1;

and wherein Q is selected from those of the following formulae:

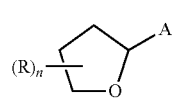

$Q_1$

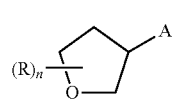

$Q_2$

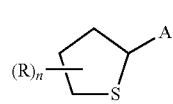

$Q_3$

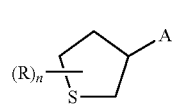

$Q_4$

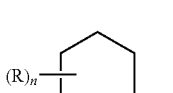

$Q_5$

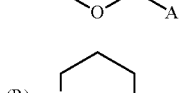

$Q_6$

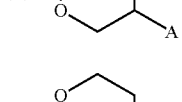

$Q_7$

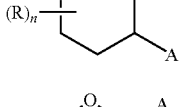

$Q_{25}$

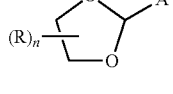

$Q_{26}$

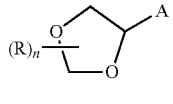

$Q_{27}$

| 225 -continued | | 226 -continued | |
|---|---|---|---|
| 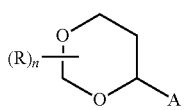 | Q28 | 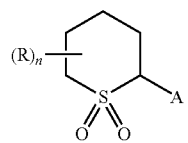 | Q40 |
| 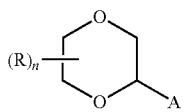 | Q29 | 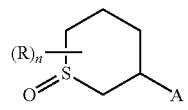 | Q41 |
| 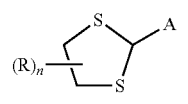 | Q30 | 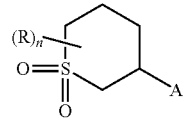 | Q42 |
| 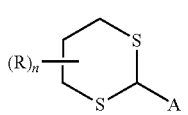 | Q31 | 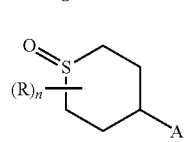 | Q43 |
| 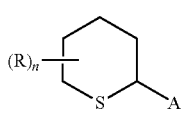 | Q32 | 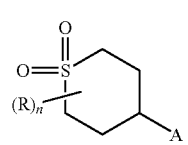 | Q44 |
| 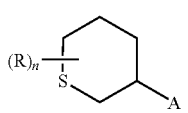 | Q33 | 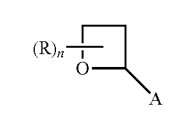 | Q46 |
| 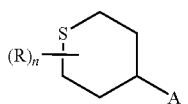 | Q34 | 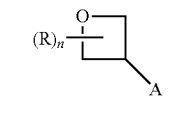 | Q47 |
| 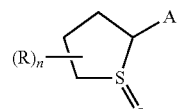 | Q35 | 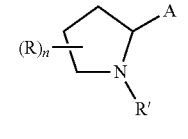 | Q86 |
| 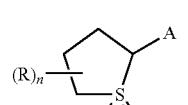 | Q36 | 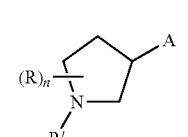 | Q87 |
| 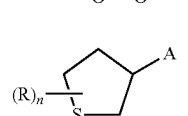 | Q37 | 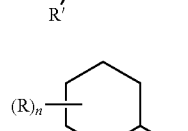 | Q88 |
| 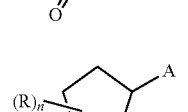 | Q38 | 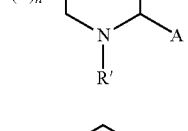 | Q89 |
| 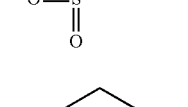 | Q39 | 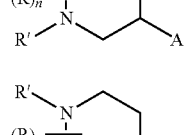 | Q90 |
| 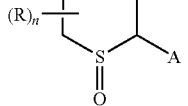 | | | |

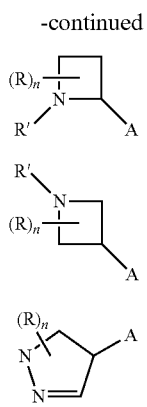

wherein:
R is hydrogen, $C_1$-$C_4$alkyl, $C_1$haloalkyl, $C_1$-$C_4$alkoxy or $C_1$haloalkoxy;
R' is $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_6$arylsulfonyl, $C_6$-$C_{10}$arylcarbonyl, $C_6$-$C_{10}$arylaminocarbonyl, $C_7$-$C_{16}$arylalkylaminocarbonyl, $C_1$-$C_9$heteroarylcarbonyl, $C_1$-$C_9$heteroarylaminocarbonyl or $C_2$-$C_{16}$heteroarylalkylaminocarbonyl;
n is 0, 1 or 2; and
A denotes the position of attachment to the —$(CR^6R^7)_m$— moiety; and
G is hydrogen or an agriculturally acceptable metal, sulfonium, ammonium or latentiating group;
wherein, when G is a latentiating group then G is selected from the groups phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$alkenyl, $C_3$haloalkenyl, $C_3$alkynyl, $C(X^a)$—$R^a$, $C(X^b)$—$X^c$—$R^b$, $C(X^d)$—$N(R^c)$—$R^d$, —$SO_2$—Re, —$P(X^e)(R^f)$—$R^g$ and $CH_2$—$X^f$—$R^h$;
wherein:
$X^a$, $X^b$, $X^c$, $X^d$, $X^e$ and $X^f$ are independently of each other oxygen or sulfur;
$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_6$alkylamino$C_1$-$C_6$alkyl, $C_2$-$C_8$dialkylamino$C_1$-$C_6$alkyl, $C_3$-$C_7$cycloalkyl$C_1$-$C_5$alkyl, $C_1$-$C_6$alkoxy$C_1$-$C_6$alkyl, $C_3$-$C_6$alkenyloxy$C_1$-$C_6$alkyl, $C_1$-$C_6$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;
$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and
$R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ are joined together to form a 3-7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_8$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino;

or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_5$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein:

the term "heteroaryl" means an aromatic ring system containing at least one heteroatom and consisting either of a single ring or of two fused rings.

2. A compound according to claim 1, wherein:

haloalkyl groups are $CF_3$, $CF_2Cl$, $CF_2H$, $CCl_2H$, $FCH_2$, $ClCH_2$, $BrCH_2$, $CH_3CHF$, $CF_3CH_2$ or $CHF_2CH_2$;

the term "heteroaryl" means an aromatic ring system containing at least one heteroatom and consisting either of a single ring or of two fused rings; wherein a single ring contains up to three heteroatoms chosen from nitrogen, oxygen and sulphur, and a bicyclic system contains up to four heteroatoms chosen from nitrogen, oxygen and sulphur.

3. A compound according to claim 1, wherein $R^1$ is methyl, ethyl or methoxy.

4. A compound according to claim 1, wherein $R^2$ and $R^3$ are independently hydrogen, halogen, $C_1$-$C_6$alkyl, $C_1$-$C_6$alkoxy, $C_2$-$C_6$alkenyl, $C_2$-$C_6$alkynyl, $C_2$-$C_6$haloalkynyl, phenyl, or phenyl substituted by $C_1$-$C_4$alkyl, $C_1$-$C_3$haloalkyl, cyano, nitro, halogen or $C_1$-$C_3$alkylsulfonyl.

5. A compound according to claim 4, wherein $R^2$ and $R^3$ are independently hydrogen, chlorine, bromine, methyl, methoxy, ethyl, ethoxy, ethenyl, ethynyl, phenyl, or phenyl substituted by methyl, trifluoromethyl, cyano, nitro, fluorine, chlorine or methylsulfonyl.

6. A compound according to claim 3, wherein $R^3$ is hydrogen; and $R^2$ is halogen, $C_1$-$C_6$alkyl, $C_1$alkoxy, $C_2$-$C_6$alkenyl, $C_2$-$C_6$alkynyl, $C_2$-$C_6$haloalkynyl, phenyl, or phenyl substituted by $C_1$alkyl, $C_1$haloalkyl, cyano, nitro, halogen or $C_1$alkylsulfonyl.

7. A compound according to claim 1, wherein $R^3$ is hydrogen.

8. A compound according to claim 1, wherein $R^4$ is hydrogen, methyl, ethyl, n-propyl, halogen, vinyl, ethynyl, methoxy, ethoxy, halomethoxy or haloethoxy.

9. A compound according to claim 8, wherein $R^4$ is hydrogen, methyl, ethyl, chlorine, bromine, ethenyl, ethynyl, methoxy or ethoxy.

10. A compound according to claim 6, wherein $R^4$ is hydrogen, methyl, ethyl, chlorine, bromine, ethenyl, ethynyl, methoxy or ethoxy.

11. A compound according to claim 1, wherein $R^6$ and $R^7$ are hydrogen.

12. A compound according to claim 1, wherein $R^8$ and $R^9$ are hydrogen.

13. A compound according to claim 1, wherein:

$R^5$ is hydrogen;

$R^6$ and $R^7$ are hydrogen; and $R^8$ and $R^9$ are hydrogen.

14. A compound according to claim 1, wherein:

R is hydrogen, $C_1$alkyl, $C_1$haloalkyl, $C_1$alkoxy or $C_1$haloalkoxy; and

R' is $C_1$-$C_6$alkoxy, $C_1$-$C_6$haloalkoxy, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_6$arylcarbonyl, or $C_1$-$C_9$heteroarylcarbonyl.

15. A compound according to claim 1, wherein Q is selected from the groups $Q_1$, $Q_2$, $Q_5$, $Q_6$, $Q_7$, $Q_{25}$, $Q_{26}$, $Q_{27}$, $Q_{28}$, $Q_{29}$, $Q_{86}$, $Q_{87}$, $Q_{88}$, $Q_{89}$, and $Q_{90}$.

16. A compound according to claim 15, wherein Q is selected from the groups $C_1$ to $C_7$.

17. A compound according to claim 15, wherein:

n is 0; and

R' is $C_1$-$C_6$alkoxy, $C_1$-$C_6$haloalkoxy, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_6$arylcarbonyl, or $C_1$-$C_9$heteroarylcarbonyl.

18. A compound according to claim 1, wherein n is 0.

19. A compound according to claim 10, wherein:

Q is selected from the groups $Q_1$, $Q_2$, $Q_5$, $Q_6$, $Q_7$, $Q_{25}$, $Q_{26}$, $Q_{27}$, $Q_{28}$, $Q_{29}$, $Q_{86}$, $Q_{87}$, $Q_{88}$, $Q_{89}$, and $Q_{90}$;

n is 0; and

R' is $C_1$-$C_6$alkoxy, $C_1$-$C_6$haloalkoxy, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_6$arylcarbonyl, or $C_1$-$C_9$heteroarylcarbonyl.

20. A compound according to claim 1, wherein, when G is a latentiating group then G is a group —$C(X^a)$—$R^a$ or —$C(X^b)$—$X^c$—$R^b$, wherein the meanings of $X^a$, $R^a$, $X^b$, $X^c$ and $R^b$ are as defined in claim 1.

21. A compound according to claim 1, wherein G is hydrogen, an alkali metal or an alkaline earth metal.

22. A herbicidal composition, which, in addition to comprising formulation adjuvants, comprises a herbicidally effective amount of a compound of formula I as defined in claim 1.

23. A compound which is one of the following compounds:

(T8)

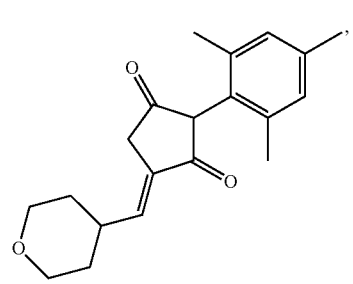

(T10) 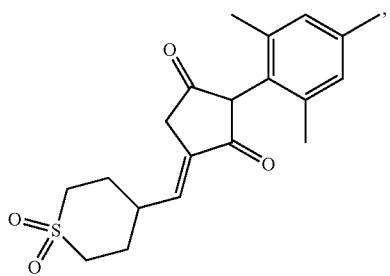
(T12) 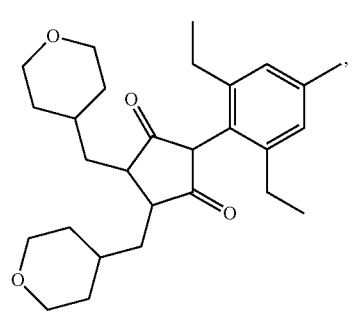
(T14) 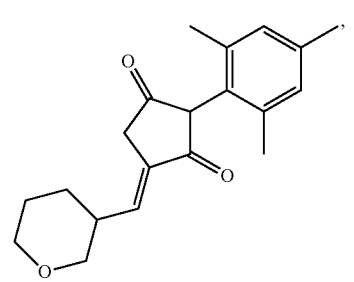
(T15) 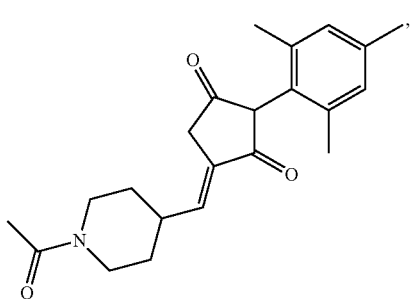
(T17) 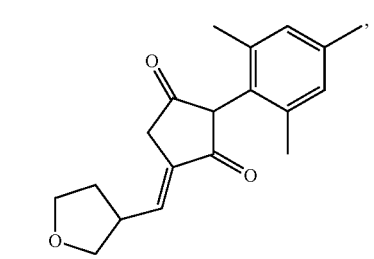
(T21) 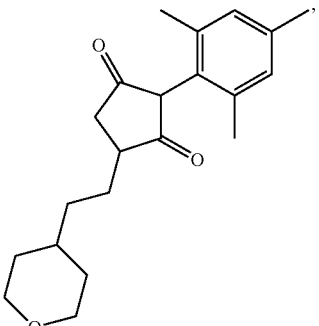
(T22) 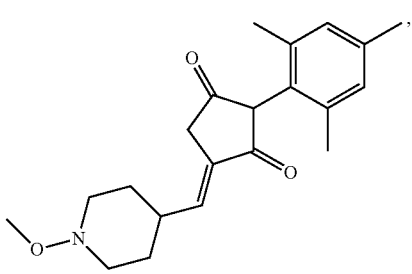
(T31) 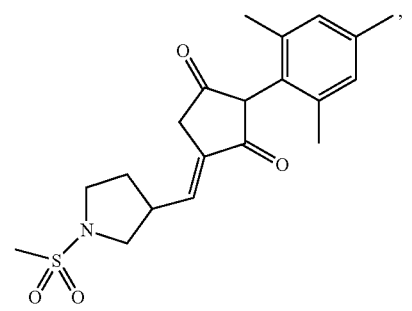
(T32) 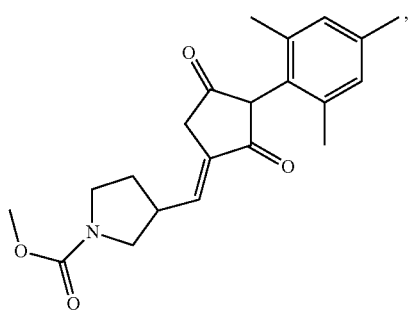
(T34) 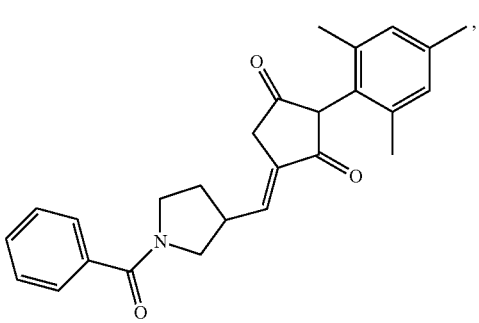

(T37)
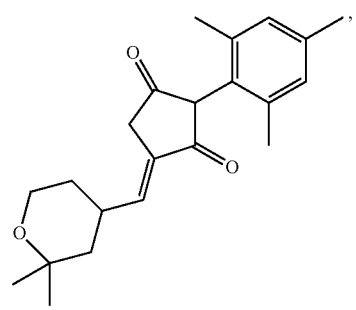
(T38)
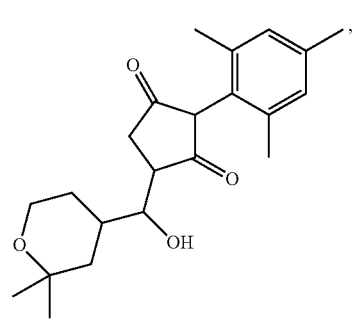
(T54)
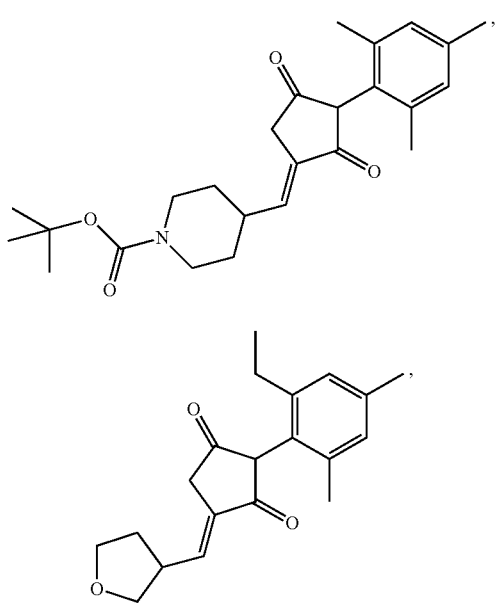
(T59)
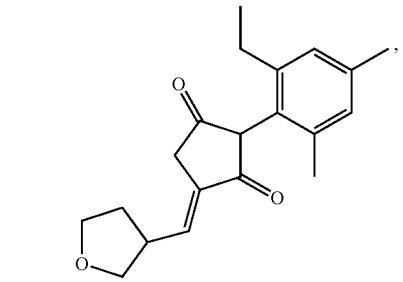
(T61)
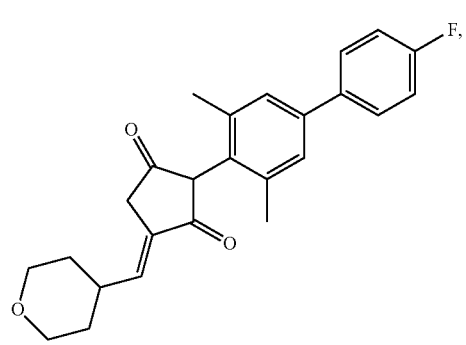
(T62)
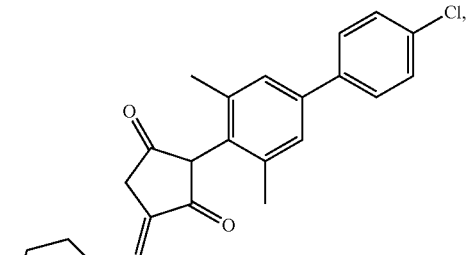
(T65)
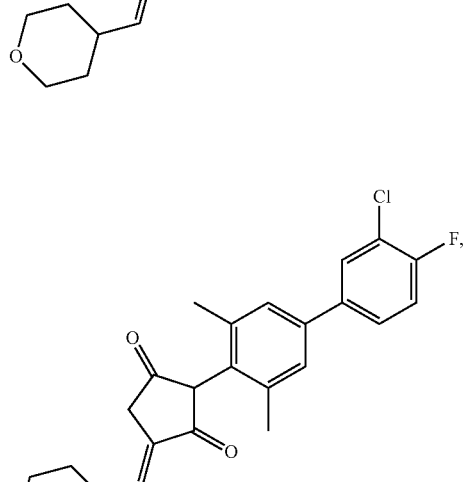
(T66)
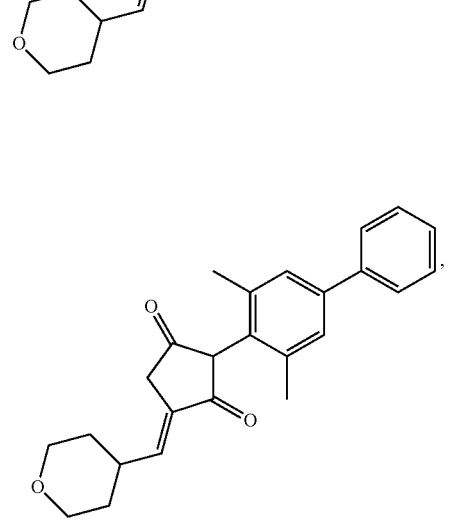
(T68)
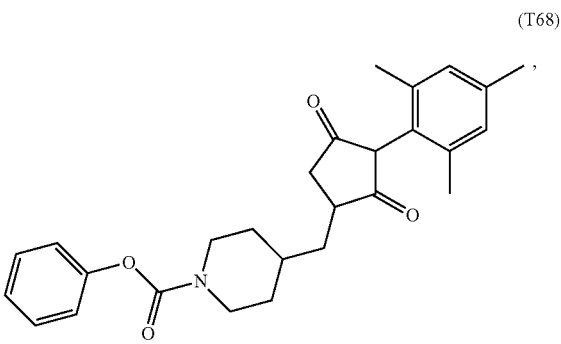

(T72) 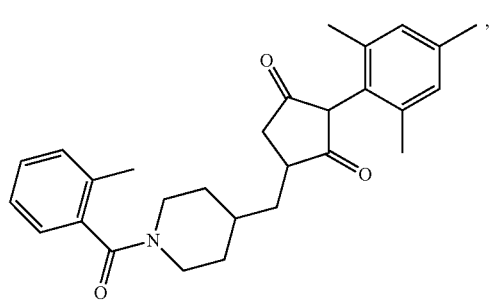
(T73) 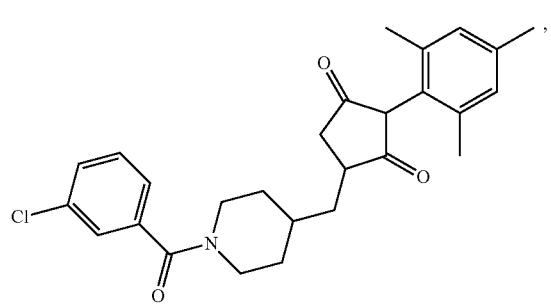
(T74) 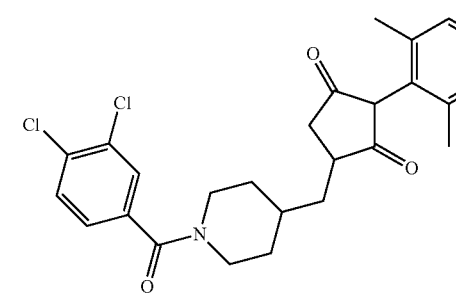
(T75) 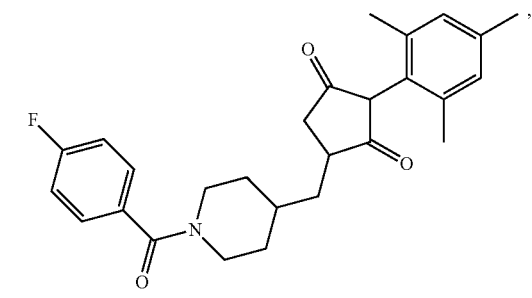
(T76) 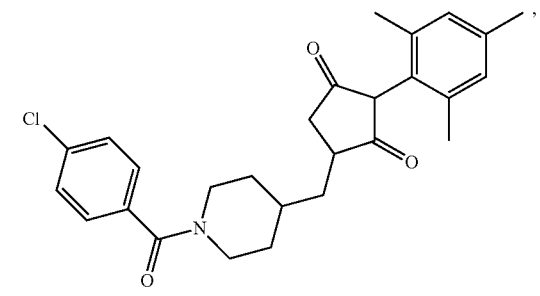
(T81) 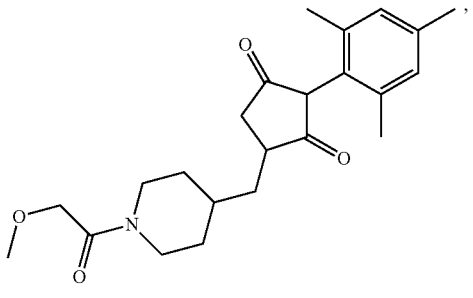
(T82) 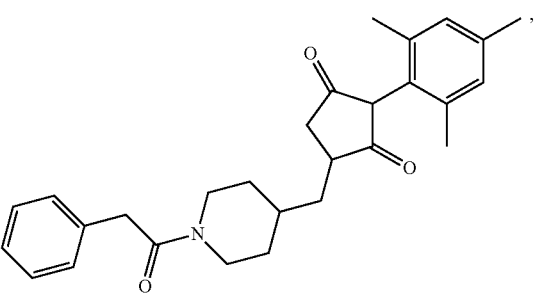
(T86) 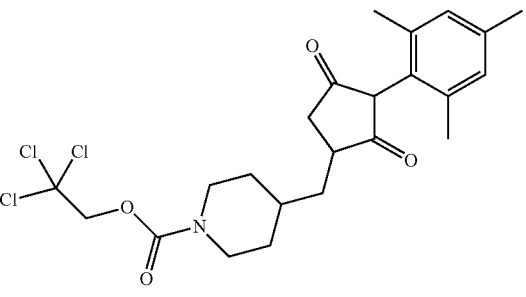
(T88) 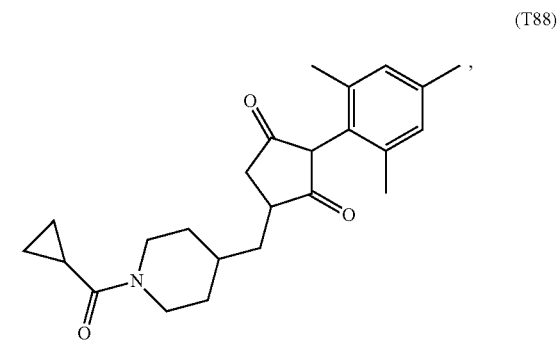
(T97) 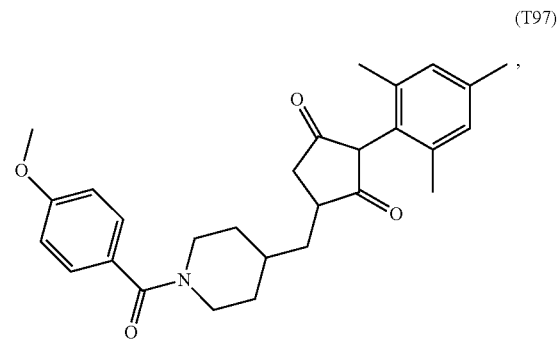

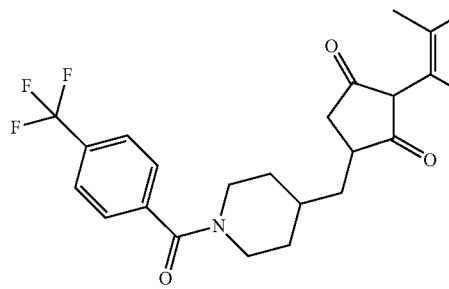
(T99)
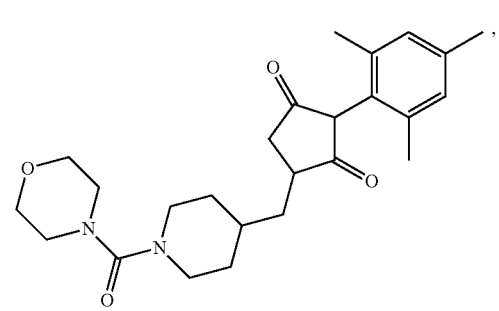
(T100)
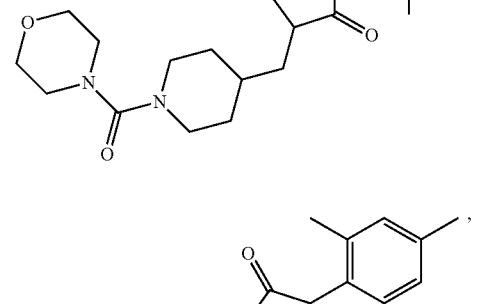
(T102)
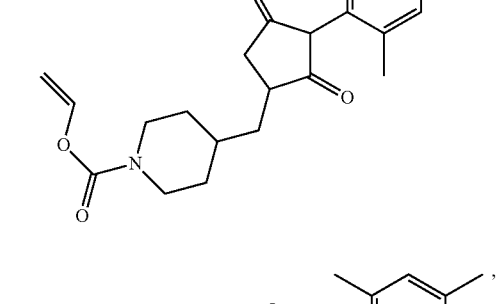
(T104)
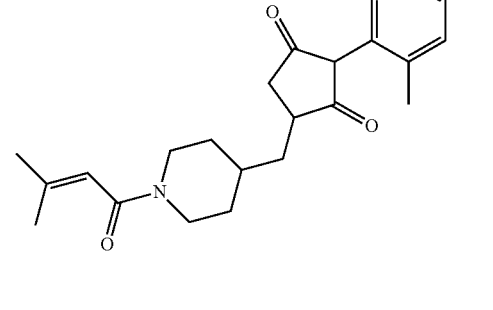
(T111)
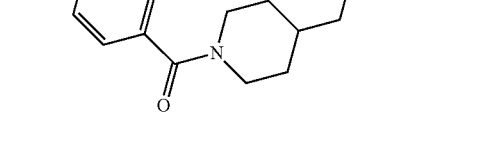
(T116)
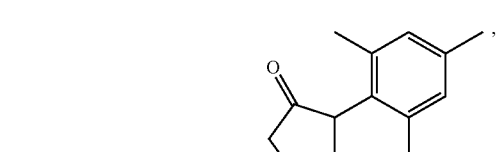
(T118)
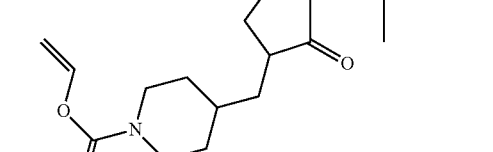
(T119)
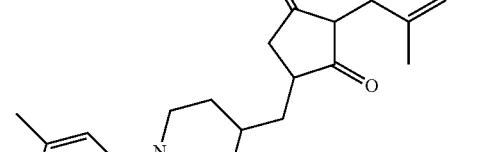
(T121)
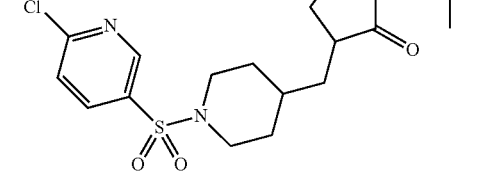
(T123)

241
-continued
(T132)
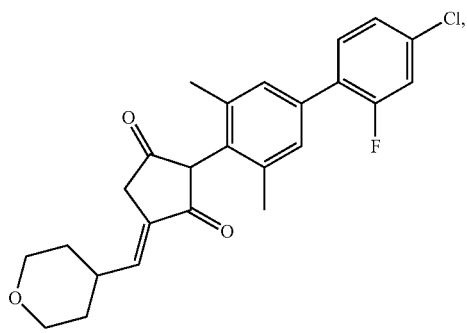
(T135)
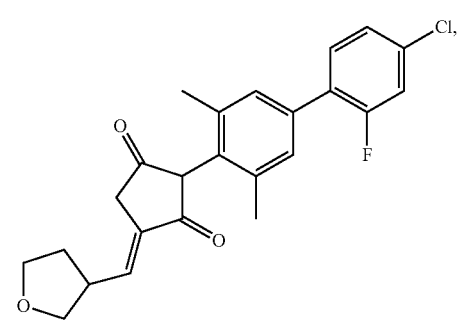
(T141)
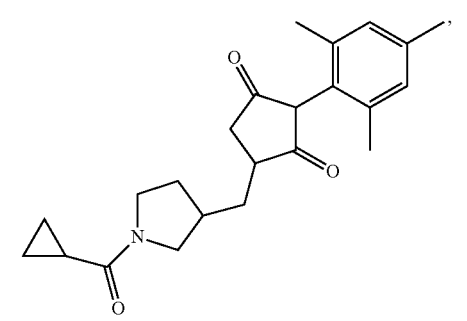
(T144)
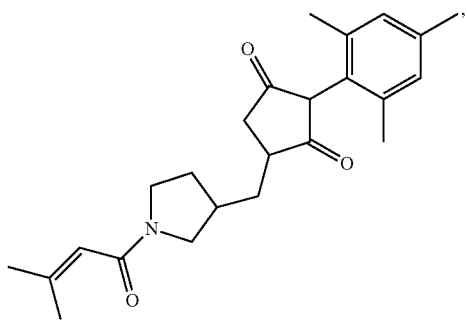
242
-continued
(T148)
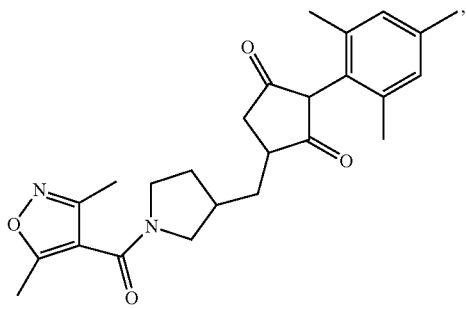
(T173)
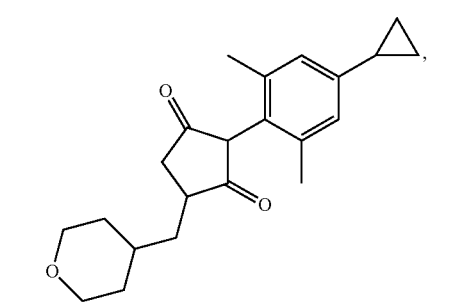
(P11)
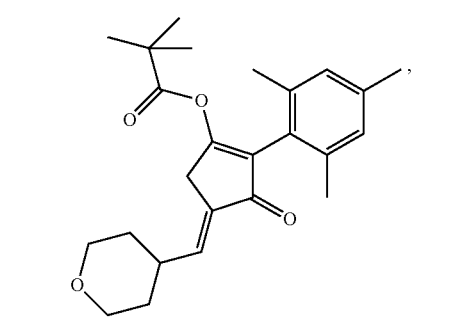
(P34)
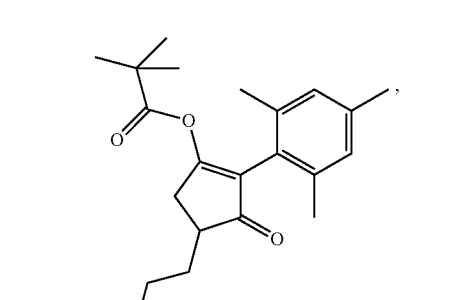
(P42)
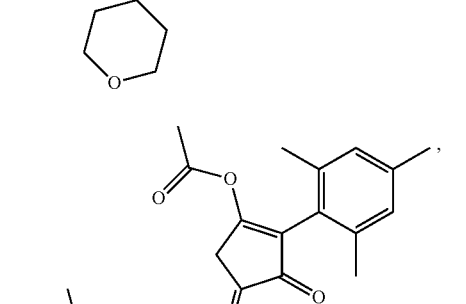

-continued
(P46) 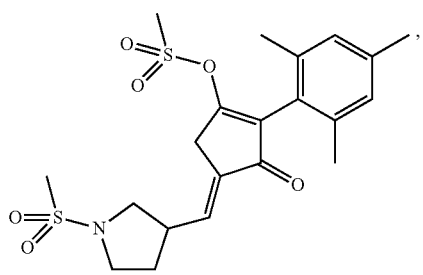
(P47) 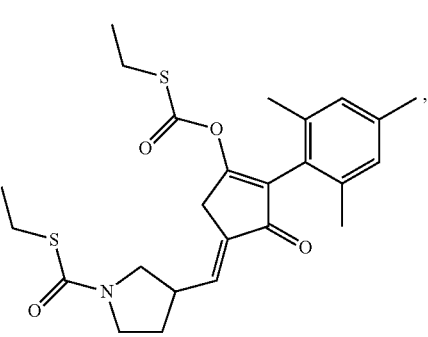
(P48) 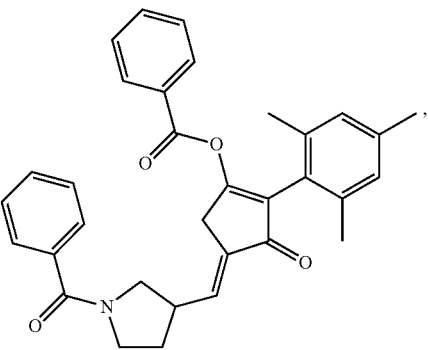
(P57) 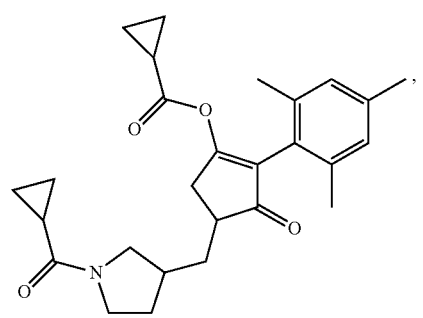
-continued
(P63) 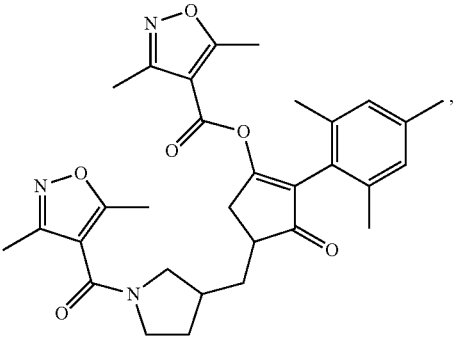
(P64) 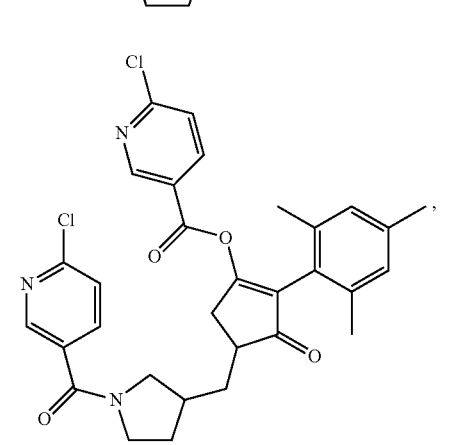
(P70) or 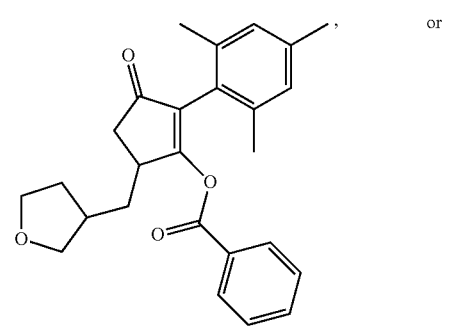
(P71) 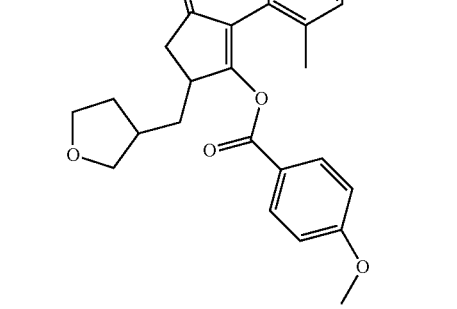
* * * * *